US012678594B2

(12) United States Patent
Misener

(10) Patent No.: US 12,678,594 B2
(45) Date of Patent: *Jul. 14, 2026

(54) ICONIC REPRESENTATIONS RELATING TO SYSTEMS FOR PLACING A MEDICAL DEVICE

(71) Applicant: C. R. Bard, Inc., Franklin Lakes, NJ (US)

(72) Inventor: Anthony K. Misener, Bountiful, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1588 days.

This patent is subject to a terminal disclaimer.

(21) Appl. No.: 16/930,209

(22) Filed: Jul. 15, 2020

(65) Prior Publication Data

US 2020/0345983 A1     Nov. 5, 2020

Related U.S. Application Data

(63) Continuation of application No. 14/201,300, filed on Mar. 7, 2014, now Pat. No. 10,751,509, which is a
(Continued)

(51) Int. Cl.
*A61B 8/08* (2006.01)
*A61B 5/06* (2006.01)
(Continued)

(52) U.S. Cl.
CPC ........... *A61M 25/0102* (2013.01); *A61B 5/06* (2013.01); *A61B 5/061* (2013.01); *A61B 5/283* (2021.01);
(Continued)

(58) Field of Classification Search
CPC ........ A61N 1/37247; A61B 5/06; A61B 5/061
See application file for complete search history.

(56) References Cited

U.S. PATENT DOCUMENTS 2,619,515 A     11/1952   Doane
2,646,086 A      7/1953   Smith
(Continued)

FOREIGN PATENT DOCUMENTS

AU         642647 B2     10/1993
AU         706052 B2      6/1999
(Continued)

OTHER PUBLICATIONS

"Ascension to Launch New 3D Guidance™ Tracker at TCT 2006." Press Releases from Ascension website: www.ascension-tech.com/news/press_101106.php, last accessed Dec. 1, 2006.
(Continued)

*Primary Examiner* — William J Levicky
(74) *Attorney, Agent, or Firm* — Rutan & Tucker LLP

(57) ABSTRACT

An integrated catheter placement system for accurately placing a catheter within a patient's vasculature is disclosed. In one embodiment, the integrated system comprises a system console, a tip location sensor for temporary placement on the patient's chest, and an ultrasound probe. The tip location sensor senses a magnetic field of a stylet disposed in a lumen of the catheter when the catheter is disposed in the vasculature. The ultrasound probe ultrasonically images a portion of the vasculature prior to introduction of the catheter. ECG signal-based catheter tip guidance is included in the integrated system to enable guidance of the catheter tip to a desired position with respect to a node of the patient's heart. Iconic representations for depiction on the display of the system and relating to positional and other characteristics of the catheter or medical device are also disclosed.

19 Claims, 57 Drawing Sheets

Related U.S. Application Data continuation-in-part of application No. 12/557,401, filed on Sep. 10, 2009, now Pat. No. 8,849,382, which is a continuation-in-part of application No. 12/426, 175, filed on Apr. 17, 2009, now Pat. No. 9,649,048, which is a continuation-in-part of application No. 12/323,273, filed on Nov. 25, 2008, now Pat. No. 8,388,541.

(60) Provisional application No. 61/775,397, filed on Mar. 8, 2013, provisional application No. 61/095,921, filed on Sep. 10, 2008, provisional application No. 61/095,451, filed on Sep. 9, 2008, provisional application No. 61/091,233, filed on Aug. 22, 2008, provisional application No. 61/045,944, filed on Apr. 17, 2008, provisional application No. 60/990,242, filed on Nov. 26, 2007.

(51) Int. Cl.

| | |
|---|---|
| *A61B 5/283* | (2021.01) |
| *A61B 34/20* | (2016.01) |
| *A61M 25/01* | (2006.01) |
| *A61N 1/372* | (2006.01) |
| *A61B 46/00* | (2016.01) |
| *A61B 90/00* | (2016.01) |
| *A61B 90/40* | (2016.01) |

(52) U.S. Cl.

CPC .......... *A61B 8/0833* (2013.01); *A61B 8/0841* (2013.01); *A61B 34/20* (2016.02); *A61N 1/37247* (2013.01); *A61B 2034/2051* (2016.02); *A61B 46/00* (2016.02); *A61B 2090/378* (2016.02); *A61B 90/40* (2016.02)

(56) References Cited

U.S. PATENT DOCUMENTS

| | | | |
|---|---|---|---|
| 3,133,244 | A | 5/1964 | Wojtulewicz |
| 3,297,020 | A | 1/1967 | Mathiesen |
| 3,625,200 | A | 12/1971 | Muller |
| 3,674,014 | A | 7/1972 | Tillander |
| 3,794,041 | A | 2/1974 | Frei et al. |
| 3,795,855 | A | 3/1974 | Browning |
| 3,817,241 | A | 6/1974 | Grausz |
| 3,847,157 | A | 11/1974 | Caillouette et al. |
| 3,868,565 | A | 2/1975 | Kuipers |
| 3,896,373 | A | 7/1975 | Zelby |
| 3,902,501 | A | 9/1975 | Citron et al. |
| 3,986,373 | A | 10/1976 | Goodlaxson |
| 3,995,623 | A | 12/1976 | Blake et al. |
| 4,003,369 | A | 1/1977 | Heilman et al. |
| 4,063,561 | A | 12/1977 | McKenna |
| 4,072,146 | A | 2/1978 | Howes |
| 4,114,601 | A | 9/1978 | Abels |
| 4,149,535 | A | 4/1979 | Volder |
| 4,161,943 | A | 7/1979 | Nogier |
| 4,173,228 | A | 11/1979 | Van Steenwyk et al. |
| 4,175,566 | A | 11/1979 | Millar |
| 4,181,120 | A | 1/1980 | Kunii et al. |
| 4,224,949 | A | 9/1980 | Scott et al. |
| 4,244,362 | A | 1/1981 | Anderson |
| 4,289,139 | A | 9/1981 | Enjoji et al. |
| 4,317,078 | A | 2/1982 | Weed et al. |
| 4,327,722 | A | 5/1982 | Groshong et al. |
| 4,327,723 | A | 5/1982 | Frankhouser |
| 4,362,166 | A | 12/1982 | Furler et al. |
| 4,365,639 | A | 12/1982 | Goldreyer |
| 4,380,237 | A | 4/1983 | Newbower |
| 4,407,294 | A | 10/1983 | Vilkomerson |
| 4,417,886 | A | 11/1983 | Frankhouser et al. |
| 4,429,693 | A | 2/1984 | Blake et al. |
| 4,431,005 | A | 2/1984 | McCormick |
| 4,431,214 | A | 2/1984 | Buffington |
| 4,445,501 | A | 5/1984 | Bresler |
| 4,459,854 | A | 7/1984 | Richardson et al. |
| 4,469,106 | A | 9/1984 | Harui |
| 4,483,343 | A | 11/1984 | Beyer et al. |
| 4,491,137 | A | 1/1985 | Jingu |
| 4,565,201 | A | 1/1986 | Lass |
| 4,572,198 | A | 2/1986 | Codrington |
| 4,577,634 | A | 3/1986 | Gessman |
| 4,582,067 | A | 4/1986 | Silverstein et al. |
| 4,587,975 | A | 5/1986 | Salo et al. |
| 4,588,394 | A | 5/1986 | Schulte et al. |
| 4,593,687 | A | 6/1986 | Gray |
| 4,595,012 | A | 6/1986 | Webler et al. |
| 4,601,706 | A | 7/1986 | Aillon |
| 4,608,989 | A | 9/1986 | Drue |
| 4,608,992 | A | 9/1986 | Hakim et al. |
| 4,619,247 | A | 10/1986 | Inoue et al. |
| 4,622,644 | A | 11/1986 | Hansen |
| 4,644,960 | A | 2/1987 | Johans |
| 4,652,820 | A | 3/1987 | Maresca |
| 4,660,571 | A | 4/1987 | Hess et al. |
| 4,665,925 | A | 5/1987 | Millar |
| 4,667,230 | A | 5/1987 | Arakawa et al. |
| 4,674,518 | A | 6/1987 | Salo |
| 4,676,249 | A | 6/1987 | Arenas et al. |
| 4,681,106 | A | 7/1987 | Kensey et al. |
| 4,681,117 | A | 7/1987 | Brodman et al. |
| 4,688,578 | A | 8/1987 | Takano et al. |
| 4,692,148 | A | 9/1987 | Kantrowitz et al. |
| 4,697,595 | A | 10/1987 | Breyer et al. |
| 4,700,997 | A | 10/1987 | Strand |
| 4,706,681 | A | 11/1987 | Breyer et al. |
| 4,710,708 | A | 12/1987 | Rorden et al. |
| 4,733,669 | A | 3/1988 | Segal |
| 4,737,794 | A | 4/1988 | Jones |
| 4,741,356 | A | 5/1988 | Letzo et al. |
| 4,742,356 | A | 5/1988 | Kuipers |
| 4,753,247 | A | 6/1988 | Kirsner |
| 4,770,185 | A | 9/1988 | Silverstein et al. |
| 4,771,788 | A | 9/1988 | Millar |
| 4,781,685 | A | 11/1988 | Lehmann et al. |
| 4,784,646 | A | 11/1988 | Feingold |
| 4,787,070 | A | 11/1988 | Suzuki et al. |
| 4,787,396 | A | 11/1988 | Pidorenko |
| 4,790,809 | A | 12/1988 | Kuntz |
| 4,793,361 | A | 12/1988 | DuFault |
| 4,794,930 | A | 1/1989 | Machida et al. |
| 4,796,632 | A | 1/1989 | Boyd et al. |
| 4,798,588 | A | 1/1989 | Aillon |
| 4,798,598 | A | 1/1989 | Bonello et al. |
| 4,809,681 | A | 3/1989 | Kantrowitz et al. |
| 4,809,713 | A | 3/1989 | Grayzel |
| 4,813,729 | A | 3/1989 | Speckhart |
| 4,821,731 | A | 4/1989 | Martinelli et al. |
| 4,834,709 | A | 5/1989 | Banning et al. |
| 4,836,214 | A | 6/1989 | Sramek |
| 4,840,182 | A | 6/1989 | Carlson |
| 4,840,622 | A | 6/1989 | Hardy |
| 4,841,977 | A | 6/1989 | Griffith et al. |
| 4,849,692 | A | 7/1989 | Blood |
| 4,850,358 | A | 7/1989 | Millar |
| 4,852,580 | A | 8/1989 | Wood |
| 4,856,317 | A | 8/1989 | Pidorenko et al. |
| 4,856,529 | A | 8/1989 | Segal |
| 4,860,757 | A | 8/1989 | Lynch et al. |
| 4,867,169 | A | 9/1989 | Machida et al. |
| 4,869,263 | A | 9/1989 | Segal et al. |
| 4,869,718 | A | 9/1989 | Brader |
| 4,873,987 | A | 10/1989 | Djordjevich et al. |
| 4,887,606 | A | 12/1989 | Yock et al. |
| 4,887,615 | A | 12/1989 | Taylor |
| 4,889,128 | A | 12/1989 | Millar |
| 4,899,756 | A | 2/1990 | Sonek |
| 4,901,725 | A | 2/1990 | Nappholz et al. |
| 4,905,698 | A | 3/1990 | Strohl, Jr. et al. |
| 4,911,173 | A | 3/1990 | Terwilliger |
| 4,911,174 | A | 3/1990 | Pederson et al. |
| 4,917,669 | A | 4/1990 | Bonaldo |

(56)　　　　　References Cited

U.S. PATENT DOCUMENTS

| | | | |
|---|---|---|---|
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,110 A | 9/1990 | Vogel et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,989,610 A | 2/1991 | Patton et al. |
| 4,995,396 A | 2/1991 | Inaba et al. |
| 4,998,916 A | 3/1991 | Hammerslag et al. |
| 5,004,456 A | 4/1991 | Botterbusch et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,055,813 A | 10/1991 | Johnson |
| 5,057,095 A | 10/1991 | Fabian |
| 5,058,583 A | 10/1991 | Geddes et al. |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,090,418 A * | 2/1992 | Squires .................. A61B 5/363 |
| | | 600/515 |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| 5,125,410 A | 6/1992 | Misono et al. |
| 5,134,370 A | 7/1992 | Jefferts et al. |
| 5,144,955 A | 9/1992 | O'Hara |
| 5,146,151 A | 9/1992 | Korn |
| 5,148,809 A | 9/1992 | Biegeleisen-Knight et al. |
| 5,156,151 A | 10/1992 | Imran |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,174,299 A | 12/1992 | Nelson |
| 5,181,513 A | 1/1993 | Touboul et al. |
| 5,184,601 A | 2/1993 | Putman |
| 5,184,627 A | 2/1993 | de Toledo |
| 5,190,045 A | 3/1993 | Frazin |
| 5,202,985 A | 4/1993 | Goyal |
| 5,205,830 A | 4/1993 | Dassa et al. |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer |
| 5,217,026 A | 6/1993 | Stoy et al. |
| 5,220,924 A | 6/1993 | Frazin |
| 5,233,994 A | 8/1993 | Shmulewitz |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,246,426 A | 9/1993 | Lewis et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,269,306 A | 12/1993 | Warnking et al. |
| 5,269,759 A | 12/1993 | Hernandez et al. |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,293 A | 6/1994 | Dorne |
| 5,325,860 A | 7/1994 | Seward et al. |
| 5,325,873 A | 7/1994 | Hirschi et al. |
| 5,330,496 A | 7/1994 | Alferness |
| 5,331,491 A | 7/1994 | Hayakawa et al. |
| 5,331,966 A | 7/1994 | Bennett et al. |
| 5,333,614 A | 8/1994 | Feiring |
| 5,337,678 A | 8/1994 | Grout |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,365,935 A | 11/1994 | Righter et al. |
| 5,366,443 A | 11/1994 | Eggers et al. |
| 5,368,048 A | 11/1994 | Stoy et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,385,146 A | 1/1995 | Goldreyer |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,417,208 A | 5/1995 | Winkler |
| 5,417,701 A | 5/1995 | Holmes |
| 5,422,478 A | 6/1995 | Wlodarczyk et al. |
| 5,423,334 A | 6/1995 | Jordan |
| 5,423,877 A | 6/1995 | Mackey |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada |
| 5,437,277 A | 8/1995 | Dumoulin et al. |
| 5,438,873 A | 8/1995 | Wlodarczyk et al. |
| 5,441,052 A | 8/1995 | Miyajima |
| 5,443,066 A | 8/1995 | Dumoulin et al. |
| 5,443,489 A | 8/1995 | Ben-Haim |
| 5,445,150 A | 8/1995 | Dumoulin et al. |
| 5,445,166 A | 8/1995 | Taylor |

(56)          References Cited

U.S. PATENT DOCUMENTS

| | | | |
|---|---|---|---|
| 5,450,846 A | 9/1995 | Goldreyer |
| 5,453,575 A | 9/1995 | O'Donnell et al. |
| 5,453,576 A | 9/1995 | Krivitski |
| 5,456,256 A | 10/1995 | Schneider et al. |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,409 A | 1/1996 | Riza |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,011 A | 3/1996 | Desai |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,160 A | 5/1996 | Schulz et al. |
| 5,515,853 A | 5/1996 | Smith et al. |
| 5,517,989 A | 5/1996 | Frisbie et al. |
| 5,522,878 A | 6/1996 | Montecalvo et al. |
| 5,522,880 A | 6/1996 | Barone et al. |
| 5,526,812 A | 6/1996 | Dumoulin et al. |
| 5,531,664 A | 7/1996 | Adachi et al. |
| 5,536,248 A | 7/1996 | Weaver et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,555,618 A | 9/1996 | Winkler |
| 5,558,091 A | 9/1996 | Acker et al. |
| 5,568,809 A | 10/1996 | Ben-haim |
| D375,450 S | 11/1996 | Bidwell et al. |
| 5,570,671 A | 11/1996 | Hickey |
| 5,575,291 A | 11/1996 | Hayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,603,333 A | 2/1997 | Konings |
| 5,606,981 A | 3/1997 | Tartacower et al. |
| 5,610,967 A | 3/1997 | Moorman et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,638,819 A | 6/1997 | Manwaring et al. |
| 5,640,967 A | 6/1997 | Fine et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,103 A | 9/1997 | Lafontaine et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,682,890 A | 11/1997 | Kormos et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,701,898 A | 12/1997 | Adam et al. |
| 5,702,433 A | 12/1997 | Taylor et al. |
| 5,711,299 A | 1/1998 | Manwaring et al. |
| 5,713,362 A | 2/1998 | Vilkomerson |
| 5,713,363 A | 2/1998 | Seward et al. |
| 5,713,858 A | 2/1998 | Heruth et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,776,064 A | 7/1998 | Kalfas et al. |
| 5,776,080 A | 7/1998 | Thome et al. |
| 5,779,638 A | 7/1998 | Vesely et al. |
| 5,782,767 A | 7/1998 | Pretlow, III |
| 5,782,773 A | 7/1998 | Kuo et al. |
| 5,785,657 A | 7/1998 | Breyer et al. |
| 5,792,055 A | 8/1998 | McKinnon |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| RE35,924 E | 10/1998 | Winkler |
| 5,817,022 A | 10/1998 | Vesely |
| 5,817,024 A | 10/1998 | Ogle et al. |
| 5,820,549 A | 10/1998 | Marian, Jr. |
| 5,820,560 A | 10/1998 | Sinderby et al. |
| 5,824,031 A | 10/1998 | Cookston et al. |
| 5,827,192 A | 10/1998 | Gopakumaran et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |

(56) References Cited

U.S. PATENT DOCUMENTS

| | | | |
|---|---|---|---|
| 5,842,998 A | 12/1998 | Gopakumaran et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,851,218 A | 12/1998 | Lev |
| 5,855,553 A | 1/1999 | Tajima et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,908,387 A | 6/1999 | LeFree et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,788 A | 8/1999 | Keen et al. |
| 5,931,818 A | 8/1999 | Werp et al. |
| 5,931,863 A | 8/1999 | Griffin, III et al. |
| 5,935,160 A | 8/1999 | Auricchio et al. |
| 5,941,858 A | 8/1999 | Johnson |
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,951,472 A | 9/1999 | Van Vaals et al. |
| 5,951,598 A | 9/1999 | Bishay et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,984 A | 10/1999 | Chu et al. |
| 5,967,991 A | 10/1999 | Gardineer et al. |
| 5,969,722 A | 10/1999 | Palm |
| 5,970,119 A | 10/1999 | Hofmann |
| 5,971,933 A | 10/1999 | Gopakumaran et al. |
| 5,971,983 A | 10/1999 | Lesh |
| 5,978,705 A | 11/1999 | KenKnight et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,004,270 A | 12/1999 | Urbano et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,022,342 A | 2/2000 | Mukherjee |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,058,323 A | 5/2000 | Lemelson |
| 6,059,718 A | 5/2000 | Taniguchi et al. |
| 6,060,970 A | 5/2000 | Bell |
| 6,063,032 A | 5/2000 | Grunwald |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,081,737 A | 6/2000 | Shah |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,102,862 A | 8/2000 | Grunwald et al. |
| 6,107,699 A | 8/2000 | Swanson |
| 6,112,111 A | 8/2000 | Glantz |
| 6,112,115 A | 8/2000 | Feldman et al. |
| 6,113,504 A | 9/2000 | Kuesters |
| 6,115,624 A | 9/2000 | Lewis et al. |
| 6,120,445 A | 9/2000 | Grunwald |
| 6,122,538 A | 9/2000 | Sliwa, Jr. et al. |
| 6,128,174 A | 10/2000 | Ritter et al. |
| 6,129,668 A | 10/2000 | Haynor et al. |
| 6,129,724 A | 10/2000 | Fleischman et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,139,540 A | 10/2000 | Rost et al. |
| 6,144,300 A | 11/2000 | Dames |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,165,977 A | 12/2000 | Mochly-Rosen |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,187,744 B1 | 2/2001 | Rooney |
| 6,190,370 B1 | 2/2001 | Tsui |
| 6,191,136 B1 | 2/2001 | Marban |
| 6,193,743 B1 | 2/2001 | Brayton et al. |
| 6,197,001 B1 | 3/2001 | Wilson et al. |
| 6,200,305 B1 | 3/2001 | Berthiaume et al. |
| 6,203,499 B1 | 3/2001 | Imling et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,212,430 B1 | 4/2001 | Kung |
| 6,216,027 B1 | 4/2001 | Willis et al. |
| 6,216,028 B1 | 4/2001 | Haynor et al. |
| 6,216,029 B1 | 4/2001 | Paltieli |
| 6,217,517 B1 | 4/2001 | Grunwald |
| 6,223,087 B1 | 4/2001 | Williams |
| 6,226,547 B1 | 5/2001 | Lockhart et al. |
| 6,230,042 B1 | 5/2001 | Slettenmark |
| 6,230,046 B1 | 5/2001 | Crane et al. |
| 6,231,518 B1 | 5/2001 | Grabek et al. |
| 6,233,476 B1 | 5/2001 | Strommer et al. |
| 6,233,994 B1 | 5/2001 | Roy et al. |
| 6,236,883 B1 | 5/2001 | Ciaccio et al. |
| 6,238,344 B1 | 5/2001 | Gamelsky et al. |
| 6,241,673 B1 | 6/2001 | Williams |
| 6,245,018 B1 | 6/2001 | Lee |
| 6,246,231 B1 | 6/2001 | Ashe |
| 6,246,898 B1 | 6/2001 | Vesely et al. |

(56) References Cited

U.S. PATENT DOCUMENTS

| | | | |
|---|---|---|---|
| 6,248,072 B1 | 6/2001 | Murkin |
| 6,248,074 B1 | 6/2001 | Ohno et al. |
| 6,248,075 B1 | 6/2001 | McGee et al. |
| 6,249,234 B1 | 6/2001 | Ely et al. |
| 6,253,770 B1 | 7/2001 | Acker et al. |
| 6,254,543 B1 | 7/2001 | Grunwald et al. |
| 6,258,035 B1 | 7/2001 | Hoeksel et al. |
| 6,259,938 B1 | 7/2001 | Zarychta et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,270,493 B1 | 8/2001 | Lalonde et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,287,259 B1 | 9/2001 | Grunwald |
| 6,287,260 B1 | 9/2001 | Hascoet et al. |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,298,261 B1 | 10/2001 | Rex |
| 6,301,496 B1 * | 10/2001 | Reisfeld ................ A61B 5/287 |
| | | 600/407 |
| 6,304,768 B1 | 10/2001 | Blume et al. |
| 6,306,097 B1 | 10/2001 | Park et al. |
| 6,306,105 B1 | 10/2001 | Rooney et al. |
| 6,310,532 B1 | 10/2001 | Santa Cruz et al. |
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames |
| 6,323,770 B1 | 11/2001 | Dames |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,354,999 B1 | 3/2002 | Dgany et al. |
| 6,355,026 B1 | 3/2002 | Mick |
| 6,356,791 B1 | 3/2002 | Westlund et al. |
| 6,360,123 B1 | 3/2002 | Kimchi et al. |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,141 B1 | 4/2002 | VanAntwerp et al. |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,615 B1 | 4/2002 | Flaherty et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,385,472 B1 | 5/2002 | Hall et al. |
| 6,385,476 B1 | 5/2002 | Osadchy et al. |
| 6,398,736 B1 | 6/2002 | Seward |
| 6,398,738 B1 | 6/2002 | Millar |
| 6,401,723 B1 | 6/2002 | Garibaldi et al. |
| 6,406,422 B1 | 6/2002 | Landesberg |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,436,043 B2 | 8/2002 | Bonnefous |
| 6,438,411 B1 | 8/2002 | Guttman et al. |
| 6,442,416 B1 | 8/2002 | Schultz |
| 6,445,943 B1 | 9/2002 | Ferre et al. |
| 6,456,874 B1 | 9/2002 | Hafer et al. |
| 6,459,919 B1 | 10/2002 | Lys et al. |
| 6,463,121 B1 | 10/2002 | Milnes |
| 6,466,815 B1 | 10/2002 | Saito et al. |
| 6,471,656 B1 | 10/2002 | Shalman et al. |
| 6,471,658 B1 | 10/2002 | Daniels et al. |
| 6,471,700 B1 | 10/2002 | Burbank et al. |
| 6,473,167 B1 | 10/2002 | Odell |
| 6,474,341 B1 | 11/2002 | Hunter et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,494,832 B1 | 12/2002 | Feldman et al. |
| 6,496,715 B1 | 12/2002 | Lee et al. |
| 6,498,942 B1 | 12/2002 | Esenaliev et al. |
| 6,498,944 B1 | 12/2002 | Ben-Haim et al. |
| 6,500,141 B1 | 12/2002 | Irion et al. |
| 6,503,205 B2 | 1/2003 | Manor et al. |
| 6,505,062 B1 | 1/2003 | Ritter et al. |
| 6,506,159 B2 | 1/2003 | Hascoet et al. |
| 6,507,751 B2 | 1/2003 | Blume et al. |
| 6,508,769 B2 | 1/2003 | Bonnefous |
| 6,508,802 B1 | 1/2003 | Rosengart et al. |
| 6,511,413 B2 | 1/2003 | Landesberg |
| 6,512,958 B1 | 1/2003 | Swoyer et al. |
| 6,514,202 B2 | 2/2003 | Grunwald |
| 6,514,226 B1 | 2/2003 | Levin et al. |
| 6,514,249 B1 | 2/2003 | Maguire et al. |
| 6,515,657 B1 | 2/2003 | Zanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,249 B2 | 2/2003 | Moehring et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,529,766 B1 | 3/2003 | Guendel |
| 6,534,982 B1 | 3/2003 | Jakab |
| 6,535,625 B1 | 3/2003 | Chang et al. |
| 6,537,192 B1 | 3/2003 | Elliott et al. |

(56)          References Cited

U.S. PATENT DOCUMENTS

| | | | |
|---|---|---|---|
| 6,537,196 B1 | 3/2003 | Creighton, IV et al. |
| 6,538,634 B1 | 3/2003 | Chui et al. |
| 6,540,699 B1 | 4/2003 | Smith |
| 6,542,766 B2 | 4/2003 | Hall et al. |
| 6,544,251 B1 | 4/2003 | Crawford |
| 6,545,678 B1 | 4/2003 | Ohazama |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,569,103 B2 | 5/2003 | Hoeksel et al. |
| 6,569,160 B1 | 5/2003 | Goldin et al. |
| 6,569,862 B1 | 5/2003 | Marban |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,589,181 B2 | 7/2003 | Grunwald et al. |
| 6,592,520 B1 | 7/2003 | Peszynski et al. |
| 6,592,565 B2 | 7/2003 | Twardowski |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,616,610 B2 | 9/2003 | Steininger et al. |
| 6,618,612 B1 | 9/2003 | Acker et al. |
| 6,623,431 B1 | 9/2003 | Sakuma et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,641,538 B2 | 11/2003 | Nakaya et al. |
| 6,645,148 B2 | 11/2003 | Nguyen-Dinh et al. |
| 6,647,135 B2 | 11/2003 | Bonnefous |
| 6,648,875 B2 | 11/2003 | Simpson et al. |
| 6,649,914 B1 | 11/2003 | Moorman et al. |
| 6,652,505 B1 | 11/2003 | Tsugita |
| 6,652,506 B2 | 11/2003 | Bowe et al. |
| 6,654,643 B1 | 11/2003 | Schmid |
| 6,660,024 B1 | 12/2003 | Flaherty et al. |
| 6,662,034 B2 | 12/2003 | Segner et al. |
| 6,663,661 B2 | 12/2003 | Boneau |
| 6,666,828 B2 | 12/2003 | Greco et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo et al. |
| 6,687,386 B1 | 2/2004 | Ito et al. |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Sarin et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,458 B1 | 5/2004 | Steins et al. |
| 6,733,473 B1 | 5/2004 | Reifart et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito |
| 6,749,569 B1 | 6/2004 | Pellegretti |
| 6,754,596 B2 | 6/2004 | Ashe |
| 6,754,608 B2 | 6/2004 | Svanerudh et al. |
| 6,755,789 B2 | 6/2004 | Stringer et al. |
| 6,755,816 B2 | 6/2004 | Ritter et al. |
| 6,755,822 B2 | 6/2004 | Reu et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop |
| 6,786,219 B2 | 9/2004 | Garibaldi et al. |
| 6,786,870 B2 | 9/2004 | Miyaki et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,815,651 B2 | 11/2004 | Odell |
| 6,816,266 B2 | 11/2004 | Varshneya et al. |
| 6,817,364 B2 | 11/2004 | Garibaldi et al. |
| 6,834,201 B2 | 12/2004 | Gillies et al. |
| 6,844,713 B2 | 1/2005 | Steber et al. |
| 6,845,142 B2 | 1/2005 | Ohishi |
| 6,850,788 B2 | 2/2005 | Ai-Ali |
| 6,856,823 B2 | 2/2005 | Ashe |
| 6,857,196 B2 | 2/2005 | Dalrymple |
| 6,860,422 B2 | 3/2005 | Hull et al. |
| 6,862,467 B2 | 3/2005 | Moore et al. |
| 6,869,390 B2 | 3/2005 | Elliott et al. |
| 6,875,179 B2 | 4/2005 | Ferguson et al. |
| 6,879,160 B2 | 4/2005 | Jakab |
| 6,887,206 B2 | 5/2005 | Hoeksel et al. |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,905,469 B2 | 6/2005 | Hascoet et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,926,674 B2 | 8/2005 | Tenerz et al. |
| 6,934,575 B2 | 8/2005 | Ferre et al. |
| 6,936,010 B2 | 8/2005 | Fang et al. |
| 6,939,313 B2 | 9/2005 | Saadat et al. |
| 6,940,379 B2 | 9/2005 | Creighton |
| 6,941,166 B2 | 9/2005 | MacAdam et al. |
| 6,945,938 B2 | 9/2005 | Grunwald |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,975,197 B2 | 12/2005 | Creighton, IV |
| 6,976,962 B2 | 12/2005 | Bullis |
| 6,976,987 B2 | 12/2005 | Flores |
| 6,979,294 B2 | 12/2005 | Selzer et al. |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,986,744 B1 | 1/2006 | Krivitski |
| 6,999,821 B2 | 2/2006 | Jenney et al. |
| 7,001,355 B2 | 2/2006 | Nunomura et al. |

(56) References Cited

U.S. PATENT DOCUMENTS

| | | | |
|---|---|---|---|
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,048,733 B2 | 5/2006 | Hartley et al. |
| 7,054,228 B1 | 5/2006 | Hickling |
| 7,059,878 B1 | 6/2006 | Hendrixson |
| 7,065,403 B1 | 6/2006 | Mouchawar et al. |
| 7,066,914 B2 | 6/2006 | Andersen |
| 7,066,924 B1 | 6/2006 | Garibaldi et al. |
| 7,069,072 B2 | 6/2006 | Jansen et al. |
| D525,363 S | 7/2006 | Chaggares |
| 7,070,565 B2 | 7/2006 | Vaezy et al. |
| 7,072,704 B2 | 7/2006 | Bucholz |
| 7,074,187 B2 | 7/2006 | Selzer et al. |
| 7,082,325 B2 | 7/2006 | Hashimshony et al. |
| 7,090,639 B2 | 8/2006 | Govari |
| 7,096,059 B2 | 8/2006 | Geddes et al. |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,112,197 B2 | 9/2006 | Hartley et al. |
| 7,128,734 B1 | 10/2006 | Wilson et al. |
| 7,132,804 B2 | 11/2006 | Lys et al. |
| 7,137,976 B2 | 11/2006 | Ritter et al. |
| 7,141,019 B2 | 11/2006 | Pearlman |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,169,109 B2 | 1/2007 | Jansen et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |
| 7,189,198 B2 | 3/2007 | Harburn et al. |
| 7,189,205 B2 | 3/2007 | McMorrow et al. |
| 7,189,208 B1 | 3/2007 | Beatty et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al. |
| 7,214,191 B2 | 5/2007 | Stringer et al. |
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,236,820 B2 | 6/2007 | Mabary et al. |
| 7,237,313 B2 | 7/2007 | Skujins et al. |
| 7,238,169 B2 | 7/2007 | Takagi et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |
| 7,252,633 B2 | 8/2007 | Obata et al. |
| 7,260,428 B2 | 8/2007 | Virtanen |
| 7,261,691 B1 | 8/2007 | Asomani |
| 7,264,584 B2 | 9/2007 | Ritter et al. |
| 7,270,662 B2 | 9/2007 | Visram et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,299,085 B2 | 11/2007 | Bergelson et al. |
| 7,300,430 B2 | 11/2007 | Wilson et al. |
| 7,302,288 B1 | 11/2007 | Schellenberg |
| 7,308,296 B2 | 12/2007 | Lys et al. |
| 7,310,150 B2 | 12/2007 | Guillermo et al. |
| 7,311,702 B2 | 12/2007 | Tallarida et al. |
| 7,321,228 B2 | 1/2008 | Govari |
| 7,326,241 B2 | 2/2008 | Jang |
| 7,327,872 B2 | 2/2008 | Vaillant et al. |
| 7,331,462 B2 | 2/2008 | Steppe |
| 7,342,058 B2 | 3/2008 | Peppmoller et al. |
| 7,344,554 B2 | 3/2008 | Kuyava et al. |
| 7,349,732 B1 | 3/2008 | Kil et al. |
| 7,355,716 B2 | 4/2008 | de Boer et al. |
| 7,359,554 B2 | 4/2008 | Klingensmith et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,381,204 B2 | 6/2008 | Wilson et al. |
| 7,382,949 B2 | 6/2008 | Bouma et al. |
| 7,384,407 B2 | 6/2008 | Rodriguez et al. |
| 7,413,562 B2 | 8/2008 | Ferguson et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| 7,454,244 B2 | 11/2008 | Kassab et al. |
| D585,556 S | 1/2009 | Kosaku |
| 7,479,141 B2 | 1/2009 | Kleen et al. |
| 7,507,114 B2 | 3/2009 | Kent et al. |
| 7,519,424 B2 | 4/2009 | Dennis et al. |
| 7,529,584 B2 | 5/2009 | Laske et al. |
| 7,534,209 B2 | 5/2009 | Abend et al. |
| 7,534,223 B2 | 5/2009 | Boutilette et al. |
| 7,538,859 B2 | 5/2009 | Tearney et al. |
| 7,543,239 B2 | 6/2009 | Viswanathan et al. |
| 7,546,158 B2 | 6/2009 | Allison et al. |
| 7,547,282 B2 | 6/2009 | Lo et al. |
| 7,551,293 B2 | 6/2009 | Yelin et al. |
| D603,050 S | 10/2009 | Chen |
| 7,599,730 B2 | 10/2009 | Hunter et al. |
| 7,606,615 B2 | 10/2009 | Makower et al. |
| 7,613,478 B2 | 11/2009 | Jabri et al. |
| 7,616,992 B2 | 11/2009 | Dennis et al. |
| 7,627,376 B2 | 12/2009 | Dennis et al. |
| 7,635,336 B1 | 12/2009 | Pruter |
| 7,637,163 B2 | 12/2009 | Fetzer et al. |
| 7,637,870 B2 | 12/2009 | Flaherty et al. |
| 7,640,053 B2 | 12/2009 | Verin |
| 7,651,469 B2 | 1/2010 | Osborne et al. |
| 7,652,080 B2 | 1/2010 | Peppmoller et al. |
| 7,660,623 B2 | 2/2010 | Hunter et al. |
| 7,665,893 B2 | 2/2010 | Buchalter |
| 7,666,191 B2 | 2/2010 | Orban, III et al. |
| 7,668,583 B2 | 2/2010 | Fegert et al. |
| 7,681,579 B2 | 3/2010 | Schwartz |
| 7,691,061 B2 | 4/2010 | Hirota |
| 7,697,972 B2 | 4/2010 | Verard et al. |
| 7,699,779 B2 | 4/2010 | Sasaki et al. |

(56) References Cited

U.S. PATENT DOCUMENTS

| | | | |
|---|---|---|---|
| 7,699,782 B2 | 4/2010 | Angelsen et al. |
| 7,699,829 B2 | 4/2010 | Harris et al. |
| 7,715,925 B2 | 5/2010 | Hafer et al. |
| 7,727,153 B2 | 6/2010 | Fritz et al. |
| 7,727,192 B2 | 6/2010 | Tokumoto et al. |
| 7,729,743 B2 | 6/2010 | Sabczynski et al. |
| 7,751,865 B2 | 7/2010 | Jascob et al. |
| 7,766,839 B2 | 8/2010 | Rogers et al. |
| 7,771,437 B2 | 8/2010 | Hogg et al. |
| 7,774,051 B2 | 8/2010 | Voth |
| 7,774,055 B1 | 8/2010 | Min |
| 7,794,407 B2 | 9/2010 | Rothenberg |
| 7,798,970 B2 | 9/2010 | Lo et al. |
| 7,819,810 B2 | 10/2010 | Stringer et al. |
| 7,822,464 B2 | 10/2010 | Maschke et al. |
| 7,828,528 B2 | 11/2010 | Estes et al. |
| 7,831,294 B2 | 11/2010 | Viswanathan |
| 7,831,449 B2 | 11/2010 | Ying et al. |
| 7,833,168 B2 | 11/2010 | Taylor et al. |
| 7,833,214 B2 | 11/2010 | Wilson et al. |
| 7,840,252 B2 | 11/2010 | Strommer et al. |
| D629,526 S | 12/2010 | Ladwig et al. |
| D629,527 S | 12/2010 | Crunkilton |
| 7,846,157 B2 | 12/2010 | Kozel |
| 7,850,613 B2 | 12/2010 | Stribling |
| D630,756 S | 1/2011 | Kitayama |
| D630,757 S | 1/2011 | Kitayama |
| 7,869,854 B2 | 1/2011 | Shachar et al. |
| 7,869,865 B2 | 1/2011 | Govari et al. |
| 7,873,402 B2 | 1/2011 | Shachar |
| 7,887,516 B2 | 2/2011 | Young |
| 7,905,837 B2 | 3/2011 | Suzuki |
| 7,909,815 B2 | 3/2011 | Whitmore, III et al. |
| 7,925,327 B2 | 4/2011 | Weese |
| 7,927,278 B2 | 4/2011 | Selzer et al. |
| 7,931,596 B2 | 4/2011 | Rachlin et al. |
| 7,947,040 B2 | 5/2011 | Davies et al. |
| 7,969,142 B2 | 6/2011 | Krueger et al. |
| 7,976,469 B2 | 7/2011 | Bonde et al. |
| 7,976,518 B2 | 7/2011 | Shaughnessy et al. |
| 7,981,038 B2 | 7/2011 | Kanade et al. |
| 7,988,633 B2 | 8/2011 | Hossack et al. |
| 8,016,814 B2 | 9/2011 | Blakstvedt et al. |
| 8,046,052 B2 | 10/2011 | Verard et al. |
| 8,055,327 B2 | 11/2011 | Strommer et al. |
| 8,057,394 B2 | 11/2011 | Dala-Krishna |
| 8,060,185 B2 | 11/2011 | Hunter et al. |
| 8,075,488 B2 | 12/2011 | Burton |
| 8,078,274 B2 | 12/2011 | Kassab |
| 8,078,279 B2 | 12/2011 | Dennis et al. |
| 8,082,025 B2 | 12/2011 | Amitai et al. |
| 8,082,032 B2 | 12/2011 | Kassab et al. |
| 8,088,072 B2 | 1/2012 | Munrow et al. |
| 8,090,427 B2 | 1/2012 | Eck et al. |
| 8,090,430 B2 | 1/2012 | Makower et al. |
| 8,099,161 B2 | 1/2012 | Kassab |
| 8,105,239 B2 | 1/2012 | Specht |
| 8,105,338 B2 | 1/2012 | Anderson et al. |
| 8,114,143 B2 | 2/2012 | Kassab et al. |
| 8,118,743 B2 | 2/2012 | Park et al. |
| 8,123,691 B2 | 2/2012 | Mine et al. |
| 8,133,698 B2 | 3/2012 | Silver |
| 8,142,417 B2 | 3/2012 | Pajunk et al. |
| 8,150,522 B2 | 4/2012 | Echauz et al. |
| 8,152,724 B2 | 4/2012 | Ridley et al. |
| 8,155,732 B2 | 4/2012 | Scholz et al. |
| 8,172,754 B2 | 5/2012 | Watanabe et al. |
| 8,175,368 B2 | 5/2012 | Sathyanarayana |
| 8,200,313 B1 | 6/2012 | Rambod et al. |
| 8,204,582 B2 | 6/2012 | Zantos et al. |
| 8,211,023 B2 | 7/2012 | Swan et al. |
| 8,214,018 B2 | 7/2012 | Markowitz et al. |
| 8,221,402 B2 | 7/2012 | Francischelli et al. |
| 8,226,540 B1 | 7/2012 | Chi |
| 8,228,347 B2 | 7/2012 | Beasley et al. |
| 8,240,211 B2 | 8/2012 | Zeitner et al. |
| 8,241,274 B2 | 8/2012 | Keogh et al. |
| 8,244,339 B2 | 8/2012 | Shen et al. |
| 8,255,035 B2 | 8/2012 | Cao et al. |
| 8,260,395 B2 | 9/2012 | Markowitz et al. |
| 8,262,577 B2 | 9/2012 | Munrow et al. |
| 8,298,147 B2 | 10/2012 | Huennekens et al. |
| 8,298,149 B2 | 10/2012 | Hastings et al. |
| 8,303,502 B2 | 11/2012 | Washburn et al. |
| 8,303,505 B2 | 11/2012 | Webler et al. |
| 8,323,202 B2 | 12/2012 | Roschak et al. |
| 8,326,419 B2 | 12/2012 | Rosenberg et al. |
| 8,326,651 B2 | 12/2012 | McLaren et al. |
| 8,328,727 B2 | 12/2012 | Miele et al. |
| 8,340,751 B2 | 12/2012 | Markowitz et al. |
| 8,346,343 B2 | 1/2013 | Kimura et al. |
| 8,369,922 B2 | 2/2013 | Paul et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,400,164 B2 | 3/2013 | Osadchy et al. |
| 8,401,616 B2 | 3/2013 | Verard et al. |
| 8,409,103 B2 | 4/2013 | Grunwald et al. |
| 8,412,313 B2 | 4/2013 | Amitai et al. |
| 8,425,425 B2 | 4/2013 | Hagy et al. |
| 8,437,833 B2 | 5/2013 | Silverstein |
| 8,439,873 B1 | 5/2013 | Donovan |
| 8,442,621 B2 | 5/2013 | Gorek et al. |
| 8,447,384 B2 | 5/2013 | Xu et al. |
| 8,449,465 B2 | 5/2013 | Nair et al. |
| D684,265 S | 6/2013 | Cadera |
| 8,456,182 B2 | 6/2013 | Bar-Tal et al. |
| 8,478,382 B2 | 7/2013 | Burnside et al. |
| 8,478,388 B2 | 7/2013 | Nguyen et al. |
| 8,485,980 B2 | 7/2013 | Sinderby et al. |
| 8,494,608 B2 | 7/2013 | Markowitz et al. |
| 8,496,592 B2 | 7/2013 | Ridley et al. |
| 8,504,139 B2 | 8/2013 | Jacobsen et al. |
| 8,512,256 B2 | 8/2013 | Rothenberg |
| 8,521,122 B2 | 8/2013 | Scott et al. |
| 8,527,036 B2 | 9/2013 | Jalde et al. |
| 8,529,433 B2 | 9/2013 | Kawano et al. |
| 8,538,509 B2 | 9/2013 | Harlev et al. |
| 8,545,255 B2 | 10/2013 | Litzler et al. |
| 8,553,954 B2 | 10/2013 | Saikia |
| 8,556,815 B2 | 10/2013 | Pelissier et al. |
| 8,585,600 B2 | 11/2013 | Liu et al. |
| 8,597,193 B2 | 12/2013 | Grunwald et al. |
| 8,620,412 B2 | 12/2013 | Griffiths et al. |
| 8,622,913 B2 | 1/2014 | Dentinger et al. |
| 8,644,907 B2 | 2/2014 | Hartmann et al. |
| 8,663,116 B2 | 3/2014 | Hamilton, Jr. |
| 8,676,295 B2 | 3/2014 | Cunningham et al. |
| 8,690,776 B2 | 4/2014 | Razzaque et al. |
| 8,700,137 B2 | 4/2014 | Albert |
| 8,706,457 B2 | 4/2014 | Hart et al. |
| 8,715,195 B2 | 5/2014 | Ziv |
| 8,721,655 B2 | 5/2014 | Viswanathan et al. |
| 8,727,988 B2 | 5/2014 | Flaherty et al. |
| 8,734,357 B2 | 5/2014 | Taylor |
| 8,734,440 B2 | 5/2014 | Wu |
| 8,744,211 B2 | 6/2014 | Owen |
| 8,754,865 B2 | 6/2014 | Merritt et al. |
| 8,761,862 B2 | 6/2014 | Ridley et al. |
| 8,764,663 B2 | 7/2014 | Smok et al. |
| 8,774,907 B2 | 7/2014 | Rothenberg |
| 8,781,555 B2 | 7/2014 | Burnside et al. |
| 8,784,336 B2 | 7/2014 | Bown et al. |
| 8,790,263 B2 | 7/2014 | Randall et al. |
| 8,801,693 B2 | 8/2014 | He et al. |
| 8,849,382 B2 | 9/2014 | Cox et al. |
| 8,858,455 B2 | 10/2014 | Rothenberg |
| 8,934,961 B2 | 1/2015 | Lakin et al. |
| 8,939,908 B2 | 1/2015 | Suzuki et al. |
| 8,942,784 B2 | 1/2015 | Neidert et al. |
| 8,965,490 B2 | 2/2015 | Lee et al. |
| 8,971,994 B2 | 3/2015 | Burnside et al. |
| 9,014,794 B2 | 4/2015 | Brodnick et al. |
| 9,022,940 B2 | 5/2015 | Meier |

(56)                    References Cited

U.S. PATENT DOCUMENTS

| | | | |
|---|---|---|---|
| 9,033,889 B2 | 5/2015 | Hamilton, Jr. | |
| 9,125,578 B2 | 9/2015 | Grunwald | |
| 9,138,290 B2 | 9/2015 | Hadjicostis | |
| 9,179,860 B2 | 11/2015 | Markowitz et al. | |
| 9,198,600 B2 | 12/2015 | Grunwald et al. | |
| 9,204,858 B2 | 12/2015 | Pelissier et al. | |
| 9,220,477 B2 | 12/2015 | Urabe et al. | |
| 9,295,447 B2 | 3/2016 | Shah | |
| 9,320,493 B2 | 4/2016 | Visveshwara | |
| 9,339,206 B2 | 5/2016 | Grunwald | |
| 9,357,980 B2 | 6/2016 | Toji et al. | |
| 9,364,171 B2 | 6/2016 | Harris et al. | |
| 9,415,188 B2 | 8/2016 | He et al. | |
| 9,427,207 B2 | 8/2016 | Sheldon et al. | |
| 9,445,780 B2 | 9/2016 | Hossack et al. | |
| 9,456,766 B2 | 10/2016 | Cox et al. | |
| 9,456,804 B2 | 10/2016 | Tamada | |
| 9,459,087 B2 | 10/2016 | Dunbar et al. | |
| 9,468,413 B2 | 10/2016 | Hall et al. | |
| 9,492,097 B2 | 11/2016 | Wilkes et al. | |
| 9,521,961 B2 | 12/2016 | Silverstein et al. | |
| 9,526,440 B2 | 12/2016 | Burnside et al. | |
| 9,532,724 B2 | 1/2017 | Grunwald | |
| 9,554,716 B2 | 1/2017 | Burnside et al. | |
| 9,582,876 B2 | 2/2017 | Specht | |
| 9,610,061 B2 | 4/2017 | Ebbini et al. | |
| 9,636,031 B2 | 5/2017 | Cox | |
| 9,642,986 B2 | 5/2017 | Beasley | |
| 9,649,037 B2 | 5/2017 | Lowe et al. | |
| 9,649,048 B2 | 5/2017 | Cox et al. | |
| 9,681,823 B2 | 6/2017 | Messerly et al. | |
| 9,702,969 B2 | 7/2017 | Hope Simpson et al. | |
| 9,715,757 B2 | 7/2017 | Ng et al. | |
| 9,717,415 B2 | 8/2017 | Cohen et al. | |
| 9,731,066 B2 | 8/2017 | Liu et al. | |
| 9,814,433 B2 | 11/2017 | Benishti et al. | |
| 9,814,531 B2 | 11/2017 | Yagi et al. | |
| 9,833,169 B2 | 12/2017 | Rothenberg | |
| 9,839,372 B2 | 12/2017 | Bukhman et al. | |
| 9,861,337 B2 | 1/2018 | Patwardhan et al. | |
| 9,895,138 B2 | 2/2018 | Sasaki | |
| 9,901,714 B2 | 2/2018 | Lemon et al. | |
| 9,907,513 B2 | 3/2018 | Silverstein | |
| 9,913,605 B2 | 3/2018 | Harris et al. | |
| 9,949,720 B2 | 4/2018 | Southard et al. | |
| 9,950,139 B2 | 4/2018 | Blanchard et al. | |
| 9,999,371 B2 | 6/2018 | Messerly et al. | |
| 10,004,875 B2 | 6/2018 | Bown et al. | |
| 10,032,552 B2 | 7/2018 | Ma et al. | |
| 10,043,272 B2 | 8/2018 | Forzoni et al. | |
| 10,046,139 B2 | 8/2018 | Powers et al. | |
| 10,105,121 B2 | 10/2018 | Burnside et al. | |
| 10,165,962 B2 | 1/2019 | Messerly et al. | |
| 10,231,643 B2 | 3/2019 | Grunwald | |
| 10,231,753 B2 | 3/2019 | Burnside et al. | |
| 10,238,418 B2 | 3/2019 | Cox et al. | |
| 10,249,424 B2 | 4/2019 | Ma et al. | |
| 10,271,762 B2 | 4/2019 | Grunwald | |
| 10,349,857 B2 | 7/2019 | Grunwald | |
| 10,349,890 B2 | 7/2019 | Misener et al. | |
| 10,449,330 B2 | 10/2019 | Newman et al. | |
| 10,524,691 B2 | 1/2020 | Newman et al. | |
| 10,524,694 B2 | 1/2020 | Hunter | |
| 10,602,958 B2 | 3/2020 | Silverstein et al. | |
| 10,751,509 B2 * | 8/2020 | Misener | A61B 5/06 |
| 10,849,695 B2 | 12/2020 | Cox et al. | |
| 10,966,630 B2 | 4/2021 | Messerly et al. | |
| 11,027,101 B2 | 6/2021 | Lemon et al. | |
| 11,103,213 B2 | 8/2021 | Burnside et al. | |
| 2001/0014774 A1 | 8/2001 | Grunwald | |
| 2001/0027332 A1 | 10/2001 | Grunwald et al. | |
| 2002/0010392 A1 | 1/2002 | Desai | |
| 2002/0016549 A1 | 2/2002 | Mejia | |
| 2002/0019447 A1 | 2/2002 | Renn et al. | |
| 2002/0022777 A1 | 2/2002 | Crieghton et al. | |
| 2002/0032391 A1 | 3/2002 | McFann et al. | |
| 2002/0045810 A1 | 4/2002 | Ben-Haim | |
| 2002/0049488 A1 | 4/2002 | Boneau | |
| 2002/0055680 A1 | 5/2002 | Miele et al. | |
| 2002/0082559 A1 | 6/2002 | Chang et al. | |
| 2002/0113555 A1 | 8/2002 | Lys et al. | |
| 2002/0123679 A1 | 9/2002 | Dominguez | |
| 2002/0128554 A1 | 9/2002 | Seward | |
| 2002/0129952 A1 | 9/2002 | Matsudate et al. | |
| 2002/0133079 A1 | 9/2002 | Sandhu | |
| 2002/0138007 A1 | 9/2002 | Nguyen-Dinh et al. | |
| 2002/0156363 A1 | 10/2002 | Hunter et al. | |
| 2002/0156376 A1 | 10/2002 | Wang et al. | |
| 2002/0165448 A1 | 11/2002 | Ben-Haim et al. | |
| 2002/0165534 A1 | 11/2002 | Hayzelden et al. | |
| 2002/0165537 A1 | 11/2002 | Kelley et al. | |
| 2002/0173721 A1 | 11/2002 | Grunwald et al. | |
| 2002/0193756 A1 | 12/2002 | Prindle | |
| 2002/0198568 A1 | 12/2002 | Hafer et al. | |
| 2003/0009132 A1 | 1/2003 | Schwartz et al. | |
| 2003/0011359 A1 | 1/2003 | Ashe | |
| 2003/0013959 A1 | 1/2003 | Grunwald et al. | |
| 2003/0013966 A1 | 1/2003 | Barnes et al. | |
| 2003/0013986 A1 | 1/2003 | Saadat | |
| 2003/0018251 A1 | 1/2003 | Solomon | |
| 2003/0036696 A1 | 2/2003 | Willis et al. | |
| 2003/0040671 A1 | 2/2003 | Somogyi et al. | |
| 2003/0040743 A1 | 2/2003 | Cosman et al. | |
| 2003/0047126 A1 | 3/2003 | Tomaschko | |
| 2003/0072805 A1 | 4/2003 | Miyazawa et al. | |
| 2003/0073901 A1 * | 4/2003 | Simon | A61B 34/20 600/424 |
| 2003/0076281 A1 | 4/2003 | Morgan et al. | |
| 2003/0083698 A1 | 5/2003 | Whitehurst et al. | |
| 2003/0088195 A1 | 5/2003 | Vardi et al. | |
| 2003/0092993 A1 | 5/2003 | Grunwald | |
| 2003/0100849 A1 | 5/2003 | Jang | |
| 2003/0114742 A1 | 6/2003 | Lewkowicz et al. | |
| 2003/0114777 A1 | 6/2003 | Griffin et al. | |
| 2003/0120150 A1 | 6/2003 | Govari | |
| 2003/0120154 A1 | 6/2003 | Sauer et al. | |
| 2003/0139661 A1 | 7/2003 | Kimchy et al. | |
| 2003/0149328 A1 | 8/2003 | Elliott et al. | |
| 2003/0149368 A1 | 8/2003 | Hennemann et al. | |
| 2003/0152290 A1 | 8/2003 | Odell | |
| 2003/0160721 A1 | 8/2003 | Gilboa et al. | |
| 2003/0162414 A1 | 8/2003 | Schulz et al. | |
| 2003/0163037 A1 | 8/2003 | Bladen et al. | |
| 2003/0163142 A1 | 8/2003 | Paltieli et al. | |
| 2003/0171691 A1 | 9/2003 | Casscells et al. | |
| 2003/0173953 A1 | 9/2003 | Ashe | |
| 2003/0181892 A1 | 9/2003 | Pajunk et al. | |
| 2003/0184544 A1 | 10/2003 | Prudent | |
| 2003/0191392 A1 | 10/2003 | Haldeman | |
| 2003/0191460 A1 | 10/2003 | Hobbs et al. | |
| 2003/0195420 A1 | 10/2003 | Mendlein et al. | |
| 2003/0199746 A1 | 10/2003 | Fuimaono et al. | |
| 2003/0208142 A1 | 11/2003 | Boudewijn et al. | |
| 2003/0216639 A1 | 11/2003 | Gilboa et al. | |
| 2003/0216723 A1 | 11/2003 | Shinmura et al. | |
| 2003/0220557 A1 | 11/2003 | Cleary et al. | |
| 2003/0220578 A1 | 11/2003 | Ho et al. | |
| 2003/0229298 A1 | 12/2003 | Iwami et al. | |
| 2003/0233042 A1 | 12/2003 | Ashe | |
| 2003/0236445 A1 | 12/2003 | Couvillon | |
| 2004/0010189 A1 | 1/2004 | van Sloun et al. | |
| 2004/0015070 A1 | 1/2004 | Liang et al. | |
| 2004/0024301 A1 | 2/2004 | Hockett et al. | |
| 2004/0030319 A1 | 2/2004 | Korkor et al. | |
| 2004/0054278 A1 | 3/2004 | Kimchy et al. | |
| 2004/0059217 A1 | 3/2004 | Kessman et al. | |
| 2004/0059237 A1 | 3/2004 | Narayan et al. | |
| 2004/0082916 A1 | 4/2004 | Jenkins | |
| 2004/0087877 A1 | 5/2004 | Besz et al. | |
| 2004/0088136 A1 | 5/2004 | Ashe | |
| 2004/0092962 A1 | 5/2004 | Thornton et al. | |
| 2004/0097803 A1 | 5/2004 | Panescu | |
| 2004/0097804 A1 | 5/2004 | Sobe | |
| 2004/0097805 A1 | 5/2004 | Verard et al. | |

(56) References Cited

U.S. PATENT DOCUMENTS

| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138557 A1* | 7/2004 | Le ..................... A61B 5/02028 600/428 |
| 2004/0138564 A1 | 7/2004 | Hwang et al. |
| 2004/0138569 A1 | 7/2004 | Grunwald et al. |
| 2004/0138570 A1 | 7/2004 | Nita et al. |
| 2004/0143183 A1 | 7/2004 | Toyoda et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0162487 A1 | 8/2004 | Klingenbeck-Regn et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0225233 A1 | 11/2004 | Frankowski et al. |
| 2004/0230131 A1 | 11/2004 | Kassab et al. |
| 2004/0230271 A1 | 11/2004 | Wang et al. |
| 2004/0234453 A1 | 11/2004 | Smith |
| 2004/0243018 A1 | 12/2004 | Organ et al. |
| 2004/0243116 A1 | 12/2004 | Joye et al. |
| 2004/0243118 A1 | 12/2004 | Ayers et al. |
| 2004/0253365 A1 | 12/2004 | Warren et al. |
| 2004/0254470 A1 | 12/2004 | Drinkwater et al. |
| 2004/0254495 A1 | 12/2004 | Mabary et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |
| 2005/0033150 A1 | 2/2005 | Takahashi et al. |
| 2005/0033232 A1 | 2/2005 | Kriesel |
| 2005/0038355 A1 | 2/2005 | Gellman et al. |
| 2005/0043640 A1 | 2/2005 | Chang |
| 2005/0049486 A1 | 3/2005 | Urquhart et al. |
| 2005/0049504 A1 | 3/2005 | Lo et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085715 A1 | 4/2005 | Dukesherer et al. |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0090746 A1 | 4/2005 | Ohtake |
| 2005/0096543 A1 | 5/2005 | Jackson et al. |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0143689 A1 | 6/2005 | Ramsey |
| 2005/0148836 A1 | 7/2005 | Kleen et al. |
| 2005/0148902 A1 | 7/2005 | Minar et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0182454 A1 | 8/2005 | Gharib et al. |
| 2005/0197674 A1 | 9/2005 | McCabe et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0240102 A1 | 10/2005 | Rachlin et al. |
| 2005/0245811 A1 | 11/2005 | Scheffler |
| 2005/0256398 A1 | 11/2005 | Hastings et al. |
| 2005/0256451 A1 | 11/2005 | Adams et al. |
| 2005/0256521 A1 | 11/2005 | Kozel |
| 2005/0256541 A1 | 11/2005 | Stypulkowski |
| 2005/0267365 A1 | 12/2005 | Sokulin et al. |
| 2005/0283210 A1 | 12/2005 | Blischak et al. |
| 2005/0283216 A1 | 12/2005 | Pyles |
| 2005/0288586 A1 | 12/2005 | Ferek-Petric |
| 2005/0288695 A1 | 12/2005 | Jenson et al. |
| 2006/0009759 A1 | 1/2006 | Chrisitian et al. |
| 2006/0015003 A1 | 1/2006 | Moaddes et al. |
| 2006/0015039 A1 | 1/2006 | Cassidy et al. |
| 2006/0025677 A1 | 2/2006 | Verard et al. |
| 2006/0025697 A1 | 2/2006 | Kurzweil et al. |
| 2006/0058633 A1 | 3/2006 | Hoshino et al. |
| 2006/0058654 A1 | 3/2006 | Di Marco et al. |
| 2006/0065275 A1 | 3/2006 | Lamprich et al. |
| 2006/0068074 A1 | 3/2006 | Stefandl |
| 2006/0079781 A1 | 4/2006 | Germond-Rouet et al. |
| 2006/0084867 A1 | 4/2006 | Tremblay et al. |
| 2006/0106306 A1 | 5/2006 | Essner et al. |
| 2006/0116571 A1 | 6/2006 | Maschke et al. |
| 2006/0116576 A1 | 6/2006 | McGee et al. |
| 2006/0116578 A1 | 6/2006 | Grunwald et al. |
| 2006/0122514 A1 | 6/2006 | Byrd et al. |
| 2006/0142656 A1 | 6/2006 | Malackowski et al. |
| 2006/0149134 A1 | 7/2006 | Soper et al. |
| 2006/0173251 A1 | 8/2006 | Govari et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184029 A1 | 8/2006 | Haim et al. |
| 2006/0184074 A1 | 8/2006 | Vaezy et al. |
| 2006/0206037 A1 | 9/2006 | Braxton |
| 2006/0210130 A1 | 9/2006 | Germond-Rouet et al. |
| 2006/0211944 A1 | 9/2006 | Mauge et al. |
| 2006/0217655 A1 | 9/2006 | Vitullo et al. |
| 2006/0217755 A1 | 9/2006 | Eversull et al. |
| 2006/0224188 A1 | 10/2006 | Libbus et al. |
| 2006/0241397 A1 | 10/2006 | Govari et al. |
| 2006/0241432 A1 | 10/2006 | Herline et al. |
| 2006/0247746 A1 | 11/2006 | Danek et al. |
| 2006/0253029 A1 | 11/2006 | Altmann et al. |
| 2006/0253115 A1 | 11/2006 | Avitall et al. |
| 2006/0258895 A1 | 11/2006 | Maschke |
| 2006/0276867 A1 | 12/2006 | Viswanathan |
| 2006/0287595 A1 | 12/2006 | Maschke |
| 2007/0010753 A1 | 1/2007 | MacAdam |
| 2007/0013540 A1 | 1/2007 | Altmann et al. |
| 2007/0015960 A1 | 1/2007 | Gornert et al. |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0016131 A1 | 1/2007 | Munger et al. |
| 2007/0032746 A1 | 2/2007 | Sell |
| 2007/0038113 A1 | 2/2007 | Donuki et al. |
| 2007/0049817 A1 | 3/2007 | Preiss et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |

(56)          References Cited

U.S. PATENT DOCUMENTS

| | | |
|---|---|---|
| 2007/0055294 A1 | 3/2007 | Giap |
| 2007/0060992 A1 | 3/2007 | Pappone |
| 2007/0062544 A1 | 3/2007 | Rauk Bergstrom et al. |
| 2007/0066888 A1 | 3/2007 | Maschke |
| 2007/0073155 A1 | 3/2007 | Park et al. |
| 2007/0078343 A1 | 4/2007 | Kawashima et al. |
| 2007/0087038 A1 | 4/2007 | Richardson et al. |
| 2007/0093710 A1 | 4/2007 | Maschke |
| 2007/0100236 A1 | 5/2007 | McMorrow et al. |
| 2007/0100285 A1 | 5/2007 | Griffin et al. |
| 2007/0112282 A1 | 5/2007 | Skujins et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161853 A1 | 7/2007 | Yagi et al. |
| 2007/0161914 A1 | 7/2007 | Zdeblick et al. |
| 2007/0161915 A1 | 7/2007 | Desai |
| 2007/0167738 A1 | 7/2007 | Timinger et al. |
| 2007/0167743 A1 | 7/2007 | Honda et al. |
| 2007/0167762 A1 | 7/2007 | Kim et al. |
| 2007/0167769 A1 | 7/2007 | Ikuma et al. |
| 2007/0167801 A1 | 7/2007 | Webler et al. |
| 2007/0167997 A1 | 7/2007 | Forsberg et al. |
| 2007/0197891 A1 | 8/2007 | Shachar et al. |
| 2007/0197905 A1 | 8/2007 | Timinger et al. |
| 2007/0197926 A1 | 8/2007 | Danehorn et al. |
| 2007/0199848 A1 | 8/2007 | Ellswood et al. |
| 2007/0208255 A1 | 9/2007 | Ridley et al. |
| 2007/0219453 A1 | 9/2007 | Kremliovsky et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232896 A1 | 10/2007 | Gilboa et al. |
| 2007/0238984 A1 | 10/2007 | Maschke et al. |
| 2007/0239004 A1 | 10/2007 | Kakee et al. |
| 2007/0239018 A1 | 10/2007 | Fetzer et al. |
| 2007/0244387 A1 | 10/2007 | Rodriguez Ponce et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0250150 A1 | 10/2007 | Pal et al. |
| 2007/0255270 A1 | 11/2007 | Carney |
| 2007/0265526 A1 | 11/2007 | Govari et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2007/0299353 A1 | 12/2007 | Harlev et al. |
| 2008/0004652 A1 | 1/2008 | Abboud et al. |
| 2008/0008745 A1 | 1/2008 | Stinchcomb et al. |
| 2008/0009720 A1 | 1/2008 | Schefelker et al. |
| 2008/0015442 A1 | 1/2008 | Watson et al. |
| 2008/0021283 A1 | 1/2008 | Kuranda |
| 2008/0021322 A1 | 1/2008 | Stone et al. |
| 2008/0027320 A1 | 1/2008 | Bolorforosh et al. |
| 2008/0033282 A1 | 2/2008 | Bar-Tal et al. |
| 2008/0033283 A1 | 2/2008 | Dellaca et al. |
| 2008/0033316 A1 | 2/2008 | Kassab et al. |
| 2008/0033350 A1 | 2/2008 | Wilson et al. |
| 2008/0033759 A1 | 2/2008 | Finlay |
| 2008/0045908 A1 | 2/2008 | Gould et al. |
| 2008/0051626 A1 | 2/2008 | Sato et al. |
| 2008/0077158 A1 | 3/2008 | Haider et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0114095 A1 | 5/2008 | Peppmoller et al. |
| 2008/0119697 A1 | 5/2008 | Vadodaria et al. |
| 2008/0125772 A1 | 5/2008 | Stone et al. |
| 2008/0137927 A1 | 6/2008 | Altmann et al. |
| 2008/0139944 A1 | 6/2008 | Weymer et al. |
| 2008/0146915 A1 | 6/2008 | McMorrow |
| 2008/0146925 A1 | 6/2008 | Byrd et al. |
| 2008/0146939 A1 | 6/2008 | McMorrow et al. |
| 2008/0146940 A1 | 6/2008 | Jenkins et al. |
| 2008/0146941 A1 | 6/2008 | Dala-Krishna |
| 2008/0146942 A1 | 6/2008 | Dala-Krishna |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0188830 A1 | 8/2008 | Rosenblatt et al. |
| 2008/0190438 A1 | 8/2008 | Harlev et al. |
| 2008/0195169 A1 | 8/2008 | Pinter et al. |
| 2008/0200754 A1 | 8/2008 | Buchalter |
| 2008/0200801 A1 | 8/2008 | Wildes et al. |
| 2008/0200913 A1 | 8/2008 | Viswanathan |
| 2008/0228082 A1 | 9/2008 | Scheirer et al. |
| 2008/0236598 A1 | 10/2008 | Gobel |
| 2008/0255404 A1 | 10/2008 | Nogawa et al. |
| 2008/0255446 A1 | 10/2008 | Akins |
| 2008/0255475 A1 | 10/2008 | Kondrosky et al. |
| 2008/0262338 A1 | 10/2008 | Paitel et al. |
| 2008/0269581 A1 | 10/2008 | Wood et al. |
| 2008/0269611 A1 | 10/2008 | Pedrizzetti et al. |
| 2008/0275465 A1 | 11/2008 | Paul et al. |
| 2008/0275765 A1 | 11/2008 | Kuchar |
| 2008/0288038 A1 | 11/2008 | Paul et al. |
| 2008/0294041 A1 | 11/2008 | Kassab |
| 2008/0319350 A1 | 12/2008 | Wallace et al. |
| 2009/0005674 A1 | 1/2009 | Saadat et al. |
| 2009/0005675 A1* | 1/2009 | Grunwald ............. A61B 5/349 |
| | | 600/467 |
| 2009/0005679 A1 | 1/2009 | Dala-Krishna |
| 2009/0012399 A1 | 1/2009 | Sunagawa et al. |
| 2009/0018497 A1 | 1/2009 | Birchard et al. |
| 2009/0024018 A1 | 1/2009 | Boyden et al. |
| 2009/0030380 A1 | 1/2009 | Binmoeller |
| 2009/0043205 A1 | 2/2009 | Pelissier et al. |
| 2009/0062646 A1 | 3/2009 | Creighton, IV et al. |
| 2009/0062684 A1 | 3/2009 | Gregersen et al. |
| 2009/0062772 A1 | 3/2009 | Wakeford et al. |
| 2009/0080738 A1 | 3/2009 | Zur et al. |
| 2009/0082661 A1 | 3/2009 | Saladin et al. |
| 2009/0084382 A1 | 4/2009 | Jalde et al. |
| 2009/0099468 A1 | 4/2009 | Thiagalingam et al. |
| 2009/0101577 A1 | 4/2009 | Fulkerson et al. |
| 2009/0115406 A1 | 5/2009 | Anderson et al. |
| 2009/0118612 A1 | 5/2009 | Grunwald et al. |
| 2009/0118637 A1 | 5/2009 | Kassab et al. |
| 2009/0118706 A1 | 5/2009 | Schweikert et al. |
| 2009/0124901 A1 | 5/2009 | Fink et al. |
| 2009/0143672 A1 | 6/2009 | Harms et al. |
| 2009/0143736 A1 | 6/2009 | Mittermeyer et al. |
| 2009/0156926 A1 | 6/2009 | Messerly et al. |
| 2009/0163810 A1 | 6/2009 | Kanade et al. |
| 2009/0171217 A1 | 7/2009 | Kim et al. |
| 2009/0177083 A1 | 7/2009 | Matsumura |
| 2009/0177090 A1 | 7/2009 | Grunwald et al. |
| 2009/0182224 A1 | 7/2009 | Shmarak et al. |
| 2009/0203989 A1 | 8/2009 | Burnside et al. |
| 2009/0204113 A1 | 8/2009 | MacAdam et al. |
| 2009/0209872 A1 | 8/2009 | Pop |
| 2009/0209950 A1 | 8/2009 | Starksen |
| 2009/0221908 A1 | 9/2009 | Glossop |
| 2009/0227952 A1 | 9/2009 | Blakstvedt et al. |
| 2009/0234328 A1 | 9/2009 | Cox et al. |
| 2009/0247835 A1 | 10/2009 | Voipio |
| 2009/0253976 A1 | 10/2009 | Harlev et al. |
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0269949 A1 | 10/2009 | Schmidgall et al. |
| 2009/0270729 A1 | 10/2009 | Corbucci et al. |
| 2009/0270746 A1 | 10/2009 | Min |
| 2009/0275828 A1 | 11/2009 | Shachar et al. |
| 2009/0281419 A1 | 11/2009 | Troesken et al. |
| 2009/0297441 A1 | 12/2009 | Canham et al. |
| 2009/0312629 A1 | 12/2009 | Razzaque et al. |
| 2010/0004543 A1 | 1/2010 | Ahlund et al. |
| 2010/0004547 A1 | 1/2010 | Scholz et al. |

(56) References Cited

U.S. PATENT DOCUMENTS

| | | |
|---|---|---|
| 2010/0010355 A1 | 1/2010 | Kassab |
| 2010/0010444 A1 | 1/2010 | Bettuchi |
| 2010/0010612 A1 | 1/2010 | Gelbart et al. |
| 2010/0016726 A1 | 1/2010 | Meier |
| 2010/0036227 A1 | 2/2010 | Cox et al. |
| 2010/0036238 A1 | 2/2010 | Neidert et al. |
| 2010/0036284 A1 | 2/2010 | Laynes et al. |
| 2010/0041973 A1 | 2/2010 | Vu et al. |
| 2010/0041984 A1 | 2/2010 | Shapland et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0063401 A1 | 3/2010 | Nishina et al. |
| 2010/0076305 A1 | 3/2010 | Maier-Hein et al. |
| 2010/0076328 A1 | 3/2010 | Matsumura et al. |
| 2010/0081934 A1 | 4/2010 | Soltani et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0113917 A1 | 5/2010 | Anderson |
| 2010/0114573 A1 | 5/2010 | Huang et al. |
| 2010/0117659 A1 | 5/2010 | Osadchy et al. |
| 2010/0130858 A1 | 5/2010 | Arai et al. |
| 2010/0143119 A1 | 6/2010 | Kooijman et al. |
| 2010/0152596 A1 | 6/2010 | Griffiths et al. |
| 2010/0152604 A1 | 6/2010 | Kaula et al. |
| 2010/0160772 A1 | 6/2010 | Gardeski et al. |
| 2010/0168557 A1 | 7/2010 | Deno et al. |
| 2010/0168767 A1 | 7/2010 | Yassinzadeh et al. |
| 2010/0185097 A1 | 7/2010 | Hall |
| 2010/0198048 A1 | 8/2010 | Togawa |
| 2010/0198346 A1 | 8/2010 | Keogh et al. |
| 2010/0204569 A1 | 8/2010 | Burnside et al. |
| 2010/0204614 A1 | 8/2010 | Lindquist et al. |
| 2010/0210938 A1 | 8/2010 | Verard et al. |
| 2010/0210950 A1 | 8/2010 | Dunbar et al. |
| 2010/0217116 A1 | 8/2010 | Eck et al. |
| 2010/0222664 A1 | 9/2010 | Lemon et al. |
| 2010/0222786 A1 | 9/2010 | Kassab |
| 2010/0234724 A1 | 9/2010 | Jacobsen et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0268059 A1 | 10/2010 | Ryu et al. |
| 2010/0273895 A1 | 10/2010 | Stinchcomb et al. |
| 2010/0274150 A1 | 10/2010 | Harlev et al. |
| 2010/0291521 A1 | 11/2010 | Simon |
| 2010/0298702 A1 | 11/2010 | Rogers et al. |
| 2010/0298704 A1 | 11/2010 | Pelissier et al. |
| 2010/0298705 A1 | 11/2010 | Pelissier et al. |
| 2010/0298712 A1 | 11/2010 | Pelissier et al. |
| 2010/0312086 A9 | 12/2010 | Beatty et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0002518 A1 | 1/2011 | Ziv-Ari et al. |
| 2011/0015496 A1 | 1/2011 | Sherman et al. |
| 2011/0015527 A1 | 1/2011 | Heasty et al. |
| 2011/0015533 A1 | 1/2011 | Cox et al. |
| 2011/0034823 A1 | 2/2011 | Gelbart et al. |
| 2011/0034940 A1 | 2/2011 | Payner |
| 2011/0040212 A1 | 2/2011 | Dietz et al. |
| 2011/0052694 A1 | 3/2011 | Stinchcomb et al. |
| 2011/0087105 A1 | 4/2011 | Ridley et al. |
| 2011/0087106 A1 | 4/2011 | Ridley et al. |
| 2011/0087107 A1 | 4/2011 | Lindekugel et al. |
| 2011/0106101 A1 | 5/2011 | Tortonese et al. |
| 2011/0112396 A1 | 5/2011 | Shachar et al. |
| 2011/0136242 A1 | 6/2011 | Marx et al. |
| 2011/0137156 A1 | 6/2011 | Razzaque et al. |
| 2011/0196235 A1 | 8/2011 | Dunbar et al. |
| 2011/0196248 A1 | 8/2011 | Grunwald |
| 2011/0196255 A1 | 8/2011 | Kassab |
| 2011/0224564 A1 | 9/2011 | Moon et al. |
| 2011/0237935 A1* | 9/2011 | Kalpin ................... A61B 5/061 |
| | | 600/424 |
| 2011/0245659 A1 | 10/2011 | Ma et al. |
| 2011/0263164 A1 | 10/2011 | Lenhert et al. |
| 2011/0282187 A1 | 11/2011 | Harlev et al. |
| 2011/0282188 A1 | 11/2011 | Burnside et al. |
| 2011/0282285 A1 | 11/2011 | Blanchard et al. |
| 2011/0282686 A1 | 11/2011 | Venon et al. |
| 2011/0295108 A1* | 12/2011 | Cox ......................... A61B 5/06 |
| | | 600/424 |
| 2011/0306859 A1 | 12/2011 | Saldivar et al. |
| 2011/0306867 A1 | 12/2011 | Gopinathan et al. |
| 2011/0313293 A1 | 12/2011 | Lindekugel et al. |
| 2012/0004564 A1 | 1/2012 | Dobak, III |
| 2012/0035460 A1 | 2/2012 | Stangenes et al. |
| 2012/0035539 A1 | 2/2012 | Tegg |
| 2012/0046562 A1 | 2/2012 | Powers et al. |
| 2012/0059249 A1 | 3/2012 | Verard et al. |
| 2012/0059270 A1 | 3/2012 | Grunwald |
| 2012/0059271 A1 | 3/2012 | Amitai et al. |
| 2012/0071751 A1 | 3/2012 | Sra et al. |
| 2012/0071759 A1 | 3/2012 | Hagy et al. |
| 2012/0071782 A1 | 3/2012 | Patil et al. |
| 2012/0078342 A1 | 3/2012 | Vollkron et al. |
| 2012/0095319 A1 | 4/2012 | Kondrosky et al. |
| 2012/0108950 A1 | 5/2012 | He et al. |
| 2012/0115007 A1 | 5/2012 | Felder et al. |
| 2012/0136242 A1 | 5/2012 | Qi et al. |
| 2012/0143029 A1 | 6/2012 | Silverstein et al. |
| 2012/0143078 A1 | 6/2012 | Kassab et al. |
| 2012/0172727 A1 | 7/2012 | Hastings et al. |
| 2012/0197132 A1 | 8/2012 | O'Connor |
| 2012/0220854 A1 | 8/2012 | Messerly et al. |
| 2012/0220874 A1 | 8/2012 | Hancock et al. |
| 2012/0265084 A1 | 10/2012 | Stewart et al. |
| 2012/0283582 A1 | 11/2012 | Mahapatra et al. |
| 2012/0296200 A1 | 11/2012 | Shachar et al. |
| 2012/0296213 A1 | 11/2012 | Mauldin, Jr. et al. |
| 2012/0310052 A1 | 12/2012 | Mahapatra et al. |
| 2012/0310066 A1 | 12/2012 | Shachar et al. |
| 2012/0310660 A1 | 12/2012 | Liu et al. |
| 2012/0316440 A1 | 12/2012 | Munrow et al. |
| 2013/0006100 A1 | 1/2013 | Shachar et al. |
| 2013/0006102 A1 | 1/2013 | Wilkes et al. |
| 2013/0018248 A1 | 1/2013 | Hurezan |
| 2013/0035590 A1 | 2/2013 | Ma et al. |
| 2013/0041250 A1 | 2/2013 | Pelissier et al. |
| 2013/0041254 A1 | 2/2013 | Hagy et al. |
| 2013/0041269 A1 | 2/2013 | Stahmann et al. |
| 2013/0060116 A1 | 3/2013 | Messerly et al. |
| 2013/0079628 A1 | 3/2013 | Groszmann et al. |
| 2013/0085416 A1 | 4/2013 | Mest |
| 2013/0090938 A1 | 4/2013 | Fishman et al. |
| 2013/0102890 A1 | 4/2013 | Dib |
| 2013/0102967 A1 | 4/2013 | Hanlon et al. |
| 2013/0123597 A1 | 5/2013 | Rothenberg |
| 2013/0131502 A1 | 5/2013 | Blaivas et al. |
| 2013/0131503 A1 | 5/2013 | Schneider et al. |
| 2013/0150724 A1 | 6/2013 | Blaivas et al. |
| 2013/0169272 A1 | 7/2013 | Eichler et al. |
| 2013/0213147 A1 | 8/2013 | Rice et al. |
| 2013/0217999 A1 | 8/2013 | Burnside et al. |
| 2013/0223702 A1 | 8/2013 | Holsing et al. |
| 2013/0245434 A1 | 9/2013 | Messerly et al. |
| 2013/0281787 A1 | 10/2013 | Avneri et al. |
| 2013/0281837 A1 | 10/2013 | Ridley et al. |
| 2013/0289417 A1 | 10/2013 | Grunwald et al. |
| 2013/0296691 A1 | 11/2013 | Ashe |
| 2013/0296693 A1 | 11/2013 | Wenzel et al. |
| 2013/0303878 A1 | 11/2013 | Nevo et al. |
| 2013/0303896 A1 | 11/2013 | Kalpin et al. |
| 2013/0303945 A1 | 11/2013 | Blumenkranz et al. |
| 2013/0317338 A1 | 11/2013 | Silverstein |
| 2013/0324841 A1 | 12/2013 | Kamen et al. |
| 2013/0338503 A1 | 12/2013 | Cohen et al. |
| 2013/0338517 A1 | 12/2013 | Rothenberg |
| 2013/0345555 A1 | 12/2013 | Kanade et al. |
| 2014/0005530 A1 | 1/2014 | Liu et al. |

(56)           References Cited

U.S. PATENT DOCUMENTS

| | | |
|---|---|---|
| 2014/0031674 A1 | 1/2014 | Newman et al. |
| 2014/0046261 A1 | 2/2014 | Newman et al. |
| 2014/0066798 A1 | 3/2014 | Albert |
| 2014/0073976 A1 | 3/2014 | Fonte et al. |
| 2014/0089836 A1 | 3/2014 | Damani et al. |
| 2014/0094694 A1 | 4/2014 | Moctezuma de la Barrera |
| 2014/0094768 A1 | 4/2014 | Stangenes et al. |
| 2014/0107475 A1 | 4/2014 | Cox et al. |
| 2014/0128712 A1 | 5/2014 | Banet et al. |
| 2014/0163356 A2 | 6/2014 | Burnside et al. |
| 2014/0180074 A1 | 6/2014 | Green et al. |
| 2014/0180098 A1 | 6/2014 | Flaherty et al. |
| 2014/0187917 A1 | 7/2014 | Clark et al. |
| 2014/0187990 A1 | 7/2014 | Banet et al. |
| 2014/0188133 A1 | 7/2014 | Misener |
| 2014/0221862 A1 | 8/2014 | Tambe |
| 2014/0228689 A1 | 8/2014 | Ishikawa et al. |
| 2014/0243659 A1 | 8/2014 | Rothenberg |
| 2014/0249428 A1 | 9/2014 | Ingold, Jr. et al. |
| 2014/0249505 A1 | 9/2014 | Bukhman |
| 2014/0253270 A1 | 9/2014 | Nicholls et al. |
| 2014/0257080 A1 | 9/2014 | Dunbar et al. |
| 2014/0275957 A1 | 9/2014 | Lupotti |
| 2014/0275990 A1 | 9/2014 | Hagy et al. |
| 2014/0276010 A1 | 9/2014 | Anderson |
| 2014/0276059 A1 | 9/2014 | Sheehan |
| 2014/0276081 A1 | 9/2014 | Tegels |
| 2014/0303492 A1 | 10/2014 | Burnside et al. |
| 2014/0309624 A1 | 10/2014 | Bown et al. |
| 2014/0343398 A1 | 11/2014 | He et al. |
| 2014/0343431 A1 | 11/2014 | Vajinepalli et al. |
| 2015/0005621 A1 | 1/2015 | Liu |
| 2015/0011887 A1 | 1/2015 | Ahn et al. |
| 2015/0018701 A1 | 1/2015 | Cox et al. |
| 2015/0025365 A1 | 1/2015 | Esguerra Wilczynski et al. |
| 2015/0025402 A1 | 1/2015 | Rothenberg |
| 2015/0051489 A1 | 2/2015 | Caluser et al. |
| 2015/0065916 A1 | 3/2015 | Maguire et al. |
| 2015/0073279 A1 | 3/2015 | Cai et al. |
| 2015/0073285 A1 | 3/2015 | Albert et al. |
| 2015/0080716 A1 | 3/2015 | Powers et al. |
| 2015/0173723 A1 | 6/2015 | Bates et al. |
| 2015/0209008 A1 | 7/2015 | Ridley et al. |
| 2015/0209113 A1 | 7/2015 | Burkholz et al. |
| 2015/0209526 A1 | 7/2015 | Matsubara et al. |
| 2015/0216445 A1 | 8/2015 | Carmeli et al. |
| 2015/0216446 A1 | 8/2015 | Bukhman et al. |
| 2015/0223775 A1 | 8/2015 | Hamilton, Jr. |
| 2015/0245809 A1 | 9/2015 | Hagy et al. |
| 2015/0245872 A1 | 9/2015 | Hagy et al. |
| 2015/0246247 A1 | 9/2015 | Binnekamp et al. |
| 2015/0282734 A1 | 10/2015 | Schweikert et al. |
| 2015/0289781 A1 | 10/2015 | Grunwald et al. |
| 2015/0297097 A1 | 10/2015 | Matsubara et al. |
| 2015/0297114 A1 | 10/2015 | Cox et al. |
| 2015/0317810 A1 | 11/2015 | Grunwald et al. |
| 2015/0335310 A1 | 11/2015 | Bernstein et al. |
| 2015/0335383 A9 | 11/2015 | Cohen |
| 2016/0000399 A1 | 1/2016 | Halmann et al. |
| 2016/0067449 A1 | 3/2016 | Misener et al. |
| 2016/0120607 A1 | 5/2016 | Sorotzkin et al. |
| 2016/0166232 A1 | 6/2016 | Merritt |
| 2016/0202053 A1 | 7/2016 | Walker et al. |
| 2016/0278869 A1 | 9/2016 | Grunwald |
| 2016/0296208 A1 | 10/2016 | Sethuraman et al. |
| 2016/0331344 A1 | 11/2016 | Hadzic |
| 2016/0374589 A1 | 12/2016 | Misener et al. |
| 2016/0374644 A1 | 12/2016 | Mauldin, Jr. et al. |
| 2017/0000367 A1 | 1/2017 | Grunwald |
| 2017/0020561 A1 | 1/2017 | Cox et al. |
| 2017/0079548 A1 | 3/2017 | Silverstein et al. |
| 2017/0079552 A1 | 3/2017 | Grunwald |
| 2017/0079615 A1 | 3/2017 | Burnside et al. |
| 2017/0079681 A1 | 3/2017 | Burnside et al. |
| 2017/0086782 A1 | 3/2017 | Hagy et al. |
| 2017/0151022 A1 | 6/2017 | Jascob et al. |
| 2017/0151027 A1 | 6/2017 | Walker et al. |
| 2017/0215762 A1 | 8/2017 | Burnside et al. |
| 2017/0231700 A1 | 8/2017 | Cox et al. |
| 2017/0238996 A1 | 8/2017 | Frame et al. |
| 2017/0281029 A1 | 10/2017 | Messerly et al. |
| 2017/0347914 A1 | 12/2017 | Isaacson et al. |
| 2017/0348510 A1 | 12/2017 | Shevgoor et al. |
| 2017/0348511 A1 | 12/2017 | Burkholz et al. |
| 2017/0367678 A1 | 12/2017 | Sirtori et al. |
| 2018/0070856 A1 | 3/2018 | Grunwald |
| 2018/0103869 A1 | 4/2018 | Bukhman et al. |
| 2018/0116551 A1 | 5/2018 | Newman et al. |
| 2018/0116723 A1 | 5/2018 | Hettrick et al. |
| 2018/0116744 A1 | 5/2018 | Taya |
| 2018/0125450 A1 | 5/2018 | Blackbourne et al. |
| 2018/0145443 A1 | 5/2018 | Andreason et al. |
| 2018/0161012 A1 | 6/2018 | Bang et al. |
| 2018/0161502 A1 | 6/2018 | Nanan et al. |
| 2018/0169389 A1 | 6/2018 | Lemon et al. |
| 2018/0199914 A1 | 7/2018 | Ramachandran et al. |
| 2018/0214119 A1 | 8/2018 | Mehrmohammadi et al. |
| 2018/0296122 A1 | 10/2018 | Messerly et al. |
| 2018/0304043 A1 | 10/2018 | Bown et al. |
| 2018/0310955 A1 | 11/2018 | Lindekugel et al. |
| 2018/0325604 A1 | 11/2018 | Atarot et al. |
| 2018/0333559 A1 | 11/2018 | Makey |
| 2019/0069877 A1 | 3/2019 | Burnside et al. |
| 2019/0099108 A1 | 4/2019 | Messerly et al. |
| 2019/0216423 A1 | 7/2019 | Ko et al. |
| 2019/0246945 A1 | 8/2019 | Grunwald |
| 2019/0261886 A1 | 8/2019 | King et al. |
| 2019/0290208 A1 | 9/2019 | Toth et al. |
| 2019/0320982 A1 | 10/2019 | Misener et al. |
| 2020/0054858 A1 | 2/2020 | Newman et al. |
| 2020/0119488 A1 | 4/2020 | Stats et al. |
| 2020/0138332 A1 | 5/2020 | Newman et al. |
| 2020/0237255 A1 | 7/2020 | Silverstein et al. |
| 2020/0237403 A1 | 7/2020 | Southard et al. |
| 2020/0246588 A1 | 8/2020 | Akins et al. |
| 2021/0077201 A1 | 3/2021 | Cox et al. |
| 2021/0082860 A1 | 3/2021 | Audette et al. |
| 2021/0401456 A1 | 12/2021 | Cox et al. |
| 2022/0096800 A1 | 3/2022 | Tran et al. |
| 2022/0347433 A1 | 11/2022 | Davis et al. |
| 2023/0233262 A9 | 7/2023 | Cox et al. |

FOREIGN PATENT DOCUMENTS

| | | | |
|---|---|---|---|
| AU | 1860597 | B2 | 6/1999 |
| AU | 20009592 | | 9/2000 |
| AU | 20015250 | | 6/2001 |
| AU | 768362 | B2 | 12/2003 |
| AU | 2001229024 | B2 | 9/2005 |
| AU | 2001283703 | B2 | 5/2006 |
| AU | 2006904933 | | 9/2006 |
| AU | 2006202149 | B2 | 3/2009 |
| AU | 2006283022 | B2 | 2/2012 |
| CA | 1197745 | A | 12/1985 |
| CA | 2420676 | C | 7/2010 |
| CA | 2619909 | C | 1/2014 |
| CN | 2031655 | U | 2/1989 |
| CN | 1672649 | A | 9/2005 |
| CN | 1913833 | A | 2/2007 |
| CN | 101854853 | A | 10/2010 |
| CN | 102209490 | A | 10/2011 |
| CN | 102802514 | A | 11/2012 |
| CN | 102821679 | A | 12/2012 |
| CN | 103037761 | A | 4/2013 |
| CN | 103037762 | A | 4/2013 |
| CN | 103118591 | A | 5/2013 |
| CN | 103189009 | A | 7/2013 |
| CN | 104013425 | A | 9/2014 |
| DE | 4319033 | C1 | 6/1994 |
| EP | 0153021 | A1 | 8/1985 |
| EP | 0362821 | A1 | 4/1990 |
| EP | 0399536 | A1 | 11/1990 |
| EP | 0359697 | B1 | 11/1994 |
| EP | 0823261 | A2 | 2/1998 |

(56)              References Cited

FOREIGN PATENT DOCUMENTS

| | | | |
|----|----|----|----|
| EP | 10043310 | | 2/1998 |
| EP | 0928976 | A2 | 7/1999 |
| EP | 1025805 | A1 | 8/2000 |
| EP | 1015967 | B1 | 4/2002 |
| EP | 1311226 | A1 | 5/2003 |
| EP | 1504713 | A1 | 2/2005 |
| EP | 1117331 | B1 | 5/2005 |
| EP | 1117332 | B1 | 8/2005 |
| EP | 1118019 | B1 | 5/2006 |
| EP | 1717601 | A2 | 11/2006 |
| EP | 1887940 | A2 | 2/2008 |
| EP | 1932477 | A1 | 6/2008 |
| EP | 2337491 | A1 | 6/2011 |
| EP | 2440122 | A1 | 4/2012 |
| EP | 2464407 | A2 | 6/2012 |
| EP | 2482719 | A1 | 8/2012 |
| EP | 2531098 | A1 | 12/2012 |
| EP | 2575610 | A1 | 4/2013 |
| EP | 2575611 | A1 | 4/2013 |
| EP | 2603145 | A2 | 6/2013 |
| EP | 2605699 | A2 | 6/2013 |
| EP | 2474268 | B1 | 7/2013 |
| EP | 2618727 | A1 | 7/2013 |
| EP | 2632360 | A1 | 9/2013 |
| EP | 2219526 | B1 | 3/2014 |
| EP | 2712547 | A1 | 4/2014 |
| EP | 2313143 | B1 | 9/2014 |
| EP | 2913000 | A2 | 9/2015 |
| EP | 2992825 | B1 | 5/2017 |
| EP | 2170162 | B1 | 8/2017 |
| EP | 2265175 | B1 | 8/2017 |
| FR | 2545349 | B1 | 9/1986 |
| JP | 01097440 | | 4/1989 |
| JP | 03173542 | A | 7/1991 |
| JP | 9-503054 | | 3/1997 |
| JP | 09-094298 | A | 4/1997 |
| JP | 10290839 | A | 11/1998 |
| JP | 11128237 | A | 5/1999 |
| JP | 2001-145630 | A | 5/2001 |
| JP | 2001161683 | A | 6/2001 |
| JP | 2001514533 | A | 9/2001 |
| JP | 2001-524339 | A | 12/2001 |
| JP | 2001340334 | A | 12/2001 |
| JP | 2002520893 | A | 7/2002 |
| JP | 2002-224069 | A | 8/2002 |
| JP | 2002529133 | A | 9/2002 |
| JP | 2002-541947 | A | 12/2002 |
| JP | 2003-010138 | A | 1/2003 |
| JP | 2003501127 | A | 1/2003 |
| JP | 2003061752 | A | 3/2003 |
| JP | 2003299654 | A | 10/2003 |
| JP | 2003334191 | A | 11/2003 |
| JP | 2004505748 | T | 2/2004 |
| JP | 2004515298 | A | 5/2004 |
| JP | 2006508744 | A | 3/2006 |
| JP | 2006-338526 | A | 12/2006 |
| JP | 2007-000226 | A | 1/2007 |
| JP | 2007-068989 | A | 3/2007 |
| JP | 2007-105450 | A | 4/2007 |
| JP | 2007-313122 | A | 12/2007 |
| JP | 4090741 | B2 | 5/2008 |
| JP | 2009/271123 | A | 11/2009 |
| JP | 5010604 | B2 | 8/2012 |
| JP | 2012-529929 | A | 11/2012 |
| JP | 2013-518676 | A | 5/2013 |
| JP | 2013-526959 | A | 6/2013 |
| JP | 2013-526961 | A | 6/2013 |
| KR | 20100047436 | A | 5/2010 |
| RU | 2009101949 | A | 7/2010 |
| WO | 1980002376 | A1 | 11/1980 |
| WO | 1991012836 | A1 | 9/1991 |
| WO | 1992003090 | A1 | 3/1992 |
| WO | 1994003159 | A1 | 2/1994 |
| WO | 1994004938 | A1 | 3/1994 |
| WO | 1996005768 | A1 | 2/1996 |
| WO | 1996007352 | A1 | 3/1996 |
| WO | 1996041119 | A1 | 12/1996 |
| WO | 1997/22395 | A1 | 6/1997 |
| WO | 1997029683 | A1 | 8/1997 |
| WO | 1997043989 | A1 | 11/1997 |
| WO | 9748438 | A2 | 12/1997 |
| WO | 1998025159 | A1 | 6/1998 |
| WO | 9829032 | A1 | 7/1998 |
| WO | 1998035611 | A1 | 8/1998 |
| WO | 1999016495 | A1 | 4/1999 |
| WO | 1999027837 | A2 | 6/1999 |
| WO | 1999049407 | A1 | 9/1999 |
| WO | 2000019906 | A1 | 4/2000 |
| WO | 2000027281 | A1 | 5/2000 |
| WO | 2000040155 | A1 | 7/2000 |
| WO | 2000063658 | A2 | 10/2000 |
| WO | 2000074775 | A1 | 12/2000 |
| WO | 2001013792 | A1 | 3/2001 |
| WO | 2001039683 | A1 | 6/2001 |
| WO | 2001076479 | A1 | 10/2001 |
| WO | 02/07794 | A2 | 1/2002 |
| WO | 2002015973 | A1 | 2/2002 |
| WO | 2002019905 | A1 | 3/2002 |
| WO | 2002025277 | A1 | 3/2002 |
| WO | 2002085442 | A1 | 10/2002 |
| WO | 2003061752 | A1 | 7/2003 |
| WO | 2003077759 | A1 | 9/2003 |
| WO | 03/088833 | A1 | 10/2003 |
| WO | 2003091495 | A1 | 11/2003 |
| WO | 2004002303 | A1 | 1/2004 |
| WO | 2004049970 | A2 | 6/2004 |
| WO | 2005033524 | A1 | 4/2005 |
| WO | 2005033574 | A1 | 4/2005 |
| WO | 2005/089851 | A1 | 9/2005 |
| WO | 2005117690 | A1 | 12/2005 |
| WO | 2005117733 | A2 | 12/2005 |
| WO | 2006074509 | A1 | 7/2006 |
| WO | 2006074510 | A1 | 7/2006 |
| WO | 2006078677 | A2 | 7/2006 |
| WO | 2006103661 | A2 | 10/2006 |
| WO | 2006111056 | A1 | 10/2006 |
| WO | 2007002541 | A2 | 1/2007 |
| WO | 2007005976 | A1 | 1/2007 |
| WO | 2007014447 | A1 | 2/2007 |
| WO | 2007034196 | A2 | 3/2007 |
| WO | 2007067324 | A1 | 6/2007 |
| WO | 2007069168 | A2 | 6/2007 |
| WO | 2007109123 | A2 | 9/2007 |
| WO | 2007126536 | A2 | 11/2007 |
| WO | 2007144894 | A1 | 12/2007 |
| WO | 2008005480 | A1 | 1/2008 |
| WO | 2008024596 | A2 | 2/2008 |
| WO | 2008028253 | A1 | 3/2008 |
| WO | 2008083111 | A1 | 7/2008 |
| WO | 2008097767 | A2 | 8/2008 |
| WO | 2008118992 | A1 | 10/2008 |
| WO | 2008126074 | A2 | 10/2008 |
| WO | 2008129326 | A1 | 10/2008 |
| WO | 2008131017 | A2 | 10/2008 |
| WO | 2008136008 | A2 | 11/2008 |
| WO | 2009000439 | A1 | 12/2008 |
| WO | 2009002514 | A2 | 12/2008 |
| WO | 2009003138 | A1 | 12/2008 |
| WO | 2009009064 | A1 | 1/2009 |
| WO | 2009057774 | A1 | 5/2009 |
| WO | 2009063166 | A1 | 5/2009 |
| WO | 2009067654 | A1 | 5/2009 |
| WO | 2009070616 | A2 | 6/2009 |
| WO | 2009100158 | A1 | 8/2009 |
| WO | 2009123819 | A2 | 10/2009 |
| WO | 2009126340 | A1 | 10/2009 |
| WO | 2009129176 | A1 | 10/2009 |
| WO | 2009129477 | A1 | 10/2009 |
| WO | 2009134605 | A2 | 11/2009 |
| WO | 2009137262 | A2 | 11/2009 |
| WO | 2010002313 | A1 | 1/2010 |
| WO | 2010018500 | A1 | 2/2010 |
| WO | 2010022370 | A1 | 2/2010 |
| WO | 2010027349 | A1 | 3/2010 |

(56)            References Cited

FOREIGN PATENT DOCUMENTS

| | | | |
|---|---|---|---|
| WO | 2010027471 | A2 | 3/2010 |
| WO | 2010029906 | A1 | 3/2010 |
| WO | 2010030820 | A1 | 3/2010 |
| WO | 2010132857 | A1 | 11/2010 |
| WO | 2010132985 | A1 | 11/2010 |
| WO | 2010/144922 | A1 | 12/2010 |
| WO | 2010143196 | A1 | 12/2010 |
| WO | 2011019760 | A2 | 2/2011 |
| WO | 2011041450 | A1 | 4/2011 |
| WO | 2011044421 | A1 | 4/2011 |
| WO | 2011057289 | A2 | 5/2011 |
| WO | 2011064209 | A1 | 6/2011 |
| WO | 2011084593 | A2 | 7/2011 |
| WO | 2011097312 | A1 | 8/2011 |
| WO | 2011128052 | A2 | 10/2011 |
| WO | 2011150358 | A1 | 12/2011 |
| WO | 2011150376 | A1 | 12/2011 |
| WO | 2012021542 | A2 | 2/2012 |
| WO | 2012024577 | A2 | 2/2012 |
| WO | 2012039866 | A1 | 3/2012 |
| WO | 2012040487 | A1 | 3/2012 |
| WO | 2012058461 | A1 | 5/2012 |
| WO | 2012083245 | A1 | 6/2012 |
| WO | 2012088535 | A1 | 6/2012 |
| WO | 2012110955 | A1 | 8/2012 |
| WO | 2012173697 | A1 | 12/2012 |
| WO | 2013006713 | A2 | 1/2013 |
| WO | 2013006817 | A1 | 1/2013 |
| WO | 2013034175 | A1 | 3/2013 |
| WO | 2014042329 | A1 | 3/2014 |
| WO | 2014052894 | A2 | 4/2014 |
| WO | 2014062728 | A1 | 4/2014 |
| WO | 2014072238 | A1 | 5/2014 |
| WO | 2014137977 | A1 | 9/2014 |
| WO | 2014138652 | A1 | 9/2014 |
| WO | 2014138918 | A1 | 9/2014 |
| WO | 2015/055797 | A1 | 4/2015 |
| WO | 2015048514 | A1 | 4/2015 |
| WO | 2015073962 | A1 | 5/2015 |
| WO | 2015/120256 | A2 | 8/2015 |
| WO | 2016/210325 | A1 | 12/2016 |
| WO | 2017079732 | A1 | 5/2017 |
| WO | 2017096487 | A1 | 6/2017 |
| WO | 2017214428 | A1 | 12/2017 |
| WO | 2018/112252 | A1 | 6/2018 |
| WO | 2018134726 | A1 | 7/2018 |
| WO | 2020/160315 | A1 | 8/2020 |
| WO | 2022232325 | A1 | 11/2022 |

OTHER PUBLICATIONS

Acuson—The Value of Vision, AcuNav Diagnostic Ultrasound Catheter, 2000.

Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.

Alexander, GD et al., The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.

Allan, P.L. et al, Role of Ultrsound in the Assessment of Chronic Venous Insufficiency, Ultrasound Quarterly, vol. 17, No. 1, pp. 3-10, 2001.

Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.

Anonymous author, Correct Catheter Placement with a low-impact, reliable and economical method, <http://www.cvc-partner.com/index. cfm?103A955CC6844BF58ACFE3C9C1471959>, last accessed Dec. 22, 2011.

Arai, J et al, Detection of Peripherally Inserted Central Catheter Occlusion by in-line Pressure Monitoring, Paediatr Anaesth, pp. 621-624, vol. 12 No. 7, Sep. 2002.

Arrow International, Inc., The Arrow-Johans RAECG Adapter-Making Proper Central Venous Catheter Placement More Reliable (Modle No. EG-04900), Technical Report 1987, USA.

Aslamy, et al. "MRI of Central Venous Anatomy: Implications for Central Venous Catheter Insertion." American College of Chest Physicians, Jun. 8, 2009.

AU 2006283022 filed Aug. 24, 2006 Office Action dated Dec. 22, 2010.

AU 2008329807 exam requested Aug. 13, 2012 Examination Report No. 1 dated Feb. 15, 2013.

AU 2008329807 exam requested Aug. 13, 2012 Notice of Acceptance dated Feb. 14, 2014.

AU 2010300677 filed Mar. 12, 2012 First Examination Report dated Mar. 9, 2014.

AU 2011289513 filed Jan. 21, 2013 Examiner's Report dated Jul. 5, 2013.

AU 2012202293 filed Apr. 19, 2012 Examination Report No. 1 dated Apr. 24, 2013.

AU 2012278809 filed Nov. 12, 2013 Notice of Acceptance dated Sep. 13, 2016.

AU 2013201648 filed Mar. 19, 2013 Examiner's Report dated Mar. 5, 2014.

AU 2013201648 filed Mar. 19, 2013 Examiner's Report dated Oct. 14, 2013.

AU 2013202824 filed Apr. 6, 2013 First Examiner's Report dated Mar. 10, 2014.

AU 2013204243 filed Apr. 12, 2013 Examiner's Report dated Jun. 5, 2013.

AURORA® System Technical Specifications, Oct. 2003.

AZoMaterials. Nickel-Based Super Alloy Inconel 625—Properties and Applications by United Performance Alloys. Oct. 27, 2015. Last accessed Mar. 23, 2018. <URL:https://web.archive.org/web/20151027202821/https://www.azom.com/article.aspx?ArticleID=4461>.

B. Braun Website, "The Optimal Position of the Central Venous Catheter." http://www.cvcpartner.com/index.cfm18F1BDEA1310466194960A39F4E90968 (2009).

B. Braun, Certofix Central Venous Catheter for Placement Using the Seldinger Technique with Simultaneous ECG Lead Option, Feb. 2010.

Bailey, SH et al, Is Immediate Chest Radiograph Necessary after Central Venous Catheter Placement in a Surgical Intensive Care Unit?, Am J Surg, pp. 517-522, vol. 180 No 6, Dec. 2000.

Bankier, Alexander A., Azygos Arch Cannulation by Central Venous Catheters: Radiographic Detection of Malposition and Subsequent Complications, Journal of Thoracic Imaging 12:64-69 (1997).

Barber, JM et al, A Nurse led Peripherally Inserted Central Catheter Line Insertion Service is Effective with Radiological Support, Clin Radiol, pp. 352-354, vol. 57 No. 5, May 2002.

Bard Access Systems, Sherlock Tip Location System, 5 pages, 2006.

Bard Access Systems, Site Rite Vascular Acess Ultrasound System, 4 pages, 2005.

Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.

Benzadon, M. N. et al: "Comparison of the Amplitude of the P-Wave from Intracardiac Electrocardiogram Obtained by Means of a Central Venous Catheter Filled With Saline Solution to That Obtained Via Esophageal Electrocardiogram", American Journal of Cardiology, Cahners Publishing Co., Newton, MA, US, vol. 98, No. 7, Oct. 1, 2006 (Oct. 1, 2006), pp. 978-981.

BioAdvance Lumen Vu, Greenhouse Fund Feb. 2004 Recipient, www.bioadvance.com <http://www.bioadvance.com>, 2005.

Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.

(56)　　　　　References Cited

OTHER PUBLICATIONS

Buehrle, Douglas, PICC Placement in Humans using Electromagnetic Detection, <http://www.corpakmedsystems.com/supplement_material/supplementpages/navigator/navarticle.html>, 2008.

C.R. Bard, CathTrack™ Catheter Location System at www.bardaccess.com <http://www.bardaccess.com>, last accessed Apr. 28, 2011.

C.R. Bard, Inc., Bard Electrophysiology Product Catalogue, Bard Catheters, pp. 74-75 (2002), USA.

CA 2,619,909 filed Aug. 24, 2006 Examiner's Report dated Oct. 26, 2012.

CA 2,721,715 filed Apr. 17, 2009 Examiner's Report dated Aug. 18, 2015.

CA 2,721,715 filed Apr. 17, 2009 Examiner's Report dated Oct. 25, 2016.

CA 2800810 filed Nov. 26, 2012 Office Action dated Mar. 13, 2018.

CA 2800810 filed Nov. 26, 2012 Office Action dated Mar. 30, 2017.

CA 2800813 filed Nov. 26, 2012 Office Action dated Mar. 5, 2018.

Cadman, A et al, To Clot or Not to Clot? That is the question in Central Venous Catheters, Clinical Radiology, pp. 349-355, vol. 59 No. 4, Apr. 2004.

Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.

Cardella, John F. et al., Interventinal Radiologic Placement of Peripherally Inserted Central Catheters, Journal of Vascular and Interventional Radiology 1993; 4:653-660.

Carlon, R et al, Secondary Migration of a Central Venous Catheter—A Case Report, Minerva Anestesiol, pp. 927-931, vol. 69 No. 12, Dec. 2003.

Caruso, LJ et al, A Better Landmark for Positioning a Central Venous Catheter, J Clinical Monitoring and Computing, pp. 331-334, vol. 17 No. 6, Aug. 2002.

Cavatorta, et al., "Central Venous Catheter Placement in Hemodialysis: Evaluation of Electrocardiograming a Guidewire." The Journal of Vascular Access, vol. 2, pp. 45-50, 2001.

Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.

U.S. Appl. No. 14/141,046, filed Dec. 26, 2013 Notice of Allowance dated May 12, 2021.

U.S. Appl. No. 16/017,695, filed Jun. 25, 2018 Non-Final Office Action dated May 21, 2021.

U.S. Appl. No. 16/017,695, filed Jun. 25, 2018 Notice of Allowance dated Nov. 2, 2021.

U.S. Appl. No. 16/164,592, filed Oct. 18, 2018 Notice of Allowability dated Jun. 23, 2021.

U.S. Appl. No. 16/164,592 filed Oct. 18, 2018 Notice of Allowance dated Jun. 8, 2021.

U.S. Appl. No. 16/394,861, filed Apr. 25, 2019 Non-Final Office Action dated Aug. 5, 2021.

KR 10-2014-7002789 filed Feb. 3, 2014 Office Action dated Jun. 21, 2018.

Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.

Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.

Liu , Ji-Bin et al, Catheter-Based Intralumincal Sonography, J Ultrasound Med, pp. 145-160, vol. 23, 2004.

Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.

Lum, Phillip, A New Formula-Based Measurement Guide for Optimal Positioning of Central Venous Catheters, JAVA, vol. 9, No. 2, pp. 80-85, 2004.

Lynch, RE et al., A Procedure for Placing Pediatric Femoral Venous Catheter Tips near the Right Atrium, Pediatr Emerg Care, pp. 130-132, vol. 18 No. 2, Apr. 2002.

Madan, et al. "Right Atrial Electrocardiograma Technique for the Placement of Central Venous Catheters for Chemotherapy or Intravenous Nutrition." British Journal of Surgery, vol. B1, pp. 1604-1605, 1994.

Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, CHEST, 2003.

Markovich, Mary B., Central Venous Catheter Tip Placement: Determination of Posterior Malposition—A Case Study, JAVA, vol. 11, No. 2, pp. 85-89, 2006.

Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.

Mcdonnall, "Intra-Atrial Electrocardiogramar Catheter Placement." Literature review prepared for Bard Access Systems, Oct. 2007.

Mcgee et al., "Accurate Placement of Central Venous Catheters: A Prospective, Randomize, Multicenter Trail." Critical Care Medicine, vol. 21 No. 8, Aug. 1993.

MedGraphics, CardioPerfect® Resting/Stress ECG System, 3 pages, 2001.

Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.

Michenfelder, John et al, Air Embolism During Neurosurgery. A New Method of Treatment, Anesthesia and Analgesia. Current Researches, pp. 390-395, vol. 45, No. 4, Jul.-Aug. 1966.

MICROBIRD™ Miniaturized DC Magnetic Sensors for Intra-body Navigation and Localization, Specifications, 2005.

MICRONIX CathRite™ Cardiac Access Device Brochure. Jun. 2004.

Micronix Pty Ltd "CathRite" Guiding Styled Core Manufacturing, Jun. 15, 2006.

Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.

Murthy, Vrudhula et al, Analysis of Power Spectral Densities of Electrocardiograms, Mathematical Biosciences, pp. 41-51, vol. 12 No. 1-2, Oct. 1971.

MX/a/2012/013672 filed Nov. 23, 2012 First Office Action dated Aug. 10, 2015.

MX/a/2012/013858 filed Nov. 28, 2012 First Office Action dated Sep. 26, 2014.

MX/a/2012/013858 filed Nov. 28, 2012 Second Office Action dated Jun. 10, 2015.

MX/a/2013/001317 filed Jan. 31, 2013 First Office Action dated Nov. 26, 2015.

MX/a/2015/004864 filed Apr. 16, 2015 Office Action dated Apr. 24, 2018.

MX/a/2015/004864 filed Apr. 16, 2015 Office Action dated Dec. 18, 2017.

Nadroo, AM et al., Changes in Upper Extremity Position Cause Migration of Peripherally Inserted Central Catheters in Neonates, Pediatrics, pp. 131-136, vol. 110, Jul. 2002.

Nakatani, K et al, Accurate Placement of Central Venous Catheters—ECG-guided method vs Patient Height Method, MASUI, pp. 34-38, vol. 51 No. 1, Jan. 2002.

Nazarian, GK et al, Changes in Tunneled Catheter Tip Position when a patient is Upright, J Vasc Interv Radiol, pp. 437-441, vol. 8 No. 3, May-Jun. 1997.

Neurometer® CPT, Clinical Applications. Neurotron , Inc. website: www.neurotron.com/CLINAPS.html, last accessed Oct. 23, 2006.

Neurometer® CPT, Frequently Asked Questions. Neurotron , Inc. website: www.neurotron.com/CPTFAQ/html, last accessed Oct. 23, 2006.

(56)　　　　　References Cited

OTHER PUBLICATIONS

Neurometer® CPT, Products Page. Neurotron , Inc. website: www.neurotron.com/products.html, last accessed Oct. 23, 2006.
Neurometer® Electrodiagnostic Neuroselective Sensory Nerve Evaluation: Charts, Tables, Documents & Downloads. Neurotron , Inc. website: www.neurotron.com/downloads.html, last accessed Oct. 23, 2006.
NOT Resource Center. Magnetic Permeability. Oct. 18, 2014. Last accessed Mar. 23, 2018. <URL:https://web.archive.org/web/20141018213902/https://www.nde-ed.org/EducationResources/CommunityCollege/Materials/Physical_Chemical/Permeability.htm>.
Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Palesty, JA et al., Routine Chest Radiographs Following Central Venous Recatheterization over a Wire are not Justified, Am J Surg, pp. 618-621, vol. 176 No. 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid Column Electrocardiograms." European Journal of Anaesthesiology, vol. 41, pp. 594-599, 2004.
PCT/US13/62409 filed Sep. 27, 2013 International Search Report and Written Opinion dated Feb. 24, 2014.
PCT/US2006/033079 filed Aug. 24, 2006 International Preliminary Report on Patentability dated Feb. 26, 2008.
PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/060502 filed Apr. 16, 2008 International Search Report and Written Opinion dated Oct. 16, 2008.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
VIASYS MedSystems, Cortrak™ Systems Brochure, 2005.
Volcano ComboMap Features and Benefits/Technical Specifications, 2 pages, 2011.
Watters, et al. "Use of Electrocardiogram to Position Right Atrial Catheters During Surgery." Annals of Surgery, vol. 225, No. 2, pp. 165-171, 1997.
Welch Allyn Cardioperfect® PC-Based Resting ECG, 2003.
Wilson, R. G. et al, Right Atrial Electrocardiogram Placement of Central Venous Catheters, The Lancet, pp. 162-463, Feb. 27, 1988.
Wong, Jeffrey J. et al., Azygos Tip Placement for Hemodialysis Catheters in Patients with Superior Vena Cava Occlusion, Cardiovasc Intervent Radiol (2006) 29:143-146.
Worley, Seth J. "Use of a Real-Time Three-Dimensional Magenetic Navigation System for Radiofrequency Ablation of Accessory Pathways." PACE, vol. 21 pp. 1636-1643, Aug. 1998.
Yilmazlar A et al, Complications of 1303 Central Venous Cannulations, J R Soc Med, pp. 319-321, vol. 90 No. 6, Jun. 1997 (Abstract only).
Yoon, SZ et al, Usefulness of the Carina as a Radiographic Landmark for Central Venous Catheter Placement in Paediatric Patients, Br J Anaesth, Jul. 2005.

Yoshida, Teruhisa et al, Detection of Concealed Left Sided Accessory Atrioventricular Pathway by P Wave Signal Averaged Electrocardiogram, J Am Coll Cardiol, pp. 55-62, 1999.
Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.
Zachariou, Zacharias et al., Intra-atrial ECG recording: a new and safe method for implantation of Broviac catheters in children, Pediatr Surg Int (1994) 9: 457-458.
Zaidi, Naveed A., et al. "Room temperature magnetic order in an organic magnet derived from polyaniline." 2004, Polymer, vol. 45, pp. 5683-5689.
PCT/US2020/015947 filed Jan. 30, 2020 International Search Report and Written Opinion dated Jun. 11, 2020.
U.S. Appl. No. 16/011,380, filed Jun. 18, 2018 Notice of Allowance dated Apr. 3, 2023.
U.S. Appl. No. 16/011,380, filed Jun. 18, 2018 Notice of Allowance dated May 17, 2023.
U.S. Appl. No. 16/653,594, filed Oct. s15, 2019 Non-Final Office Action dated Feb. 1, 2023.
U.S. Appl. No. 16/734,011, filed Jan. 3, 2020, Final Office Action dated May 18, 2023.
U.S. Appl. No. 16/734,011, filed Jan. 3, 2020, Non-Final Office Action dated Oct. 28, 2022.
U.S. Appl. No. 16/777,685, filed Jan. 30, 2020 Examiner's Answer dated Apr. 11, 2023.
U.S. Appl. No. 16/830,040, filed Mar. 25, 2020 Notice of Allowance dated Sep. 29, 2022.
U.S. Appl. No. 17/105,221, filed Nov. 25, 2020 Non-Final Office Action dated Oct. 6, 2022.
U.S. Appl. No. 17/127,587, filed Dec. 18, 2020 Final Office Action dated Sep. 21, 2022.
U.S. Appl. No. 17/127,587, filed Dec. 18, 2020 Non-Final Office Action dated Apr. 7, 2023.
U.S. Appl. No. 17/240,894, filed Apr. 26, 2021 Notice of Allowance dated Dec. 13, 2022.
U.S. Appl. No. 17/317,591, filed May 11, 2021, Restriction Requirement dated Feb. 24, 2023.
U.S. Appl. No. 17/484,868, filed Sep. 24, 2021 Non-Final Office Action dated Jan. 20, 2023.
U.S. Appl. No. 16/653,594, filed Oct. 15, 2019 Non-Final Office Action dated Aug. 16, 2023.
U.S. Appl. No. 16/734,011, filed Jan. 3, 2020, Advisory Action dated Aug. 10, 2023.
U.S. Appl. No. 17/105,221, filed Nov. 25, 2020 Notice of Allowance dated Jun. 2, 2023.
U.S. Appl. No. 17/317,591, filed May 11, 2021 Non-Final Office Action dated Jun. 20, 2023.
U.S. Appl. No. 17/484,868, filed Sep. 24, 2021 Final Office Action dated Aug. 1, 2023.
EP 211857735 filed Jul. 16, 2021 Extended European Search Report dated Nov. 5, 2021.
U.S. Appl. No. 16/394,861, filed Apr. 25, 2019 Notice of Allowance dated Apr. 11, 2022.
U.S. Appl. No. 16/830,040, filed Mar. 25, 2020 Non-Final Office Action dated May 5, 2022.
U.S. Appl. No. 17/127,587, filed Dec. 18, 2020 Non-Final Office Action dated May 11, 2022.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Pittiruti, et al. "The electrocardiogramethod for positioning the tip of central venous catheters" JAVA, pp. 1-12, Feb. 12, 2011.
Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Pop, Gheorghe A. et al., Catheter-based impedance measurements in the right atrium for continuously monitoring hematocrit and esti-

(56)         References Cited

OTHER PUBLICATIONS mating blood viscosity changes; an in vivo feasibility study in swine, Biosensors and Bioelectronics 19 (2004) 1685-1693.

Popp, M. B. et al., Accuracy of implanted port placement with the use of the electromagnetic CathTrack® catheter locator system, The Journal of Vascular Access 2005; 6: 9-12.

Randolph AG et al., Ultrasound guidance for placement of central venous catheters: a meta-analysis of the literature, Critcal Care Medicine, pp. 2053-2058, vol. 24, Dec. 1996.

Reece, A et al, Posititioning Long Lines: Contrast Versus Plain Radiography, Arch Dis Child Fetal Neonatal Ed, pp. 129-130, vol. 84 No. 2, Mar. 2001.

Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.

RU 2011150917 filed Dec. 15, 2011 First Office Action dated Apr. 24, 2014.

RU 2011150917 filed Dec. 15, 2011 Second Office Action dated Aug. 28, 2014.

RU 2013158008 filed Dec. 26, 2013 First Office Action dated May 27, 2016.

RU 2015110633 filed Mar. 26, 2015 Office Action dated Oct. 25, 2018.

RU 2015111669 filed Apr. 1, 2015 Office Action dated Jan. 25, 2018.

RU 2015111669 filed Apr. 1, 2015 Office Action dated May 18, 2018.

RU 2015111669 filed Apr. 1, 2015 Office Action dated Sep. 5, 2017.

Ruschulte, Heiner et al, Prevention of Central Venous Catheter related infections with chlorhex idine gluconate impregnated wound dressings: A randomized controlled trial, presented as an abstract at the Annual meeting of the European Society of Anesthesiologists (ESA) in Madrid, Spain in Jun. 2006, 12 pages, Annals of Hematology, Jul. 14, 2008.

Rutherford, J. S. et al., Depth of Central Venous Catheterization: An Audit of Practice in a Cardiac Surgical Unit, Anaesth Intens Care 1994; 22: 267-271.

Sacolick, et al. "Electromagnetically Tracked Placement of a Peripherally Inserted Central Catheter." SPIE Medical Imaging, 2004 Proceedings.

Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.

Savary, D et al, Intra-atrial Monitoring to Add Insertion of a Central Venous Line in Pre-Hospital Emergency Care Journal Europeen des Urgences, pp. 75-78, vol. 17 No. 2, 2004.

Schafer et al. "Incorrect placement of a vena cava catheter and its prevention by intra-atrial ECG." Anaesthesist. Jan. 1988;37(1):49-51.

Schummer, et al. "Central Venous Catheters—The inability of 'intra-atrial ECG' to prove adequate positioning." British Journal of Anaesthesia, vol. 93, No. 2, pp. 193-198, 2004.

Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).

Schummer, W et al, Intra-Atrial ECG is not a Reliable Method for Positioning Left Internal Jugular Vein Catheters, Br J Anaesth, pp. 481-486, vol. 91 No. 4, Oct. 2003.

Schummer, W, Central Venous Catheter—the Inability of "Intra-Atrial ECG" to prove Adequate Positioning, Br J Anaesth, pp. 193-198, vol. 93 No. 2, Aug. 2004.

Schuster, M. et al., The carina as a landmark in central venous catheter placement, British Journal of Anaesthesia 85 (2): 192-4 (2000).

Siela, Debra, Using Chest Radiography in the Intensive Care Unit, Crit Care Nurse Aug. 1, 2002 vol. 22 No. 4, pp. 18-27.

Simon, et al., "Central Venous Catheter Placement in Children: Evaluation of Electrocardiogramaing J-Wire." Paediatric Anaesthesia vol. 9, pp. 501-504, 1999.

Smith, Brigham, et al., Intravenous electrocardiogramce for placement of peripherally inserted central catheters, Journal of Electrocardiology 43 (2010) 274-278.

Stark, DD et al, Radiographic Assessment of Venous Catheter Position in Children: Value of the Lateral View, Pediatric Radiology, pp. 76-80, vol. 14 No. 2, 1984.

Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.

Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.

Starr, David S et al, EKG Guided Placement of Subclavian CVP Catheters Using J-Wire, pp. 673-676, Ann. Surg, Dec. 1986.

Stas, M et al, Peroperative Intravasal Electrographic Control of Catheter Tip Position in Access Ports Placed by Venous Cut-Down Technique, EJSO, pp. 316-320, vol. 27, 2001.

Stereotaxis Magetic Navigation System with Navigant™ User Interface, 2005 Brochure.

Stereotaxis, Expanding the Possibilites of Interventional Medicine: Remote Navigation and Automation, pp. 1-8, Apr. 2011.

Tepa® Health Innovation PC based ECG System Introduction and Technical Specifications, EKG Master USB, 2 pages, Nov. 2003.

Thakor, N. V., et al. "Ground-Free ECG Recording with Two Electrodes." IEEE Transactions on Biomedical Engineering, vol. BME-27, No. 12, Dec. 1980.

The FloWire Doppler Guide Wire located <http://www.volcanocorp.com/products/flowire-doppler-guide-wire.php>, 2011.

Traxal Technologies, Tracking Technology website overview: www.traxal.com/rd/rd_classroom_trackingtechnology.htm, last accessed Dec. 1, 2006.

UAB Health Systems, Arrhythmias, retrieved from http://www.health,uab.edu/14564/ on Nov. 15, 2007, 12 pages.

U.S. Appl. No. 11/466,602, filed Aug. 23, 2006 Advisory Action dated Jun. 22, 2009.

U.S. Appl. No. 11/466,602, filed Aug. 23, 2006 Appeal Board Decision dated Sep. 17, 2012.

U.S. Appl. No. 11/466,602, filed Aug. 23, 2006 Final Office Action dated Apr. 8, 2010.

U.S. Appl. No. 11/466,602, filed Aug. 23, 2006 Final Office Action dated Jan. 30, 2009.

U.S. Appl. No. 11/466,602, filed Aug. 23, 2006 Final Office Action dated Oct. 28, 2013.

U.S. Appl. No. 11/466,602, filed Aug. 23, 2006 Non-Final Office Action dated Mar. 28, 2013.

U.S. Appl. No. 11/466,602, filed Aug. 23, 2006 Non-Final Office Action dated Sep. 25, 2009.

U.S. Appl. No. 11/466,602, filed Aug. 23, 2006 Notice of Allowance dated Dec. 3, 2012.

PCT/US2022/026606 filed Apr. 27, 2022, International Search Report and Written Opinion dated Jul. 21, 2022.

U.S. Appl. No. 16/011,380, filed Jun. 18, 2018 Final Office Action dated Jul. 21, 2022.

U.S. Appl. No. 16/734,011, filed Jan. 3, 2020, Restriction Requirement dated Jul. 20, 2022.

U.S. Appl. No. 16/777,685, filed Jan. 30, 2020 Final Office Action dated Jul. 12, 2022.

EP 10786978.6 filed Dec. 19, 2011 Office Action dated Jan. 16, 2019.

EP 10821193.9 filed Mar. 27, 2012 Partial European Search Report dated Oct. 9, 2015.

EP 11 818 828.3 filed Mar. 18, 2013 Extended European Search Report dated Dec. 10, 2014.

EP 11740309.7 filed Aug. 23, 2012 Extended European Search Report dated Aug. 3, 2015.

EP 11787515.3 filed Dec. 12, 2012 partial European search report dated Jun. 23, 2015.

EP 11787515.3 filed Dec. 12, 2012 partial European search report dated Oct. 27, 2015.

(56) References Cited

OTHER PUBLICATIONS

EP 11787527.8 filed Dec. 19, 2012 Extended European Search Report dated Oct. 9, 2015.
EP 11787527.8 filed Dec. 19, 2012 partial European search report dated May 26, 2015.
EP 11827551.0 filed Feb. 7, 2013 Extended European Search Report dated Sep. 19, 2017.
EP 11827551.0 filed Feb. 7, 2013 Office Action dated Mar. 13, 2020.
EP 11837113.7 filed May 28, 2013 Extended European Search Report dated Apr. 24, 2014.
EP 11850625.2 filed Jul. 22, 2013 Extended European Search Report dated Jun. 21, 2017.
EP 11850625.2 filed Jul. 22, 2013 Office Action dated Feb. 25, 2019.
EP 11850625.2 filed Jul. 22, 2013 Office Action dated Sep. 24, 2018.
EP 12177438.4 filed Jul. 23, 2012 Communication dated Jan. 13, 2014.
EP 12177438.4 filed Jul. 23, 2012 European Search Report dated Dec. 4, 2012.
EP 12177438.4 filed Jul. 23, 2012 European Search Report dated Jun. 7, 2015.
EP 12177438.4 filed Jul. 23, 2012 Examination Report dated Dec. 5, 2014.
EP 12177438.4 filed Jul. 23, 2012 extended European Search Report dated Mar. 25, 2013.
EP 12807886.2 filed Jan. 15, 2014 Extended European Search Report dated Feb. 6, 2015.
EP 13194818.4 filed Nov. 28, 2013 extended European search report dated Feb. 28, 2014.
EP 13840356.3 filed Apr. 27, 2015 Extended European Search Report dated Mar. 22, 2017.
EP 13840356.3 filed Apr. 27, 2015 Partial European Search Report dated Oct. 19, 2016.
EP 13846380.7 filed May 15, 2015 Extended European Search Report dated Sep. 30, 2016.
EP 13846380.7 filed May 15, 2015 Partial European Search Report dated Sep. 30, 2016.
EP 14151268.1 filed Jan. 15, 2014 European Search Report dated Feb. 21, 2014.
EP 14197137.4 filed Dec. 10, 2014 Extended European Search Report dated Nov. 4, 2015.
EP 14197137.4 filed Dec. 10, 2014 Office Action dated Apr. 5, 2018.
EP 14197137.4 filed Dec. 10, 2014 Office Action dated, Sep. 20, 2017.
EP 14197137.4 filed Dec. 10, 2014, Office Action dated Nov. 21, 2018.
EP 14197137.4 filed Dec. 10, 2014, Partial European Search Report dated May 29, 2015.
EP 14761249.3 Filed Sep. 3, 2015 Extended European Search Report dated Sep. 19, 2016.
EP 14761249.3 Filed Sep. 3, 2015 Office Action dated Sep. 28, 2017.
EP 15179061.5 filed Jul. 30, 2015 Extended European Search Report dated Jan. 14, 2016.
EP 15179061.5 filed Jul. 30, 2015 Partial European Search Report dated Jan. 17, 2018.
EP 15746326.6 filed Jul. 1, 2016 Extended European Search Report dated Jun. 9, 2017.
EP 15746326.6 filed Jul. 1, 2016 Office Action dated Jan. 29, 2019.
EP 17157118.5 filed Feb. 21, 2017 Extended European Search Report Jun. 8, 2017.
EP 17186624.7 filed Aug. 17, 2017 Extended European Search Report dated Jan. 17, 2018.
EP 17186624.7 filed Aug. 17, 2017 Partial European Search Report dated Jan. 17, 2018.
EP 20154593.6 filed Jan. 30, 2020 Extended European Search Report dated Jun. 2, 2020.
EP14197136.6 filed Dec. 10, 2014 Extended European Search Report dated May 26, 2015.
EP14197136.6 filed Dec. 10, 2014 Office Action dated Nov. 21, 2018.

Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiogramacement Control of Central Venous Catheters in Austria, Acta Med Austriaca, pp. 109-113, vol. 26 No. 3, 1999 (Abstract only).
Forauer, AR et al, Change in Peripherally Inserted Central Catheter Tip Location with Abduction and Adduction of the Upper Extremity, J Vasc Interv Radiol, pp. 1315-1318, vol. 11 No. 10, Nov.-Dec. 2000.
Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
PCT/US2020/066186 filed Dec. 18, 2020 International Search Report dated Mar. 23, 2021.
U.S. Appl. No. 15/842,685, filed Dec. 14, 2017 Non-Final Office Action dated Mar. 31, 2021.
U.S. Appl. No. 15/900,623, filed Feb. 20, 2018 Notice of Allowance dated Mar. 4, 2021.
U.S. Appl. No. 16/017,695, filed Jun. 25, 2018 Advisory Action dated Feb. 23, 2021.
U.S. Appl. No. 16/164,592, filed Oct. 18, 2018 Non-Final Office Action dated Feb. 19, 2021.
U.S. Appl. No. 16/457,606, filed Jun. 28, 2017 Notice of Allowance dated Mar. 17, 2021.
U.S. Appl. No. 16/598,952, filed Oct. 10, 2019 Supplemental Notice of Allowance dated Feb. 24, 2021.
U.S. Appl. No. 16/598,952, filed Oct. 10, 2019 Supplemental Notice of Allowance dated Jan. 29, 2021.
CN 201180052587.5 filed Apr. 28, 2013 Office Action dated Feb. 24, 2016.
CN 201180052587.5 filed Apr. 28, 2013 Second Office Action dated Aug. 19, 2015.
CN 201180068309.9 filed Aug. 22, 2013 First Office Action dated Oct. 16, 2014.
CN 201180068309.9 filed Aug. 22, 2013 Second Office Action dated May 6, 2015.
CN 201180068309.9 filed Aug. 22, 2013 Third Office Action dated Sep. 2, 2015.
CN 201280033189.3 filed Jan. 3, 2014 First Office Action dated Apr. 3, 2014.
CN 201280033189.3 filed Jan. 3, 2014 Second Office Action dated Sep. 14, 2015.
CN 201380051172.5 filed Mar. 30, 2015 Office Action dated Jan. 16, 2018.
CN 201380051172.5 filed Mar. 30, 2015 Office Action dated Jul. 30, 2018.
CN 201380051172.5 filed Mar. 30, 2015 Office Action dated May 2, 2017.
CN 201380065663.5 filed Jun. 15, 2015 Office Action dated Mar. 15, 2017.
CN 201380065663.5 filed Jun. 15, 2015 Office Action dated Oct. 10, 2017.
CN 201410009216.4 filed Jan. 8, 2014 Office Action dated Jun. 15, 2016.
CN 201410009216.4 filed Jan. 8, 2014 Second Office Action dated Sep. 25, 2015.
CN 201480010988.8 filed Aug. 27, 2015 Office Action dated Aug. 17, 2018.
CN 201480010988.8 filed Aug. 27, 2015 Office Action dated Dec. 13, 2017.
CN 201510144728.6 filed Apr. 17, 2015 Office Action dated Aug. 29, 2017.
CN 201510144728.6 filed Apr. 17, 2015 Office Action dated Jan. 23, 2017.
CN 201580007645.0 filed Aug. 8, 2016 Office Action dated Sep. 12, 2018.

(56)         References Cited

OTHER PUBLICATIONS

CN 201610127217.8 filed Mar. 7, 2016 Office Action dated Dec. 28, 2017.
CN 201610127217.8 filed Mar. 7, 2016 Office Action dated Jun. 11, 2018.
CN 201610127217.8 filed Mar. 7, 2016 Office Action dated Nov. 19, 2018.
CN 201610166569.4 filed Dec. 23, 2010, Office Action dated Nov. 1, 2017.
CO 15110530 filed May 14, 2015 Office Action dated May 8, 2017.
CO 15110530 filed May 14, 2015 Office Action dated Nov. 25, 2016.
Colley, Peter S et al, ECG-Guided Placement of Sorenson CVP Catheters via Arm Veins, Anesthesia and Analgesia, pp. 953-956, vol. 63, 1984.
Collier, PE et al., Cardiac Tamponade from Central Venous Catheters, Am J Surg, pp. 212-214, vol. 176 No. 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No. 3, Sep. 1998.
Curet, Myriam J. et al., University and Practice-based Physicians' Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
DELTEC Cath-Finder® Tracking System Operation Manual, 1994.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
Enrique Company-Bosch, "ECG Front-End Design is Simplified with MicroConverter." Analog Dialogue 37-11, (dated Nov. 2003).
EP 08855396.1 filed Jun. 15, 2010 European Search Report dated Jul. 31, 2012.
EP 08855396.1 filed Jun. 15, 2010 Intent to Grant dated Jul. 5, 2013.
EP 09707467.8 supplemental European search report dated Jun. 18, 2013.
EP 09743249.6 filed Oct. 18, 2010 Extended European Search Report dated Jan. 13, 2016.
EP 09743249.6 filed Oct. 18, 2010 Intention to Grant dated Mar. 2, 2017.
EP 09808901.4 filed Aug. 21, 2009 European Search Report dated May 23, 2012.
EP 09808901.4 filed Aug. 21, 2009 Examination Report dated May 10, 2013.
EP 09813632.8 filed Apr. 5, 2011 European Search Report dated Jul. 4, 2012.
EP 09813632.8 filed Apr. 5, 2011 Office Action dated Apr. 30, 2013.
EP 09813632.8 filed Apr. 5, 2011 Summons to Attend Oral Proceedings dated Apr. 16, 2014.
EP 10 808 660.4 filed Feb. 15, 2012 Extended European Search Report dated Mar. 4, 2014.
EP 10786978.6 filed Dec. 19, 2011 Extended European Search Report dated Mar. 7, 2014.
EP 10786978.6 filed Dec. 19, 2011 Office Action dated Aug. 11, 2017.

U.S. Appl. No. 11/466,602, filed Aug. 23, 2006 Notice of Allowance dated Mar. 14, 2014.
U.S. Appl. No. 11/552,094, filed Oct. 23, 2006 Notice of Allowability dated Apr. 2, 2010.
U.S. Appl. No. 11/552,094, filed Oct. 23, 2006 Non-Final Office Action dated Apr. 27, 2009.
U.S. Appl. No. 11/552,094, filed Oct. 23, 2006 Notice of Allowance dated May 20, 2010.
U.S. Appl. No. 12/104,253, filed Apr. 16, 2008 Final Office Action dated Jul. 27, 2011.
U.S. Appl. No. 12/104,253, filed Apr. 16, 2008 Non-Final Office Action dated Nov. 29, 2010.
U.S. Appl. No. 12/323,273, filed Nov. 25, 2008 Non-Final Office Action dated Jun. 8, 2012.
U.S. Appl. No. 12/369,625, filed Feb. 11, 2009 Final Office Action dated Feb. 23, 2012.
U.S. Appl. No. 12/369,625, filed Feb. 11, 2009 Notice of Allowance dated Oct. 5, 2012.
U.S. Appl. No. 12/369,625, filed Feb. 11, 2009 Notice of Panel Decision dated Aug. 1, 2012.
U.S. Appl. No. 12/369,625, filed Feb. 11, 2009 Non-Final Office Action dated Jul. 20, 2011.
U.S. Appl. No. 12/426,175, filed Apr. 17, 2009 Advisory Action dated Nov. 26, 2013.
U.S. Appl. No. 12/426,175, filed Apr. 17, 2009 Decision on Appeal dated Nov. 7, 2016.
U.S. Appl. No. 12/426,175, filed Apr. 17, 2009 Examiner's Answer dated Oct. 7, 2014.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/427,244, filed Apr. 21, 2009 Non-Final Office Action dated Jan. 19, 2012.
U.S. Appl. No. 12/545,762, filed Aug. 21, 2009 Final Office Action dated Apr. 10, 2017.
U.S. Appl. No. 12/545,762, filed Aug. 21, 2009 Final Office Action dated Mar. 7, 2013.
U.S. Appl. No. 12/545,762, filed Aug. 21, 2009 Non-Final Office Action dated Aug. 1, 2012.
U.S. Appl. No. 12/545,762, filed Aug. 21, 2009 Non-Final Office Action dated Dec. 13, 2013.
U.S. Appl. No. 12/545,762, filed Aug. 21, 2009 Non-Final Office Action dated Feb. 16, 2016.
U.S. Appl. No. 12/545,762, filed Aug. 21, 2009 Non-Final Office Action dated Nov. 7, 2014.
U.S. Appl. No. 12/545,762, filed Aug. 21, 2009 Non-Final Office Action dated Sep. 11, 2015.
U.S. Appl. No. 12/545,762, filed Aug. 21, 2009 Non-Final Office Action dated Sep. 26, 2016.
U.S. Appl. No. 12/545,762, filed Aug. 21, 2009 Notice of Panel Decision dated Jul. 14, 2017.
U.S. Appl. No. 12/557,401, filed Sep. 10, 2009 Non-Final Office Action dated Apr. 24, 2012.
U.S. Appl. No. 12/557,401, filed Sep. 10, 2009 Non-Final Office Action dated Jan. 6, 2014.
U.S. Appl. No. 12/575,456, filed Oct. 7, 2009 Non-Final Office Action dated Oct. 5, 2012.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 12/815,331, filed Jun. 14, 2010 Advisory Action dated Mar. 5, 2015.
U.S. Appl. No. 12/815,331, filed Jun. 14, 2010 Advisory Action dated Oct. 4, 2013.
U.S. Appl. No. 12/815,331, filed Jun. 14, 2010 Final Office Action dated Dec. 23, 2014.

(56)    References Cited

OTHER PUBLICATIONS

U.S. Appl. No. 12/815,331, filed Jun. 14, 2010 Final Office Action dated Jul. 26, 2013.

U.S. Appl. No. 12/815,331, filed Jun. 14, 2010 Final Office Action dated Nov. 4, 2015.

U.S. Appl. No. 12/815,331, filed Jun. 14, 2010 Non-Final Office Action dated Jan. 22, 2013.

U.S. Appl. No. 12/815,331, filed Jun. 14, 2010 Non-Final Office Action dated Jul. 2, 2014.

U.S. Appl. No. 12/815,331, filed Jun. 14, 2010 Non-Final Office Action dated Jun. 1, 2015.

U.S. Appl. No. 12/854,083, filed Aug. 10, 2010 Advisory Action dated Sep. 8, 2014.

U.S. Appl. No. 12/854,083, filed Aug. 10, 2010 Final Office Action dated Aug. 15, 2013.

U.S. Appl. No. 12/854,083, filed Aug. 10, 2010 Final Office Action dated Aug. 21, 2015.

U.S. Appl. No. 12/854,083, filed Aug. 10, 2010 Final Office Action dated Jul. 1, 2014.

U.S. Appl. No. 12/854,083, filed Aug. 10, 2010 Non-Final Office Action dated Feb. 1, 2016.

U.S. Appl. No. 12/854,083, filed Aug. 10, 2010 Non-Final Office Action dated Jan. 29, 2013.

U.S. Appl. No. 12/854,083, filed Aug. 10, 2010 Non-Final Office Action dated Jan. 29, 2014.

U.S. Appl. No. 12/854,083, filed Aug. 10, 2010 Non-Final Office Action dated Mar. 16, 2015.

U.S. Appl. No. 12/878,915, filed Sep. 9, 2010 Final Office Action dated Sep. 26, 2012.

U.S. Appl. No. 13/469,932, filed May 11, 2012 Non-Final Office Action dated Jul. 31, 2014.

U.S. Appl. No. 13/469,932, filed May 11, 2012 Non-Final Office Action dated Sep. 4, 2015.

U.S. Appl. No. 13/469,932, filed May 11, 2012 Notice of Allowance dated Jan. 31, 2017.

U.S. Appl. No. 13/469,932, filed May 11, 2012 Final Office Action dated Apr. 7, 2016.

U.S. Appl. No. 13/665,420, filed Oct. 31, 2012 Final Office Action dated Apr. 8, 2016.

U.S. Appl. No. 13/665,420, filed Oct. 31, 2012 Non-Final Office Action dated Jan. 6, 2014.

U.S. Appl. No. 13/665,420, filed Oct. 31, 2012 Non-Final Office Action dated Jul. 9, 2015.

U.S. Appl. No. 13/665,420, filed Oct. 31, 2012 Non-Final Office Action dated Mar. 15, 2017.

U.S. Appl. No. 13/665,420, filed Oct. 31, 2012 Non-Final Office Action dated Oct. 9, 2014.

U.S. Appl. No. 13/665,420, filed Oct. 31, 2012 Notice of Allowance dated Feb. 7, 2018.

U.S. Appl. No. 13/737,806, filed Jan. 9, 2013 Notice of Allowance dated Oct. 31, 2013.

U.S. Appl. No. 13/858,782, filed Apr. 8, 2013 Notice of Allowance dated Oct. 9, 2014.

U.S. Appl. No. 13/887,166, filed May 3, 2013 Advisory Action dated Aug. 27, 2014.

U.S. Appl. No. 13/887,166, filed May 3, 2013 Appeal Decision dated Aug. 17, 2017.

U.S. Appl. No. 13/887,166, filed May 3, 2013 Examiner's Answer dated Jul. 16, 2015.

U.S. Appl. No. 13/887,166, filed May 3, 2013 Final Office Action dated Jun. 23, 2014.

U.S. Appl. No. 13/887,166, filed May 3, 2013 Non-Final Office Action dated Jan. 7, 2014.

U.S. Appl. No. 13/887,166, filed May 3, 2013 Notice of Allowance dated Nov. 6, 2017.

U.S. Appl. No. 13/890,158, filed May 8, 2013 Advisory Action dated Feb. 13, 2018.

U.S. Appl. No. 13/890,158, filed May 8, 2013 Advisory Action dated Jul. 26, 2016.

U.S. Appl. No. 13/890,158, filed May 8, 2013 Final Office Action dated Nov. 21, 2017.

U.S. Appl. No. 13/890,158, filed May 8, 2013 Non-Final Office Action dated Apr. 7, 2017.

U.S. Appl. No. 13/890,158, filed May 8, 2013 Non-Final Office Action dated Aug. 15, 2014.

U.S. Appl. No. 13/890,158, filed May 8, 2013 Non-Final Office Action dated Jul. 9, 2015.

U.S. Appl. No. 13/890,158, filed May 8, 2013 Notice of Allowance dated May 30, 2018.

U.S. Appl. No. 13/969,265, filed Aug. 16, 2013 Non-Final Office Action dated Dec. 19, 2013.

U.S. Appl. No. 13/969,265, filed Aug. 16, 2013 Notice of Allowance dated Jun. 23, 2014.

U.S. Appl. No. 14/040,205, filed Sep. 27, 2013 Advisory Action dated Dec. 15, 2016.

U.S. Appl. No. 14/040,205, filed Sep. 27, 2013 Board Decision dated May 1, 2019.

U.S. Appl. No. 14/040,205, filed Sep. 27, 2013 Examiner's Answer dated Jul. 20, 2017.

U.S. Appl. No. 14/040,205, filed Sep. 27, 2013 Final Office Action dated Oct. 19, 2016.

U.S. Appl. No. 14/040,205, filed Sep. 27, 2013 Non-Final Office Action dated Mar. 10, 2016.

U.S. Appl. No. 14/040,205, filed Sep. 27, 2013 Notice of Allowance dated Aug. 21, 2019.

U.S. Appl. No. 14/054,700, filed Oct. 15, 2013 Advisory Action dated Dec. 15, 2016.

U.S. Appl. No. 14/054,700, filed Oct. 15, 2013 Board Decision dated May 1, 2019.

U.S. Appl. No. 14/054,700, filed Oct. 15, 2013 Examiner's Answer dated Jul. 3, 2017.

U.S. Appl. No. 14/054,700, filed Oct. 15, 2013 Final Office Action dated Oct. 19, 2016.

U.S. Appl. No. 14/054,700, filed Oct. 15, 2013 Notice of Allowance dated Jun. 6, 2019.

U.S. Appl. No. 14/141,046, filed Dec. 26, 2013 Advisory Action dated Aug. 4, 2016.

U.S. Appl. No. 14/141,046, filed Dec. 26, 2013 Board Decision dated Nov. 26, 2019.

U.S. Appl. No. 14/141,046, filed Dec. 26, 2013 Examiner's Answer dated Oct. 15, 2018.

U.S. Appl. No. 14/141,046, filed Dec. 26, 2013 Final Office Action dated Dec. 11, 2017.

U.S. Appl. No. 14/141,046, filed Dec. 26, 2013 Final Office Action dated May 11, 2016.

U.S. Appl. No. 14/141,046, filed Dec. 26, 2013 Non-Final Office Action dated Apr. 7, 2017.

U.S. Appl. No. 14/141,046, filed Dec. 26, 2013 Non-Final Office Action dated Feb. 11, 2015.

U.S. Appl. No. 14/141,046, filed Dec. 26, 2013 Non-Final Office Action dated Jun. 20, 2014.

U.S. Appl. No. 14/141,046, filed Dec. 26, 2013 Non-Final Office Action dated Nov. 5, 2015.

U.S. Appl. No. 14/201,300, filed Mar. 7, 2014 Advisory Action dated Jul. 18, 2016.

U.S. Appl. No. 14/201,300, filed Mar. 7, 2014 Advisory Action dated Mar. 2, 2017.

U.S. Appl. No. 14/201,300, filed Mar. 7, 2014 Board Decision dated Apr. 12, 2019.

U.S. Appl. No. 14/996,247, filed Jan. 15, 2016 Non-Final Office Action dated Sep. 1, 2020.

U.S. Appl. No. 14/996,247, filed Jan. 15, 2016 Notice of Allowance dated Dec. 4, 2020.

U.S. Appl. No. 15/418,475, filed Jan. 27, 2017 Non-Final Office Action dated Sep. 1, 2020.

U.S. Appl. No. 15/418,475, filed Jan. 27, 2017 Notice of Allowance dated Jan. 28, 2021.

U.S. Appl. No. 15/625,842, filed Jun. 16, 2017 Final Office Action dated Nov. 5, 2020.

U.S. Appl. No. 15/625,842, filed Jun. 16, 2017 Notice of Allowance dated Dec. 11, 2020.

(56) References Cited

OTHER PUBLICATIONS

U.S. Appl. No. 15/816,932, filed Nov. 17, 2017 Corrected Notice of Allowance dated Nov. 16, 2020.

U.S. Appl. No. 15/816,932, filed Nov. 17, 2017 Notice of Allowance dated Oct. 29, 2020.

U.S. Appl. No. 15/836,741, filed Jan. 8, 2017 Notice of Allowance dated Sep. 10, 2020.

U.S. Appl. No. 15/842,685, filed Dec. 14, 2017 Non-Final Office Action dated Jan. 7, 2021.

U.S. Appl. No. 16/017,695, filed Jun. 25, 2018 Final Office Action dated Dec. 18, 2020.

U.S. Appl. No. 16/457,606, filed Jun. 28, 2017 Final Office Action dated Dec. 21, 2020.

U.S. Appl. No. 16/457,606, filed Jun. 28, 2017 Non-Final Office Action dated Sep. 15, 2020.

U.S. Appl. No. 16/598,952, filed Oct. 10, 2019 Notice of Allowance dated Dec. 23, 2020.

U.S. Appl. No. 16/598,952, filed Oct. 10, 2019 Supplemental Notice of Allowance dated Jan. 25, 2021.

Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.

Chang, Thomas C. et al., Are Routine Ch Ladiographs Necessary After Image-Guided Placement of Internal Jugular Central Venous Access Devices?, AJR Feb. 1998;170:335-337.

Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.

Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.

Cheng, Ki et al, A Novel Approach of Intravenous Electrocardiogramique in Correct Position the Long-Term Central Venous Catheter, Kaohsiung J Med Sci, pp. 241-247, vol. 16 No. 5, May 2000 (Abstract only).

Cheung, P., et al., The Effect of a Disposable Probe Cover on Pulse Oximetry, Anaesth Intensive Care 2002; 30: 211-214.

Chu, et al., "Accurate Central Venous Port-A Catheter Placement: Intravenous Electrocardiogramand Surface Landmark Techniques Compared by Using Transesophageal Echocardiography." The International Anesthesia Research Society, vol. 98, pp. 910-914, 2004.

Claasz, Antonia et al, A Study of the Relationship of the Superior Vena Cava to the Bony Landmarks of the Sternum In the Supine Adult: Implications for Magnetic Guidance Systems, Journal, vol. 12 No. 3, JAVA, Jul. 24, 2007.

Clifford, et al. "Assessment of Hepatic Motion Secondary to Respiration for Computer Assisted Interventions." Computer Aided Surgery, vol. 7, pp. 291-299, 2002.

CN 200880012117.4 filed Apr. 16, 2008 First Office Action dated Dec. 23, 2011.

CN 200880012117.4 filed Apr. 16, 2008 Fourth Office Action dated Sep. 4, 2013.

CN 200880012117.4 filed Apr. 16, 2008 Second Office Action dated Oct. 8, 2012.

CN 200880012117.4 filed Apr. 16, 2008 Third Office Action dated Apr. 27, 2013.

CN 200880125528.4 filed Nov. 25, 2008 First Office Action dated Jun. 5, 2012.

CN 200880125528.4 filed Nov. 25, 2008 Second Office Action dated Mar. 6, 2013.

CN 200880125528.4 filed Nov. 25, 2008 Third Office Action dated Jul. 1, 2013.

CN 200980123021.X filed Dec. 17, 2010 First Office Action dated Nov. 19, 2012.

CN 200980123021 X filed Dec. 17, 2010 Second Office Action dated Aug. 13, 2013.

CN 200980123021.X filed Dec. 17, 2010 Third Office Action dated Apr. 22, 2014.

CN 200980144663.8 filed May 9, 2011 Decision of Re-Examination dated Feb. 21, 2017.

CN 200980144663.8 filed May 9, 2011 Fifth Office Action dated May 26, 2015.

CN 200980144663.8 filed May 9, 2011 First Office Action dated Dec. 5, 2012.

CN 200980144663.8 filed May 9, 2011 Fourth Office Action dated Nov. 15, 2014.

CN 200980144663.8 filed May 9, 2011 Notice of Reexamination dated Aug. 5, 2016.

CN 200980144663.8 filed May 9, 2011 Second Office Action dated Aug. 22, 2013.

CN 200980144663.8 filed May 9, 2011 Third Office Action dated May 4, 2014.

CN 201080035659.0 filed Feb. 10, 2012 First Office Action dated Jan. 26, 2014.

CN 201080035659.0 filed Feb. 10, 2012 Second Office Action dated Oct. 9, 2014.

CN 201080035659.0 filed Feb. 10, 2012 Third Office Action dated Mar. 19, 2015.

CN 201080053838.7 filed May 28, 2012 First Office Action dated Jan. 6, 2014.

CN 201080053838.7 filed May 28, 2012 Fourth Office Action dated Jun. 2, 2015.

CN 201080053838.7 filed May 28, 2012 Second Office Action dated Jun. 17, 2014.

CN 201080053838.7 filed May 28, 2012 Third Office Action dated Dec. 4, 2014.

CN 201180016462.7 filed Sep. 27, 2012 First Office Action dated Mar. 21, 2014.

CN 201180016462.7 filed Sep. 27, 2012 Second Office Action dated Dec. 9, 2014.

CN 201180016462.7 filed Sep. 27, 2012 Third Office Action dated Jun. 10, 2015.

CN 201180037065.8 filed Jan. 28, 2013 First Office Action dated Sep. 28, 2014.

CN 201180037065.8 filed Jan. 28, 2013 Fourth Office Action dated May 5, 2016.

CN 201180037065.8 filed Jan. 28, 2013 Notice of Grant dated Aug. 30, 2016.

CN 201180037065.8 filed Jan. 28, 2013 Second Office Action dated Jun. 2, 2015.

CN 201180037065.8 filed Jan. 28, 2013 Third Office Action dated Nov. 24, 2015.

CN 201180037068.1 filed Jan. 28, 2013 First Office Action dated Apr. 20, 2015.

CN 201180037068.1 filed Jan. 28, 2013 First Office Action dated Sep. 9, 2014.

CN 201180037068.1 filed Jan. 28, 2013 Third Office Action dated Oct. 19, 2015.

CN 201180040151.4 filed Feb. 19, 2013 First Office Action dated Oct. 28, 2014.

CN 201180040151.4 filed Feb. 19, 2013 Office Action dated Dec. 10, 2015.

CN 201180040151.4 filed Feb. 19, 2013 Second Office Action dated Jun. 19, 2015.

CN 201180043512.0 filed Mar. 8, 2013 First Office Action dated Jul. 31, 2014.

CN 201180043512.0 filed Mar. 8, 2013 Second Office Action dated Apr. 14, 2015.

CN 201180052587.5 filed Apr. 28, 2013 First Office Action dated Jan. 26, 2015.

U.S. Appl. No. 15/192,561, filed Jun. 24, 2016 Final Office Action dated Nov. 1, 2018.

U.S. Appl. No. 15/192,561, filed Jun. 24, 2016 Non-Final Office Action dated Apr. 6, 2018.

U.S. Appl. No. 15/266,977, filed Sep. 15, 2016 Non-Final Office Action dated Oct. 30, 2018.

U.S. Appl. No. 15/284,355, filed Oct. 3, 2016 Advisory Action dated Aug. 13, 2018.

U.S. Appl. No. 15/284,355, filed Oct. 3, 2016 Final Office Action dated May 24, 2018.

(56)　　　　　References Cited

OTHER PUBLICATIONS

U.S. Appl. No. 15/284,355, filed Oct. 3, 2016 Non-Final Office Action dated Apr. 24, 2017.

U.S. Appl. No. 15/284,355, filed Oct. 3, 2016 Non-Final Office Action dated Nov. 17, 2017.

U.S. Appl. No. 15/284,355, filed Oct. 3, 2016 Notice of Allowance dated Feb. 21, 2019.

U.S. Appl. No. 15/365,698, filed Nov. 30, 2016 Final Office Action dated Jul. 12, 2018.

U.S. Appl. No. 15/365,698, filed Nov. 30, 2016 Non-Final Office Action dated Apr. 18, 2019.

U.S. Appl. No. 15/365,698, filed Nov. 30, 2016 Non-Final Office Action dated Dec. 14, 2017.

U.S. Appl. No. 15/365,698, filed Nov. 30, 2016 Notice of Allowance dated Nov. 4, 2019.

U.S. Appl. No. 15/365,734, filed Nov. 30, 2016 Non-Final Office Action dated Feb. 23, 2018.

U.S. Appl. No. 15/365,734, filed Nov. 30, 2016 Notice of Allowance dated Jun. 4, 2018.

U.S. Appl. No. 15/365,752, filed Nov. 30, 2016 Final Office Action dated Jul. 12, 2018.

U.S. Appl. No. 15/365,752, filed Nov. 30, 2016 Non-Final Office Action dated Dec. 13, 2017.

U.S. Appl. No. 15/365,752, filed Nov. 30, 2016 Notice of Allowance dated Nov. 6, 2018.

U.S. Appl. No. 15/365,872, filed Nov. 30, 2016 Non-Final Office Action dated Aug. 27, 2018.

U.S. Appl. No. 15/365,872, filed Nov. 30, 2016 Notice of Allowance dated Dec. 21, 2018.

U.S. Appl. No. 15/365,872, filed Nov. 30, 2016 Restriction Requirement dated Apr. 5, 2018.

U.S. Appl. No. 15/418,475, filed Jan. 27, 2017 Advisory Action dated May 28, 2020.

U.S. Appl. No. 15/418,475, filed Jan. 27, 2017 Final Office Action dated Apr. 2, 2020.

U.S. Appl. No. 15/418,475, filed Jan. 27, 2017 Non-Final Office Action dated Oct. 18, 2019.

U.S. Appl. No. 15/418,475, filed Jan. 27, 2017 Restriction Requirement dated Jul. 23, 2019.

U.S. Appl. No. 15/585,051, filed May 2, 2017 Board Decision dated Apr. 21, 2020.

U.S. Appl. No. 15/585,051, filed May 2, 2017 Examiner's Answer dated May 2, 2019.

U.S. Appl. No. 15/585,051, filed May 2, 2017 Final Office Action dated Feb. 28, 2018.

U.S. Appl. No. 15/585,051, filed May 2, 2017 Final Office Action dated Mar. 15, 2018.

U.S. Appl. No. 15/585,051, filed May 2, 2017 Non-Final Office Action dated Jul. 14, 2017.

U.S. Appl. No. 15/585,051, filed May 2, 2017 Notice of Allowance dated Jul. 31, 2020.

U.S. Appl. No. 15/625,842, filed Jun. 16, 2017 Non-Final Office Action dated Mar. 18, 2020.

U.S. Appl. No. 15/816,932, filed Nov. 17, 2017 Advisory Action dated Jun. 18, 2020.

U.S. Appl. No. 15/816,932, filed Nov. 17, 2017 Final Office Action dated Feb. 28, 2020.

U.S. Appl. No. 15/816,932, filed Nov. 17, 2017 Non-Final Office Action dated Aug. 22, 2019.

U.S. Appl. No. 15/836,741, filed Jan. 8, 2017 Non-Final Office Action dated Jun. 12, 2020.

U.S. Appl. No. 15/836,741, filed Jan. 8, 2017 Restriction Requirement dated Mar. 3, 2020.

U.S. Appl. No. 15/900,623, filed Feb. 20, 2018 Advisory Action dated Aug. 7, 2020.

U.S. Appl. No. 15/900,623, filed Feb. 20, 2018 Final Office Action dated Jun. 12, 2020.

U.S. Appl. No. 15/900,623, filed Feb. 20, 2018 Final Office Action dated Sep. 20, 2018.

U.S. Appl. No. 15/900,623, filed Feb. 20, 2018 Non-Final Office Action dated Dec. 30, 2019.

U.S. Appl. No. 15/900,623, filed Feb. 20, 2018 Non-Final Office Action dated Jul. 16, 2019.

U.S. Appl. No. 15/900,623, filed Feb. 20, 2018 Non-Final Office Action dated May 3, 2018.

U.S. Appl. No. 16/017,695, filed Jun. 25, 2018 Non-Final Office Action dated Jul. 20, 2020.

U.S. Appl. No. 29/428,649, filed Aug. 1, 2012 Notice of Allowance dated Jul. 5, 2013.

Valdivieso, J.R. Perez, et al., Evaluation of a formula for optimal positioning of a central venous catheter inserted through the right internal jugular vein, Rev. Esp. Anestesiol. Reanim. 2003; 50: 77-79.

VasoNova Inc, Vascular navigation system for accurate placement of PICCs, Start-Up Emerging Medical Ventures, pp. 44-45, vol. 14 No. 7, Jul.-Aug. 2009.

Vesely, Thomas M. et al., Central Venous Catheter Tip Position: A Continuing Controversy, J Vasc Intery Radiol 2003; 14:527-534.

VIASYS Health Care Inc. Cortrak © Fact Sheet, 2005.

VIASYS Healthcare MedSystems, Navigator® Benefits, 2008.

VIASYS Healthcare MedSystems, Navigator® Research in Cost Justification, 2008.

U.S. Appl. No. 14/201,300, filed Mar. 7, 2014 Board Decision dated Jul. 23, 2019.

U.S. Appl. No. 14/201,300, filed Mar. 7, 2014 Examiner's Answer dated Apr. 19, 2018.

U.S. Appl. No. 14/201,300, filed Mar. 7, 2014 Final Office Action dated Dec. 19, 2016.

U.S. Appl. No. 14/201,300, filed Mar. 7, 2014 Final Office Action dated Jul. 10, 2017.

U.S. Appl. No. 14/201,300, filed Mar. 7, 2014 Final Office Action dated Mar. 9, 2020.

U.S. Appl. No. 14/201,300, filed Mar. 7, 2014 Final Office Action dated May 5, 2016.

U.S. Appl. No. 14/201,300, filed Mar. 7, 2014 Non-Final Office Action dated Aug. 24, 2016.

U.S. Appl. No. 14/201,300, filed Mar. 7, 2014 Non-Final Office Action dated Jan. 6, 2016.

U.S. Appl. No. 14/201,300, filed Mar. 7, 2014 Non-Final Office Action dated Mar. 30, 2017.

U.S. Appl. No. 14/201,300, filed Mar. 7, 2014 Non-Final Office Action dated Nov. 27, 2019.

U.S. Appl. No. 14/201,300, filed Mar. 7, 2014 Notice of Allowance dated May 8, 2020.

U.S. Appl. No. 14/270,241, filed May 5, 2014 Non-Final Office Action dated Apr. 23, 2015.

U.S. Appl. No. 14/270,241, filed May 5, 2014 Notice of Allowance dated Oct. 7, 2015.

U.S. Appl. No. 14/309,511, filed Jun. 19, 2014 Non-Final Office Action, dated Sep. 24, 2015.

U.S. Appl. No. 14/309,511, filed Jun. 19, 2014 Notice of Allowance, dated Jul. 26, 2016.

U.S. Appl. No. 14/317,501, filed Jun. 27, 2014 Advisory Action dated Sep. 16, 2015.

U.S. Appl. No. 14/317,501, filed Jun. 27, 2014 Decision on Appeal dated Nov. 17, 2017.

U.S. Appl. No. 14/317,501, filed Jun. 27, 2014 Examiner's Answer dated Jun. 30, 2016.

U.S. Appl. No. 14/317,501, filed Jun. 27, 2014 Final Office Action dated Jul. 1, 2015.

U.S. Appl. No. 14/317,501, filed Jun. 27, 2014 Non-Final Office Action dated Mar. 3, 2015.

U.S. Appl. No. 14/317,501, filed Jun. 27, 2014 Non-Final Office Action dated Sep. 12, 2014.

U.S. Appl. No. 14/317,501, filed Jun. 27, 2014 Notice of Allowance dated Feb. 9, 2018.

U.S. Appl. No. 14/449,061, filed Jul. 31, 2014 Final Office Action dated Nov. 6, 2015.

U.S. Appl. No. 14/449,061, filed Jul. 31, 2014 Non-Final Office Action dated Apr. 27, 2015.

U.S. Appl. No. 14/449,061, filed Jul. 31, 2014 Notice of Allowance dated Apr. 13, 2016.

(56)            References Cited

OTHER PUBLICATIONS

U.S. Appl. No. 14/498,887, filed Sep. 26, 2014 Advisory Action dated Aug. 22, 2016.
U.S. Appl. No. 14/498,887, filed Sep. 26, 2014 Final Office Action dated Jun. 15, 2016.
U.S. Appl. No. 14/498,887, filed Sep. 26, 2014 Non-Final Office Action dated Feb. 19, 2016.
U.S. Appl. No. 14/506,552, filed Oct. 3, 2014 Non-Final Office Action dated Oct. 1, 2015.
U.S. Appl. No. 14/548,151, filed Nov. 19, 2014 Advisory Action dated Aug. 1, 2017.
U.S. Appl. No. 14/548,151, filed Nov. 19, 2014 Advisory Action dated Jul. 22, 2016.
U.S. Appl. No. 14/548,151, filed Nov. 19, 2014 Final Office Action dated Apr. 19, 2017.
U.S. Appl. No. 14/548,151, filed Nov. 19, 2014 Non-Final Office Action dated Jun. 5, 2015.
U.S. Appl. No. 14/548,151, filed Nov. 19, 2014 Non-Final Office Action dated Sep. 21, 2017.
U.S. Appl. No. 14/548,151, filed Nov. 19, 2014 Non-Final Office Action dated Sep. 28, 2016.
U.S. Appl. No. 14/615,932, filed Feb. 6, 2015 Non-Final Office dated Dec. 29, 2016.
U.S. Appl. No. 14/788,305, filed Jun. 30, 2015 Advisory Action dated Oct. 19, 2018.
U.S. Appl. No. 14/788,305, filed Jun. 30, 2015 Final Office Action dated Jul. 27, 2018.
U.S. Appl. No. 14/788,305, filed Jun. 30, 2015 Non-Final Office Action dated Jan. 10, 2018.
U.S. Appl. No. 14/788,305, filed Jun. 30, 2015 Notice of Allowance dated Nov. 15, 2018.
U.S. Appl. No. 14/788,305, filed Jun. 30, 2015 Restriction Requirement dated Aug. 25, 2017.
U.S. Appl. No. 14/846,496, filed Sep. 4, 2015 Non-Final Office Action dated Nov. 25, 2016.
U.S. Appl. No. 14/996,247, filed Jan. 15, 2016 Advisory Action dated Feb. 20, 2020.
U.S. Appl. No. 14/996,247, filed Jan. 15, 2016 Final Office Action dated Dec. 11, 2019.
U.S. Appl. No. 14/996,247, filed Jan. 15, 2016 Non-Final Office Action dated Jul. 18, 2019.
U.S. Appl. No. 14/996,247, filed Jan. 15, 2016 Restriction Requirement dated Mar. 22, 2019.
U.S. Appl. No. 15/160,958, filed May 20, 2016 Advisory Action dated Jul. 10, 2017.
U.S. Appl. No. 15/160,958, filed May 20, 2016 Final Office Action dated Apr. 21, 2017.
U.S. Appl. No. 15/160,958, filed May 20, 2016 Non-Final Office Action dated Dec. 15, 2016.
U.S. Appl. No. 15/160,958, filed May 20, 2016 Notice of Allowance dated Jul. 26, 2017.
U.S. Appl. No. 12/878,915, filed Sep. 9, 2010 Non-Final Office Action dated Mar. 15, 2012.
U.S. Appl. No. 12/878,915, filed Sep. 9, 2010 Notice of Allowance dated Jan. 8, 2013.
U.S. Appl. No. 12/893,916, filed Sep. 29, 2010 Advisory Action dated Aug. 15, 2014.
U.S. Appl. No. 12/893,916, filed Sep. 29, 2010 Advisory Action dated Jun. 2, 2016.
U.S. Appl. No. 12/893,916, filed Sep. 29, 2010 Final Office Action dated Jan. 15, 2015.
U.S. Appl. No. 12/893,916, filed Sep. 29, 2010 Final Office Action dated Jun. 18, 2014.
U.S. Appl. No. 12/893,916, filed Sep. 29, 2010 Final Office Action dated Mar. 25, 2016.
U.S. Appl. No. 12/893,916, filed Sep. 29, 2010 Non-Final Office Action dated Aug. 31, 2016.
U.S. Appl. No. 12/893,916, filed Sep. 29, 2010 Non-Final Office Action dated Dec. 24, 2013.

U.S. Appl. No. 12/893,916, filed Sep. 29, 2010 Non-Final Office Action dated Sep. 10, 2015.
U.S. Appl. No. 12/893,916, filed Sep. 29, 2010 Non-Final Office Action dated Sep. 25, 2014.
U.S. Appl. No. 12/900,750, filed Oct. 8, 2010 Non-Final Office Action dated Jun. 3, 2013.
U.S. Appl. No. 13/019,939, filed Feb. 2, 2011 Final Office Action dated Apr. 2, 2014.
U.S. Appl. No. 13/019,939, filed Feb. 2, 2011 Non-Final Office Action dated February 9. 2015.
U.S. Appl. No. 13/019,939, filed Feb. 2, 2011 Non-Final Office Action dated Oct. 11, 2013.
U.S. Appl. No. 13/118,033, filed May 27, 2011 Final Office Action dated Apr. 1, 2016.
U.S. Appl. No. 13/118,033, filed May 27, 2011 Non-Final Office Action dated Aug. 1, 2013.
U.S. Appl. No. 13/118,033, filed May 27, 2011 Non-Final Office Action dated Feb. 3, 2015.
U.S. Appl. No. 13/118,033, filed May 27, 2011 Non-Final Office Action dated Jul. 8, 2015.
U.S. Appl. No. 13/118,033, filed May 27, 2011 Non-Final Office Action dated May 22, 2014.
U.S. Appl. No. 13/118,033, filed May 27, 2011 Notice of Allowance dated Sep. 2, 2016.
U.S. Appl. No. 13/118,138, filed May 27, 2011 Final Office Action dated Apr. 1, 2016.
U.S. Appl. No. 13/118,138, filed May 27, 2011 Final Office Action dated Apr. 3, 2013.
U.S. Appl. No. 13/118,138, filed May 27, 2011 Non-Final Office Action dated Jul. 15, 2015.
U.S. Appl. No. 13/118,138, filed May 27, 2011 Non-Final Office Action dated Oct. 3, 2012.
U.S. Appl. No. 13/118,138, filed May 27, 2011 Non-Final Office Action dated Oct. 9, 2014.
U.S. Appl. No. 13/213,622, filed Aug. 19, 2011 Final Office Action dated Feb. 19, 2013.
U.S. Appl. No. 13/213,622, filed Aug. 19, 2011 Non-Final Office Action dated Jul. 31, 2012.
U.S. Appl. No. 13/213,622, filed Aug. 19, 2011 Non-Final Office Action dated May 22, 2014.
U.S. Appl. No. 13/240,171, filed Sep. 22, 2011 Advisory Action dated Aug. 18, 2015.
U.S. Appl. No. 13/240,171, filed Sep. 22, 2011 Advisory Action dated Jul. 22, 2016.
U.S. Appl. No. 13/240,171, filed Sep. 22, 2011 Final Office Action dated Jun. 10, 2015.
U.S. Appl. No. 13/240,171, filed Sep. 22, 2011 Final Office Action dated May 6, 2016.
U.S. Appl. No. 13/240,171, filed Sep. 22, 2011 Non-Final Office Action dated Dec. 1, 2015.
U.S. Appl. No. 13/240,171, filed Sep. 22, 2011 Non-Final Office Action dated Dec. 26, 2014.
U.S. Appl. No. 13/283,395, filed Oct. 27, 2011 Advisory Action dated Jan. 28, 2014.
U.S. Appl. No. 13/283,395, filed Oct. 27, 2011 Final Office Action dated Nov. 14, 2013.
U.S. Appl. No. 13/283,395, filed Oct. 27, 2011 Non-Final Office Action dated Apr. 23, 2013.
U.S. Appl. No. 13/336,919, filed Dec. 23, 2011 Advisory Action dated May 23, 2013.
U.S. Appl. No. 13/336,919, filed Dec. 23, 2011 Final Office Action dated Dec. 19, 2014.
U.S. Appl. No. 13/336,919, filed Dec. 23, 2011 Final Office Action dated Mar. 1, 2013.
U.S. Appl. No. 13/336,919, filed Dec. 23, 2011 Non-Final Office Action dated Dec. 27, 2013.
U.S. Appl. No. 13/336,919, filed Dec. 23, 2011 Non-Final Office Action dated Jul. 9, 2015.
U.S. Appl. No. 13/336,919, filed Dec. 23, 2011 Non-Final Office Action dated Oct. 16, 2012.
U.S. Appl. No. 13/336,919, filed Dec. 23, 2011 Notice of Allowance dated Jul. 26, 2016.

(56) References Cited

OTHER PUBLICATIONS

U.S. Appl. No. 13/337,987, filed Dec. 27, 2011 Examiner's Answer dated Jul. 2, 2014.

U.S. Appl. No. 13/337,987, filed Dec. 27, 2011 Final Office Action dated Sep. 19, 2013.

U.S. Appl. No. 13/337,987, filed Dec. 27, 2011 Non-Final Office Action dated Mar. 15, 2013.

U.S. Appl. No. 13/469,932, filed May 11, 2012 Advisory Action dated Jun. 27, 2016.

U.S. Appl. No. 13/469,932, filed May 11, 2012 Non-Final Office Action dated Jan. 3, 2014.

GB Application 0800474.9 filed Aug. 24, 2006 Office Action dated Mar. 17, 2010.

Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).

Gebhard, et al., "The accuracy of Electrocardiogram-Controlled Central Line Placement." The International Anesthesia Research Society, vol. 104, No. 1 Jan. 2007.

Gjendemsjo, Anders, et al., Energy and Power, The Connexions Project, Version 1.2, Feb. 20, 2004.

Gladwin, MT et al, Cannulation of the Internal Jugular Vein: is postpocedural chest radiography always necessary?, Crit Care Med, 33 pages, Oct. 2000.

Gonzales, et al. "Peripherally Inserted Central Catheter Placement in Swine Using Magnet Detection." Journal of Intravenous Nursing, vol. 22, No. 3, May/Jun. 1999.

Greenall, M.J. et al, Cardiac Tamponade and Central Venous Catheters, British Medical Journal, pp. 595-597, Jun. 14, 1975.

Guillory, "Basic Principles of Technologies for Catheter Localization." C.R. Bard internal paper, Oct. 20, 2004.

Guth, AA, Routine Chest X-rays after Insertion of Implantable Long-Term Venous Catheters: Necessary or Not?, Am Burg, pp. 26-29, vol. 67 No. 1, Jan. 2001 (Abstract only).

Hamza, N. et al. "Interference reduction in ECG signal acquisition: Ground electrode removal." 2013 International Conference on Computer Medical Applications (ICCMA), Jan. 2013.

Hill, Bradley et al, Abstract of article discussing VasaNova VPS as guide for placement of PICCs. 2009.

Hill, Bradley, Identifying the Caval-Atrial Junction Using Smart-Catheter Technology presentation, 22nd Annual Scientific Meeting of the AVA in Savannah, Georgia, Sep. 13, 2008.

Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.

Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.

Honeywell, "1, 2 and 3 Axis Magnetic Sensors HMC1051/HMC1052L/HMC1053" dated Jan. 2010.

Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.

Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.

Joosting, Jean-Pierre, "Dual-interface RFID-compatible EEPROM enables remote access to electronic device parameters," EE Times, Mar. 8, 2010.

JP 2008-528151 filed Aug. 24, 2006 Notice of Grant dated May 6, 2012.

JP 2010-504220 filed Sep. 3, 2009 Final Office Action dated Apr. 18, 2013.

JP 2010-504220 filed Sep. 3, 2009 Office Action dated Apr. 1, 2014.

JP 2010-504220 filed Sep. 3, 2009 Office Action dated Apr. 18, 2013.

JP 2010-504220 filed Sep. 3, 2009 Office Action dated May 21, 2012.

JP 2010-535117 filed May 26, 2011 First Office Action dated Aug. 5, 2013.

JP 2012-515222 filed Dec. 9, 2011 Office Action dated Feb. 23, 2015.

JP 2012-515222 filed Dec. 9, 2011 Office Action dated Mar. 24, 2014.

JP 2012-552060 filed Aug. 1, 2012 Office Action dated Nov. 12, 2014.

JP 2012-552060 filed Aug. 1, 2012 Second Office Action dated Nov. 6, 2015.

JP 2013-512046 filed Nov. 26, 2012 First Office Action dated Mar. 23, 2015.

JP 2013-512046 filed Nov. 26, 2012 Office Action dated Dec. 8, 2015.

JP 2013-512046 filed Nov. 26, 2012 Office Action dated May 16, 2016.

JP 2013-512051 filed Nov. 26, 2012 First Office Action dated Mar. 23, 2015.

JP 2013-524999 filed Jan. 22, 2013 First Office Action dated Jun. 1, 2015.

JP 2013-530322 filed Mar. 18, 2013, Office Action dated Jul. 6, 2018.

JP 2013-530322 filed Mar. 18, 2013, Office Action dated Mar. 2, 2017.

JP 2013-530322 filed Mar. 18, 2013, Office Action dated Nov. 6, 2017.

JP 2014-519081 filed Dec. 27, 2013 First Office Action dated Apr. 26, 2016.

JP 2015-534770 filed Mar. 26, 2015 Office Action dated Feb. 21, 2018.

JP 2015-534770 filed Mar. 26, 2015 Office Action dated Jun. 12, 2017.

JP2013-530322 filed Mar. 18, 2013, Office Action dated May 2, 2016.

JP2013-530322 filed Mar. 18, 2013, First Office Action dated Jul. 31, 2015.

Kim, Ko et al, Positioning Internal Jugular Venous Catheters using the Right Third Intercostal Space in Children, Acta Anaesthesiol Scand, pp. 1284-1286, vol. 47 No. 10, Nov. 2003.

Nelstrup T et al, Positioning of Central Venous Catheters using ECG, Tidssk Nor Laegeforen, pp. 599-601, vol. 111 No. 5, Feb. 1999 (Abstract only).

Kofler, Julia, et al., Epinephrine application via an endotracheal airway and via the Combitube in esophageal position, Critical Care Medicine: May 2000, vol. 28: Issue 5, pp. 1445-1449.

Konings, MK, et al., Development of an intravascular impedance catheter for detection of fatty lesions in arteries, IEEE Trans Med Imaging Aug. 1997; 16(4):439-46.

Kowalski, CM et al, Migration of Central Venous Catheters: Implications for Initial Catheter Tip Positioning, J Vasc Interv Radiol, pp. 443-447, vol. 8 No. 3, May-Jun. 1997.

KR 10-2012-7000866 filed Jan. 11, 2012 First Office Action dated Jun. 16, 2016.

KR 10-2012-7000866 filed Jan. 11, 2012 Second Office Action dated Nov. 3, 2016.

KR 10-2013-7006933 filed Mar. 19, 2013 Office Action dated Aug. 7, 2017.

KR 10-2014-7002789 filed Feb. 3, 2014 Office Action dated Feb. 22, 2019.

PCT/US2021/052066 filed Sep. 24, 2021 International Search Report and Written Opinion dated Jan. 10, 2022.

U.S. Appl. No. 16/011,380, filed Jun. 18, 2018 Non-Final Office Action dated Dec. 24, 2021.

U.S. Appl. No. 16/394,861, filed Apr. 25, 2019 Final Office Action dated Jan. 31, 2022.

U.S. Appl. No. 16/777,685, filed Jan. 30, 2020 Non-Final Office Action dated Jan. 18, 2022.

PCT/US2009/033116 filed Feb. 4, 2009 Written Opinion dated Mar. 13, 2009.

(56)          References Cited

OTHER PUBLICATIONS

PCT/US2009/041051 filed Apr. 17, 2009 International Preliminary Report on Patentability dated Apr. 8, 2014.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.
PCT/US2011/038415 filed May 27, 2011 International Preliminary Report on Patentability dated Dec. 13, 2012.
PCT/US2011/038415 filed May 27, 2011 International Search Report dated Sep. 28, 2011.
PCT/US2011/038415 filed May 27, 2011 Written Opinion dated Sep. 28, 2011.

PCT/US2011/047127 filed Aug. 9, 2011 International Preliminary Report on Patentability dated Apr. 18, 2013.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Preliminary Report on Patentability dated Jul. 30, 2013.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Preliminary Report on Patentability dated Apr. 4, 2013.
PCT/US2011/052793 filed Sep. 22, 2011 International Search Report dated Jan. 6, 2012.
PCT/US2011/052793 filed Sep. 22, 2011 Written Opinion dated Jan. 6, 2012.
PCT/US2011/058138 filed Oct. 27, 2011 International Preliminary Report on Patentability dated May 10, 2013.
PCT/US2011/058138 filed Oct. 27, 2011 International Search Report dated Feb. 7, 2012.
PCT/US2011/058138 filed Oct. 27, 2011 Written Opinion dated Feb. 7, 2012.
PCT/US2011/067268 filed Dec. 23, 2011 International Preliminary Report on Patentability dated Jul. 4, 2013.
PCT/US2011/067268 filed Dec. 23, 2011 International Search Report and Written Opinion dated Apr. 27, 2012.
PCT/US2012/045814 filed Jul. 6, 2012 International Search Report and Written Opinion dated Oct. 1, 2012.
PCT/US2013/065121 filed Oct. 15, 2013 International Search Report and Written Opinion dated Jan. 16, 2014.
PCT/US2014/022019 filed Mar. 7, 2014 International Search Report and Written Opinion dated Jun. 11, 2014.
PCT/US2015/014795 filed Feb. 6, 2015 International Search Report and Written Opinion dated May 14, 2015.
PCT/US2016/039356 filed Jun. 24, 2016 International Search Report and Written Opinion dated Sep. 16, 2016.
PCT/US2017/066503 filed Dec. 14, 2017 International Search Report and Written Opinion dated Feb. 20, 2018.
PCT/US2019/055716 filed Oct. 10, 2019 International Search Report and Written Opinion dated Feb. 4, 2020.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, "The intracavitary ECG method for positioning the tip of central venous catheters: results of an Italian multicenter study," J Vasc Access, pp. 1-9, Nov. 21, 2011.

* cited by examiner

114

114A

114A

114A

114B

114B

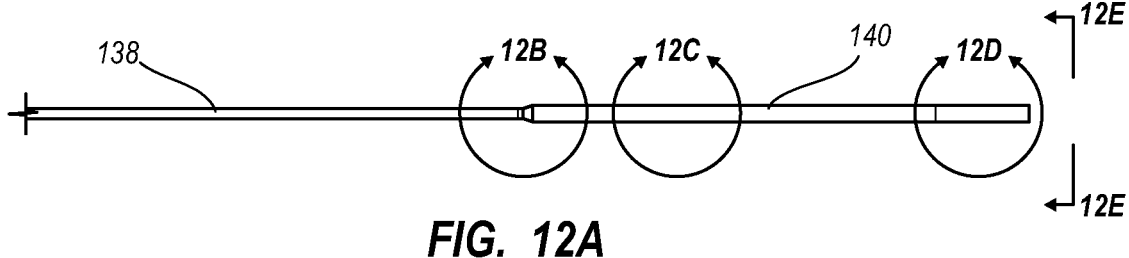
FIG. 12A
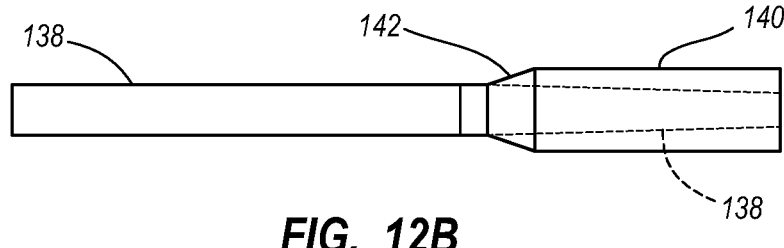
FIG. 12B
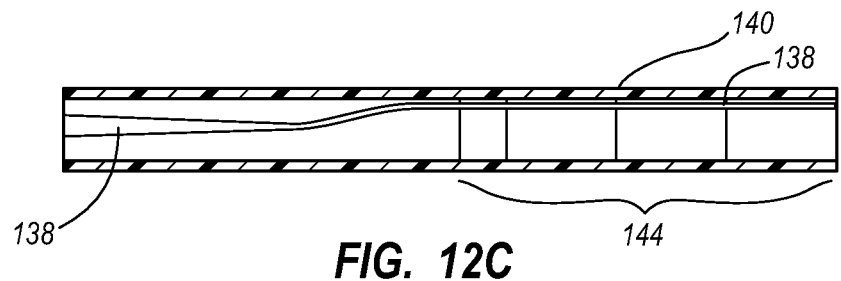
FIG. 12C
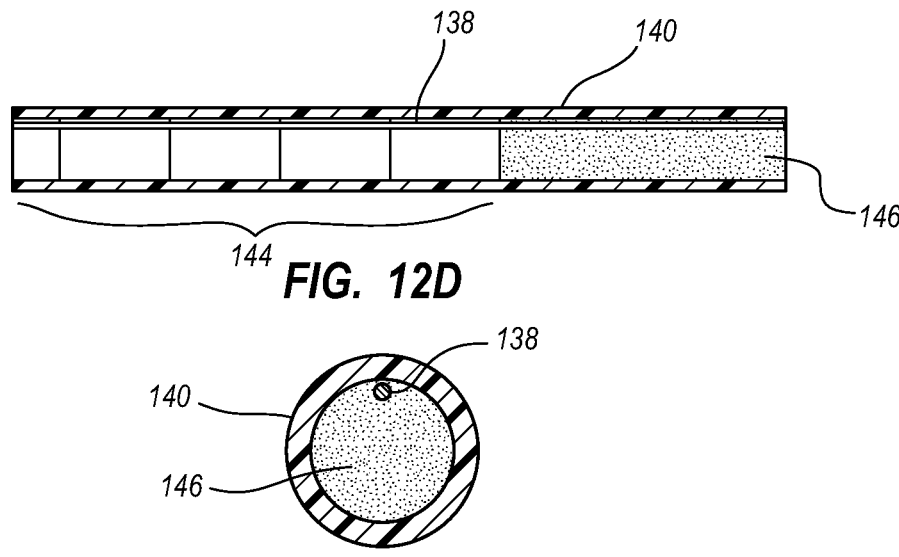
FIG. 12D
FIG. 12E

156

158

158

166

164

169

162

156

169

160

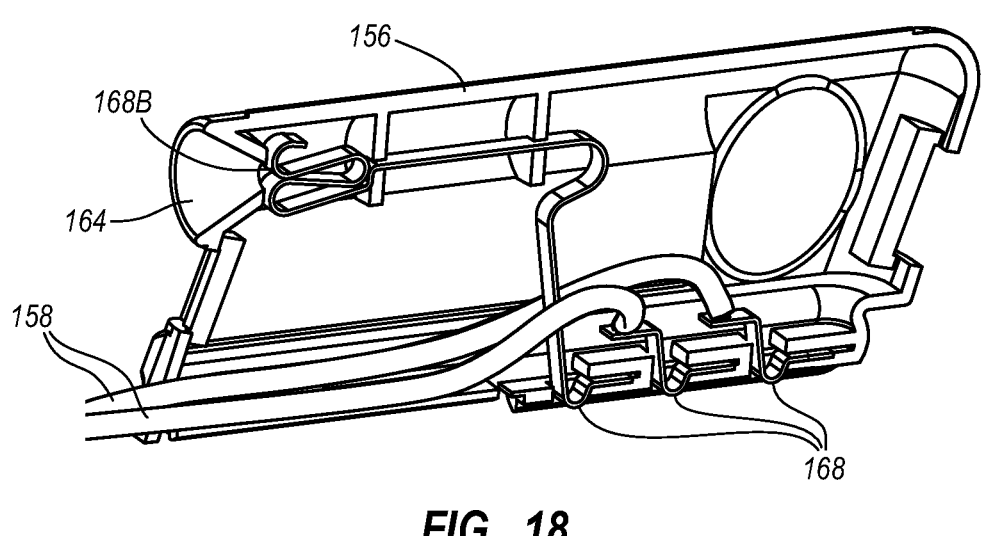
FIG. 18
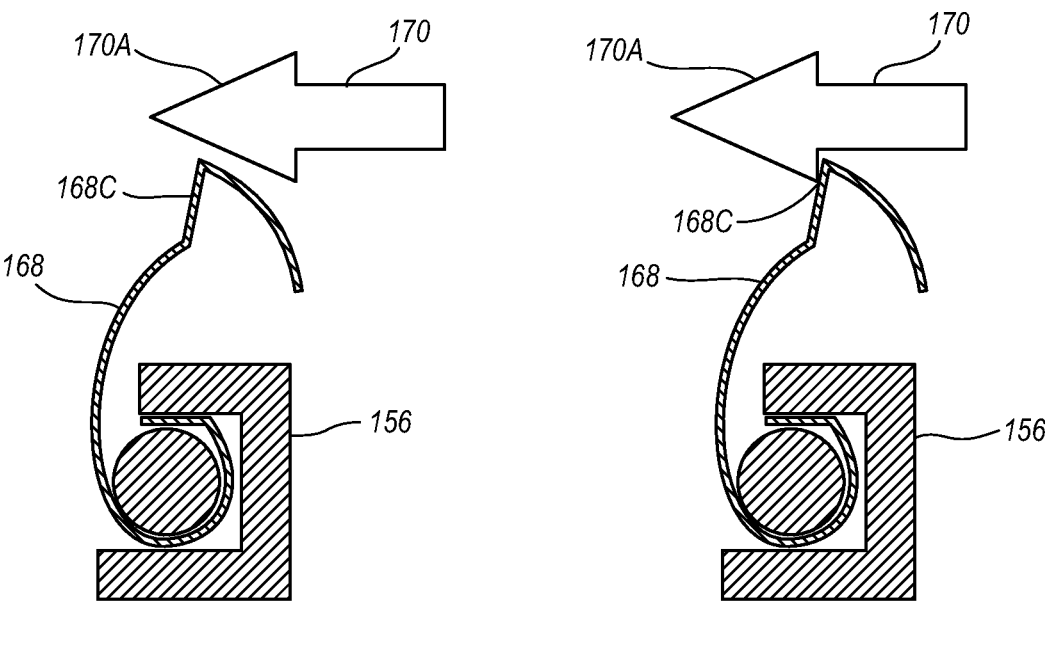
FIG. 19A                    FIG. 19B

982

982B

986

984

982

994A          994B          994C

982B

990

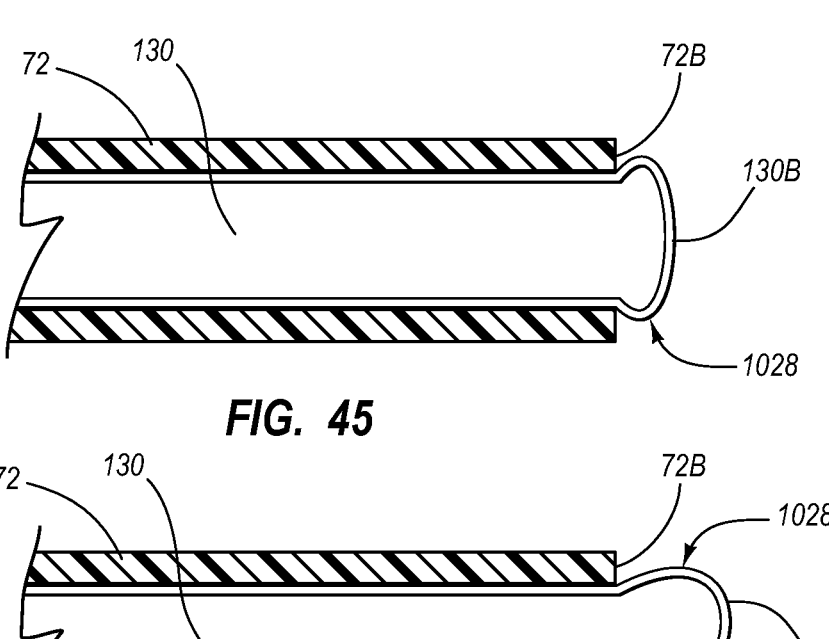
FIG. 45
FIG. 46
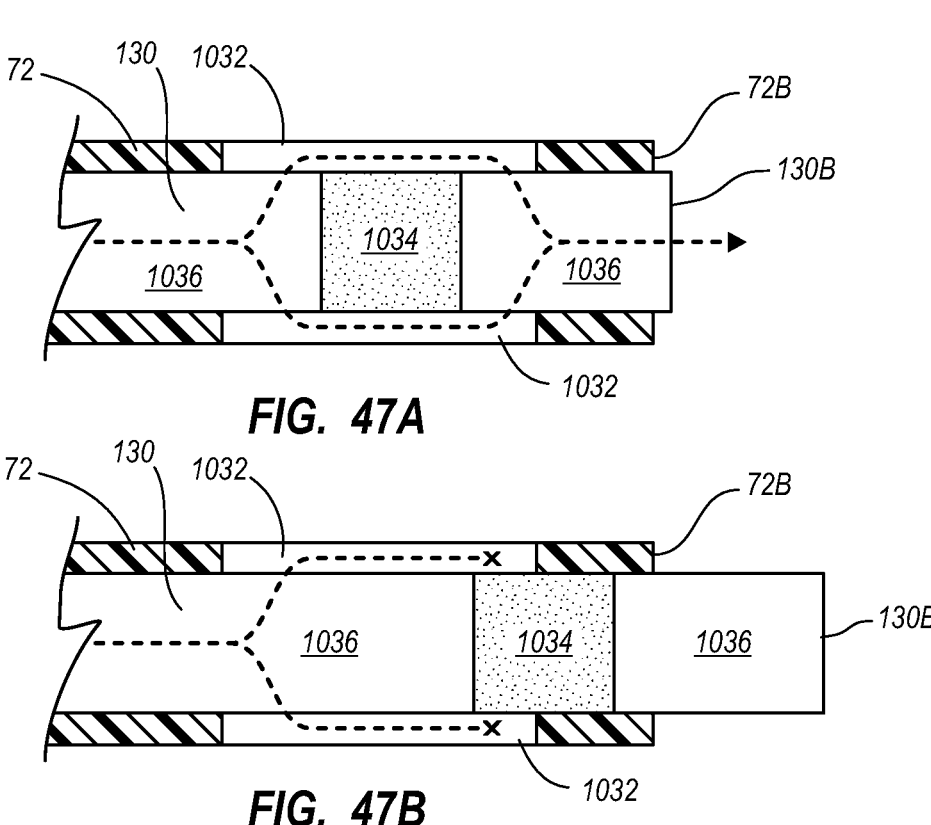
FIG. 47A
FIG. 47B

1056 — Sample ECG Signal Data

1058 — Identify An ECG Waveform

1060 — Identify P-wave Portion Of ECG Waveform

1062 — Determine Amplitude Peak Of P-wave

1064 — Correlate P-wave Amplitude Peak To Corresponding Output

1066 — Produce Output

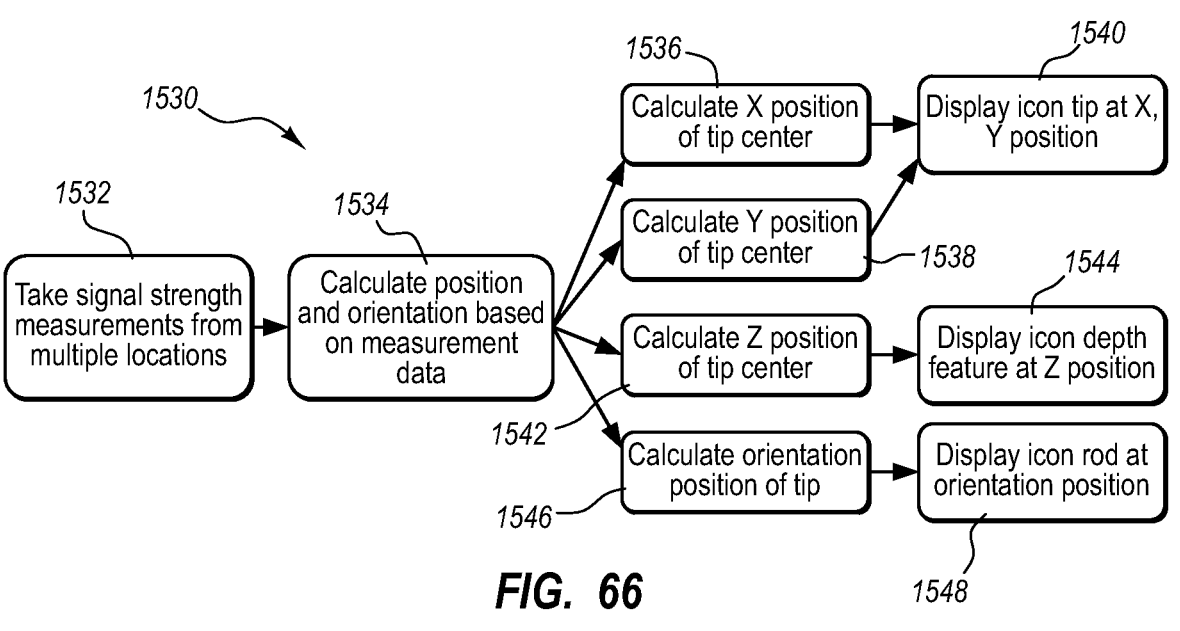
FIG. 66
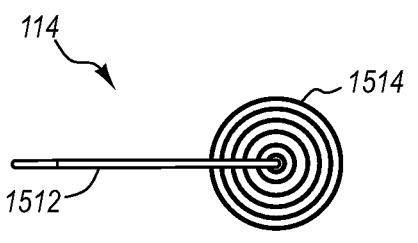
FIG. 67A
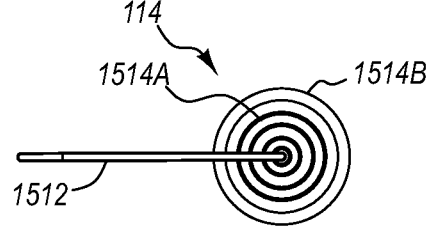
FIG. 67B
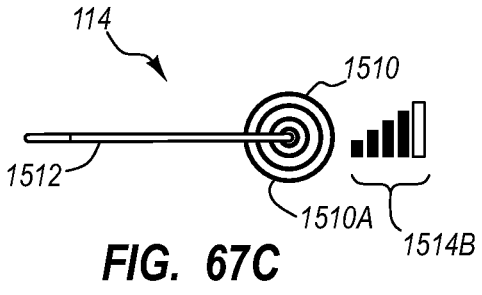
FIG. 67C
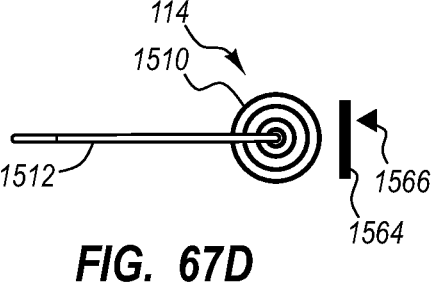
FIG. 67D
FIG. 67E
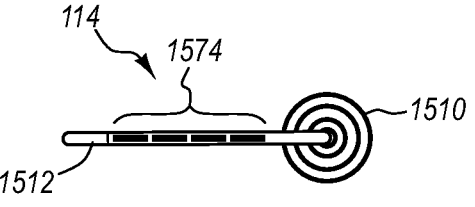
FIG. 67F

ICONIC REPRESENTATIONS RELATING TO SYSTEMS FOR PLACING A MEDICAL DEVICE

CROSS-REFERENCE TO RELATED APPLICATIONS

This application is a continuation of U.S. patent application Ser. No. 14/201,300, filed Mar. 7, 2014, now U.S. Pat. No. 10,751,509, which claims the benefit of U.S. Provisional Application No. 61/775,397, filed Mar. 8, 2013, and which is a continuation-in-part of U.S. application Ser. No. 12/557, 401, filed Sep. 10, 2009, now U.S. Pat. No. 8,849,382, which claims the benefit of U.S. Provisional Application No. 61/095,921, filed Sep. 10, 2008, and which is a continuation-in-part of U.S. application Ser. No. 12/426,175, filed Apr. 17, 2009, now U.S. Pat. No. 9,649,048, which claims the benefit of: 1) U.S. Provisional Application No. 61/045,944, filed Apr. 17, 2008; 2) U.S. Provisional Application No. 61/095,921, filed Sep. 10, 2008; 3) U.S. Provisional Application No. 61/091,233, filed Aug. 22, 2008; and 4) U.S. Provisional Application No. 61/095,451, filed Sep. 9, 2008; and which is a continuation-in-part of U.S. application Ser. No. 12/323,273, filed Nov. 25, 2008, now U.S. Pat. No. 8,388,541, which claims the benefit of: 1) U.S. Provisional Application No. 60/990,242, filed Nov. 26, 2007; 2) U.S. Provisional Application No. 61/095,921, filed Sep. 10, 2008; 3) U.S. Provisional Application No. 61/091,233, filed Aug. 22, 2008; 4) U.S. Provisional Application No. 61/095,451, filed Sep. 9, 2008; and 5) U.S. Provisional Application No. 61/045,944, filed Apr. 17, 2008. Each of the aforementioned applications is incorporated by reference in its entirety into this application.

BRIEF SUMMARY

Briefly summarized, embodiments of the present invention are directed to an integrated catheter placement system configured for accurately placing a catheter within the vasculature of a patient. The integrated system employs at least two modalities for improving catheter placement accuracy: 1) ultrasound-assisted guidance for introducing the catheter into the patient's vasculature; and 2) a tip location system ("TLS"), or magnetically-based (e.g., via permanent magnet(s) or electromagnet(s)) tracking of the catheter tip during its advancement through the vasculature to detect and facilitate correction of any tip malposition during such advancement.

In one embodiment, the integrated system comprises a system console including a control processor, a tip location sensor for temporary placement on a portion of a body of the patient, and an ultrasound probe. The tip location sensor senses a magnetic field of a stylet disposed in a lumen of the catheter when the catheter is disposed in the vasculature. The ultrasound probe ultrasonically images a portion of the vasculature prior to introduction of the catheter into the vasculature. In addition, the ultrasound probe includes user input controls for controlling use of the ultrasound probe in an ultrasound mode and use of the tip location sensor in a tip location mode.

In another embodiment, a third modality, i.e., ECG signal-based catheter tip guidance, is included in the system to enable guidance of the catheter tip to a desired position with respect to a node of the patient's heart from which the ECG signals originate. Various means for establishing a conductive pathway between a sterile field of the patient and a non-sterile field to enable passage of ECG signals from the catheter to the tip location sensor are also disclosed. Such means include, for example, connector schemes that establish the conductive pathway through a perforation defined in a sterile barrier, such as a surgical drape, wherein the perforation is isolated by the connector scheme so as to prevent contamination or compromise of the sterile field of the patient.

In further embodiments, various aspects for visualizing and manipulating display of the ECG signal data acquired via the present catheter placement system are disclosed. These display aspects enable a clinician placing the catheter or other invasive medical device to ascertain information relating to the proximity of the device relative to the ECG signal-emitting node. In yet other embodiments, aspects of various ECG sensor configurations are also disclosed. In further embodiments, iconic representations for depiction on the display of the system and relating to positional and other characteristics of the catheter or medical device are also disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 12A-12E are various views of portions of the stylet of FIG. 11;

FIG. 18 is a cross sectional view of a fin connector including electrical contacts configured in accordance with one embodiment;

FIGS. 19A and 19B are simplified views of an electrical contact retention system for engagement of a tether connector with a fin connector, in accordance with one embodiment;

FIG. 45 is a cross sectional view of a catheter including a stylet with a distal interference feature according to one embodiment;

FIG. 46 is a cross sectional view of a catheter including a stylet with a distal interference feature according to another embodiment;

FIGS. 47A and 47B are cross sectional views of distal portions of a catheter and stylet configured to maintain alignment of the distal ends of the catheter and stylet according to one embodiment.

FIGS. 56A-57B are ECG traces showing details regarding ECG waveform scaling according to one embodiment;

FIG. 66 shows a simplified flow chart of a method for determining and depicting the icons of FIG. 65, according to one embodiment;

FIGS. 67A-67F depict various example icons that can be depicted on the display of the integrated system of FIG. 63 during catheter tip placement procedures to indicate a four-dimensional position and orientation of the distal end of a stylet associated with the catheter of FIG. 64;

DETAILED DESCRIPTION OF SELECTED EMBODIMENTS

Figures 1, 2:
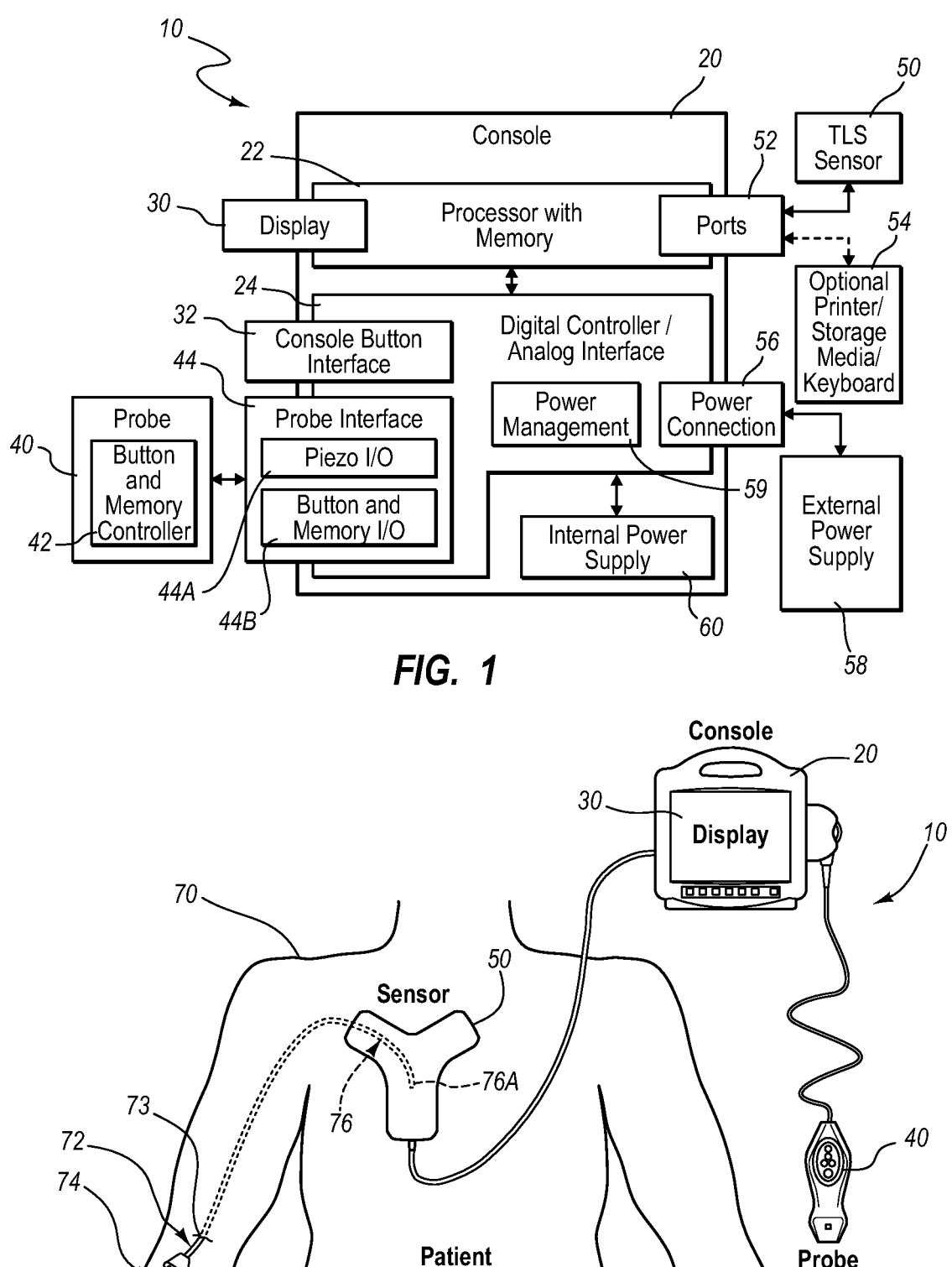
FIG. 1 is a block diagram depicting various elements of an integrated system for intravascular placement of a catheter, according to one example embodiment of the present invention.
FIG. 2 is a simplified view of a patient and a catheter being inserted therein with assistance of the integrated system of FIG. 1.

Reference will now be made to figures wherein like structures will be provided with like reference designations. It is understood that the drawings are diagrammatic and schematic representations of exemplary embodiments of the present invention, and are neither limiting nor necessarily drawn to scale.

Embodiments of the present invention are generally directed to a catheter placement system configured for accurately placing a catheter within the vasculature of a patient. In one embodiment, the catheter placement system employs at least two modalities for improving catheter placement accuracy: 1) ultrasound-assisted guidance for introducing the catheter into the patient's vasculature; and 2) a tip location/navigation system ("TLS"), or magnetically-based tracking of the catheter tip during its advancement through the tortuous vasculature path to detect and facilitate correction of any tip malposition during such advancement. The ultrasound guidance and tip location features of the present system according to one embodiment are integrated into a single device for use by a clinician placing the catheter. Integration of these two modalities into a single device simplifies the catheter placement process and results in relatively faster catheter placements. For instance, the integrated catheter placement system enables ultrasound and TLS activities to be viewed from a single display of the integrated system. Also, controls located on an ultrasound probe of the integrated device, which probe is maintained within the sterile field of the patient during catheter placement, can be used to control functionality of the system, thus precluding the need for a clinician to reach out of the sterile field in order to control the system.

In another embodiment, a third modality, i.e., ECG signal-based catheter tip guidance, is included in the integrated system to enable guidance of the catheter tip to a desired position with respect to a node of the patient's heart from which the ECG signals originate. Such ECG-based positional assistance is also referred to herein as "tip confirmation."

Combination of the three modalities above according to one embodiment enables the catheter placement system to facilitate catheter placement within the patient's vasculature with a relatively high level of accuracy, i.e., placement of the distal tip of the catheter in a predetermined and desired position. Moreover, because of the ECG-based guidance of the catheter tip, correct tip placement may be confirmed without the need for a confirmatory X-ray. This, in turn, reduces the patient's exposure to potentially harmful x-rays, the cost and time involved in transporting the patient to and from the x-ray department, costly and inconvenient catheter repositioning procedures, etc.

As the ECG signal-based modality includes a need for passing ECG signals from a catheter assembly disposed in a sterile field of a patient to a data-receiving component of the system disposed in a non-sterile field, embodiments of the present invention are further concerned with various connector systems for establishing a conductive pathway through a sterile barrier separating the sterile and non-sterile fields. Various aspects for visualizing and manipulating display of the ECG signal data acquired via the present system, together with aspects of various ECG sensor configurations, are also disclosed. Example iconic representations relating to the system's detection of the indwelling catheter or other medical device are also disclosed.

For clarity it is to be understood that the word "proximal" as used herein refers to a direction relatively closer to a clinician, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Reference is first made to FIGS. 1 and 2 which depict various components of a catheter placement system ("system"), generally designated at 10, configured in accordance with one example embodiment of the present invention. As shown, the system 10 generally includes a console 20, display 30, probe 40, and sensor 50, each of which is described in further detail below.

FIG. 2 shows the general relation of these components to a patient 70 during a procedure to place a catheter 72 into the patient vasculature through a skin insertion site 73. FIG. 2 shows that the catheter 72 generally includes a proximal portion 74 that remains exterior to the patient and a distal potion 76 that resides within the patient vasculature after placement is complete. The system 10 is employed to ultimately position a distal tip 76A of the catheter 72 in a desired position within the patient vasculature. In one embodiment, the desired position for the catheter distal tip 76A is proximate the patient's heart, such as in the lower one-third ($1/3^{rd}$) portion of the Superior Vena Cava ("SVC"). Of course, the system 10 can be employed to place the catheter distal tip in other locations. The catheter proximal portion 74 further includes a hub 74A that provides fluid communication between the one or more lumens of the catheter 72 and one or more extension legs 74B extending proximally from the hub.

Figure 8A:
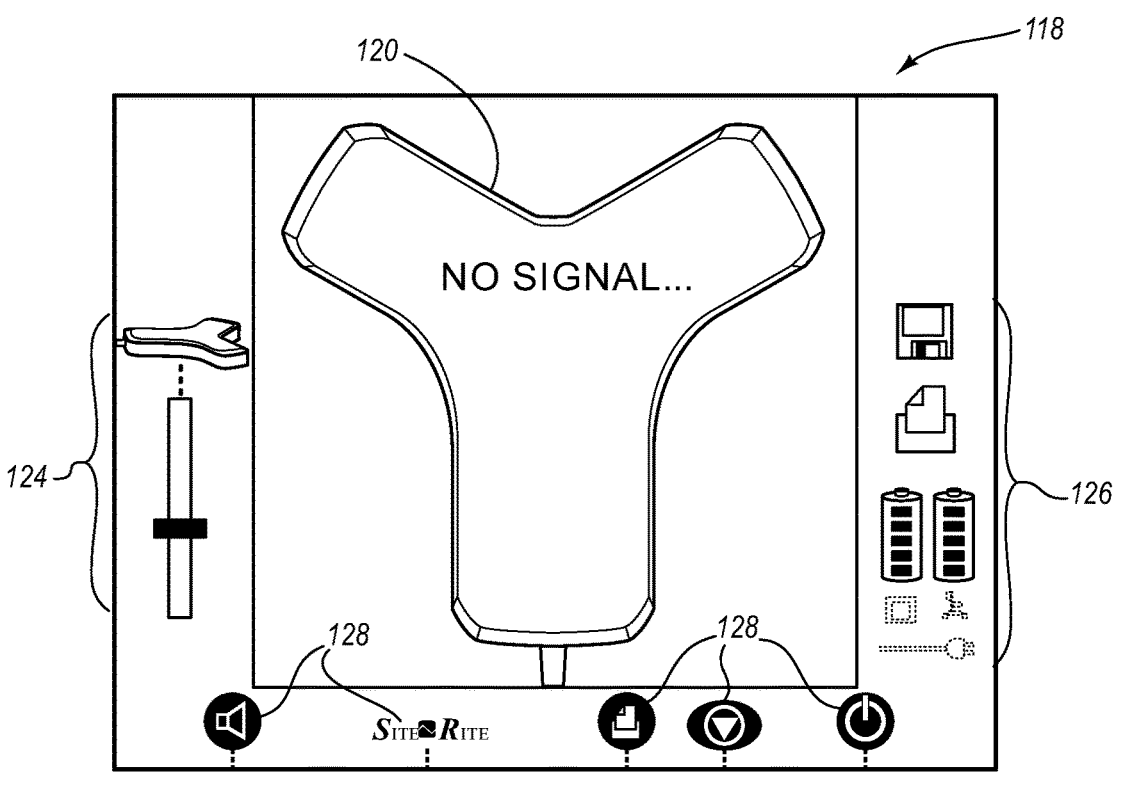
FIGS. 8A-8C are screenshots of images depicted on a display of the integrated system of FIG. 1 during catheter tip placement procedures.
Figure 8B:
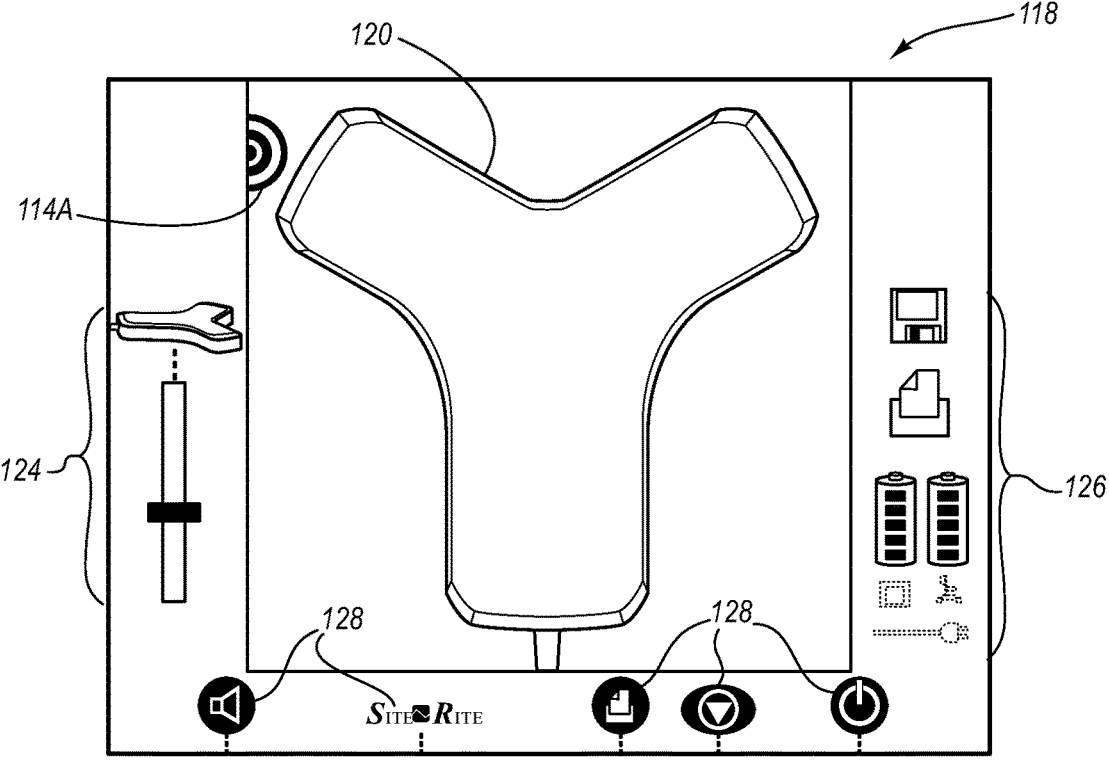
Figure 8C:
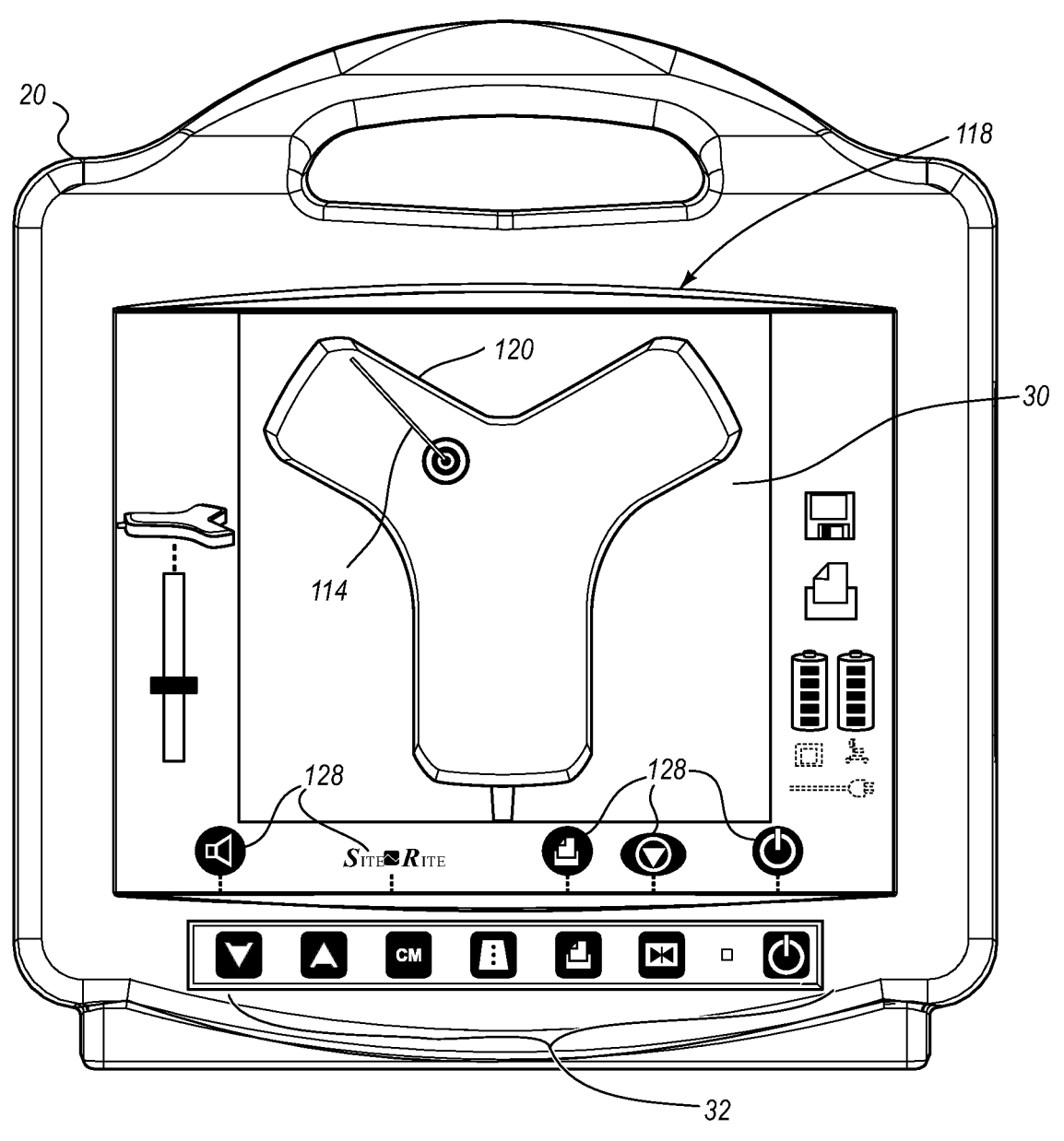

An example implementation of the console 20 is shown in FIG. 8C, though it is appreciated that the console can take one of a variety of forms. A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 (see FIGS. 1, 8C) and buttons included on the probe 40 can be used to immediately call up a desired mode to the display 30 by the clinician to assist in the placement procedure. In one embodiment, information from multiple modes, such as TLS and ECG, may be displayed simultaneously, such as in FIG. 17. Thus, the single display 30 of the system console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 30 is an LCD device.

Figure 3A:
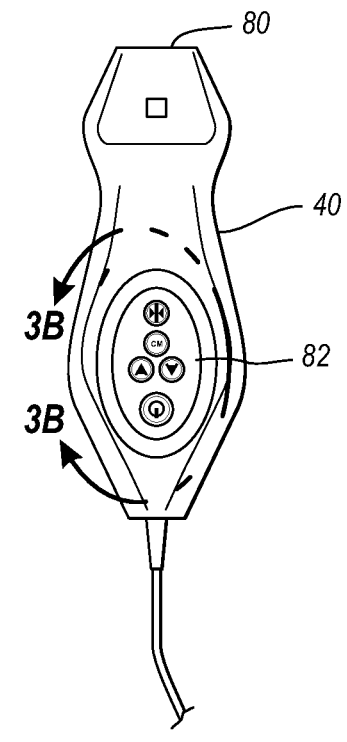
FIGS. 3A and 3B are views of a probe of the integrated system of FIG. 1.
Figure 3B:
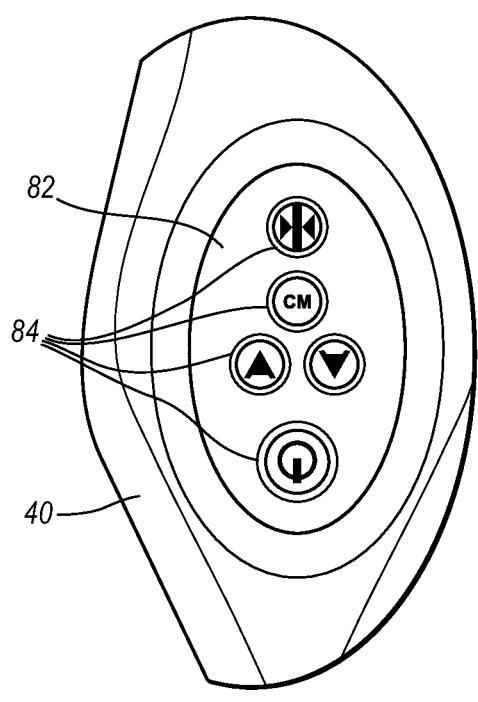

FIGS. 3A and 3B depict features of the probe 40 according to one embodiment. The probe 40 is employed in connection with the first modality mentioned above, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, etc.

The handheld probe 40 includes a head 80 that houses a piezoelectric array for producing ultrasonic pulses and for receiving echoes thereof after reflection by the patient's body when the head is placed against the patient's skin proximate the prospective insertion site 73 (FIG. 2). The probe 40 further includes a plurality of control buttons 84, which can be included on a button pad 82. In the present embodiment, the modality of the system 10 can be controlled by the control buttons 84, thus eliminating the need for the clinician to reach out of the sterile field, which is established about the patient insertion site prior to catheter placement, to change modes via use of the console button interface 32.

As such, in one embodiment a clinician employs the first (US) modality to determine a suitable insertion site and establish vascular access, such as with a needle or introducer, then with the catheter. The clinician can then seamlessly switch, via button pushes on the probe button pad 82, to the second (TLS) modality without having to reach out of the sterile field. The TLS mode can then be used to assist in advancement of the catheter 72 through the vasculature toward an intended destination.

FIG. 1 shows that the probe 40 further includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Figure 4:
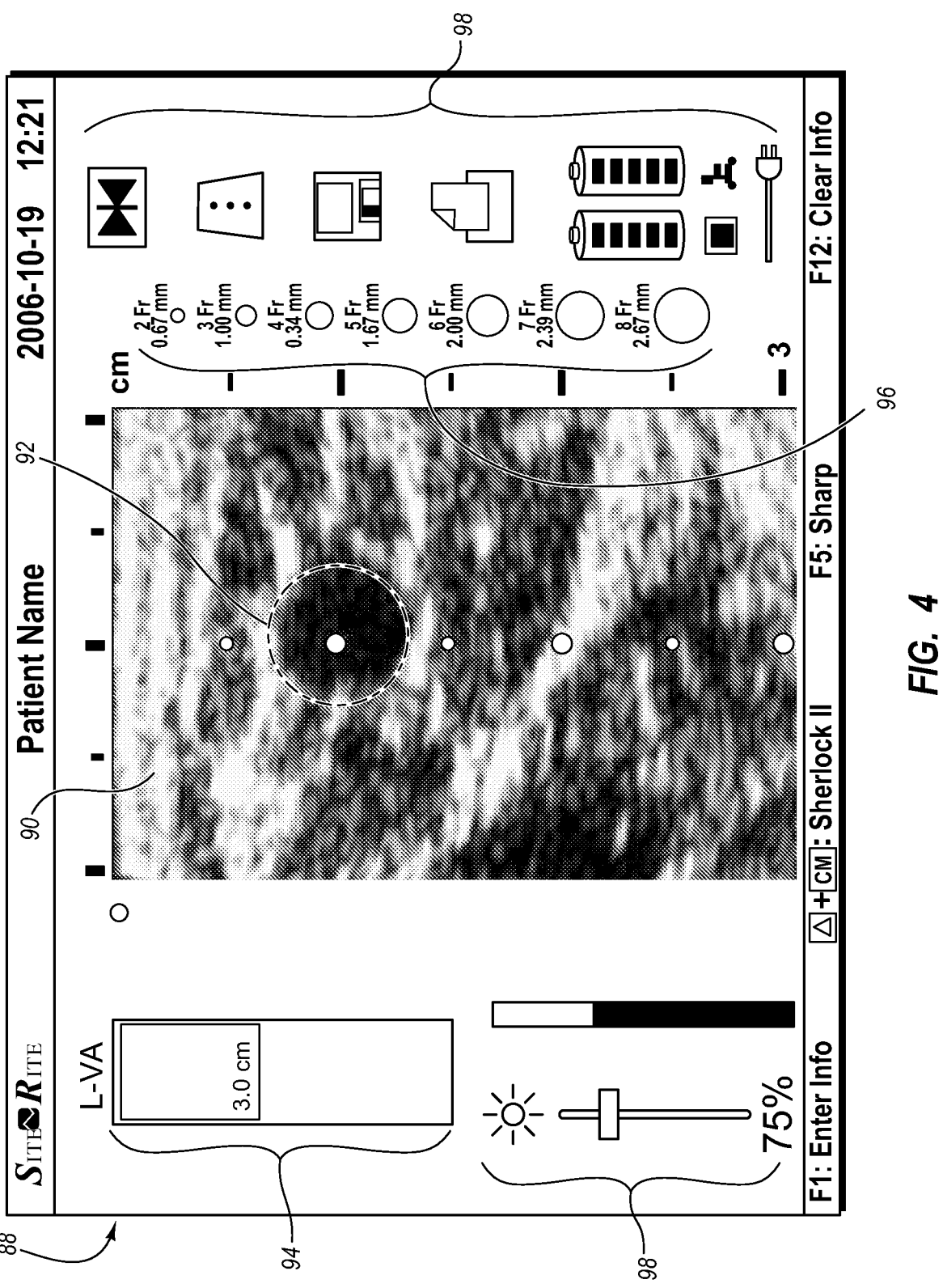
FIG. 4 is a screenshot of an ultrasound image as depicted on a display of the integrated system of FIG. 1.

FIG. 4 shows an example screenshot 88 as depicted on the display 30 while the system 10 is in its first ultrasound modality. An image 90 of a subcutaneous region of the patient 70 is shown, depicting a cross section of a vein 92. The image 90 is produced by operation of the piezoelectric array of the probe 40. also included on the display screenshot 88 is a depth scale indicator 94, providing information regarding the depth of the image 90 below the patient's skin, a lumen size scale 96 that provides information as to the size of the vein 92 relative to standard catheter lumen sizes, and other indicia 98 that provide information regarding status of the system 10 or possible actions to be taken, e.g., freeze frame, image templates, data save, image print, power status, image brightness, etc.

Note that while a vein is depicted in the image 90, other body lumens or portions can be imaged in other embodiments. Note that the US mode shown in FIG. 4 can be simultaneously depicted on the display 30 with other modes, such as the TLS mode, if desired. In addition to the visual display 30, aural information, such as beeps, tones, etc., can also be employed by the system 10 to assist the clinician during catheter placement. Moreover, the buttons included on the probe 40 and the console button interface 32 can be configured in a variety of ways, including the use of user input controls in addition to buttons, such as slide switches, toggle switches, electronic or touch-sensitive pads, etc. Additionally, both US and TLS activities can occur simultaneously or exclusively during use of the system 10.

As just described, the handheld ultrasound probe 40 is employed as part of the integrated catheter placement system 10 to enable US visualization of the peripheral vasculature of a patient in preparation for transcutaneous introduction of the catheter. In the present example embodiment, however, the probe is also employed to control functionality of the TLS portion, or second modality, of the system 10 when navigating the catheter toward its desired destination within the vasculature as described below. Again, as the probe 40 is used within the sterile field of the patient, this feature enables TLS functionality to be controlled entirely from within the sterile field. Thus the probe 40 is a dual-purpose device, enabling convenient control of both US and TLS functionality of the system 10 from the sterile field. In one embodiment, the probe can also be employed to control some or all ECG-related functionality, or third modality, of the catheter placement system 10, as described further below.

The catheter placement system 10 further includes the second modality mentioned above, i.e., the magnetically-based catheter TLS, or tip location system. The TLS enables the clinician to quickly locate and confirm the position and/or orientation of the catheter 72, such as a peripherally-inserted central catheter ("PICC"), central venous catheter ("CVC"), or other suitable catheter, during initial placement into and advancement through the vasculature of the patient 70. Specifically, the TLS modality detects a magnetic field generated by a magnetic element-equipped tip location stylet, which is pre-loaded in one embodiment into a longitudinally defined lumen of the catheter 72, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

Figure 5:
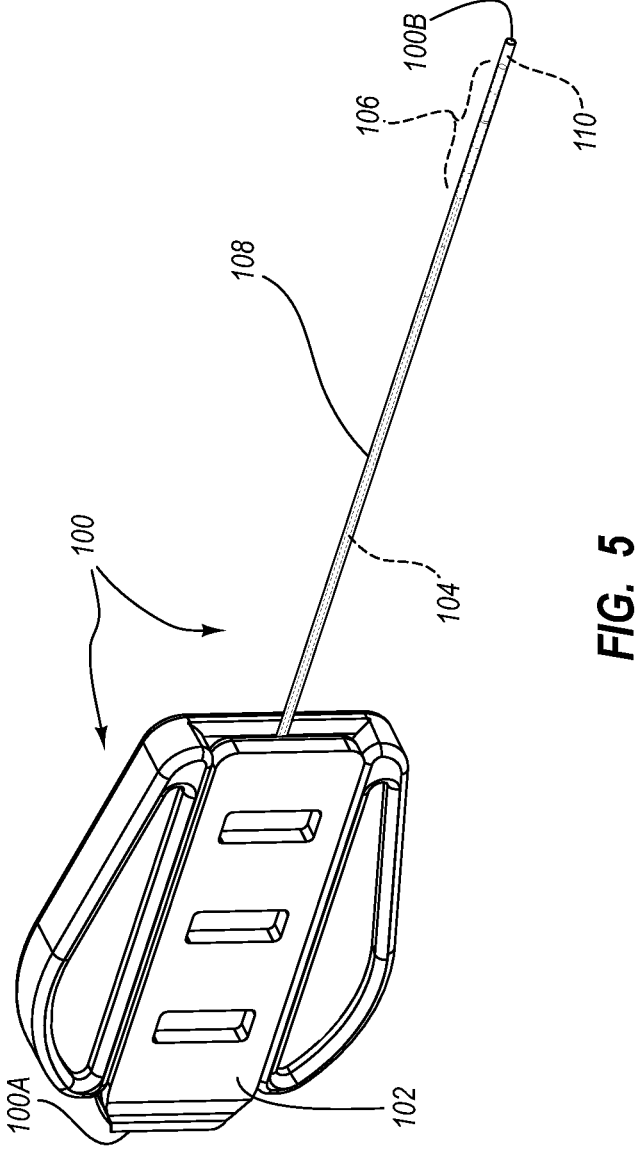
FIG. 5 is a perspective view of a stylet employed in connection with the system of FIG. 1 in placing a catheter within a patient vasculature.

As mentioned, the TLS utilizes a stylet to enable the distal end of the catheter 72 to be tracked during its advancement through the vasculature. FIG. 5 gives an example of such a stylet 100, which includes a proximal end 100A and a distal end 100B. A handle is included at the stylet proximal end 100A, with a core wire 104 extending distally therefrom. A magnetic assembly is disposed distally of the core wire 104. The magnetic assembly includes one or more magnetic elements 106 disposed adjacent one another proximate the stylet distal end 100B and encapsulated by tubing 108. In the present embodiment, a plurality of magnetic elements 106 is included, each element including a solid, cylindrically shaped ferromagnetic stacked end-to-end with the other magnetic elements. An adhesive tip 110 can fill the distal tip of the tubing 108, distally to the magnetic elements 106.

Note that in other embodiments, the magnetic elements may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845 titled "Medical Instrument Location Means," which is incorporated herein by reference in its entirety. Yet other examples of stylets including magnetic elements that can be employed with the TLS modality can be found in U.S. Pat. No. 8,784,336 titled "Stylet Apparatuses and Methods of Manufacture," which is incorporated herein by reference in its entirety. These and other variations are therefore contemplated by embodiments of the present invention. It should appreciated herein that "stylet" as used herein can include any one of a variety of devices configured for removable placement within a lumen of the catheter to assist in placing a distal end of the catheter in a desired location within the patient's vasculature.

FIG. 2 shows disposal of the stylet 100 substantially within a lumen in the catheter 72 such that the proximal portion thereof extends proximally from the catheter lumen, through the hub 74A and out through a selected one of the extension legs 74B. So disposed within a lumen of the catheter, the distal end 100B of the stylet 100 is substantially co-terminal with the distal catheter end 76A such that detection by the TLS of the stylet distal end correspondingly indicates the location of the catheter distal end.

The TLS sensor 50 is employed by the system 10 during TLS operation to detect a magnetic field produced by the magnetic elements 106 of the stylet 100. As seen in FIG. 2, the TLS sensor 50 is placed on the chest of the patient during catheter insertion. The TLS sensor 50 is placed on the chest of the patient in a predetermined location, such as through the use of external body landmarks, to enable the magnetic field of the stylet magnetic elements 106, disposed in the catheter 72 as described above, to be detected during catheter transit through the patient vasculature. Again, as the magnetic elements 106 of the stylet magnetic assembly are co-terminal with the distal end 76A of the catheter 72 (FIG. 2), detection by the TLS sensor 50 of the magnetic field of the magnetic elements provides information to the clinician as to the position and orientation of the catheter distal end during its transit.

In greater detail, the TLS sensor 50 is operably connected to the console 20 of the system 10 via one or more of the ports 52, as shown in FIG. 1. Note that other connection schemes between the TLS sensor and the system console can also be used without limitation. As just described, the magnetic elements 106 are employed in the stylet 100 to enable the position of the catheter distal end 76A (FIG. 2) to be observable relative to the TLS sensor 50 placed on the patient's chest. Detection by the TLS sensor 50 of the stylet magnetic elements 106 is graphically displayed on the display 30 of the console 20 during TLS mode. In this way, a clinician placing the catheter is able to generally determine the location of the catheter distal end 76A within the patient vasculature relative o the TLS sensor 50 and detect when catheter malposition, such as advancement of the catheter along an undesired vein, is occurring.

Figure 6:
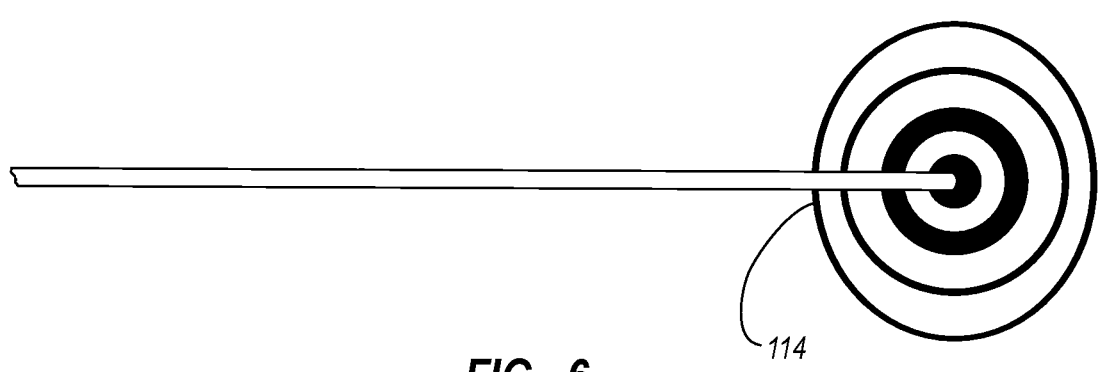
FIG. 6 is an icon as depicted on a display of the integrated system of FIG. 1, indicating a position of a distal end of the stylet of FIG. 5 during catheter tip placement procedures.
Figure 7A:
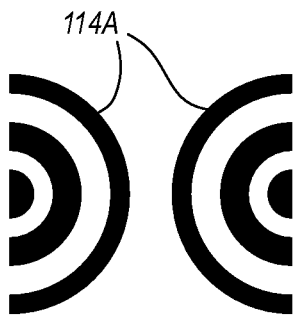
FIGS. 7A-7E depict various example icons that can be depicted on the display of the integrated system of FIG. 1 during catheter tip placement procedures.
Figure 7B:
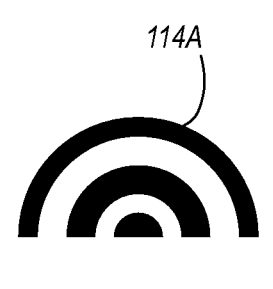
Figure 7C:
Figure 7D:
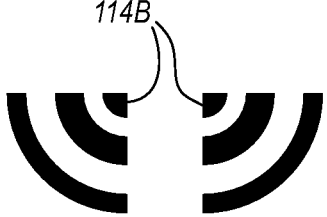
Figure 7E:
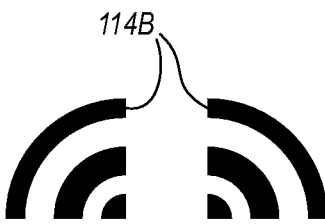

FIGS. 6 and 7A-7E show examples of icons that can be used by the console display 30 to depict detection of the stylet magnetic elements 106 by the TLS sensor 50. In particular, FIG. 6 shows an icon 114 that depicts the distal portion of the stylet 100, including the magnetic elements 106 as detected by the TLS sensor 50 when the magnetic elements are positioned under the TLS sensor. As the stylet distal end 100B is substantially co-terminal with the distal end 76A of the catheter 72, the icon indicates the position and orientation of the catheter distal end. FIGS. 7A-7E show various icons that can be depicted on the on the console display 30 when the magnetic elements 106 of the stylet 100 are not positioned directly under a portion of the TLS sensor 50, but are nonetheless detected nearby. The icons can include half-icons 114A and quarter-icons 114B that are displayed according to the position of the stylet magnetic assembly, i.e., the magnetic elements 106 in the present embodiment, relative to the TLS sensor 50.

FIGS. 8A-8C depict screenshots taken from the display 30 of the system 10 while in TLS mode, showing how the magnetic assembly of the stylet 100 is depicted. The screenshot 118 of FIG. 8A shows a representative image 120 of the TLS sensor 50. Other information is provided on the display screenshot 118, including a depth scale indicator 124, status/ action indicia 126, and icons 128 corresponding to the button interface 32 included on the console 20 (FIG. 8C). Though the icons 128 in the present embodiment are simply indicators to guide the user in identifying the purpose of the corresponding buttons of the button interface 32, in another embodiment the display can be made touch-sensitive so that the icons themselves can function as button interfaces and can change according to the mode the system is in.

During initial stages of catheter advancement through the patient's vasculature after insertion therein, the distal end 76A of the catheter 72, having the stylet distal end 100B substantially co-terminal therewith, is relatively distant from the TLS sensor 50. As such, the display screenshot will indicate "no signal," indicating that the magnetic field from the stylet magnetic assembly has not been detected. In FIG. 8B, the magnetic assembly proximate the stylet distal end 100B has advanced sufficiently close to the TLS sensor 50 to be detected thereby, though it is not yet under the sensor. This is indicated by the half-icon 114A shown to the left of the sensor image 120, representing the stylet magnetic assembly being positioned to the right of the TLS sensor 50 from the perspective of the patient.

In FIG. 8C, the magnetic assembly proximate the stylet distal end 100B has advanced under the TLS sensor 50 such that its position and orientation relative thereto is detected by the TLS sensor. This is indicated by the icon 114 on the sensor image 120. Note that the button icons 128 provide indications of the actions that can be performed by pressing the corresponding buttons of the console button interface 32. As such, the button icons 128 can change according to which modality the system 10 is in, thus providing flexibility of use for the button interface 32. Note further that, as the button pad 82 of the probe 40 (FIG. 3A, 3B) includes buttons 84 that mimic several of the buttons of the button interface 32, the button icons 128 on the display 30 provide a guide to the clinician for controlling the system 10 with the probe buttons 84 while remaining in the sterile field. For instance, if the clinician has need to leave TLS mode and return to US (ultrasound) mode, the appropriate control button 84 on the probe button pad 82 can be depressed, and the US mode can be immediately called up, with the display 30 refreshing to accommodate the visual information needed for US functionality, such as that shown in FIG. 4. This is accomplished without a need for the clinician to reach out of the sterile field.

Figure 9:
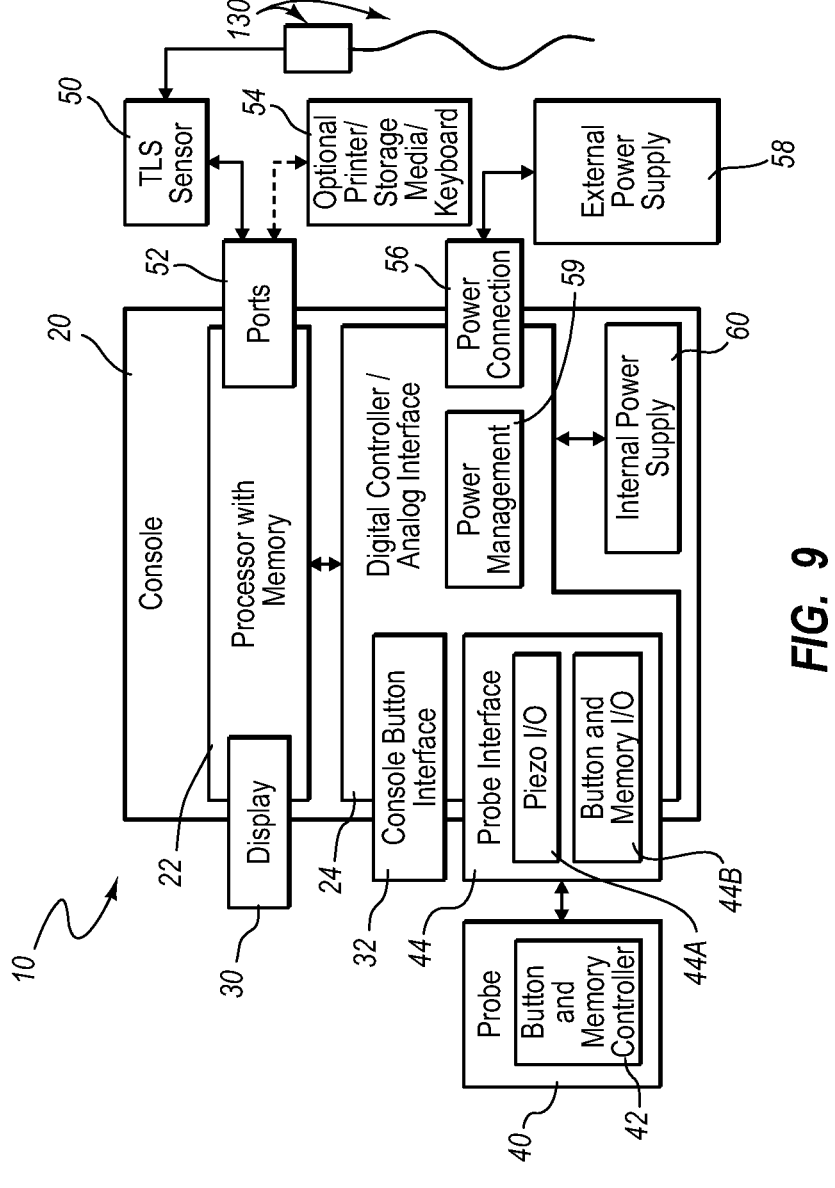
FIG. 9 is a block diagram depicting various elements of an integrated system for intravascular placement of a catheter, according to another example embodiment of the present invention.
Figure 10:
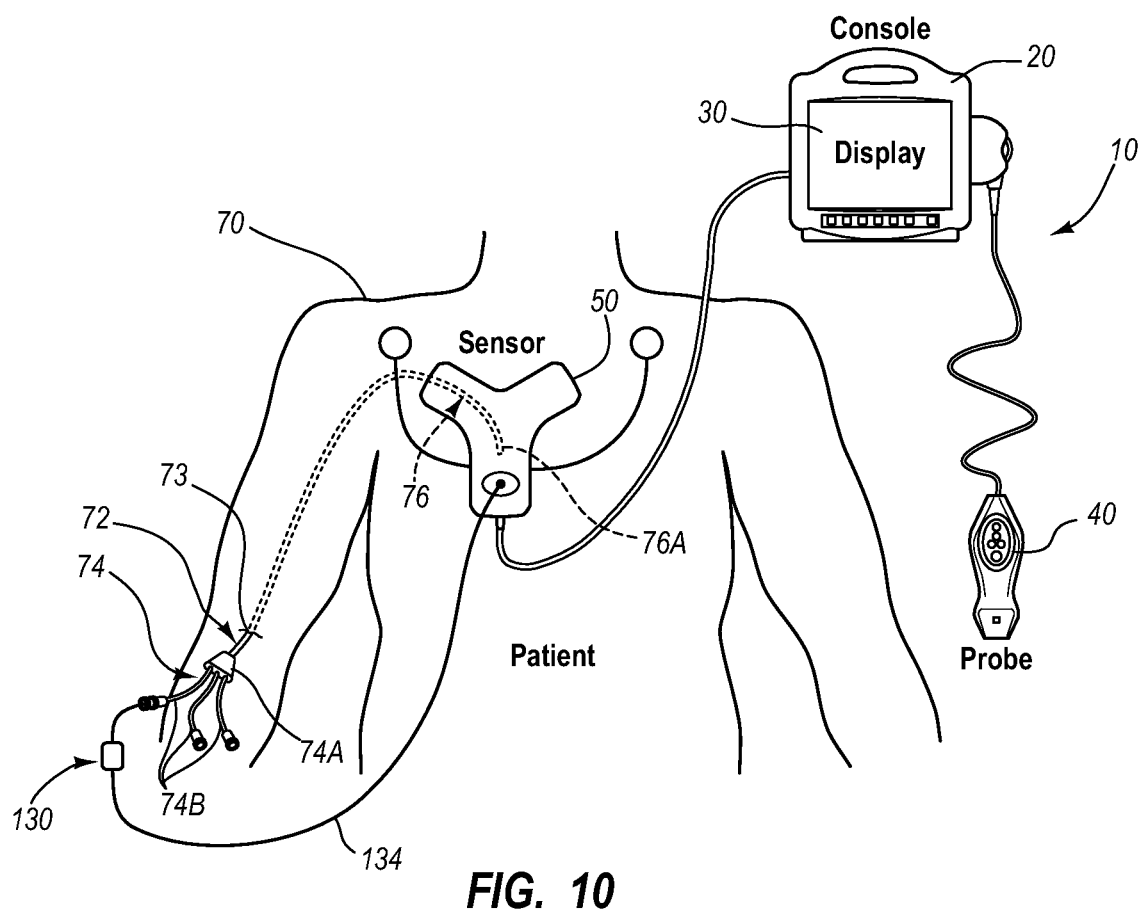
FIG. 10 is a simplified view of a patient and a catheter being inserted therein with assistance of the integrated system of FIG. 9.

Reference is now made to FIGS. 9 and 10 in describing the integrated catheter placement system 10 according to another example embodiment. As before, the integrated system 10 includes the console 20, display 30, probe 40 for US functionality, and the TLS sensor 50 for tip location functionality as described above. Note that the system 10 depicted in FIGS. 9 and 10 is similar in many respects to the system shown in FIGS. 1 and 2. As such, only selected differences will be discussed below. The system 10 of FIGS. 9 and 10 includes additional functionality wherein determination of the proximity of the catheter distal tip 76A relative to a sino-atrial ("SA") or other electrical impulse-emitting node of the heart of the patient 70 can be determined, thus providing enhanced ability to accurately place the catheter distal tip in a desired location proximate the node. Also referred to herein as "ECG" or "ECG-based tip confirmation," this third modality of the system 10 enables detection of ECG signals from the SA node in order to place the catheter distal tip in a desired location within the patient vasculature. Note that the US, TLS, and ECG modalities are seamlessly combined in the present system 10, but can be employed in concert or individually to assist in catheter placement. In one embodiment, it is understood that the ECG modality as described herein can be included in a stand-alone system without the inclusion of the US and TLS modalities. Thus, the environments in which the embodiments herein are described are understood as merely example environments and are not considered limiting of the present disclosure.

FIGS. 9 and 10 show the addition to the system 10 of a stylet 130 configured in accordance with the present embodiment. As an overview, the catheter stylet 130 is removably predisposed within the lumen of the catheter 72 being inserted into the patient 70 via the insertion site 73. The stylet 130, in addition to including a magnetic assembly for the magnetically-based TLS modality, includes a sensing component, i.e., an ECG sensor assembly, proximate its distal end and including a portion that is co-terminal with the distal end of the catheter tip for sensing ECG signals produced by the SA node. In contrast to the previous embodiment, the stylet 130 includes a tether 134 extending from its proximal end that operably connects to the TLS sensor 50. As will be described in further detail, the stylet tether 134 permits ECG signals detected by the ECG sensor assembly included on a distal portion of the stylet 130 to be conveyed to the TLS sensor 50 during confirmation of the catheter tip location as part of the ECG signal-based tip confirmation modality. Reference and ground ECG lead/ electrode pairs 158 attach to the body of the body of the patient 70 and are operably attached to the TLS sensor 50 to enable the system to filter out high level electrical activity unrelated to the electrical activity of the SA node of the heart, thus enabling the ECG-based tip confirmation functionality. Together with the reference and ground signals received from the ECG lead/electrode pairs 158 placed on the patient's skin, the ECG signals sensed by the stylet ECG sensor assembly are received by the TLS sensor 50 positioned on the patient's chest (FIG. 10) or other designated component of the system 10. The TLS sensor 50 and/or console processor 22 can process the ECG signal data to produce an electrocardiogram waveform on the display 30, as will be described. In the case where the TLS sensor 50 processes the ECG signal data, a processor is included therein to perform the intended functionality. If the console 20 processes the ECG signal data, the processor 22, controller 24, or other processor can be utilized in the console to process the data.

Thus, as it is advanced through the patient vasculature, the catheter 72 equipped with the stylet 130 as described above can advance under the TLS sensor 50, which is positioned on the chest of the patient as shown in FIG. 10. This enables the TLS sensor 50 to detect the position of the magnetic assembly of the stylet 130, which is substantially co-terminal with the distal tip 76A of the catheter as located within the patient's vasculature. The detection by the TLS sensor 50 of the stylet magnetic assembly is depicted on the display 30 during ECG mode. The display 30 further depicts during ECG mode an ECG electrocardiogram waveform produced as a result of patient heart's electrical activity as detected by the ECG sensor assembly of the stylet 130. In greater detail, the ECG electrical activity of the SA node, including the P-wave of the waveform, is detected by the ECG sensor assembly of the stylet (described below) and forwarded to the TLS sensor 50 and console 20. The ECG electrical activity is then processed for depiction on the display 30. A clinician placing the catheter can then observe the ECG data to determine optimum placement of the distal tip 76A of the catheter 72, such as proximate the SA node in one embodiment. In one embodiment, the console 20 includes the electronic components, such as the processor 22 (FIG. 9), necessary to receive and process the signals detected by the stylet ECG sensor assembly. In another embodiment, the TLS sensor 50 can include the necessary electronic components processing the ECG signals.

As already discussed, the display 30 is used to display information to the clinician during the catheter placement procedure. The content of the display 30 changes according to which mode the catheter placement system is in: US, TLS, or ECG. Any of the three modes can be immediately called up to the display 30 by the clinician, and in some cases information from multiple modes, such as TLS and ECG, may be displayed simultaneously. In one embodiment, as before, the mode the system is in may be controlled by the control buttons 84 included on the handheld probe 40, thus eliminating the need for the clinician to reach out of the sterile field (such as touching the button interface 32 of the console 20) to change modes. Thus, in the present embodiment the probe 40 is employed to also control some or all ECG-related functionality of the system 10. Note that the button interface 32 or other input configurations can also be used to control system functionality. Also, in addition to the visual display 30, aural information, such as beeps, tones, etc., can also be employed by the system to assist the clinician during catheter placement.

Figure 11:
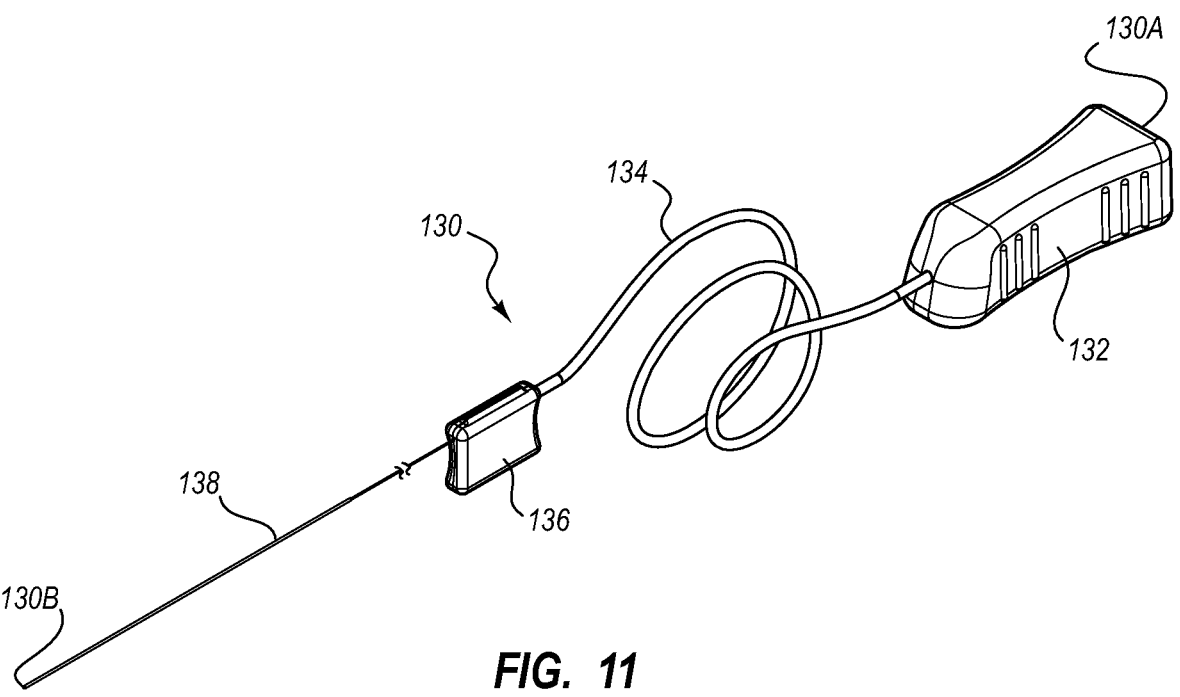
FIG. 11 is a perspective view of a stylet employed in connection with the integrated system of FIG. 9 in placing a catheter within a patient vasculature.

Reference is now made to FIGS. 11-12E in describing various details of one embodiment of the stylet 130 that is removably loaded into the catheter 72 and employed during insertion to position the distal tip 76A of the catheter in a desired location within the patient vasculature. As shown, the stylet 130 as removed from the catheter defines a proximal end 130A and a distal end 130B. A connector 132 is included at the proximal stylet end 130A, and a tether 134 extends distally from the connector and attaches to a handle 136. A core wire 138 extends distally from the handle 136. The stylet 130 is pre-loaded within a lumen of the catheter 72 in one embodiment such that the distal end 130B is substantially flush, or co-terminal, with the catheter opening at the distal end 76A thereof (FIG. 10), and such that a proximal portion of the core wire 138, the handle 136, and the tether 134 extend proximally from a selected one of the extension tubes 74B. Note that, though described herein as a stylet, in other embodiments a guidewire or other catheter guiding apparatus could include the principles of the embodiment described herein.

The core wire 138 defines an elongate shape and is composed of a suitable stylet material including stainless steel or a memory material such as, in one embodiment, a nickel and titanium-containing alloy commonly known by the acronym "nitinol." Though not shown here, manufacture of the core wire 138 from nitinol in one embodiment enables the portion of the core wire corresponding to a distal segment of the stylet to have a pre-shaped bent configuration so as to urge the distal portion of the catheter 72 into a similar bent configuration. In other embodiments, the core wire includes no pre-shaping. Further, the nitinol construction lends torqueability to the core wire 138 to enable a distal segment of the stylet 130 to be manipulated while disposed within the lumen of the catheter 72, which in turn enables the distal portion of the catheter to be navigated through the vasculature during catheter insertion.

The handle 136 is provided to enable insertion/removal of the stylet from the catheter 72. In embodiments where the stylet core wire 138 is torqueable, the handle 136 further enables the core wire to be rotated within the lumen of the catheter 72, to assist in navigating the catheter distal portion through the vasculature of the patient 70.

The handle 136 attaches to a distal end of the tether 134. In the present embodiment, the tether 134 is a flexible, shielded cable housing one or more conductive wires electrically connected both to the core wire 138, which acts as the ECG sensor assembly referred to above, and the tether connector 132. As such, the tether 134 provides a conductive pathway from the distal portion of the core wire 138 through to the tether connector 132 at proximal end 130A of the stylet 130. As will be explained, the tether connector 132 is configured for operable connection to the TLS sensor 50 on the patient's chest for assisting in navigation of the catheter distal tip 76A to a desired location within the patient vasculature.

As seen in FIGS. 12B-12D, a distal portion of the core wire 138 is gradually tapered, or reduced in diameter, distally from a junction point 142. A sleeve 140 is slid over the reduced-diameter core wire portion. Though of relatively greater diameter here, the sleeve in another embodiment can be sized to substantially match the diameter of the proximal portion of the stylet core wire. The stylet 130 further includes a magnetic assembly disposed proximate the distal end 130B thereof for use during TLS mode. The magnetic assembly in the illustrated embodiment includes a plurality of magnetic elements 144 interposed between an outer surface of the reduced-diameter core wire 138 and an inner surface of the sleeve 140 proximate the stylet distal end 130B. In the present embodiment, the magnetic elements 144 include 20 ferromagnetic magnets of a solid cylindrical shape stacked end-to-end in a manner similar to the stylet 100 of FIG. 2. In other embodiments, however, the magnetic element(s) may vary from this design in not only shape, but also composition, number, size, magnetic type, and position in the stylet. For example, in one embodiment the plurality of magnets of the magnetic assembly is replaced with an electromagnetic coil that produces a magnetic field for detection by the TLS sensor. These and other variations are therefore contemplated by embodiments of the present invention.

The magnetic elements 144 are employed in the stylet 130 distal portion to enable the position of the stylet distal end 130B to be observable relative to the TLS sensor 50 placed on the patient's chest. As has been mentioned, the TLS sensor 50 is configured to detect the magnetic field of the magnetic elements 144 as the stylet advances with the catheter 72 through the patient vasculature. In this way, a clinician placing the catheter 72 is able to generally determine the location of the catheter distal end 76A within the patient vasculature and detect when catheter malposition is occurring, such as advancement of the catheter along an undesired vein, for instance.

The stylet 130 further includes the afore-mentioned ECG sensor assembly, according to one embodiment. The ECG sensor assembly enables the stylet 130, disposed in a lumen of the catheter 72 during insertion, to be employed in detecting an intra-atrial ECG signal produced by an SA or other node of the patient's heart, thereby allowing for navigation of the distal tip 76A of the catheter 72 to a predetermined location within the vasculature proximate the patient's heart. Thus, the ECG sensor assembly serves as an aide in confirming proper placement of the catheter distal tip 76A.

In the embodiment illustrated in FIGS. 11-12E, the ECG sensor assembly includes a distal portion of the core wire 138 disposed proximate the stylet distal end 130B. The core wire 138, being electrically conductive, enables ECG signals to be detected by the distal end thereof and transmitted proximally along the core wire. A conductive material 146, such as a conductive epoxy, fills a distal portion of the sleeve 140 adjacent the distal termination of the core wire 138 so as to be in conductive communication with the distal end of the core wire. This in turn increases the conductive surface of the distal end 130B of the stylet 130 so as to improve its ability to detect ECG signals.

Before catheter placement, the stylet 130 is loaded into a lumen of the catheter 72. Note that the stylet 130 can come preloaded in the catheter lumen from the manufacturer, or loaded into the catheter by the clinician prior to catheter insertion. The stylet 130 is disposed within the catheter lumen such that the distal end 130B of the stylet 130 is substantially co-terminal with the distal tip 76A of the catheter 72, thus placing the distal tips of both the stylet and the catheter in substantial alignment with one another. The co-terminality of the catheter 72 and stylet 130 enables the magnetic assembly to function with the TLS sensor 50 in TLS mode to track the position of the catheter distal tip 76A as it advances within the patient vasculature, as has been described. Note, however, that for the tip confirmation functionality of the system 10, the distal end 130B of the stylet 130 need not be co-terminal with the catheter distal end 76A. Rather, all that is required is that a conductive path between the vasculature and the ECG sensor assembly, in this case the core wire 138, be established such that electrical impulses of the SA node or other node of the patient's heart can be detected. This conductive path in one embodiment can include various components including saline solution, blood, etc.

In one embodiment, once the catheter 72 has been introduced into the patient vasculature via the insertion site 73 (FIG. 10) the TLS mode of the system 10 can be employed as already described to advance the catheter distal tip 76A toward its intended destination proximate the SA node. Upon approaching the region of the heart, the system 10 can be switched to ECG mode to enable ECG signals emitted by the SA node to be detected. As the stylet-loaded catheter is advanced toward the patient's heart, the electrically conductive ECG sensor assembly, including the distal end of the core wire 138 and the conductive material 146, begins to detect the electrical impulses produced by the SA node. As such, the ECG sensor assembly serves as an electrode for detecting the ECG signals. The elongate core wire 138 proximal to the core wire distal end serves as a conductive pathway to convey the electrical impulses produced by the SA node and received by the ECG sensor assembly to the tether 134.

The tether 134 conveys the ECG signals to the TLS sensor 50 temporarily placed on the patient's chest. The tether 134 is operably connected to the TLS sensor 50 via the tether connector 132 or other suitable direct or indirect connective configuration. As described, the ECG signal can then be processed and depicted on the system display 30 (FIG. 9, 10). Monitoring of the ECG signal received by the TLS sensor 50 and displayed by the display 30 enables a clinician to observe and analyze changes in the signal as the catheter distal tip 76A advances toward the SA node. When the received ECG signal matches a desired profile, the clinician can determine that the catheter distal tip 76A has reached a desired position with respect to the SA node. As mentioned, in one embodiment this desired position lies within the lower one-third (⅓ rd) portion of the SVC.

The ECG sensor assembly and magnetic assembly can work in concert in assisting a clinician in placing a catheter within the vasculature. Generally, the magnetic assembly of the stylet 130 assists the clinician in generally navigating the vasculature from initial catheter insertion so as to place the distal end 76A of the catheter 72 in the general region of the patient's heart. The ECG sensor assembly can then be employed to guide the catheter distal end 76A to the desired location within the SVC by enabling the clinician to observe changes in the ECG signals produced by the heart as the stylet ECG sensor assembly approaches the SA node. Again, once a suitable ECG signal profile is observed, the clinician can determine that the distal ends of both the stylet 130 and the catheter 72 have arrived at the desired location with respect to the patient's heart. Once it has been positioned as desired, the catheter 72 may be secured in place and the stylet 130 removed from the catheter lumen. It is noted here that the stylet may include one of a variety of configurations in addition to what is explicitly described herein. In one embodiment, the stylet can attach directly to the console instead of an indirect attachment via the TLS sensor. In another embodiment, the structure of the stylet 130 that enables its TLS and ECG-related functionalities can be integrated into the catheter structure itself. For instance, the magnetic assembly and/or ECG sensor assembly can, in one embodiment, be incorporated into the wall of the catheter.

FIGS. 13A-15 describe various details relating to the passage of ECG signal data from the stylet tether 134 to the TLS sensor 50 positioned on the patient's chest, according the present embodiment. In particular, this embodiment is concerned with passage of ECG signal data from a sterile field surrounding the catheter 72 and insertion site 73, which includes the stylet 130 and tether 134, and a non-sterile field, such as the patient's chest on which the TLS sensor is positioned. Such passage should not disrupt the sterile field so that the sterility thereof is compromised. A sterile drape that is positioned over the patient 70 during the catheter insertion procedure defines the majority of the sterile field: areas above the drape are sterile, while areas below (excluding the insertion site and immediately surrounding region) are non-sterile. As will be seen, the discussion below includes at least a first communication node associated with the stylet 130, and a second communication node associated with the TLS sensor 50 that operably connect with one another to enable ECG signal data transfer therebetween.

Figure 13A:
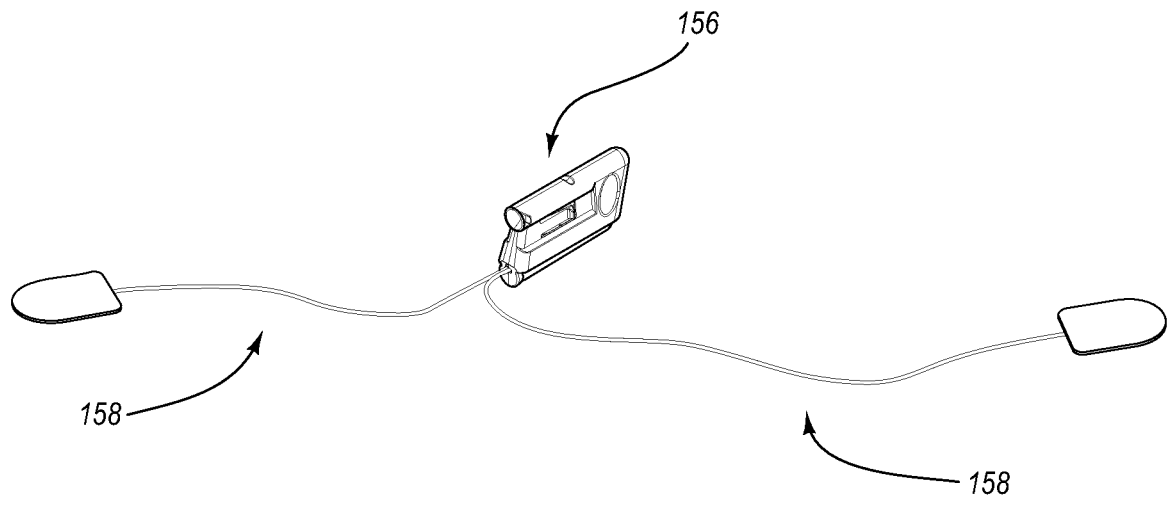
FIGS. 13A-13D are various views of a fin connector assembly for use with the integrated system of FIG. 9.
Figure 13B:
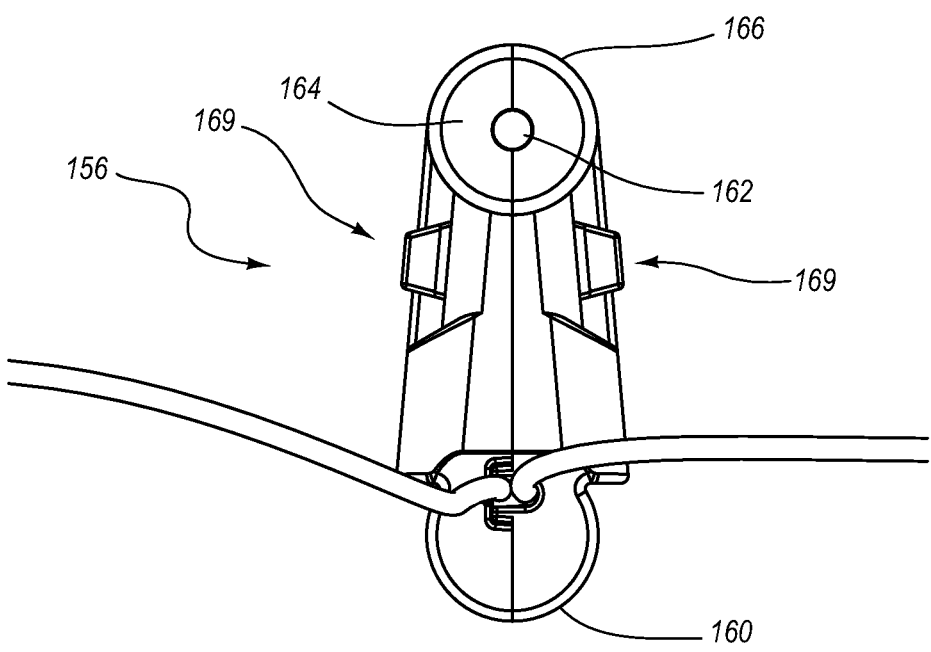
Figure 13C:
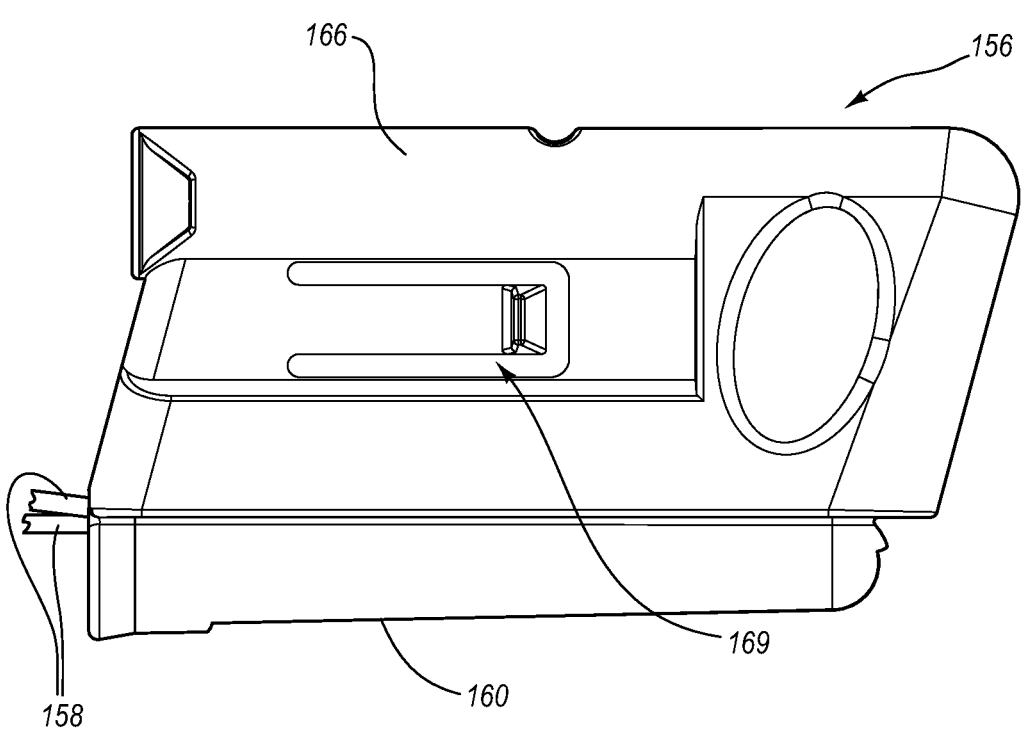
Figure 13D:
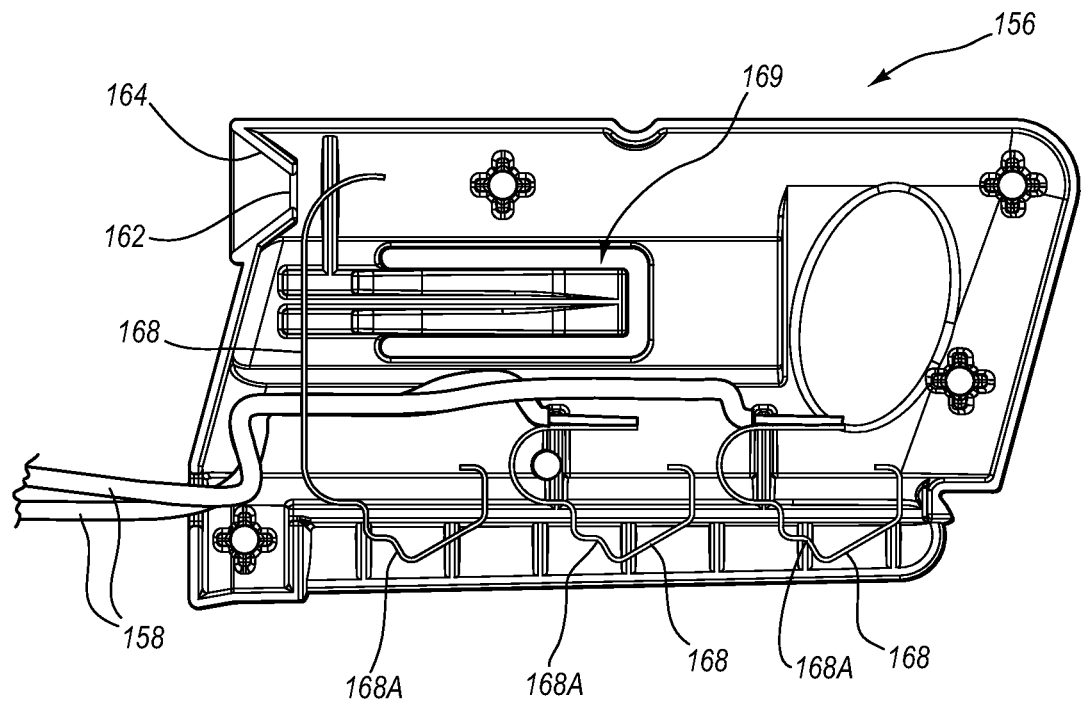
Figure 13E:
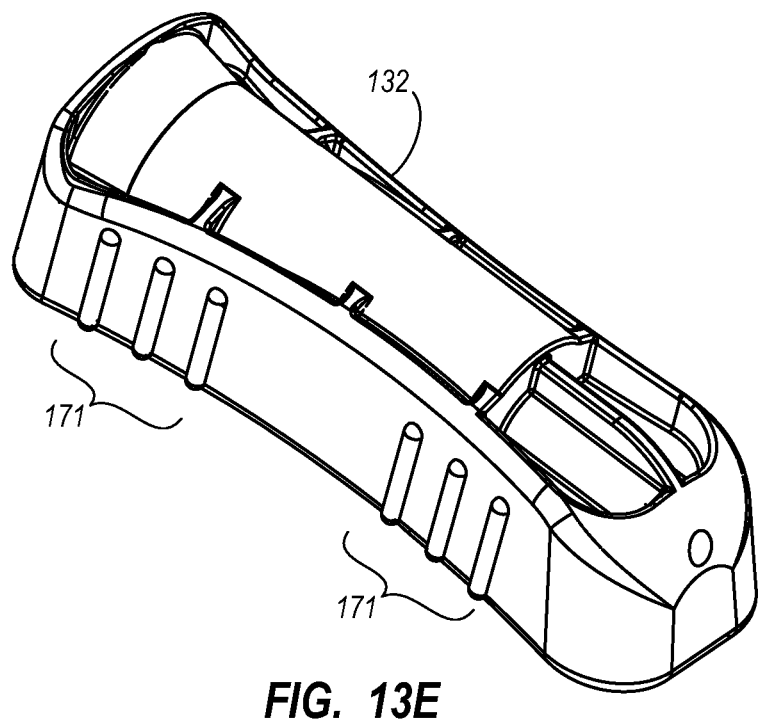
FIGS. 13E-13F are various views of a tether connector for use with the fin connector assembly shown in FIGS. 13A-13D.
Figure 13F:
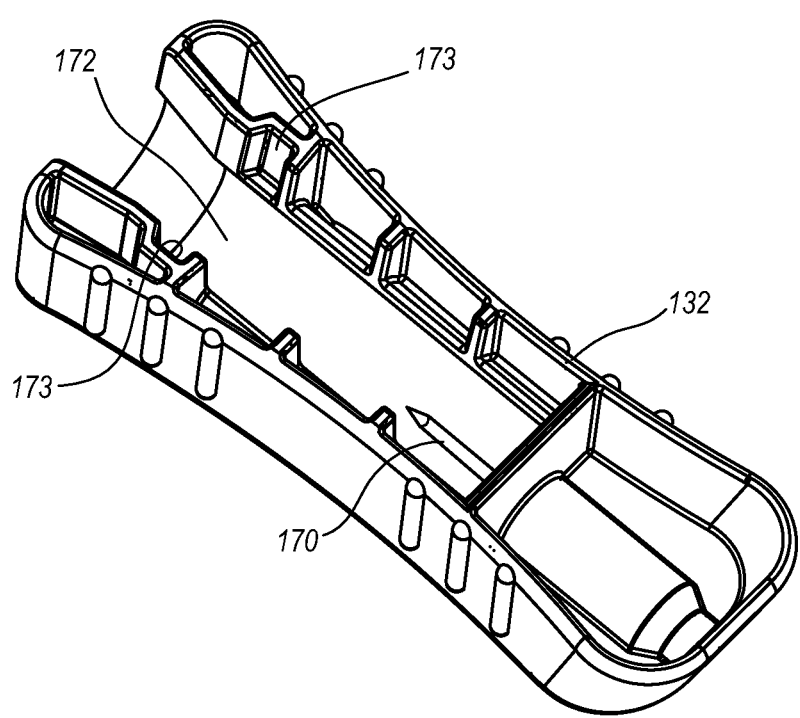
Figure 14A:
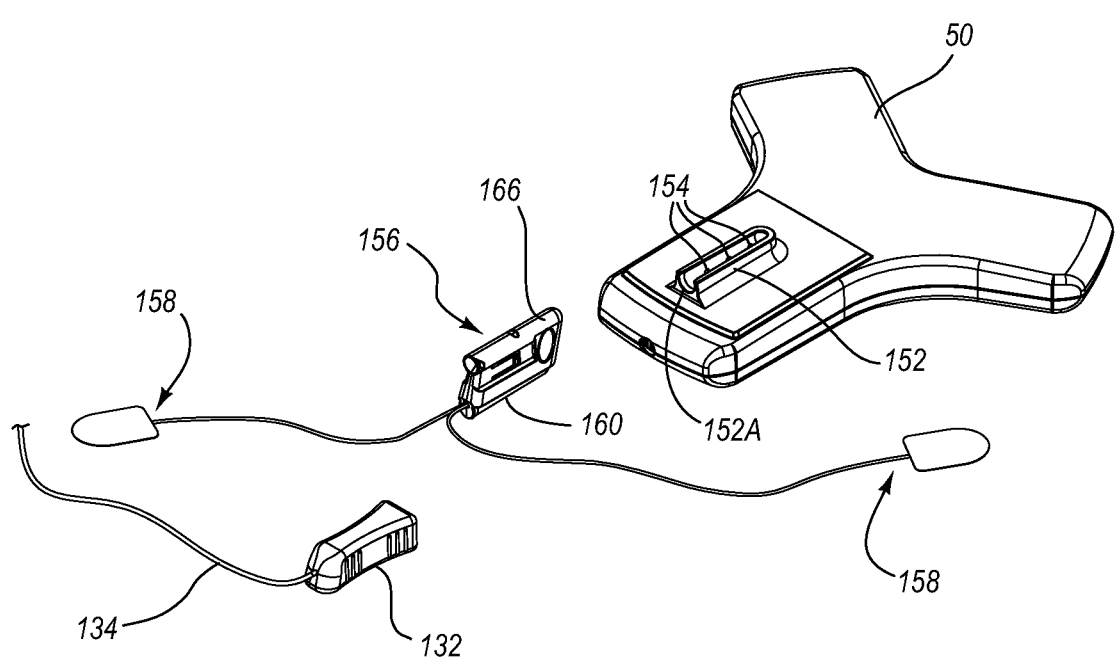
FIGS. 14A-14C are views showing the connection of a stylet tether and fin connector to a sensor of the integrated system of FIG. 9.
Figure 14B:
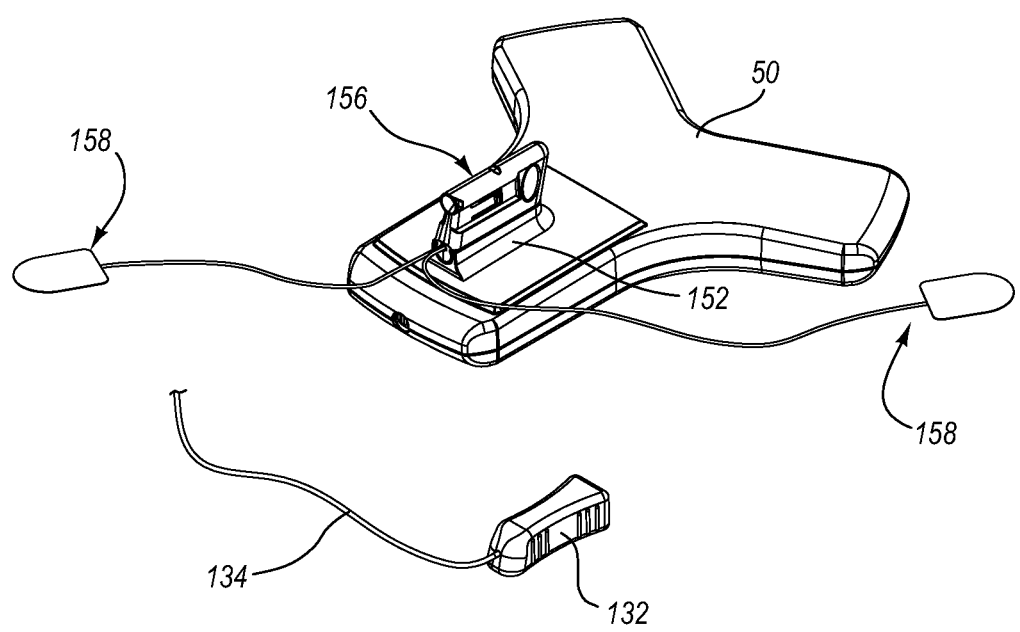
Figure 14C:
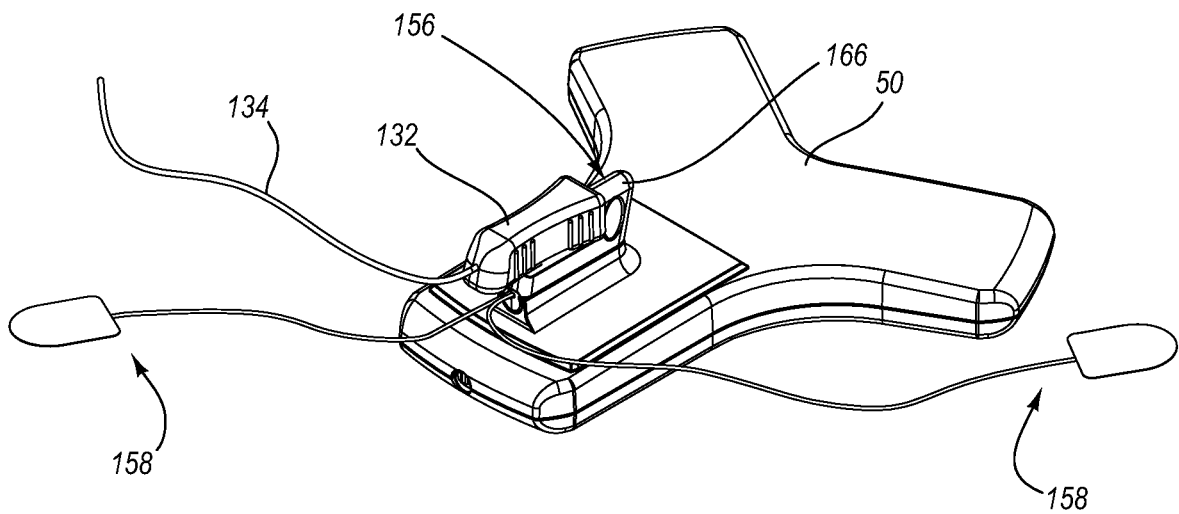
Figure 15:
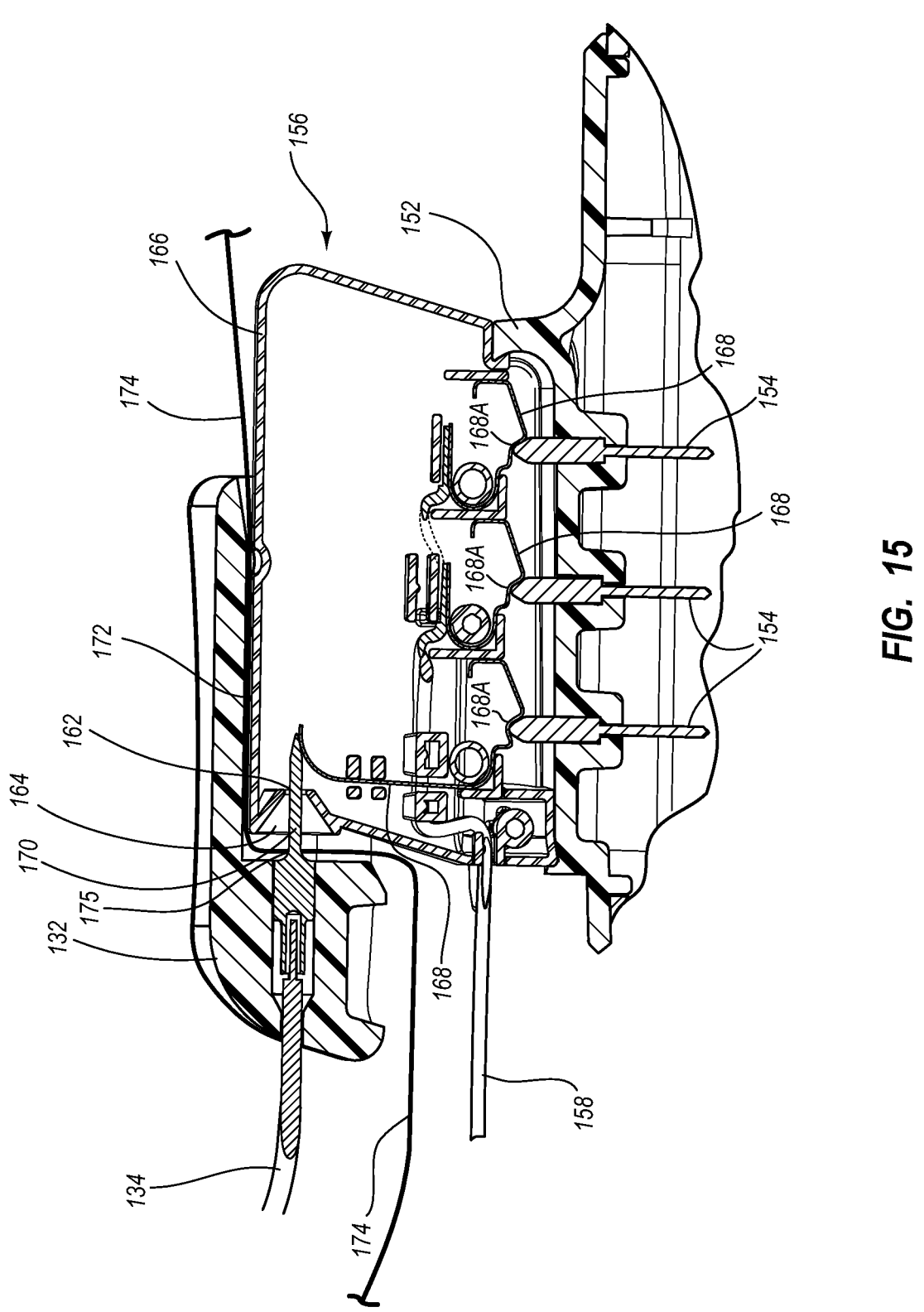
FIG. 15 is a cross sectional view of the connection of the stylet tether, fin connector, and sensor shown in FIG. 14C.

One embodiment addressing the passage of ECG signal data from the sterile field to the non-sterile field without compromising the sterility of the former is depicted in FIGS. 13A-15, which depict a "through-drape" implementation also referred to as a "shark fin" implementation. In particular, FIG. 14A shows the TLS sensor 50 as described above for placement on the chest of the patient during a catheter insertion procedure. The TLS sensor 50 includes on a top surface thereof a connector base 152 defining a channel 152A in which are disposed three electrical base contacts 154. A fin connector 156, also shown in FIGS. 13A-13D, is sized to be slidingly received by the channel 152A of the connector base 152, as shown in FIGS. 14B and 15. Two ECG lead/electrode pairs 158 extend from the fin connector 156 for placement on the shoulder and torso or other suitable external locations on the patient body. The drape-piercing tether connector 132 is configured to slidingly mate with a portion of the fin connector 156, as will be described further below, to complete a conductive pathway from the stylet 120, through the sterile field to the TLS sensor 50.

FIGS. 13A-13D show further aspects of the fin connector 156. In particular, the fin connector 156 defines a lower barrel portion 160 that is sized to be received in the channel 152A of the connector base 152 (FIGS. 14B, 15). A hole 162 surrounded by a centering cone 164 is included on a back end of an upper barrel portion 166. The upper barrel portion 166 is sized to receive the tether connector 132 of the stylet 130 (FIGS. 14C, 15) such that a pin contact 170 extending into a channel 172 of the tether connector 132 (FIG. 15) is guided by the centering hole until it seats within the hole 162 of the fin connector 156, thus interconnecting the tether connector with the fin connector. An engagement feature, such as the engagement feature 169 shown in FIGS. 13C and 13D, can be included on either side of the fin connector 156 to engage with corresponding detents 173 (FIG. 13F) on the tether connector 132 to assist with maintaining a mating between the two components. If disengagement between the two components is desired, a sufficient reverse pull force is applied to the tether connector 132 while holding or securing the fin connector 156 to prevent its removal from the channel 152A of the connector base 152.

FIG. 13D shows that the fin connector 156 includes a plurality of electrical contacts 168. In the present embodiment, three contacts 168 are included: the two forward-most contact each electrically connecting with a terminal end of one of the ECG leads 158, and the rear contact extending into axial proximity of the hole 162 so as to electrically connect with the pin contact 170 of the tether connector 132 when the latter is mated with the fin connector 156 (FIG. 15). A bottom portion of each contact 168 of the fin connector 156 is positioned to electrically connect with a corresponding one of the base contacts 154 of the TLS sensor connector base 152. In one embodiment, the bottom portion of each contact 168 includes a retention feature, such as an indentation 168A. So configured, each contact 168 can resiliently engage a respective one of the base contacts 154 when the fin connector 156 is received by the TLS sensor connector base 152 such that a tip of each base contact is received in the respective indentation 168A. This configuration provides an additional securement (FIG. 15) to assist in preventing premature separation of the fin connector 156 from the connector base 152. Note that many different retention features between the base contacts 154 and the fin contacts 168 can be included in addition to what is shown and described herein.

FIGS. 13E and 13F depict various details of the tether connector 132 according to one embodiment, including the tether connector channel 172, the pin contact 170 disposed in the channel, and detents 173 for removably engaging the engagement features 169 of the fin connector 156 (FIGS. 13A-13D), as described above. FIG. 13E further shows a plurality of gripping features 171 as an example of structure that can be included to assist the clinician in grasping the tether connector 132.

FIG. 14B shows a first connection stage for interconnecting the above described components, wherein the fin connector 156 is removably mated with the TLS sensor connector base 152 by the sliding engagement of the lower barrel portion 160 of the fin connector with the connector base channel 152A. This engagement electrically connects the connector base contacts 154 with the corresponding fin contacts 168 (FIG. 15).

FIG. 14C shows a second connection stage, wherein the tether connector 132 is removably mated with the fin connector 156 by the sliding engagement of the tether connector channel 172 with the upper barrel portion 166 of the fin connector. This engagement electrically connects the tether connector pin contact 170 with the back contact 168 of the fin connector 156, as best seen in FIG. 15. In the present embodiment, the horizontal sliding movement of the tether connector 132 with respect to the fin connector 156 is in the same engagement direction as when the fin connector is slidably mated to the sensor connector base channel 152A (FIG. 14B). In one embodiment, one or both of the stylet 130/tether connector 132 and the fin connector 156 are disposable. Also, the tether connector in one embodiment can be mated to the fin connector after the fin connector has been mated to the TLS sensor, while in another embodiment the tether connector can be first mated to the fin connector through the surgical drape before the fin connector is mated to the TLS sensor.

In the connection scheme shown in FIG. 14C, the stylet 130 is operably connected to the TLS sensor 50 via the tether connector 132, thus enabling the ECG sensor assembly of the stylet to communicate ECG signals to the TLS sensor. In addition, the ECG lead/electrode pairs 158 are operably connected to the TLS sensor 50. In one embodiment, therefore, the tether connector 132 is referred to as a first communication node for the stylet 130, while the fin connector 156 is referred to as a second communication node for the TLS sensor 50. As will be seen, various other first and second communication nodes can be employed to enable the establishment of a conductive pathway between the ECG sensor assembly and the TLS sensor or other system component.

Note that various other connective schemes and structures can be employed to establish operable communication between the stylet and the TLS sensor. For instance, the tether connector can use a slicing contact instead of a pin contact to pierce the drape. Or, the fin connector can be integrally formed with the TLS sensor. These and other configurations are therefore embraced within the scope of embodiments of the present disclosure.

As mentioned, a drape 174 is often placed over the patient 70 and employed as a barrier to separate a sterile field of the patient, e.g., areas and components above the drape and proximate to the insertion site 73 (including the catheter 72, the stylet 130, and tether 134 (FIG. 10)) from non-sterile areas outside of the sterile field, e.g., areas and components below the drape, including the patient's chest, the sensor 50 (FIG. 10) placed on the chest, and regions immediately surrounding the patient 70, also referred to herein as a non-sterile field. As seen in FIG. 15, the sterile drape 174 used during catheter placement to establish the sterile field is interposed between the interconnection of the tether connector 132 with the fin connector 156. As just described, the tether connector 132 includes the pin contact 170 that is configured to pierce the drape 174 when the two components are mated. This piercing forms a small hole, or perforation 175, in the sterile drape 174 that is occupied by the pin contact 170, thus minimizing the size of the drape perforation by the pin contact. Moreover, the fit between the tether connector 132 and the fin connector 156 is such that the perforation in sterile drape made by piercing of the pin contact 170 is enclosed by the tether connector channel 172, thus preserving the sterility of the drape and preventing a breach in the drape that could compromise the sterile barrier established thereby. The tether connector channel 172 is shaped and configured so as to fold the sterile drape 174 down prior to piercing by the pin contact 170 such that the pin contact does not pierce the drape until it is disposed proximate the hole 162 of the fin connector 156 and such that the drape does not bunch up within the channel. It is noted here that the tether connector 132 and fin connector 156 are configured so as to facilitate alignment therebetween blindly through the opaque sterile drape 174, i.e., via palpation absent visualization by the clinician of both components.

As already mentioned, note further that the fin contacts 168 of the fin connector 156 as shown in FIG. 15 include the indentations 168A, which are configured to mate with the sensor base contacts 154 in such a way as to assist in retaining the fin connector in engagement with the sensor base channel 152A. This in turn reduces the need for additional apparatus to secure the fin connector 156 to the TLS sensor 50. In other embodiments, retention features that are separate from the electrical contacts can be employed to assist in retaining the fin connector in engagement with the sensor base channel. In one embodiment, the base contacts 154 can be configured as pogo pins such that they are vertically displaceable to assist in retaining the fin connector 156.

Figure 16:
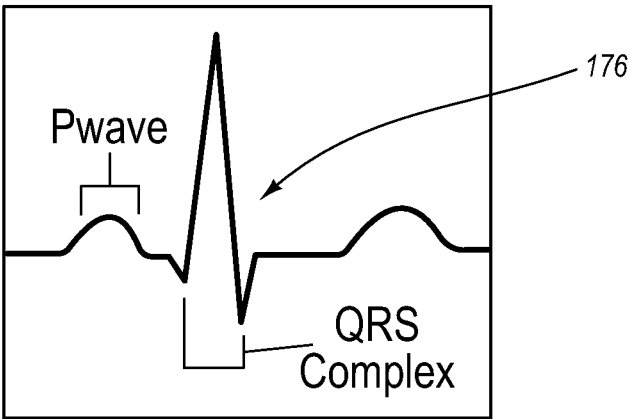
FIG. 16 is simplified view of an ECG trace of a patient.

FIG. 16 shows a typical ECG waveform 176 of a patient, including a P-wave and a QRS complex. Generally, and with respect to the present system 10, the amplitude of the P-wave varies as a function of distance of the ECG sensor assembly from the SA node, which produces the P-wave of the waveform 176. A clinician can use this relationship in determining when the catheter tip is properly positioned proximate the heart. For instance, in one implementation the catheter tip is desirably placed within the lower one-third (⅓rd) of the superior vena cava, as has been discussed. The ECG data detected by the ECG sensor assembly of the stylet 130 is used to reproduce waveforms such as the waveform 176, for depiction on the display 30 of the system 10 during ECG mode.

Figure 17:
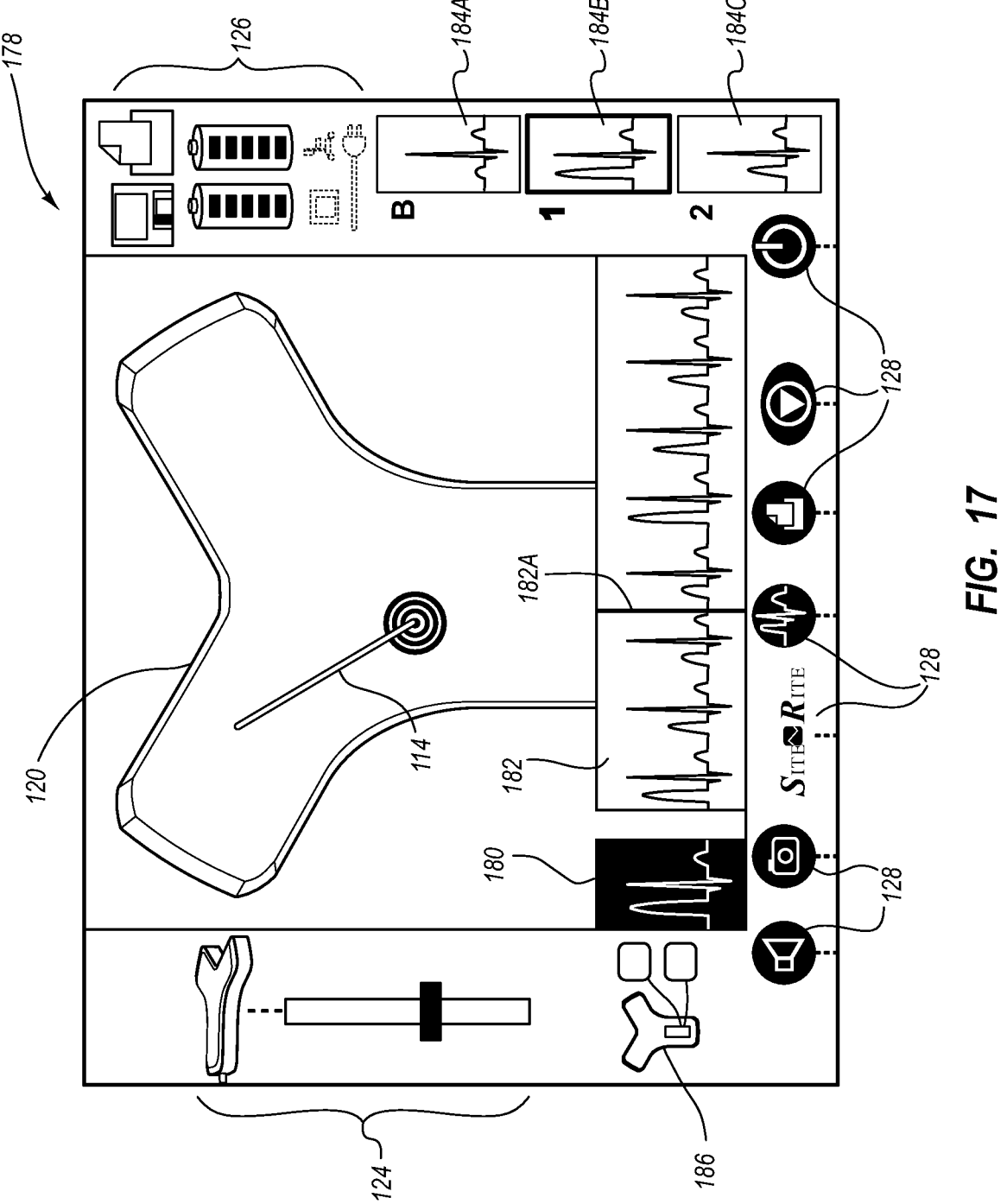
FIG. 17 is a screenshot of an image depicted on a display of the integrated system of FIG. 9 during catheter tip placement procedures.

Reference is now made to FIG. 17 in describing display aspects of ECG signal data on the display 30 when the system 10 is in ECG mode, the third modality described further above, according to one embodiment. The screenshot 178 of the display 30 includes elements of the TLS modality, including a representative image 120 of the TLS sensor 50, with the icon 114 corresponding to the position of the distal end of the stylet 130 during transit through the patient vasculature. The screenshot 178 further includes a window 180 in which the current ECG waveform captured by the ECG sensor assembly of the stylet 130 and processed by the system 10 is displayed. The window 180 is continually refreshed as new waveforms are detected.

Window 182 includes a successive depiction of the most recent detected ECG waveforms, and includes a refresh bar 182A, which moves laterally to refresh the waveforms as they are detected. Window 184A is used to display a baseline ECG waveform, captured before the ECG sensor assembly is brought into proximity with the SA node, for comparison purposes to assist the clinician in determining when the desired catheter tip location has been achieved. Windows 184B and 184C can be filled by user-selected detected ECG waveforms when the user pushes a predetermined button on the probe 40 or the console button interface 32. The waveforms in the windows 184B and 184C remain until overwritten by new waveforms as a result of user selection via button pushes or other input. As in previous modes, the depth scale 124, status/action indicia 126, and button icons 128 are included on the display 30. An integrity indicator 186 is also included on the display 30 to give an indication of whether the ECG lead/electrode pairs 158 are operably connected to the TLS sensor 50 and the patient 70.

As seen above, therefore, the display 30 depicts in one embodiment elements of both the TLS and ECG modalities simultaneously on a single screen, thus offering the clinician ample data to assist in placing the catheter distal tip in a desired position. Note further that in one embodiment a printout of the screenshot or selected ECG or TLS data can be saved, printed, or otherwise preserved by the system 10 to enable documentation of proper catheter placement.

Although the embodiments described herein relate to a particular configuration of a catheter, such as a PICC or CVC, such embodiments are merely exemplary. Accordingly, the principles of the present invention can be extended to catheters of many different configurations and designs.

FIGS. 18-19B depict examples of contact engagement configurations for the tether connector 132 and fin connector 156. Specifically, FIG. 18 depicts the fin contacts 168 of the fin connector 156 according to one embodiment, wherein the rear contact includes a spring clip configuration 168B for receiving the pin contact 170 (FIG. 15) of the tether connector 132 via the centering cone 164 or other aperture defined in the fin connector. FIGS. 19A and 19B depict an engagement scheme according to another embodiment, wherein the pin contact 170 of the tether connector 132 includes a barbed feature 170A that, when inserted into the centering cone 164 or other aperture of the fin connector 156, engages a shoulder 168C defined on the rear fin contact 168 of the fin connector so as to help prevent premature removal of the pin contact from the fin connector. These embodiments thus serve as non-limiting examples of a variety of contact configurations that can be included with the fin connector 156, the sensor connector base 152, and the tether connector 132. Note that unless referred to as otherwise, the contacts described herein are understood to include electrical contacts used in establishing a conductive pathway.

The embodiments to be described below in connection with FIGS. 20A-32 each depict an example connection scheme as a means for establishing a conductive or other communication pathway between a patient's sterile field and a non-sterile field, i.e., areas outside of the sterile field. Thus, the embodiments described herein serve as examples of structure, material, and/or compositions corresponding to the means for establishing a conductive or other communication pathway. In particular, various embodiments described herein disclose examples for breaching or otherwise circumventing a sterile barrier separating the sterile field from the non-sterile field so as to provide at least a portion of the conductive pathway for the passage of ECG signals from a sensing component such as the ECG sensor assembly of the stylet 130 to the sensor 50, also referred to herein as a TLS sensor or chest sensor, or other suitable data-receiving component of the system 10. Note that these embodiments are merely examples of a variety of means for establishing such a conductive or other communication pathway, and are not to be considered limiting of the scope of the present disclosure. It is therefore appreciated that the means for establishing a conductive or other communication pathway can be employed for transferring ECG signals or other information, electrical signals, optical signals, etc.

As will be seen, many of the embodiments to be described include a tether connector, also referred to herein as a first communication node, which is operably connected to the stylet 130 and included in the sterile field, the tether connector is configured to operably attach to a connector included on the sensor 50 or other suitable component of the system 10, also referred to herein as a second communications node, which is disposed outside of the sterile field. Note, however, that the first communication node and second communication node are contemplated as generally referring to various connector interfaces that provide a conductive pathway from the sterile field to the non-sterile field to enable the passage of ECG signals as described above. It is appreciated that the conductive pathway is a communication pathway and includes an electrical pathway, an optical pathway, etc. Further, the communication node connection schemes described and contemplated herein can be employed with systems involving the use of modalities exclusive of ECG signals for navigation or placement of a catheter or other medical device.

Note further that the embodiments to follow that describe configurations for breaching a drape or other non-transparent sterile barrier are configured such that location of a communication node disposed out-of-sight under the drape/barrier is facilitated by palpation of the clinician, thus easing location and connection of the first and second communication nodes. Also, many of the connector configurations described herein can be configured as one-use, disposable components so as to minimize concerns with infection.

Figure 20A:
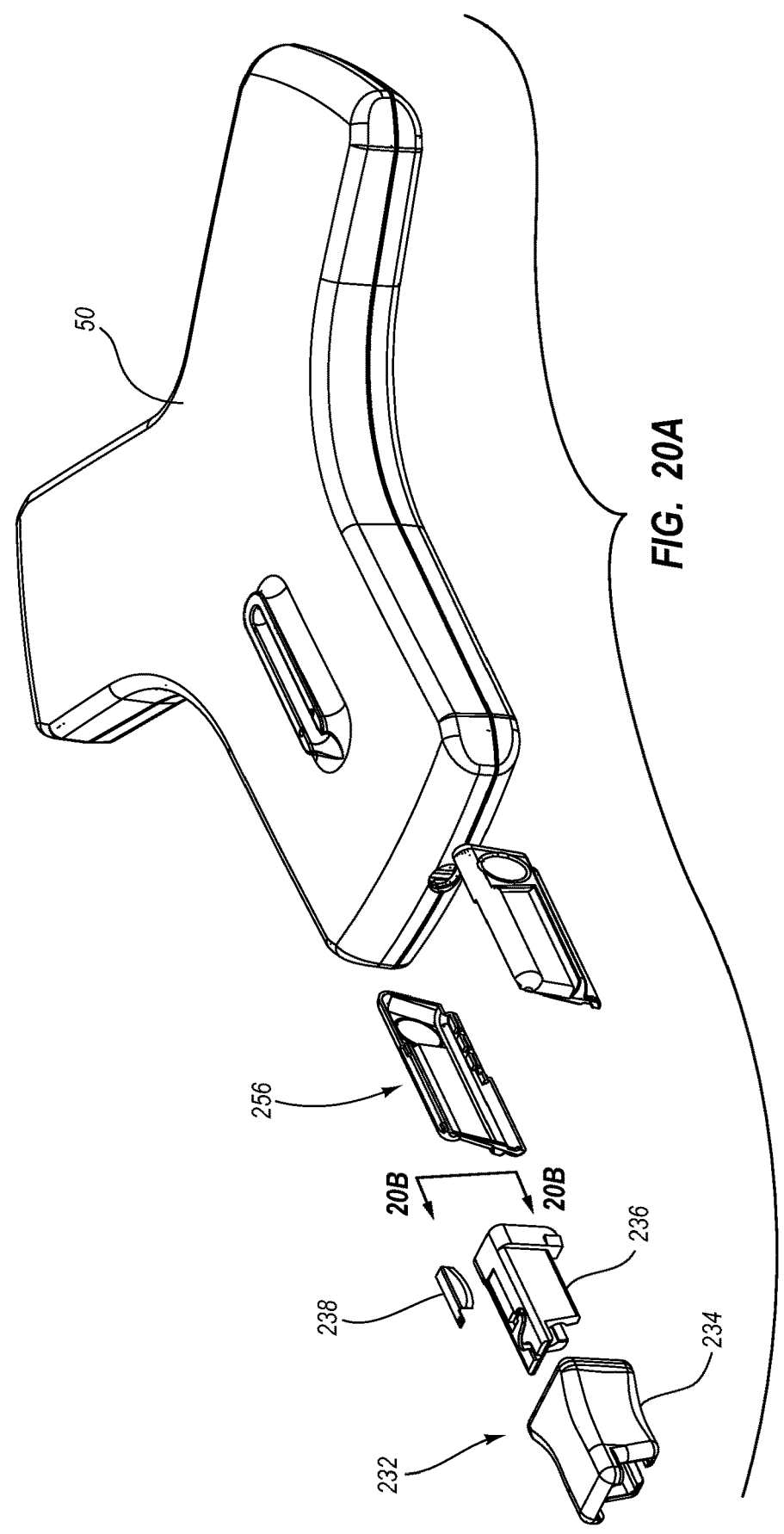
FIGS. 20A-20C are various views of one embodiment of a fin connector and a tether connector for establishing a signal pathway through a sterile barrier in connection with use of the integrated system described herein.
Figure 20B:
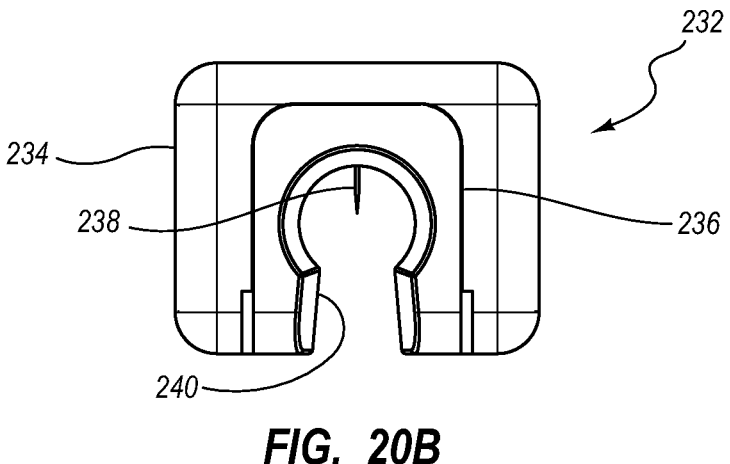
Figure 20C:
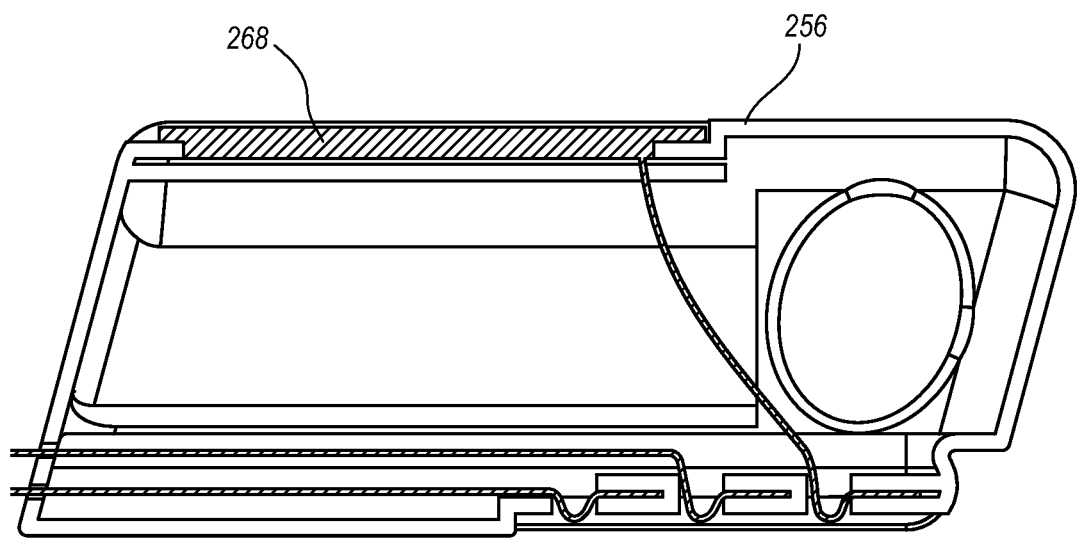

Reference is now made to FIGS. 20A-20C, which depict a connection scheme as a means for establishing a conductive pathway between sterile and non-sterile fields, according to one embodiment. In particular, FIGS. 20A-20C depict a tether connector 232 that includes an outer housing 234 and a blade holder 236 that attaches to the outer housing. A blade contact 238 is secured by the blade holder 236 such that the blade contact extends into a channel 240 of the tether connector. The blade contact 238 serves to create a slice perforation in a drape that is interposed between the tether connector and the fin connector 256 when the tether connector 232 is slid on to engage the fin connector in the manner described in previous embodiments. As before, the outer housing 234 of the tether connector envelops and protects the perforation so as to prevent contamination and compromise of the sterile field.

FIG. 20C shows that a fin connector 256 includes a fin contact 268 that is configured to physically interconnect with the blade contact 238 when the tether connector is slid on to the fin connector 256, thus establishing a conductive pathway through the sheath so as to enable ECG signals from an ECG sensing component, i.e., the ECG sensor assembly described above for instance, to pass to the sensor 50 via the blade contact 238/fin contact 268 engagement. Note that the particular configuration of the blade and fin contacts can be varied from what is described herein. For instance, the tether connector can include two or more blades or contacts for engagement with corresponding fin contacts to enable multiple conductive pathways to be established, if desired. The engagement surfaces of the tether connector and the fin connector can also vary from what is shown and described. In one embodiment, a light source can be included with the fin connector or other connectors as described herein so as to provide illumination through the drape 174 and provide visual assistance in locating the fin connector for interconnection with the tether connector.

Figures 21A, 21B:
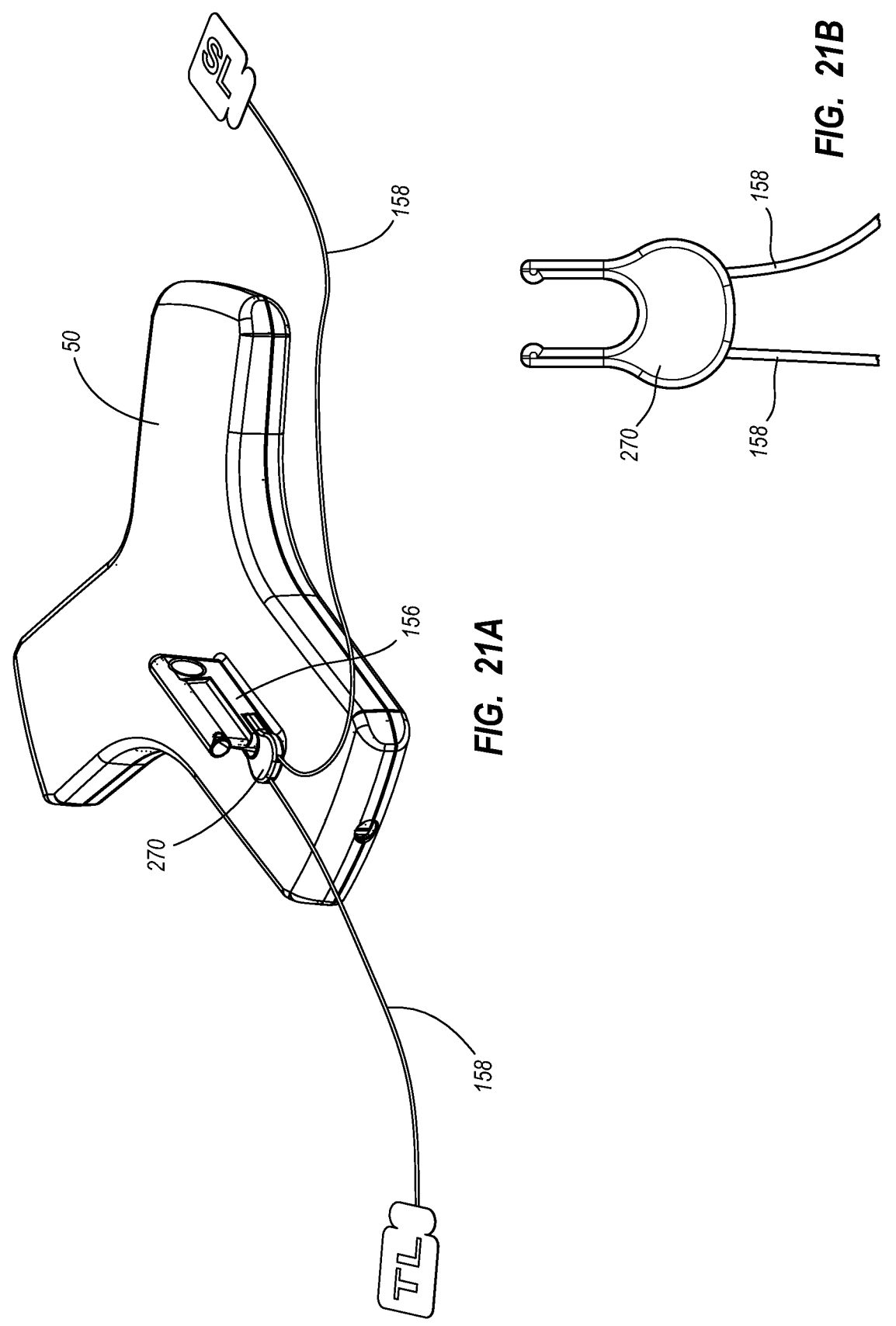
FIGS. 21A and 21B are various views of a connector for electrically connecting ECG electrodes to a sensor of the integrated system, according to one embodiment.

As seen in FIGS. 14A and 14B, in one embodiment the ECG leads 158 are permanently connected to the fin connector 156. FIG. 21A depicts another possible embodiment, wherein the ECG leads are removably attached to the fin connector 156 via a connector, such as a horseshoe connector 270, best seen in FIG. 21B. FIG. 21A further shows that the fin connector 156 is permanently attached to the sensor 50. These and other variations in the connective schemes of the various components of the system 10 are therefore contemplated as falling within the scope of the present disclosure. In another embodiment, the electrode of each lead is removably attachable from the lead, such as via a snap connection, for instance.

Figure 22A:
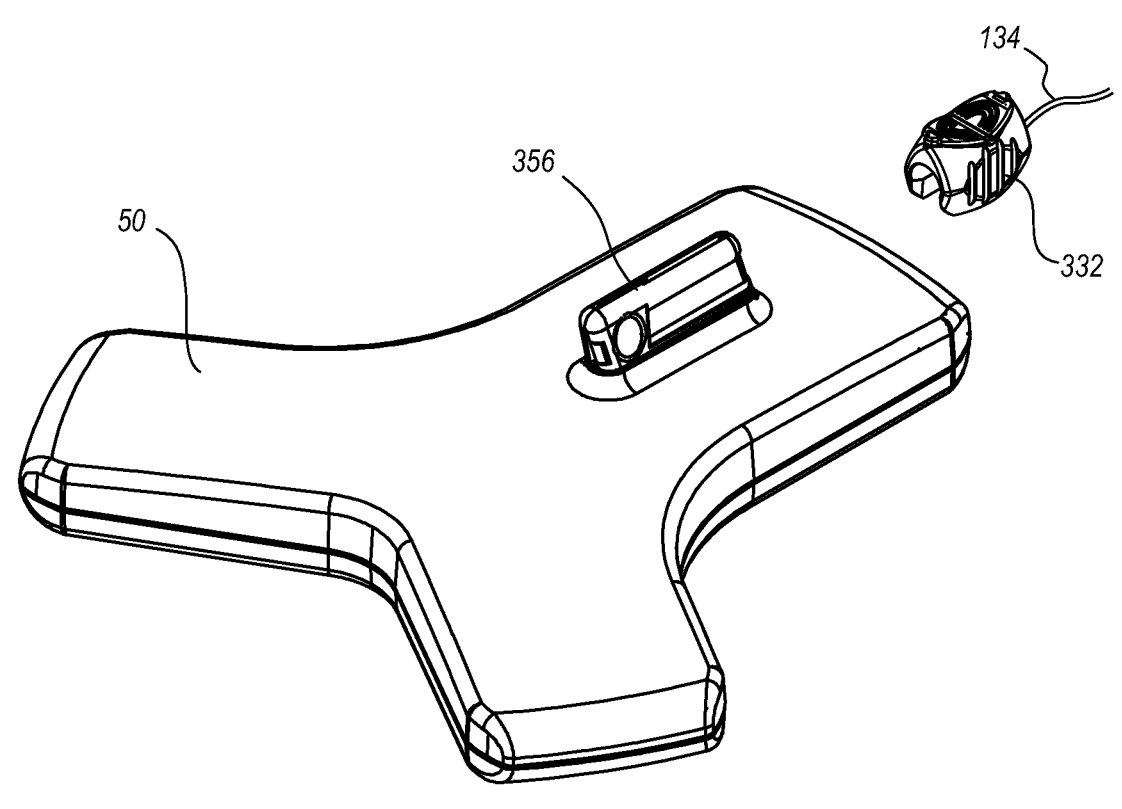
FIGS. 22A-22C are various views of one embodiment of a fin connector and a tether connector for establishing a signal pathway through a sterile barrier.
Figure 22B:
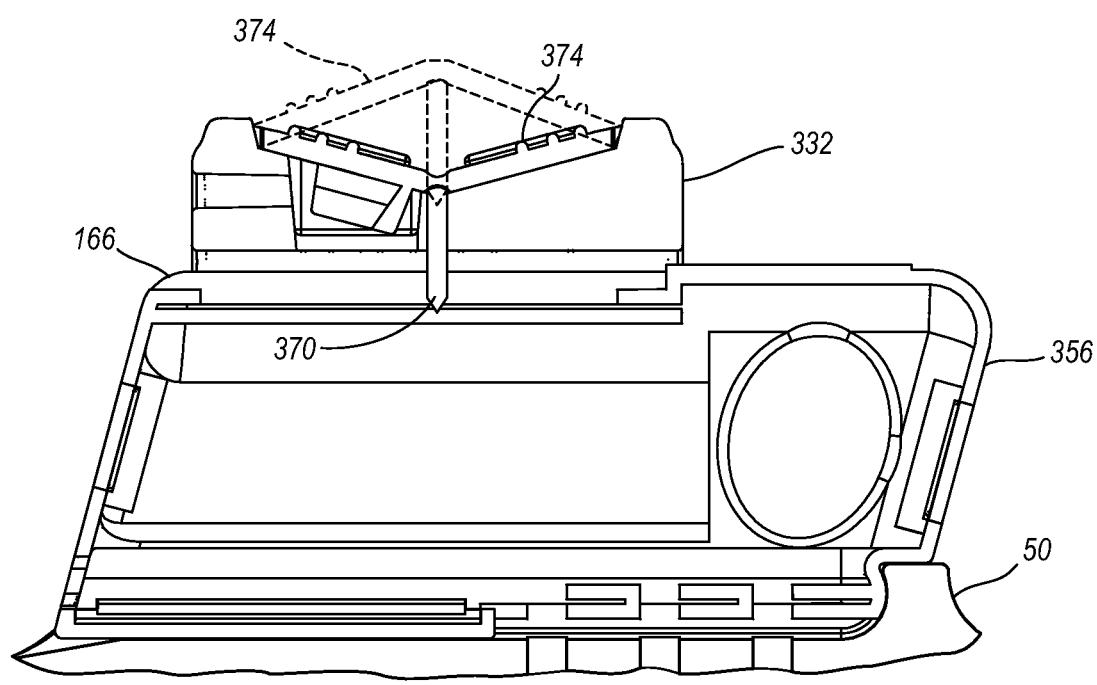
Figure 22C:
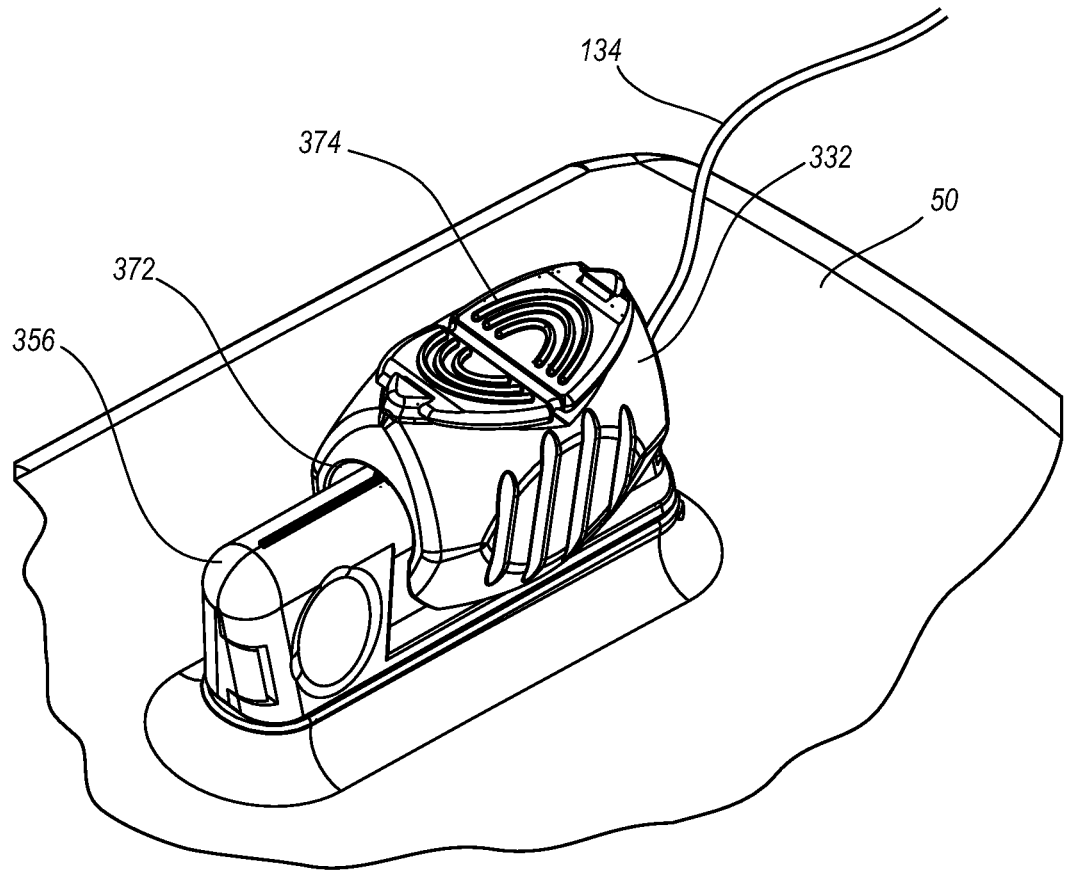

Reference is now made to FIGS. 22A-22C, which depict a connection scheme as a means for establishing a conductive pathway between sterile and non-sterile fields, according to one embodiment. In particular, FIGS. 22A-22C depict a tether connector 332 that includes a channel 372 for slidably engaging an upper barrel 166 of a fin connector 356 disposed on the sensor 50, in a manner similar to previous embodiments. The tether connector 332 includes a bi-positional top cap 374 to which is attached a pin contact 370 or other piercing contact.

The top cap 374 is positioned in an un-actuated first position, shown in phantom in FIG. 22B, when the tether connector 332 is first slid on to the fin connector 356. The drape, removed for clarity, is interposed between the upper barrel 166 of the fin connector 356 and the tether connector channel 372, similar to earlier embodiments. After the tether connector 332 is positioned on the fin connector 356, the top cap 374 can then be depressed by the clinician into an actuated second position shown in FIG. 22B, wherein the pin contact 370 is pressed downward through the drape and into operable engagement with a corresponding contact disposed in the fin connector 356. The tether connector 332 is thus positioned as shown in FIG. 22C. In addition to establishing a conductive path through the drape 174, this engagement of the pin contact 370 locks the tether connector 332 on to the fin connector 356 so as to prevent premature separation of the components.

Figure 23A:
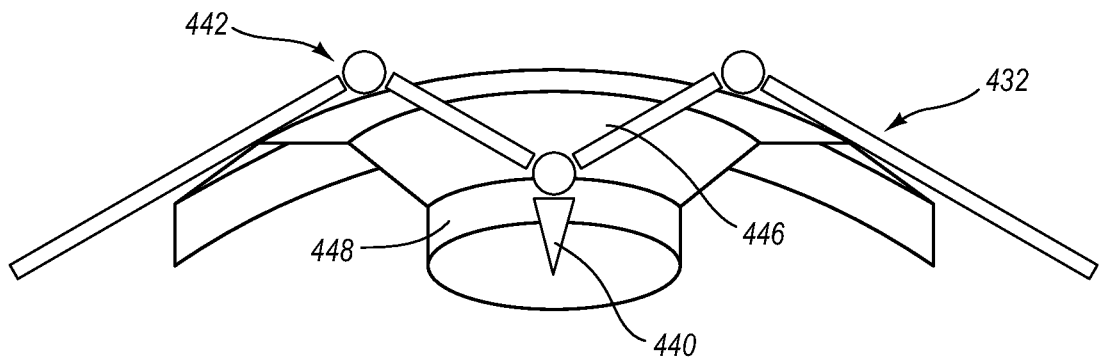
FIGS. 23A and 23B are cross sectional views of a connector system for establishing a signal pathway through a sterile barrier, according to one embodiment.
Figure 23B:
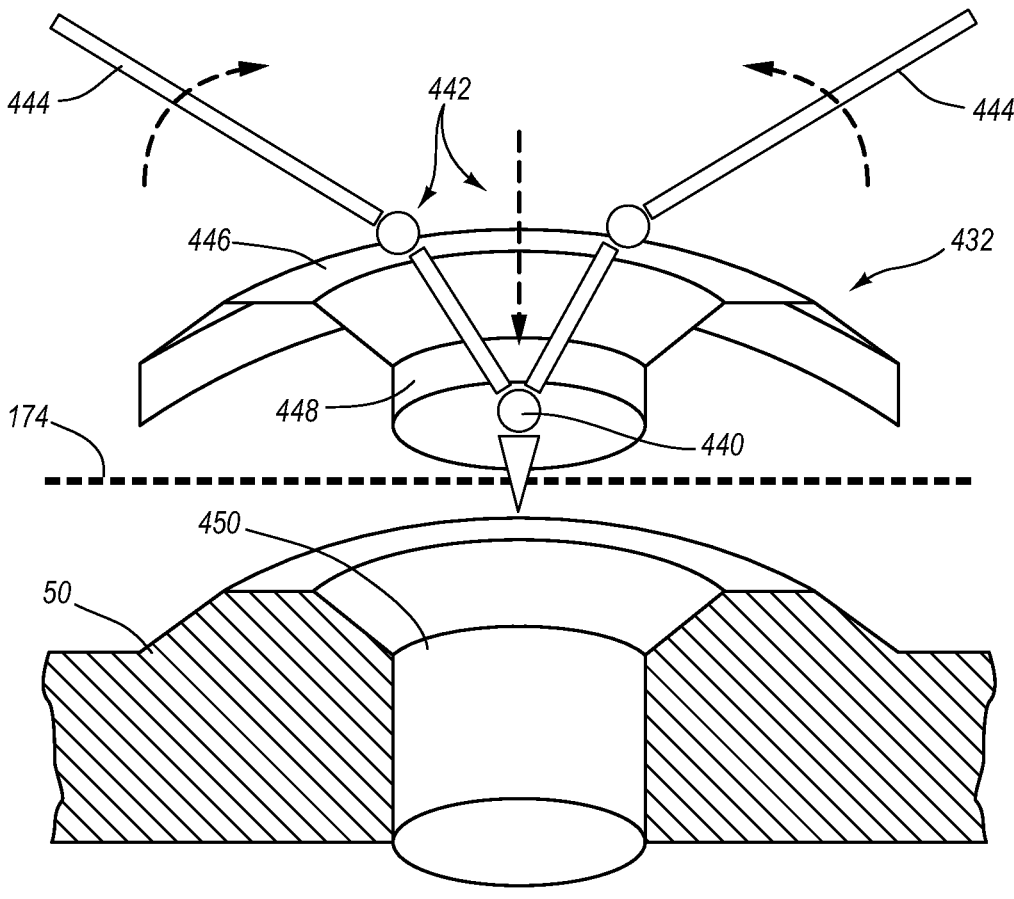

Reference is now made to FIGS. 23A and 23B, which depict a connection scheme as a means for establishing a conductive pathway between sterile and non-sterile fields, according to one embodiment. In particular, FIG. 23A depicts a tether connector 432 including a pin contact 440 or other suitable contact attached to an actuation assembly 442. The actuation assembly 442 includes lever arms for selectively lowering the pin contact 440 through an opening defined by a male end 448 of a housing 446 in which the actuation assembly is disposed. The male end 448 of the housing is configured to be received by a sensor connector receptacle 450 disposed on the sensor 50 or other suitable component of the system, such as a remote module operably connected to the sensor, for instance.

To interconnect the tether connector 432 to the sensor connector receptacle 450, the male end 448 of the tether connector 432 is brought, above the drape 174, into proximity with the receptacle 450. The actuation assembly 442 is then actuated by raising the lever arms 444, as shown in FIG. 23B. The pin contact 440 is forced downward through the drape 174, thus defining a perforation therein. The male end 448 can then be fully received into the sensor receptacle 450, wherein the pin contact 440 operably connects with a suitable contact of the sensor connector receptacle. The connector scheme shown in FIGS. 23A and 23B is useful for imposing a minimal downward force on the body of the patient during connector interconnection. Further, the actuation assembly 442 provides a predetermined force in connecting the first communication node (the tether connector 432) with the second communication node (the sensor connector receptacle 450), and thus does not rely on a clinician's estimation of force to establish the node connection. In another embodiment, the housing 446 and the sensor receptacle 450 can be aligned and mated before the actuation assembly 442 is actuated to pierce the contact 440 through the drape.

Figure 24:
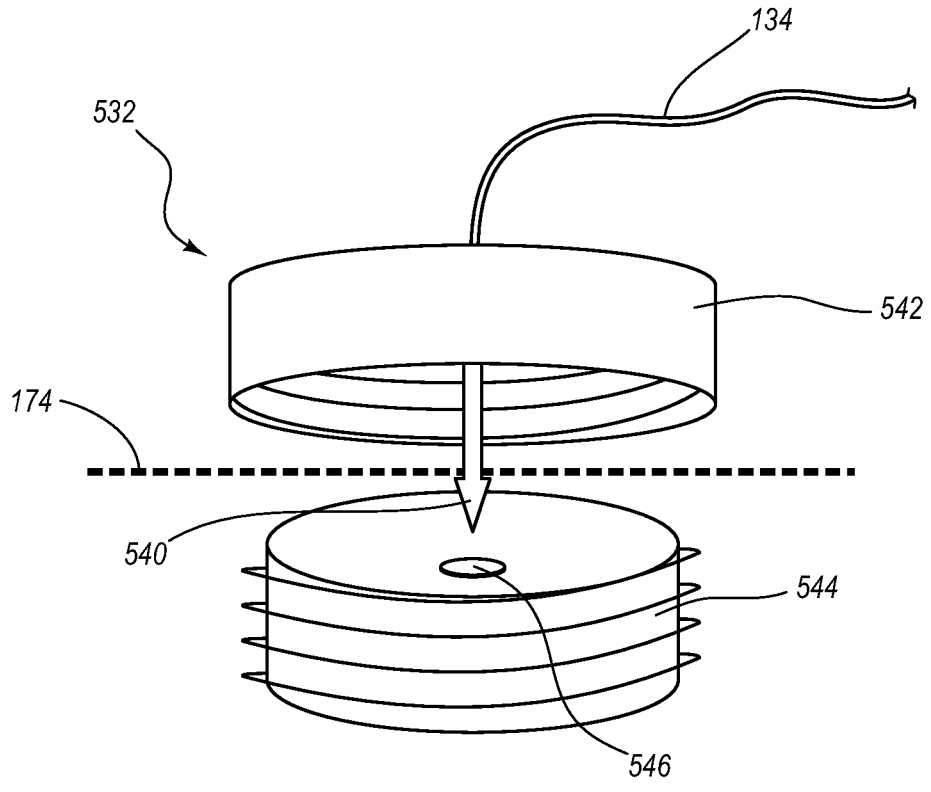
FIG. 24 is a simplified side view of a connector system for establishing a signal pathway through a sterile barrier, according to one embodiment.

Reference is now made to FIG. 24, which depicts a connection scheme as a means for establishing a conductive pathway between sterile and non-sterile fields, according to one embodiment. As in the embodiment shown in FIGS. 23A and 23B, the present interconnection scheme minimizes downward pressure on the body of the patient during interconnection of the nodes. As shown, a tether connector 532 includes a pin contact 540 or other suitable contact included with a threaded cap 542, which defines threads on an inside surface thereof. The threaded cap 542 is configured to threadingly receive a threaded base 544 disposed on the sensor 50 or other suitable component of the system, such as a remote module operably connected to the sensor, for instance. As before, the drape 174 is interposed therebetween.

To interconnect the tether connector 532 to the sensor 50, the threaded cap 542 of the tether connector is brought, above the drape 174, into proximity with the threaded base 544 and threaded on to the base. This causes the pin contact 540 to penetrate the drape 174, thus defining a perforation therein. Further threading of the cap 542 on to the base 544 causes the pin contact 540 to engage a contact receptacle 546 included in the base 544, thus operably interconnecting the two nodes. In one embodiment, the tether 134 is rotatably attached to the threaded cap 542 so as to prevent twisting of the tether during threading. The connector scheme shown in FIG. 24 is useful for imposing a minimal downward force on the body of the patient during connector interconnection as the force to join the two connectors is directed laterally with respect to the patient via the threading operation. Note further that a variety of thread configurations and locations, as well as different cap and base configurations, are contemplated by the present disclosure.

Figure 25A:
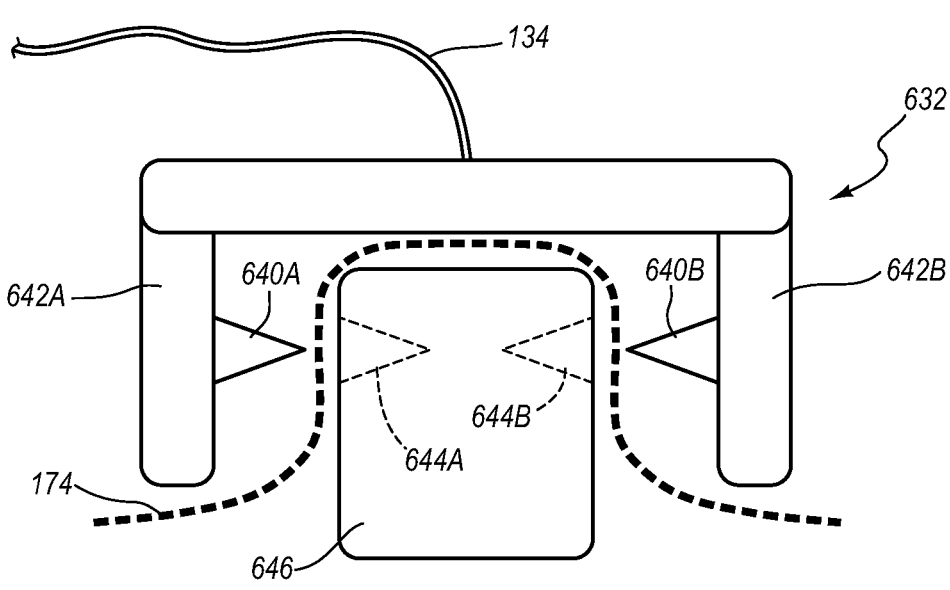
FIGS. 25A and 25B are simplified side views of a connector system for establishing a signal pathway through a sterile barrier, according to one embodiment.
Figure 25B:
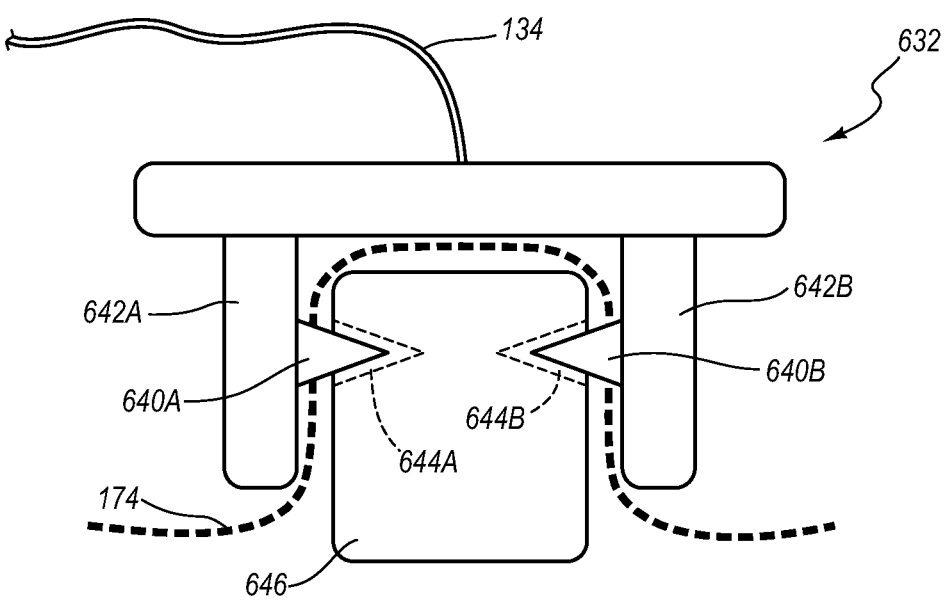

Reference is now made to FIGS. 25A and 25B, which depict a connection scheme as a means for establishing a conductive pathway between sterile and non-sterile fields, according to one embodiment. As in the previous embodiment, the present interconnection scheme minimizes downward pressure on the body of the patient during interconnection of the nodes. As depicted in FIGS. 25A and 25B, a tether connector 632 includes one or more piercing contacts, such as pin contacts 640A and 640B that are respectively included on slide arms 642A and 642B. One or more contact receptacles, such as contact receptacles 644A and 644B, are included on a portion of the sensor 50, such as a sensor fin 646, or other suitable system component. As before, the drape 174 is interposed between the tether connector 632 and the sensor fin 646 to serve as a sterile barrier.

To interconnect the tether connector 632 to the sensor fin 646, the tether connector is brought, above the drape 174, into proximity with the sensor fin such that the slide arms 642A and 642B straddle the sensor fin and such that the pin contacts 640A and 640B are aligned with corresponding contact receptacles 644A and 644B, as shown in FIG. 25A. The slide arms 642A and 642B are then slid toward one another such that the pin contacts 640A and 640B penetrate the drape 174, each defining a perforation therein. The slide arms 642A and 642B are slid inward until the pin contacts 640A and 640B seat within and operably connect with the corresponding contact receptacles 644A and 644B, as seen in FIG. 25B, thus interconnecting the two nodes. The connector scheme shown in FIGS. 25A and 25B is useful for imposing a minimal downward force on the body of the patient during connector interconnection as the force to join the two connectors is directed laterally with respect to the patient. Note that the particular configuration of the tether connector, the sensor fin, and the contacts can vary from what is explicitly described herein. For instance, in one embodiment the slide arms can be configured as bi-positional rocker arms that are connected in a see-saw configuration with respect to one another. Also, one, two, or more contacts can be included on the slide arms.

Figure 26A:
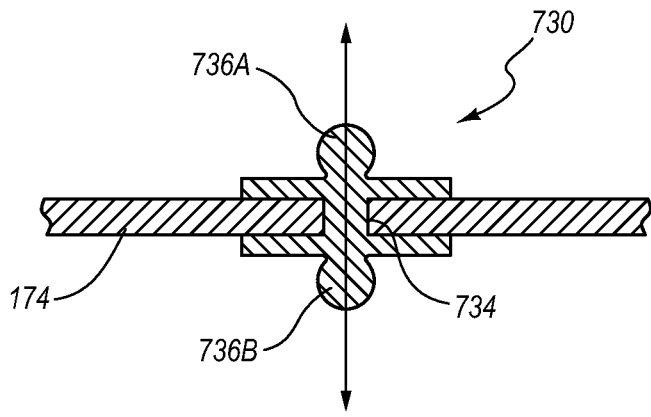
FIGS. 26A and 26B are cross sectional views of a connector system for establishing a signal pathway through a sterile barrier, according to one embodiment.
Figure 26B:
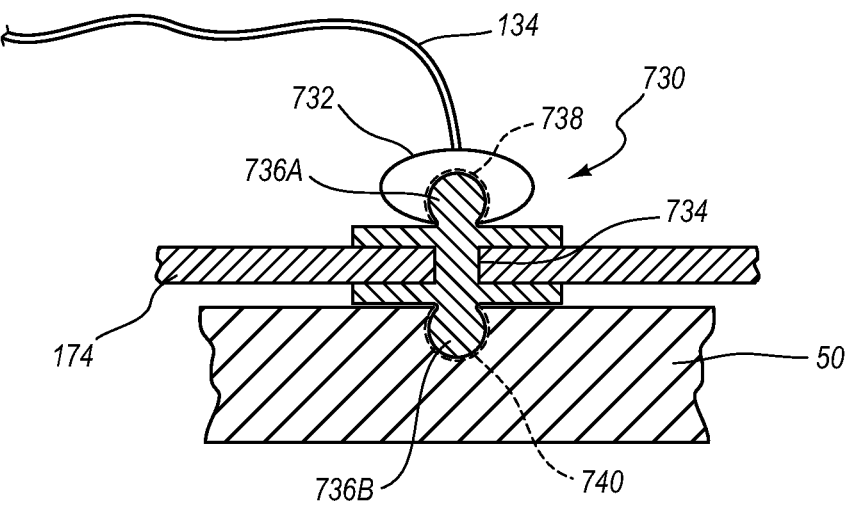

Reference is now made to FIGS. 26A and 26B, which depict a connection scheme as a means for establishing a conductive pathway between sterile and non-sterile fields, according to one embodiment. As shown, an integrated connector 730 is incorporated into the drape 174 so as to enable operable interconnection therethrough. In the illustrated embodiment, the integrated connector 730 includes a conductive base portion 734 from which extend mechanical connectors, such as snap balls 736A and 736B.

As shown in FIG. 26B, the integrated connector 730 is positioned in the drape 174 as to be connectable with both a suitable receptacle 738 of a tether connector 732 and a suitable receptacle 740 of the sensor 50 or other suitable component of the system 10. In particular, the tether connector 732 can be snap-attached to the integrated connector 730, after which the integrated connector can be attached to the sensor 50, thus providing a suitable pathway for signals from the ECG sensor assembly in the sterile field to be transmitted through the sterile barrier of the drape 174 to the sensor in the non-sterile field. It is appreciated that, in other embodiments, the integrated connector can include other configurations, such as different mechanical connectors, e.g., friction connectors, male/female connectors, etc., and as such the receptacles on the tether connector and sensor can likewise be modified to accommodate the different mechanical connectors. Also, the connective scheme described above can be reversed such that the receptacles are included on the integrated connector and the snap balls on the respective tether connector and sensor. Further, though presently depicted as a unitary component, the integrated connector in other embodiments can include two or more pieces that are attached to each other through a previously defined hole in the drape during manufacture thereof. These and other variations are therefore contemplated.

Figure 27:
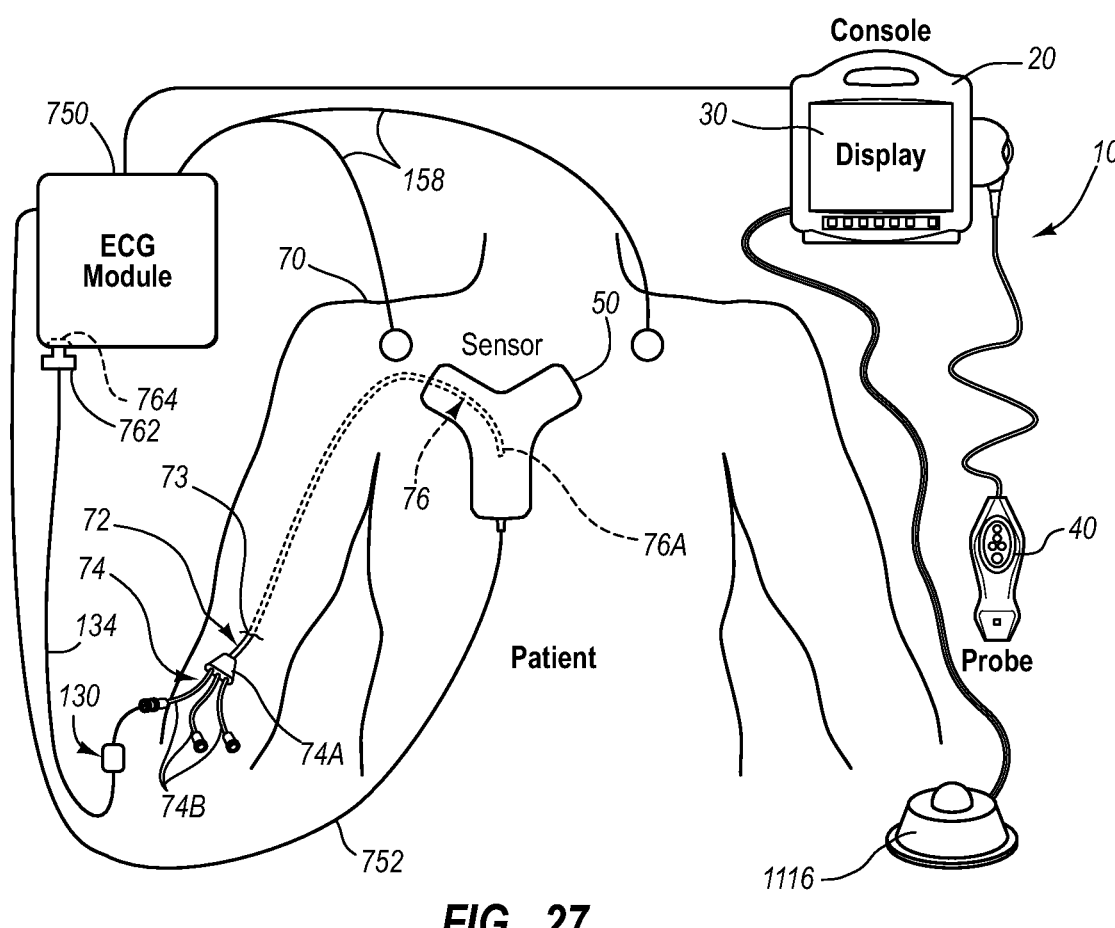
FIG. 27 is a simplified view of a connector system for establishing a signal pathway through a sterile barrier, according to one embodiment.

Reference is now made to FIG. 27, which depicts a connection scheme as a means for establishing a conductive pathway between sterile and non-sterile fields, according to one embodiment. In detail, FIG. 27 depicts an intermediate module, i.e., ECG module 750, disposed outside of the sterile field of the patient, which is operably connected to the sensor 50 of the system 10 via a sensor cable 752. The ECG module 750 is also operably connected to the ECG leads 158. In one embodiment, the ECG module 750 includes the circuitry and other components necessary for receipt and analysis of the ECG signal detected by the ECG sensor assembly of the stylet 130. As such, a conductive pathway is established between the stylet 130 and the ECG module 750 by traversing the sterile field of the patient. In the present embodiment, this is accomplished by a tether connector 762 of the tether 134.

As depicted in FIG. 27, the tether connector 762 operably attaches to a receptacle 764 of the ECG module 750. As shown, the tether connector 762 can include a sufficiently long handle that enables the clinician to attach the sterile tether connector to the receptacle 764 of the non-sterile ECG module 750 without touching the ECG module itself, thus preventing any compromise of the sterile field. In one embodiment, the handle of the tether connector 762 can include an extendable J-hook contact, for instance, that can operably connect to a suitable contact of the ECG module.

FIG. 27 further depicts a footswitch 1116, usable with any of the embodiments described herein, which may be placed on the ground near the feet of the clinician and employed to control selected aspects of system functionality during catheter placement procedures. For instance, in one embodiment, the footswitch 1116 can be used to freeze ECG waveform images on the system display 30, or to create a printout of the display during the procedure, or even after the procedure is complete so as to provide a record of final catheter placement. Of course, the design and functionality of the footswitch can be modified in many ways from what is explicitly shown and described herein.

Figure 28:
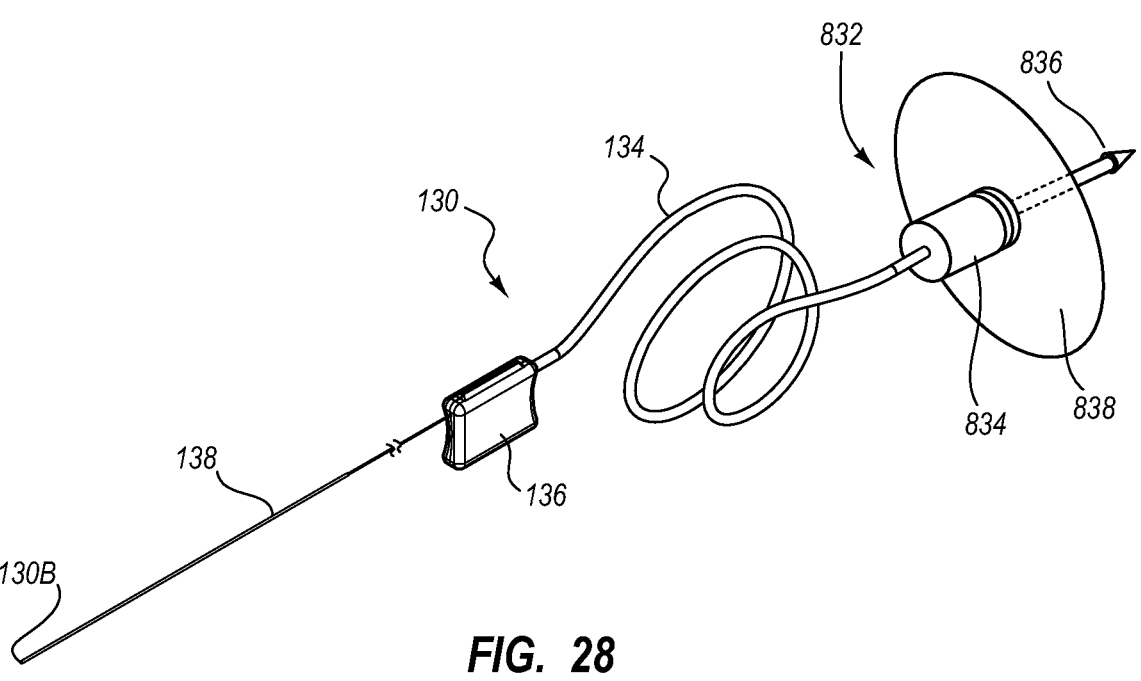
FIG. 28 is a perspective view of stylet including a sterile shield for use with the connector system shown in FIG. 28, according to one embodiment.

FIG. 28 shows another example of a tether connector that can be employed with the ECG module 750 of FIG. 27 or other suitable component of the system 10 as part of a connection scheme as a means for establishing a conductive pathway between sterile and non-sterile fields, according to one embodiment. In particular, FIG. 28 depicts a tether connector 832, which includes a handle and a barbed contact 836 or other suitable contact at a proximal end thereof. A sterile shield 838 is interposed between the handle 834 and the contact 836. The sterile shield 838 assists in protecting the hand of the clinician while inserting the contact 836 into the receptacle 764 of the ECG module 750 in a manner similar to what is shown in FIG. 27. Thus, the sterile shield 838 serves as an additional barrier to prevent inadvertent contact by the clinician with a component outside of the sterile field, such as the ECG module 750. Note that the size, shape, and particular configuration of the sterile shield and/or tether connector can vary from what is explicitly described in the present embodiment.

Figure 29A:
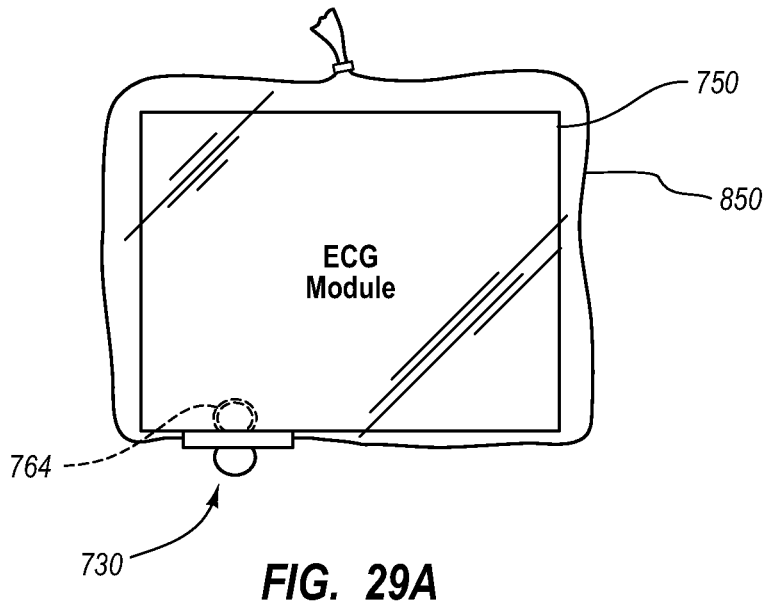
FIGS. 29A and 29B are simplified views of the ECG module of FIG. 27, including a connector system for establishing a signal pathway through a sterile barrier, according to one embodiment.
Figure 29B:
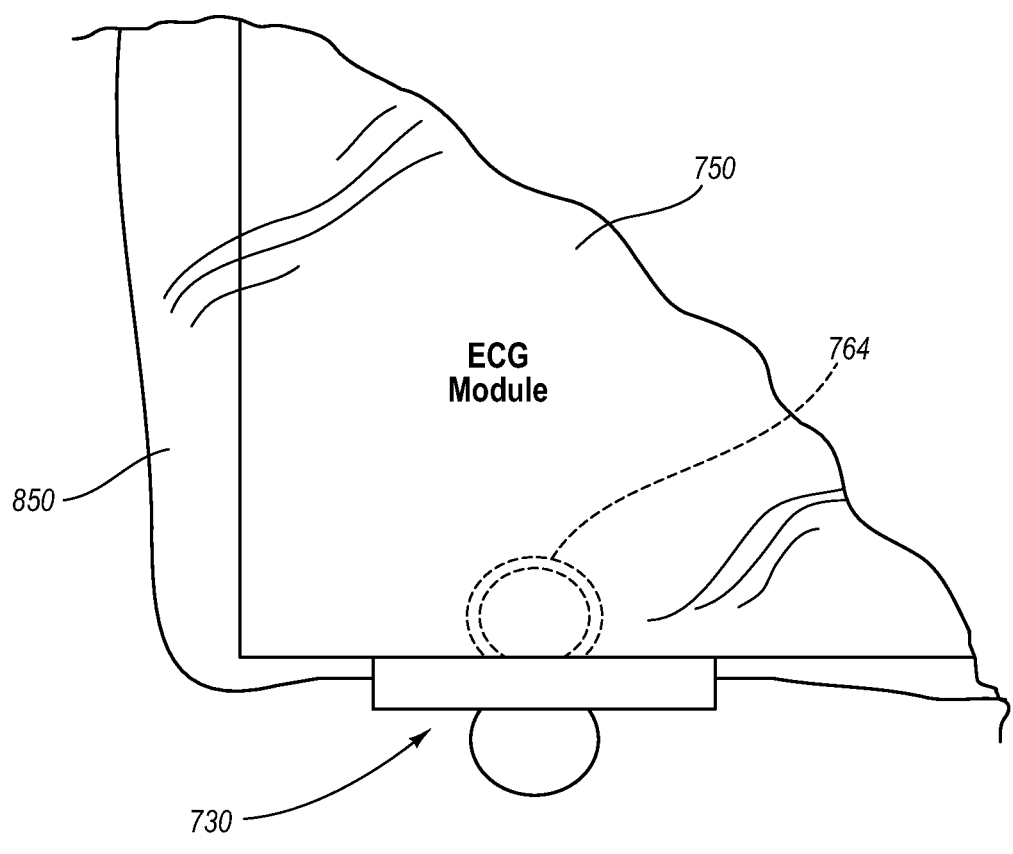

FIGS. 29A and 29B show yet another example of a connection scheme that can be employed with the ECG module 750 of FIG. 27 or other suitable component of the system 10 as a means for establishing a conductive pathway between sterile and non-sterile fields, according to one embodiment. In particular, FIG. 29A shows that the ECG module 750 can be enveloped by a sterile bag 850. A connector, such as the integrated connector 730 described above in connection with FIGS. 26A and 26B, can be incorporated into the bag. As shown in FIG. 29B, an inner snap ball or other mechanical connector of the integrated connector 730 can be received by the suitably corresponding receptacle 764 of the ECG module 750. The tether connector of the system 10 can then be operably connected with the outer snap ball or other connector of the integrated connector 730, thus establishing a conductive pathway between the sterile field and the non-sterile field without compromising sterility. Note that the sterile bag 850 can include any one or more of a variety of suitable materials, including plastic. Note also that the integrated connector can include other connector configurations in addition to what is explicitly described herein. In one embodiment, the sterile bag includes no integrated connector, but rather is pierced by a pin contact of the tether connector, such as the barbed contact 836 included on the tether connector 832 of FIG. 28.

Figures 30, 31:
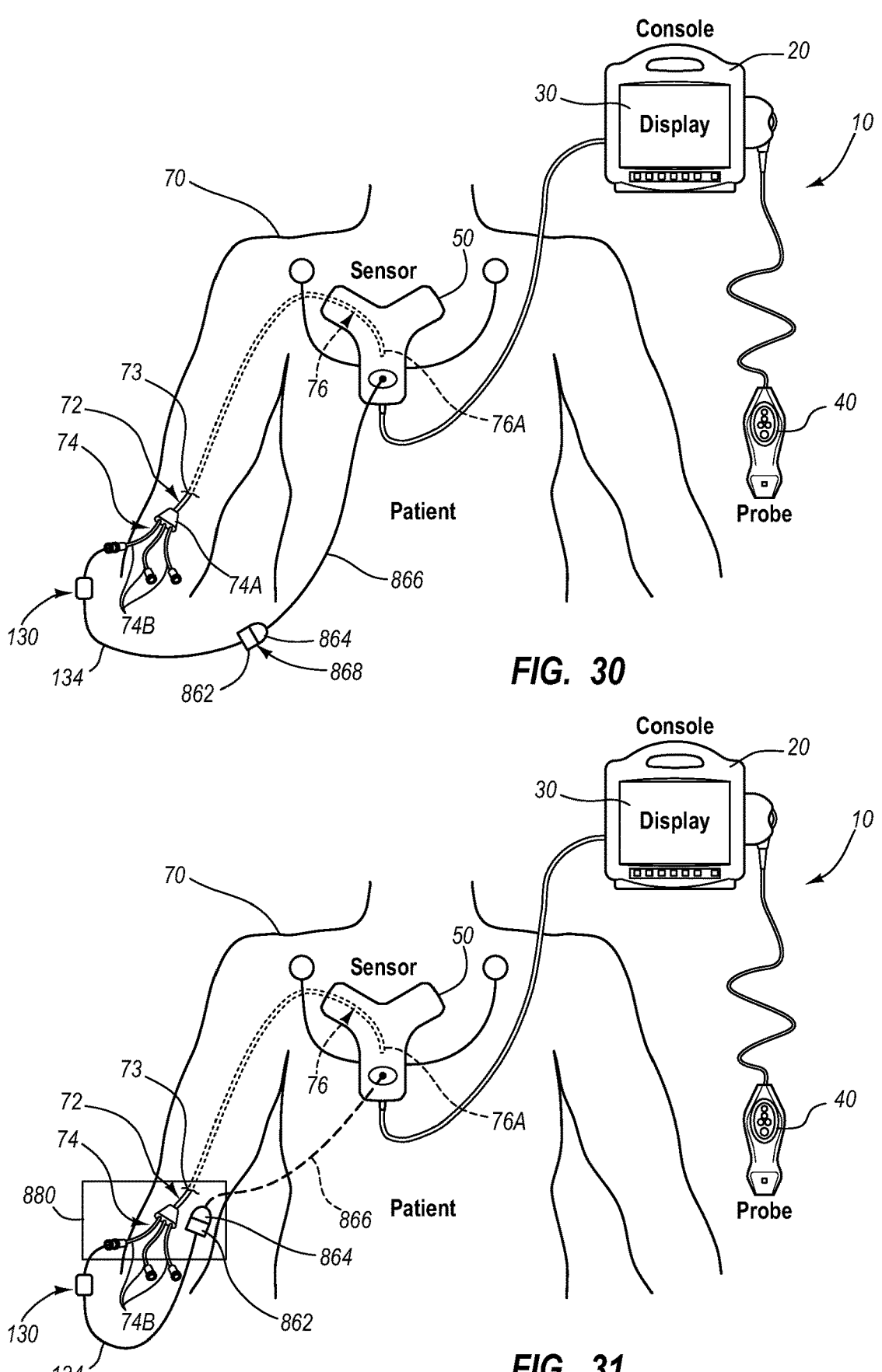
FIG. 30 is a simplified view of a connector system for establishing a signal pathway through a sterile barrier, according to one embodiment.
FIG. 31 is a simplified view of a connector system for establishing a signal pathway through a sterile barrier, according to one embodiment.

Reference is now made to FIG. 30, which depicts a connection scheme as a means for establishing a conductive pathway between sterile and non-sterile fields, according to one embodiment. Specifically, the stylet 130 includes a tether connector 862 as a first communication node, as in previous embodiments. A remote sensor connector 864 is also included as a second communications node, and is operably connected to the sensor 50 of the system 10 via a remote sensor connector cable 866. The tether connector 862 and remote sensor connector 864 operably connect to one another along a connection interface 868. The drape 174 that serves as a sterile barrier is interposed between the tether connector 862 and remote sensor connector 864 at the connection interface 868, and a suitable drape piercing configuration is included with the tether connector and the remote sensor connector to establish a conductive pathway through the drape. The present embodiment thus discloses one embodiment wherein the second communication node is located remotely with respect to the sensor 50.

Reference is now made to FIG. 31, which depicts a connection scheme as a means for establishing a conductive pathway between sterile and non-sterile fields, according to one embodiment. Specifically, the present embodiment includes the tether connector 862 and the remote sensor connector 864 that operably connect to one another along the connection interface 868, as described in connection with FIG. 30, above. The remote sensor connector 864 in the present embodiment is placed proximate the catheter insertion site 73 in a region over which a fenestration 880 defined in the drape 174 (portions of the drape omitted for clarity) is positioned to enable clinician access to the insertion site during catheter placement. The remote sensor connector 864 is adhered to the patient's skin proximate the catheter insertion site 73 with the use of an adhesive, tape, etc., before the region surrounding the insertion site is sterilized in preparation for catheter insertion. Thus, when the insertion site is sterilized, the remote sensor connector 864 is also sterilized. Later, when connection of the tether connector 862 to the remote sensor connector 864 is made, the clinician can handle the latter component without compromising the sterile field of the patient. It is appreciated that the particular configurations of the tether connector and the remote sensor connector can vary while still residing within the scope of the present embodiment.

Figures 32, 33:
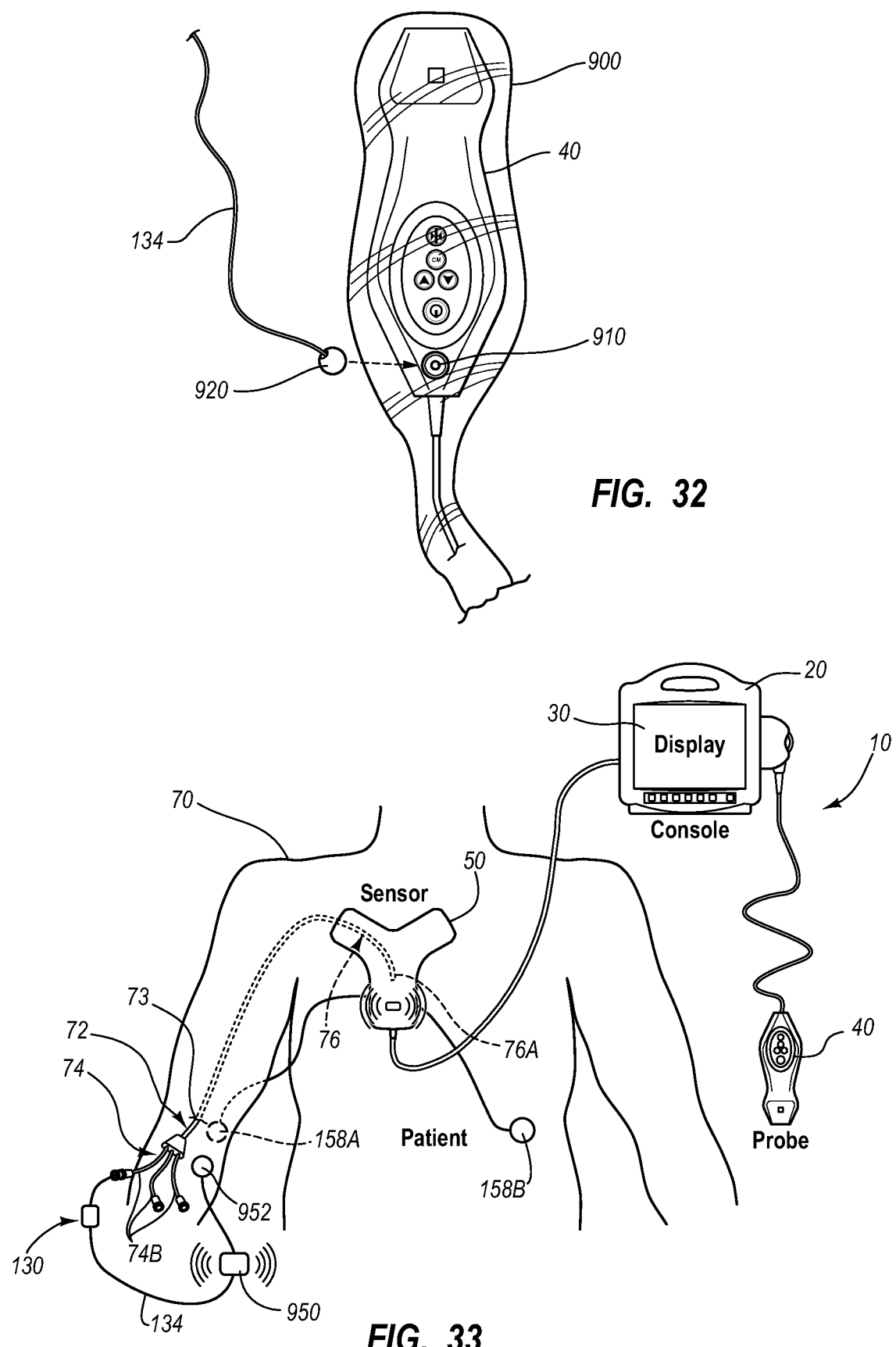
FIG. 32 is a simplified view of elements of a connector system for establishing a signal pathway through a sterile barrier, according to one embodiment.
FIG. 33 is a view of a means for establishing a conductive pathway between sterile and non-sterile fields, according to one embodiment.

Reference is now made to FIG. 32, which depicts a connection scheme as a means for establishing a conductive pathway between sterile and non-sterile fields, according to one embodiment. Specifically, FIG. 32 shows the probe 40 employed by the system 10 for US functionality, as described above in connection with FIGS. 3A and 3B. A sterile sheath 900 is placed over the probe 40 so as to bring the probe into the sterile field of the patient. A connection interface, such as a receptacle 910, is included on the probe 900 and is configured so as to be operable connectable with a tether connector 920. In one embodiment, for example, the tether connector 920 includes a pin contact that penetrates the sterile sheath 900 to mate with the receptacle 910 in such a way as to prevent contamination of the sterile field. In this way, the tether connector 920, as a first communication node, operably connects with the probe 40, as a second communications node. In turn, the probe 40 is operably connected to the system console 20, as seen in FIG. 31 for example, so as to enable ECG signals received by the ECG sensor assembly of the stylet 130 via the tether connector 920 to be forwarded to the console, the sensor 50, or other system component for processing, as described above. In another embodiment, the receptacle 910 or other suitable connection interface can be included on the cable connecting the probe 40 to the system console 20. The particular contact configuration of the receptacle 910 and tether connector 920 can be varied according to the understanding of one skilled in the art. For instance, an integrated connector such as that shown in FIGS. 26A and 26B can be incorporated into the sterile sheath in one embodiment. Note further that, though including plastic in the present embodiment, the sterile sheath as described herein can include other suitable materials for providing sterility.

Reference is now made to FIG. 33 in describing means for establishing a conductive pathway between sterile and non-sterile fields, according to one embodiment. As shown, the tether 134 includes a wireless module 950, included within the sterile field, which serves as a first communication node for wirelessly transmitting (via RF or other suitable frequency or frequency range) ECG data received from the ECG sensor assembly of the stylet 130 to a data-receiving component as a second communication node, such as the sensor 50 or other suitable component of the system 10. A wireless module ground electrode 952 is operably connected with the wireless module 950 for placement in the sterile field proximate the catheter insertion site 73. A system ground electrode 158A extends from the sensor 50 for placement outside of the sterile field but proximate both the catheter insertion site 73 and the location of the wireless module ground electrode 952. One possible placement location for the system ground electrode 158A is beneath the patient arm, as depicted in FIG. 33. The system reference electrode 158B is placed on the lower torso of the patient 70 or other suitable location, as in previous embodiments. Note that the wireless module and system console as discussed herein can be configured in one or more of a variety of ways and include components for wireless signal transmission and reception not specifically detailed herein, such as patch or other antennas, signal transducers, etc.

With the system configured as shown in FIG. 33, the system ground electrode 158A can be electrically driven such that it produces a voltage that is sensed by the passive wireless module ground electrode 952, given its proximate location with respect to the system ground electrode. This enables both ground electrodes to be at substantially equal electric potentials, thus enabling the wireless module 950 to utilize the wireless module ground electrode 952 and the ECG signals from the ECG sensor assembly of the stylet 130, e.g., the core wire 138 (FIGS. 12C-12E) in one embodiment, to detect and wirelessly transmit the ECG data to the sensor 50 for comparison with the data sensed by the system reference electrode 158B in order to obtain the desired P-wave waveform (e.g., FIG. 16). The data comparison in one embodiment is a differential comparison between the ECG data as obtained by the ECG sensor assembly of the stylet 130, the wireless module ground electrode 952, and the system reference electrode 158B. In one embodiment, the system ground electrode 158A, like the wireless module ground electrode 952, can be passive and not electrically driven. Note also that the analog ECG data can be digitized or otherwise processed by the wireless module 950 before transmission to the sensor 50 or other system component, such as the console 20.

Figures 34, 35A, 35B, 35C:
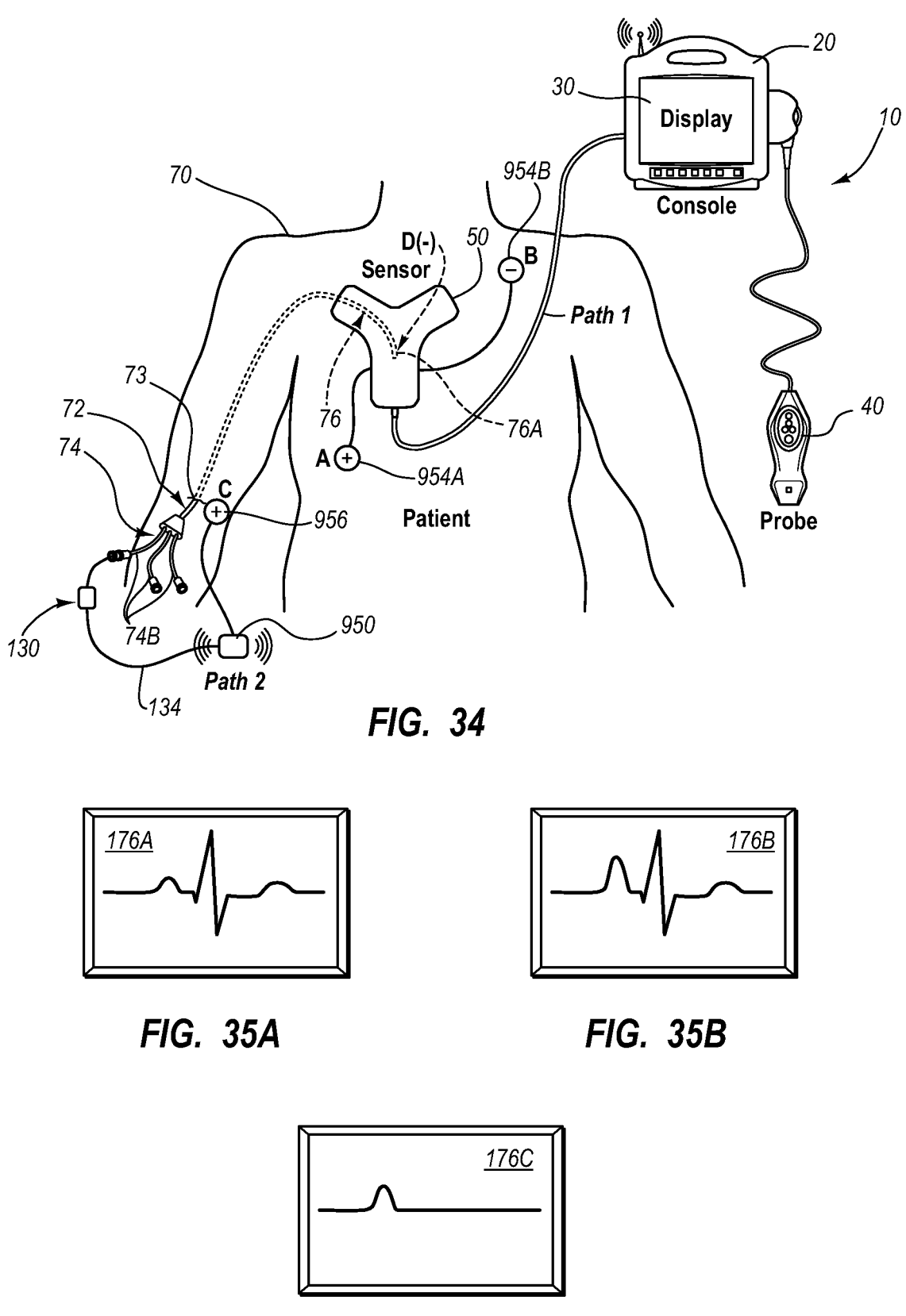
FIG. 34 is a view of another means for establishing a conductive pathway between sterile and non-sterile fields, according to one embodiment.
FIGS. 35A-35C depict exemplary P-wave waveforms.

FIG. 34 describes yet another wireless configuration as a means for establishing a conductive pathway between sterile and non-sterile fields, according to one embodiment. As shown, a positive electrode 954A at a location A and a negative electrode 954B at a location B are included with the sensor 50 and positioned on the torso of the patient 70, while a positive wireless module electrode 956 is included with the wireless node 950, as indicated at location C, positioned on or in the patient proximate the catheter insertion site 73. The ECG sensor assembly of the stylet 130, e.g., the core wire 138 in one embodiment, serves as a negative electrode for the wireless portion of the depicted configuration, indicated at D in FIG. 34 at its final position. Note that in one embodiment the locations A and B of the electrodes 954A and 954B, respectively, can be altered on the patient body to tune the system 10 for best ECG signal reception.

In the present embodiment, the electrodes 954A and 954B serve as a first independent source for sampling bipolar ECG signals. The ECG data from these electrodes are digitized and forwarded to the console 20 or other suitable system component via the cable interconnecting the sensor 50 and the console (path 1) outside of the sterile field. The wireless module electrode 956 and the ECG sensor assembly serve as a second independent source for sampling bipolar ECG signals. The ECG data from these electrodes are digitized and forwarded wirelessly to the console 20 via the wireless module 950 (path 2) within the sterile field. Thus, in the present embodiment the wireless module 950 serves as a first communication node, and a wireless receiver of the console 20 as a second communication node for the transfer of ECG signals between the two nodes. Note that the polarities of the afore-mentioned electrodes can be reversed in other embodiments.

The ECG signals received along both paths 1 and 2 are baseline corrected by appropriate circuitry of the console 20 to adjust for DC offset and drift. After such correction, a non-changing reference, or baseline, P-wave waveform 176A from path 1 can be produced, as seen in FIG. 35A, for example. Similarly, a P-wave waveform 176B as seen in FIG. 35B is produced from path 2, which waveform changes as the stylet 130 within the catheter 72 is advanced toward the heart of the patient. During such advancement, the waveform 176B from path 2 is subtracted from the P-wave waveform 176A from path 1, employing a digital differential amplifier, for instance. This subtraction removes all common components of the waveforms represented by each of the signals, and enables the console 20 to depict via its display 30 only the differences in the two signals, as seen for example by the waveform 176C shown in FIG. 35C. The change in P-wave of the waveform from path 2 can then be easily observed during catheter advancement. Thus the present embodiment enables an easily observable digital display of ECG data to be represented while preventing a physical breaching of a sterile barrier, such as a surgical drape, for the passage of such data.

Note that in other embodiments the wireless module electrode 956 can include other configurations, including a conductive element imbedded into an introducer sheath, in contact with the bloodstream of the patient, which is commonly disposed through the insertion site 73 during catheter placement. The introducer can include a connector on a proximal portion thereof to enable a connection with the wireless node 950 to be made, in one embodiment.

Note further that one or more of a variety of wireless protocols can be employed in transmitting wireless signals in accordance with the embodiments described herein, including one or more of the IEEE 802.11 family of specifications, etc. Also note that in one embodiment the wireless module can be included in a sterile sheath, as described in previous embodiments, to bring the module within the sterile field, together with connectors for operably connecting the wireless module electrode through the sheath or included in the sheath itself. Of course, other methods for maintaining the wireless module within the sterile field can also be employed. In one embodiment, the wireless module can include buttons that further enable control of the system 10 from within the sterile field.

Figure 36:
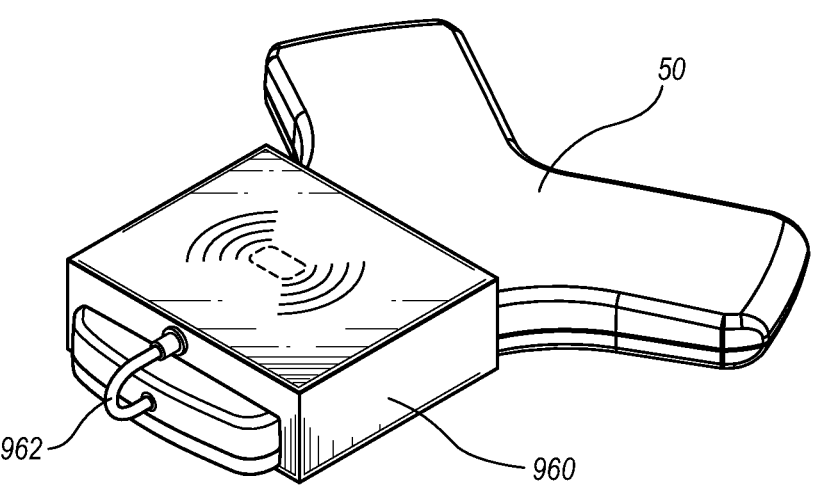
FIG. 36 is a view of a sensor retro-fitted with a wireless module, according to one embodiment.

FIG. 36 shows that in one embodiment the sensor 50 can be retro-fitted with a wireless module 960 to enable signals received by the sensor to be wirelessly transmitted to the console 20 or other suitable component of the system 10. For instance, ECG data received by the ground and reference electrodes 158A, 158B (FIG. 34) can be received by the sensor 50 then wirelessly transmitted to the system console via the wireless module 960. The wireless module 960 can include an antenna or other transmitting component and can operably connect to the sensor 50 via a sensor cable 962 or other suitable interface. Note that the wireless module 960 can be employed in connection with other embodiments described herein, including those depicted in FIGS. 10 and 33, for instance.

Figure 37:
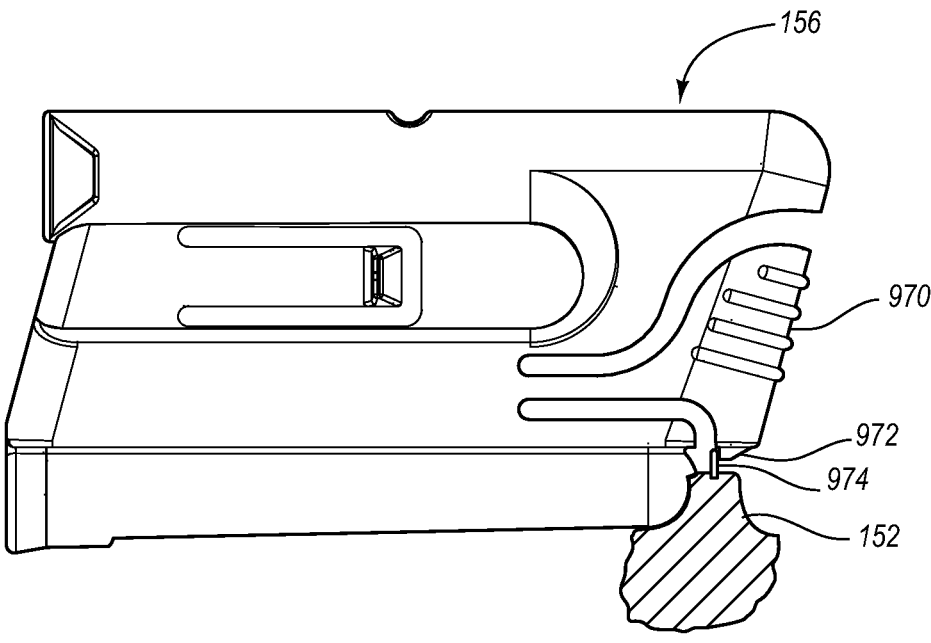
FIG. 37 is a view of a retention feature for a connector, according to one embodiment.

FIG. 37 shows a retention feature for preventing inadvertent separation of the fin connector 156 from the sensor connector base 152 or other receptacle with which the fin connector operably connects, according to one embodiment. As shown, the fin connector 156 includes a retention arm 970 that is resiliently attached to the fin connector body. The retention arm 970 includes a tab 972 that slides over and engages a lip 974 included with the connector base 152 of the sensor 50 when the fin connector 156 is slidably received in the sensor channel 152A (FIG. 14A). The engagement of the tab 972 with the lip 974 prevents inadvertent removal of the fin connector 156 during use. When removal of the fin connector 156 from the sensor connector base 152 is desired, the retention arm 970 is lifted so as to disengage the tab 972 from the lip 974, after which the fin connector can be slid out of engagement with the sensor channel 152A. This configuration can be employed either with or independent of other retention features, such as the indentations 168A (FIG. 13D). Note that in other embodiments a variety of modifications and configurations can be employed in assisting to maintain engagement between the fin connector and the connector. For instance, the retention arm in one embodiment can be operably attached to one or more of the fin contacts 168 (FIG. 13D) such that displacement, e.g., lifting laterally moving, pinching, etc., of the retention arm or other suitable fin connector component disengages the fin contact (s) from the base contacts (FIG. 15), thus reducing the overall retention force provided by the engagement of the fin contacts with the base contacts. Note further that these principles can be applied to the other connector schemes disclosed or contemplated in addition to the fin connector described here.

In addition to the above embodiments depicting various connection schemes as means for establishing a conductive pathway between sterile and non-sterile fields, other configurations can be employed, as appreciated by one skilled in the art, for performing the same functionality. Such other configurations can include, for example, wireless transmission of ECG signals from the stylet to the sensor or the system component, the inclusion of electrically conductive thread in the drape, the inclusion of an electrically conductive window (e.g., composed of an electrically conductive plastic or foil) in the sterile drape, etc. In yet another embodiment, a proximal end of the stylet/guidewire itself can be used to pierce the drape for receipt into a connector on the sensor. In this case, no tether is included on the proximal end of the stylet, and the stylet itself serves as the conductive pathway for transmitting ECG signals from the stylet sensor assembly to the sensor on the patient's chest. Such a configuration can allow for over-the-wire placement of the catheter using a stylet/guidewire as described here. As such, the above embodiments should not be construed as being limiting of the present invention in any way.

Figures 38, 39:
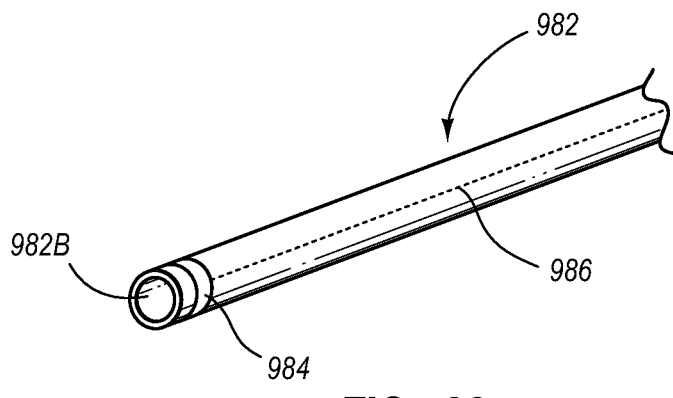
FIG. 38 is a perspective view of a catheter including an ECG sensor according to one embodiment.
FIG. 39 is a perspective view of a sensor assembly including multiple electrodes disposed on a catheter.

FIG. 38 shows a catheter 982 as one example of a catheter that can be employed with the catheter placement system 10 described in the embodiments disclosed herein. The catheter 982 includes a conductive annular band 984, positioned proximate the distal end 982B (though other locations along the catheter are also possible), which serves as an ECG sensor, or electrode, for detecting ECG signals from an emitting heart node of the patient 70 when the catheter is at least partially inserted within the patient vasculature. A conductive wire 986 extends along the length of the catheter 982 and in one embodiment is embedded in the catheter wall, such as by co-extrusion for instance, for connection with external ECG signal receiving components external to the patient. Note that this is but one example embodiment of a catheter and ECG sensor electrode configuration, in addition to those described above and appreciated by one skilled in the art. Yet other possible configurations are disclosed in U.S. Pat. No. 9,901,714 titled "Catheter Assembly Including ECG Sensor and Magnetic Assemblies," which is incorporated herein by reference in its entirety.

FIG. 39 shows the catheter 982 for use with the system 10 including an ECG sensor assembly 990 according to one embodiment, wherein the catheter includes a plurality of ECG sensors, or electrodes 994A, 994B, and 994C. The electrode 994C is positioned proximate the catheter distal end 982B, while the remaining electrodes 994A and 994B are positioned on the catheter proximal thereto. Each electrode is operably connected to a respective conductive pathway, such as a conductive wire proximally extending from the electrode along the length of the catheter so as to enable detected ECG signals to be forwarded to the external TLS sensor 50 or other suitable system component. The electrodes 994A-994C can be configured in one or more of a variety of configurations suitable to act as sensors for detecting an ECG signal of the patient's heart. Also, though shown as close-ended, the catheter 982 can be open-ended in one embodiment.

Figure 40A:
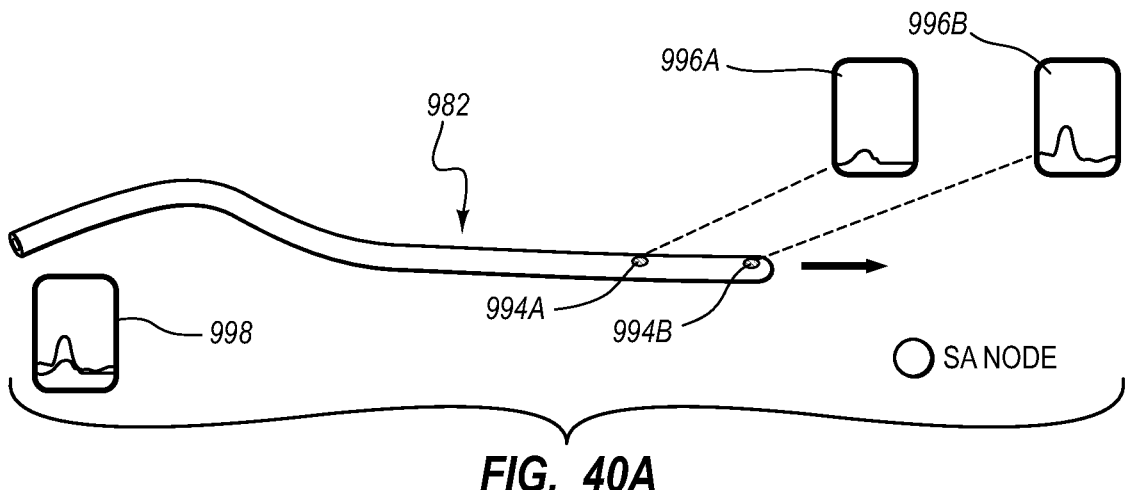
FIGS. 40A-40C depict operation of the catheter of FIG. 39.
Figure 40B:
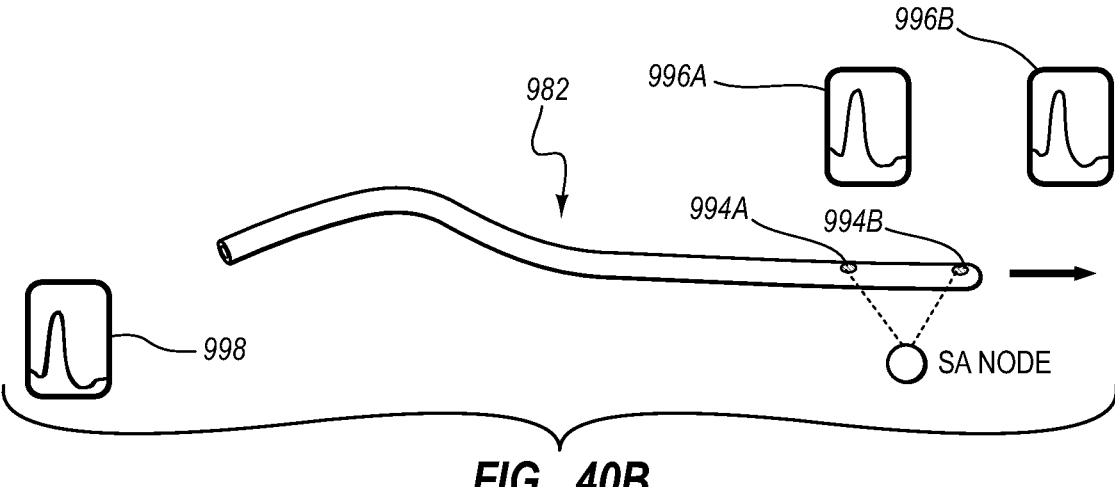
Figure 40C:
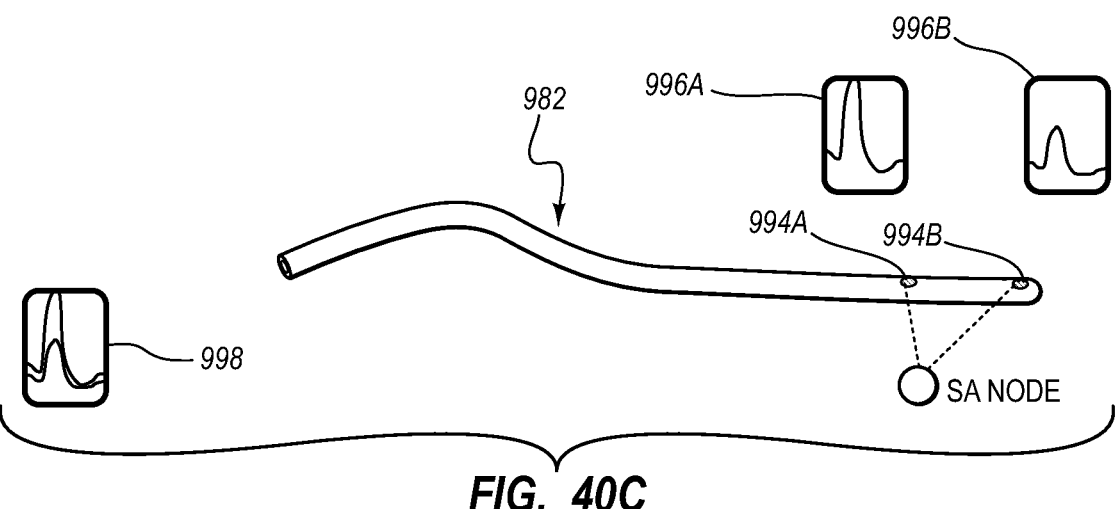

As shown in FIGS. 40A-40C, the ECG sensor assembly 990 can be employed in determining the proximity of the catheter distal end 982B to the SA node, wherein the sensor assembly of the catheter 982 includes in the illustrated embodiment two electrodes 994A and 994B. In FIG. 40A, as the catheter distal end 982B approaches the SA node, the P-waves 996A and 996B of the ECG waveforms detected by the catheter electrodes 994A and 994B, respectively, both show an increase in P-wave amplitude. Because of its relatively more proximate position to the SA node, however, the electrode 994B shows a P-wave with a relatively larger amplitude. A superposition of the P-waves 996A and 996B as detected by the system 10, for instance, is shown at 998. Observation of this relationship on the system display, for instance, can give needed information to a clinician during placement of the catheter so as to aid in advancement of the catheter distal end 982B toward the SA node.

FIG. 40B shows that when the two electrodes 994A and 994B are equidistant with respect to the SA node, the amplitudes of the P-waves 996A and 996B are approximately equal, which fact is further shown by the superposition 998 of the P-waves. In FIG. 40C, the distal electrode 994B is relatively farther from the SA node than the electrode 994A, and as such its corresponding P-wave 996B is smaller relative to the P-wave 996A. Note that the type and number of electrodes can be varied from what is shown here.

In another embodiment, a filtering process can be employed in connection with use of the ECG electrodes 994A, 994B of the catheter 982 described here, wherein portions of the ECG waveforms detected by the electrodes other than the P-wave portion are cancelled out, leaving only the differences in the detected P-waves between the two electrodes to be depicted. This process is similar to that employed in connection with FIGS. 34-35C, as described above.

Figures 41A, 41B, 41C:
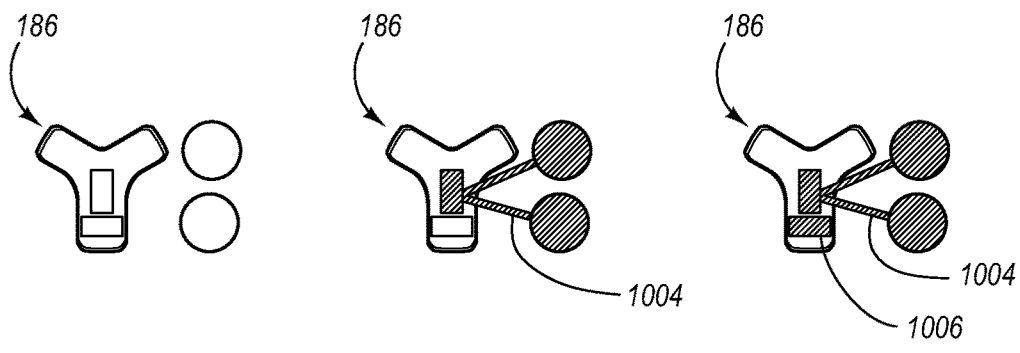
FIGS. 41A-41D are various views of an electrode connection integrity indicator and system in accordance with one embodiment.

FIGS. 41A-41C depict various possible states for the ECG electrode integrity indicator 186, also shown as displayed on the screenshot 178 of the system display 30 in FIG. 17. The integrity indicator 186 is an icon that is displayed on the system display 30 and is part of a connection integrity component to verify the status of the connections of the various ECG signal paths with the external sensor 50, i.e., whether the connections are closed and ready for use during catheter placement procedures. Such lead verification is helpful to avoid having to remove the sterile drape and reinitiate the placement procedure if the various ECG electrodes were not properly connected before placement of the sterile drape and establishment of the sterile field about the patient.

In FIG. 41A, the integrity indicator 186 shows that no connections to the external sensor 50 are currently closed. In contrast, FIG. 41B shows that the connection between the sensor 50 and the ECG electrodes 158 (FIG. 14B) is closed, indicated by the shaded connection symbol 1004. FIG. 41C shows in addition that the connection between the sensor 50 and the ECG sensor of the stylet 130 (e.g., the core wire 138 in FIGS. 12C and 12D via the tether 134 and tether connector 132) is closed, as indicated by the shaded connection symbol 1006. Thus, the integrity indicator view in FIG. 41A represents the connection status shown in FIG. 14A, the indicator view in FIG. 41B represents the connection status shown in FIG. 14B, and the indicator view in FIG. 41C represents the connection status shown in FIG. 14C.

Figure 41D:
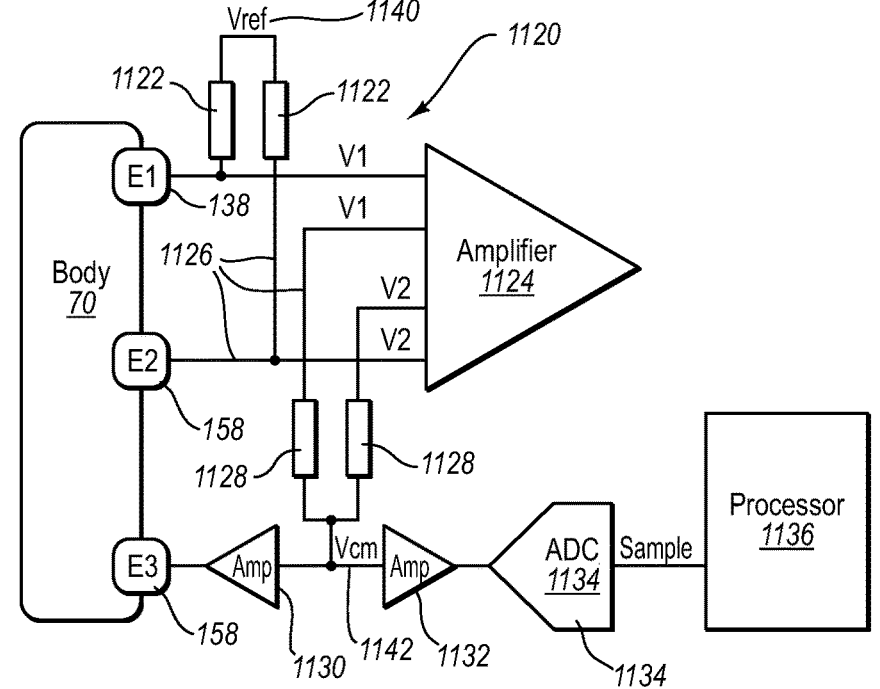

The system 10 can confirm the status of the above connections in one or more of a variety of ways using connection integrity components, including capacitive or inductive sensing circuits included with the sensor 50 and/or console 20 for instance, impedance-based methods, time or frequency reflectometry techniques, etc. One possible voltage balance-based connection integrity component system is shown at 1120 in FIG. 41D. In particular, the circuitry of the system 1120 includes a first resistor pair 1122 and an amplifier 1124, such as an instrumentation amplifier, operably connected via communication lines 1126, as are the other components of the present system, as shown in FIG. 41D. A second resistor pair 1128, amplifiers 1130 and 1132, an analog-to-digital converter ("ADC") 1134, and processor 1136 are also included in the system and interconnected as shown in FIG. 41D. The processor 1136 is included in the external TLS sensor 50 in one embodiment, but can be incorporated into other system processors or included in other components, such as the console 20 in one embodiment. The various ECG electrodes of the system 10 are shown attached to the body of the patient 70, i.e., the internal ECG sensor (E1 in FIG. 41D) such as the stylet core wire 138 in the configuration shown in FIGS. 12A-12E, and both the external reference external ECG electrode 158 (E2) and second external electrode (E3) shown in FIGS. 14A-14C.

In preparation for use of the system 10, the integrity check system 1120 can be used to ensure that the external ECG electrodes are properly connected both to the body of the patient 70 and to the external TLS sensor 50 of the system 10 in one embodiment. Reference voltage Vref, shown at 1140, is driven, such as by a voltage regulator, to a predetermined value, such as 4 volts, for instance, while the voltage at the external electrode E3 is maintained at a relatively lower value, such as 2 volts for instance. The values of the voltages V1 and V2 from the electrodes 1 and 2, respectively, in FIG. 41D are averaged to generate a common mode voltage, Vcm, indicated at 1142. In one embodiment, the processor 1136 monitors Vcm, as sampled via the ADC 1134. When the external ECG electrodes E2 and E3 are properly connected to the patient body and TLS sensor 50, Vcm will be pulled lower in value, in one embodiment approaching about 2 volts, though other values are possible. If one or both of the external electrodes E2 and E3 are not properly connected, however, Vcm will be pulled higher toward the value of Vref, or about 4 volts in the present embodiment. As such, monitoring of Vcm by the processor 1136 can determine the connectivity of the external ECG electrodes. These data relating to the connectivity status of the external ECG electrodes can be forwarded to the display 30 by the processor 1136 for depiction by the indicator 186 on the display 30 shown in FIGS. 41A-41C.

Figure 42:
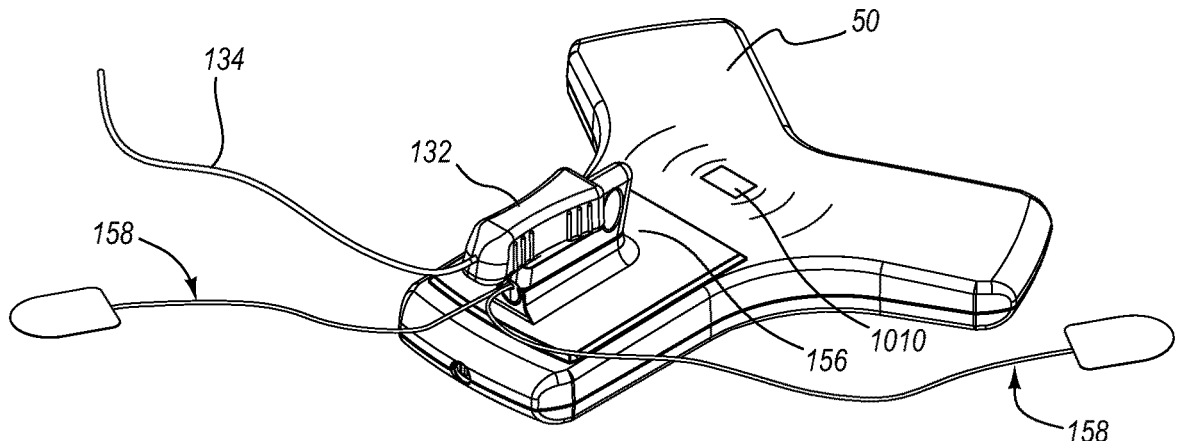
FIG. 42 is a perspective view of an electrode connection integrity system according to one embodiment.

FIG. 42 shows yet another possible connection integrity component configuration according to one embodiment, wherein a passive lead continuity check system is employed, eliminating any need for injecting current into the leads that extend from the various ECG electrodes of the system 10. As shown, a radiating element 1010 is included relatively near the ECG electrode leads, such as on the sensor 50. The radiating element 1010 is configured to emit a signal of a known frequency. The ECG lead wires, such as the wires of the external ECG electrodes 158 and the tether 134, act as antennae to passively detect the signal radiated by the radiating element 1010. When the ECG leads are properly attached to the sensor 50, the antenna effect of the ECG lead wires is minimized, such that the radiating signal present on the ECG lead wires is suppressed. Sensor and/or console circuitry is configured so as to detect the radiating signal present on the ECG leads and compare it to a threshold signal level. If the detected radiating signal is above the threshold, the system reports that the ECG leads are not properly connected. When the detected signal is below the threshold, the system reports that the leads are properly connected. The present configuration is passive and does not necessitate the passing of current down the ECG leads in order to check connection integrity for the connective path check.

In one embodiment, the connection check scheme of FIG. 42 can be configured such that different graduated levels of signal present on the leads will indicate whether subconnections upstream from the ECG electrode are closed. In another embodiment, natural signal line noise in the natural 60 Hz, 120 Hz or 180 Hz frequencies, naturally present on the lead wires, can be used for detection, thus eliminating the need for the radiating element 1010.

It is appreciated that other icons and designs can be used to implement the functionality described in connection with FIGS. 41A-41C, and that connection status checking can be varied according to modifications made to the catheter placement system. Of course, other visual or aural indications can be used to convey electrode connection status.

Figure 43A:
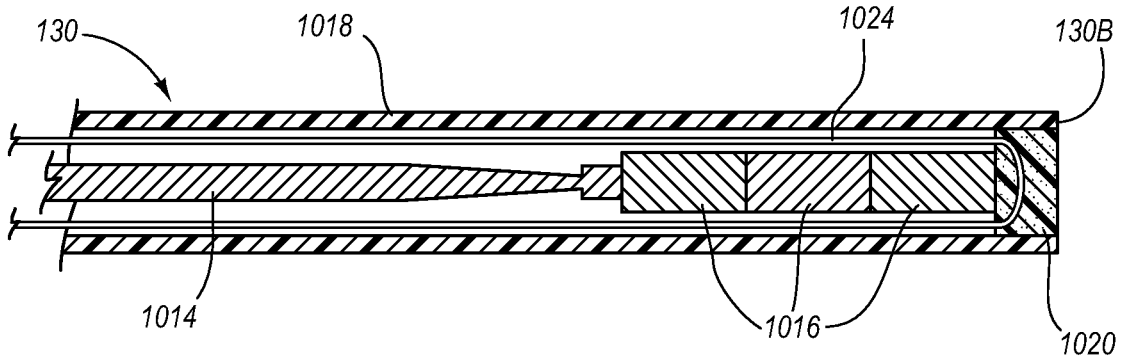
FIGS. 43A and 43B are cross sectional views of a stylet including a conductive wire loop for detecting severing of the stylet according to one embodiment.
Figure 43B:
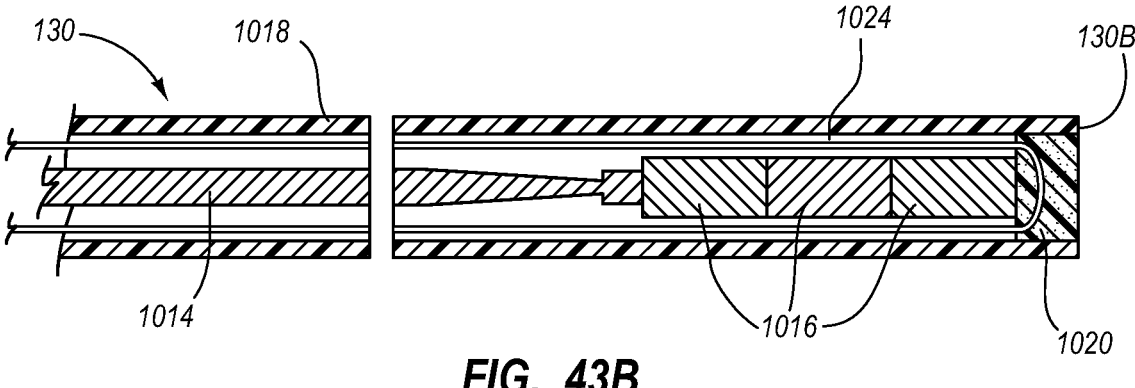

FIGS. 43A-43B depicts details of a stylet configuration including a mode for checking whether the stylet 130 has been inadvertently cut, such as when the stylet is undesirably left in the catheter lumen when the catheter 72 is trimmed before being inserted into the patient 70. As shown, in one embodiment, the stylet 130 can include a core wire 1014 and a plurality of magnetic elements 1016 covered by a tubing sleeve 1018, together with a conductive epoxy 1020 included at the stylet distal end. A conductive wire loop 1024 is included in the stylet and loops at the distal end 130B of the stylet 130 so as to form a circuit when suitably connected with the system 10. The conductive wire loop 1024 thus defines a continuity circuit that checks the continuity of the distal portion of the stylet. If the stylet has been inadvertently cut, such as by improper catheter trimming as shown in FIG. 43B, the loop is opened and the continuity check fails, indicating the catheter tip has been compromised. The continuity check can be performed before the catheter 72 is inserted into the patient vasculature so as to prevent catheter guidance problems after insertion. In another embodiment, the conductive wire loop 1024 could be configured so as to be exposed to the patient bloodstream and additionally serve as an ECG electrode.

Figure 44:
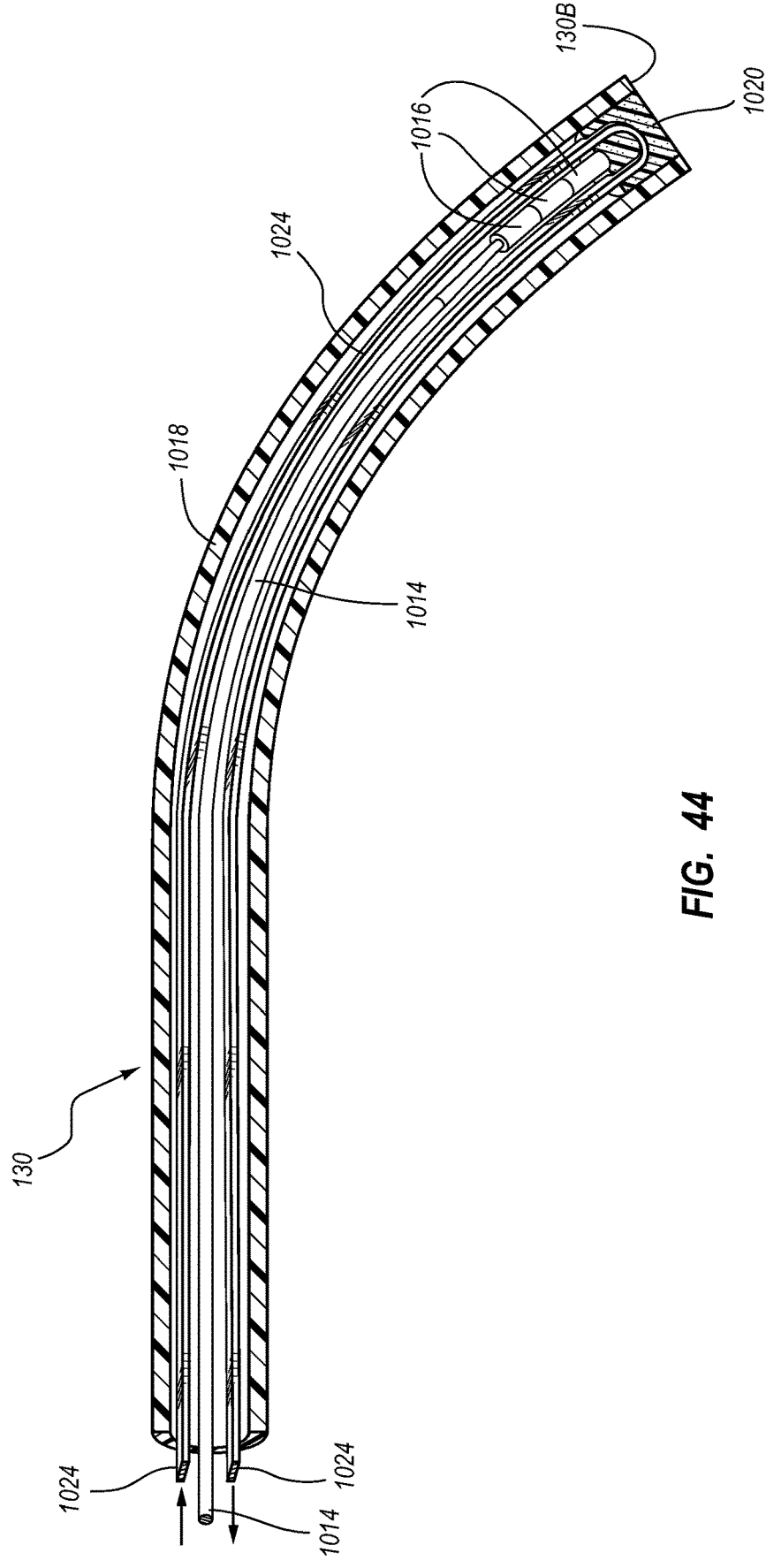
FIG. 44 is a partial cross sectional view the stylet of FIG. 43A, including a conductive wire loop with a planar wire in accordance with one embodiment.

FIG. 44 shows one of many possible variations to the previous embodiment, wherein the conductive wire loop 1024 is implemented as a planar wire, which has a bias toward bending within the plane of least thickness. Such a planar wire can be used in stylets that have a pre-curved configuration, such as that shown in FIG. 44. In addition, in one embodiment such a wire enables the direction of stylet bending to be controlled along one axis, if desired. Indeed, in one embodiment, tension can be imparted to the planar wire in order to cause the distal portion of the stylet 130 to selectively deflect from a straight to a curved configuration as shown in FIG. 44, for example. It should be noted that the embodiments just described can be implemented in stylets having one of a variety of configurations in terms of structure, size, etc. In other embodiments, Note that in other embodiments, other techniques can be employed to ensure the stylet has not been cut or otherwise compromised, including stylet checks using time or frequency domain reflectometry, for instance.

FIGS. 45 and 46 depict a mechanical solution for preventing unintended proximal advancement of the stylet 130 within the catheter 72. In particular, FIG. 45 shows a bulbous mechanical interference feature 1028 included on the stylet distal end 130B so as to impede retraction of the stylet into the catheter lumen. FIG. 46 shows another example, wherein the stylet distal end 130B includes a deflected extended portion interference feature 1028. Of course, mechanical interference features of many different sizes and shapes can be employed, including arrow-shaped, spherical, etc.

FIGS. 47A and 47B depict an electrical solution to assist in preventing misalignment of the distal ends of the catheter 72 and the stylet 130. As shown, a conduction band 1032 is embedded within the catheter so as to be in electrical communication with two conductive portions 1036 of the stylet 130 between which is interposed a nonconductive stylet portion 1034. When the stylet distal end 130B is properly aligned with the distal end 72B of the catheter 72, the more distal stylet conductive portion 1036 is conductively connected to the more proximal stylet conductive portion 1036 via the catheter-embedded conduction band 1032. Should the stylet and catheter distal ends 130B, 72B be misaligned, however, no such conductive path is established, and the absence of this path can be detected by the sensor 50, console 20, or other suitable component of the system 10 so as to enable its rectification.

Figure 48:
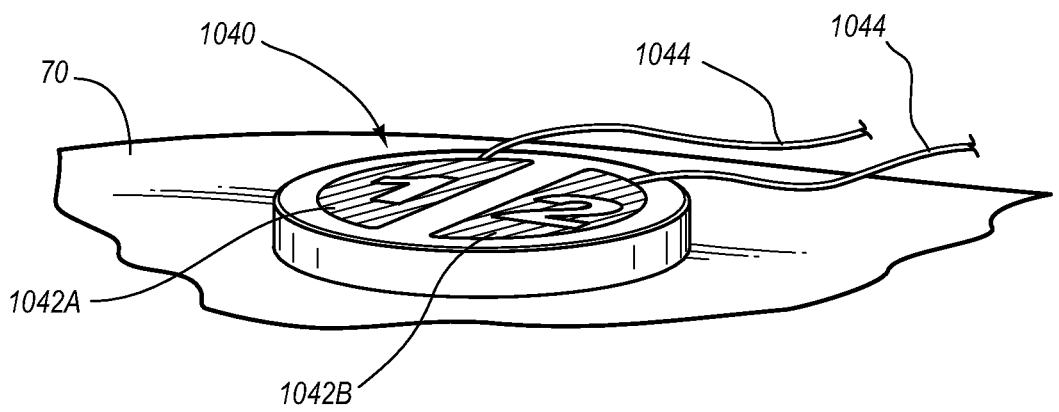
FIG. 48 is a perspective view of an external dual-ECG electrode assembly in accordance with one embodiment.

FIG. 48 depicts one possible implementation of a dual ECG electrode assembly 1040 for placement on the skin of the patient 70 during catheter placement procedures. As shown, the assembly 1040 includes dual electrodes 1042A, 1042 B a single pad, for simplifying the ECG lead placement. Corresponding leads 1044 are also included. In other embodiments, the ECG electrode assembly can include more than two electrodes, if desired.

Figure 49:
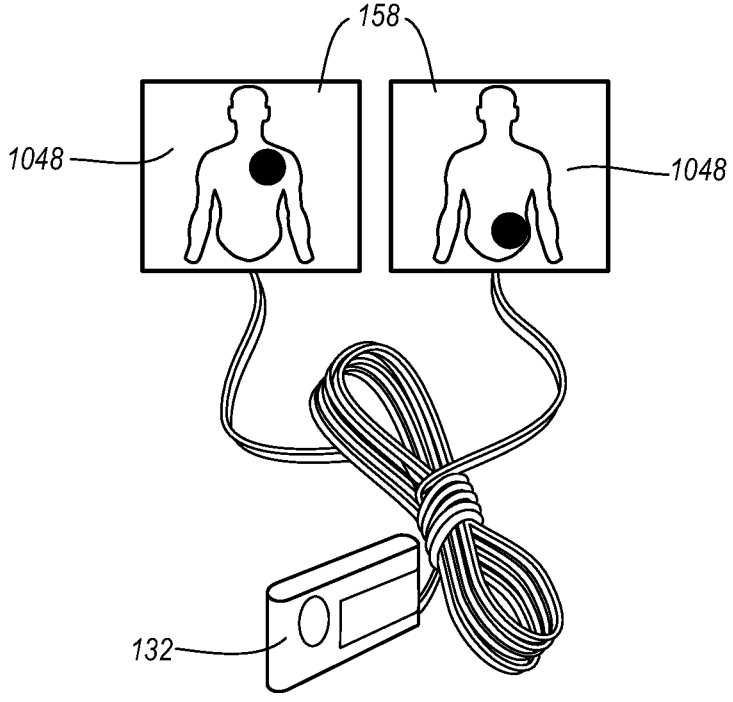
FIG. 49 is a perspective view of an external ECG electrode assembly including graphics in accordance with one embodiment.

FIG. 49 shows one example of an external ECG external electrode assembly for placement on the skin of the patient 70, including the previously-described fin connector 156, and external ECG electrodes 158. Graphics 1048 are positioned on a surface of each electrode 158 including illustrations to assist the clinician in placing the ECG electrodes in the proper location on the patient's body. This assists clinicians who may not be familiar with the proper placement locations for the electrodes on the patient's body 70. The illustrations and particular electrode configuration can vary according to system design.

FIGS. 50-61 depict various possible implementations for displaying ECG data on a display of a catheter placement system, such as the display 30 of the system 10 of FIG. 10 for instance, for assisting a clinician in placing a catheter into the vasculature of the patient 70. In many of the implementations to follow, standard methods of presenting and displaying ECG data are improved to aid in catheter placement and confirmation of tip location. As such, the following display and computing techniques may be useful in presenting data to a clinician.

Figure 50:
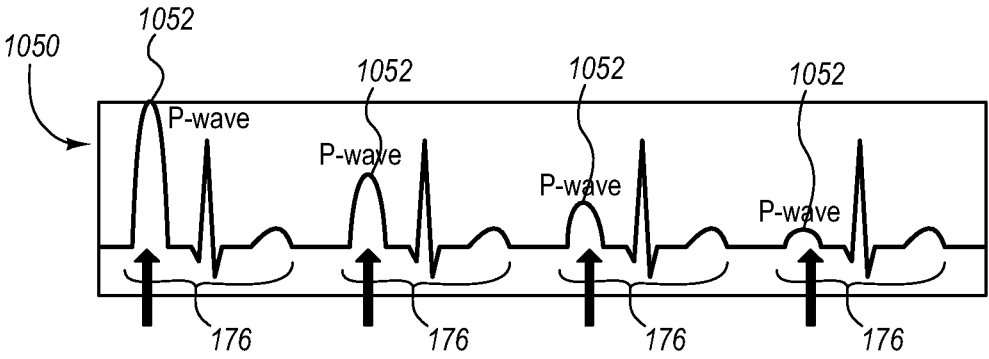
FIG. 50 is an ECG trace showing P-wave characteristics according to one embodiment.

FIG. 50 shows that audible or other suitable feedback can be employed in connection with displaying an ECG trace, such as an ECG trace 1050 shown here, which is similar to the trace history window 182 depicted on the display screenshot 178 in FIG. 17. In particular, in one embodiment a sound or other indicia can be correlated to an aspect of an ECG waveform of an ECG signal. In the present embodiment, an audible cue is associated with the amplitude of a P-wave 1052 of each waveform 176 in the ECG trace 1050. As the P-wave amplitude changes as shown in FIG. 50, the audible cue can correspondingly change. The audible cue can be modulated in frequency, volume, continuity (e.g., discrete click vs. a continuous tone), etc.

Figure 51:
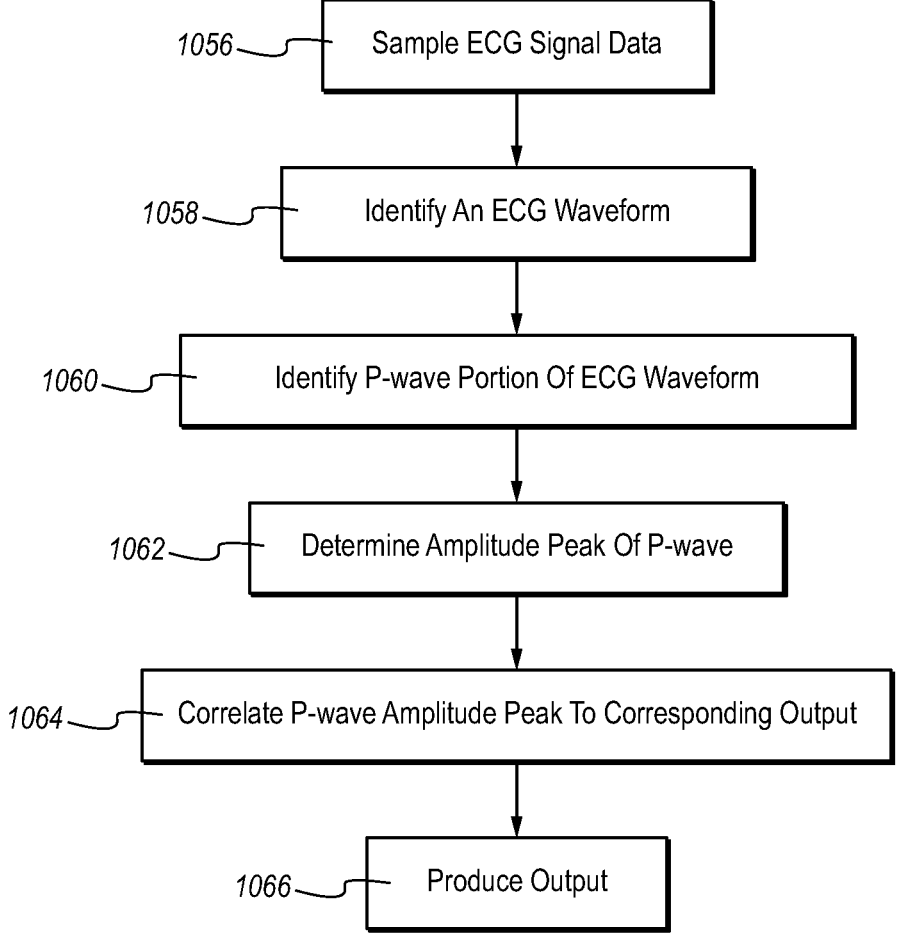
FIG. 51 is a flow chart describing one method according to one embodiment.

FIG. 51 shows a flow chart depicting one embodiment of a method for correlating and producing audible or other feedback with respect to an aspect of the ECG waveform 176, such as the amplitude of the P-wave 1052. This method in whole or in part can be performed and/or controlled by suitable components of the system 10, e.g., circuitry included in the external sensor 50 or console 20, or other suitable catheter or medical device placement system. In stage 1056, ECG signal data is sampled in a manner such as has been described above in connection with use of the system 10 during catheter placement procedures. In stage 1058, an ECG waveform is identified from the sampled ECG signal data. In stage 1060, a P-wave portion of the ECG waveform is identified. This can be accomplished, for instance, by comparing portions of the waveform with a standard, pre-loaded P-wave template to determine the existence and location of the P-wave 1052. The amplitude peak of the P-wave is then determined in stage 1062. In stage 1064, the P-wave amplitude peak is correlated to a corresponding audible or other suitable feedback output. This stage can be predetermined and stored by the system 10, or can be dynamically controlled automatically or by user input, in one embodiment. The output is then produced in stage 1066. Note that in other embodiments the output can be other than audible as has been described, including for instance visual, light/sound combinations, mechanical movement (vibratory), and/or other sensory cues, or combinations of the foregoing.

Figures 52, 53, 54, 55:
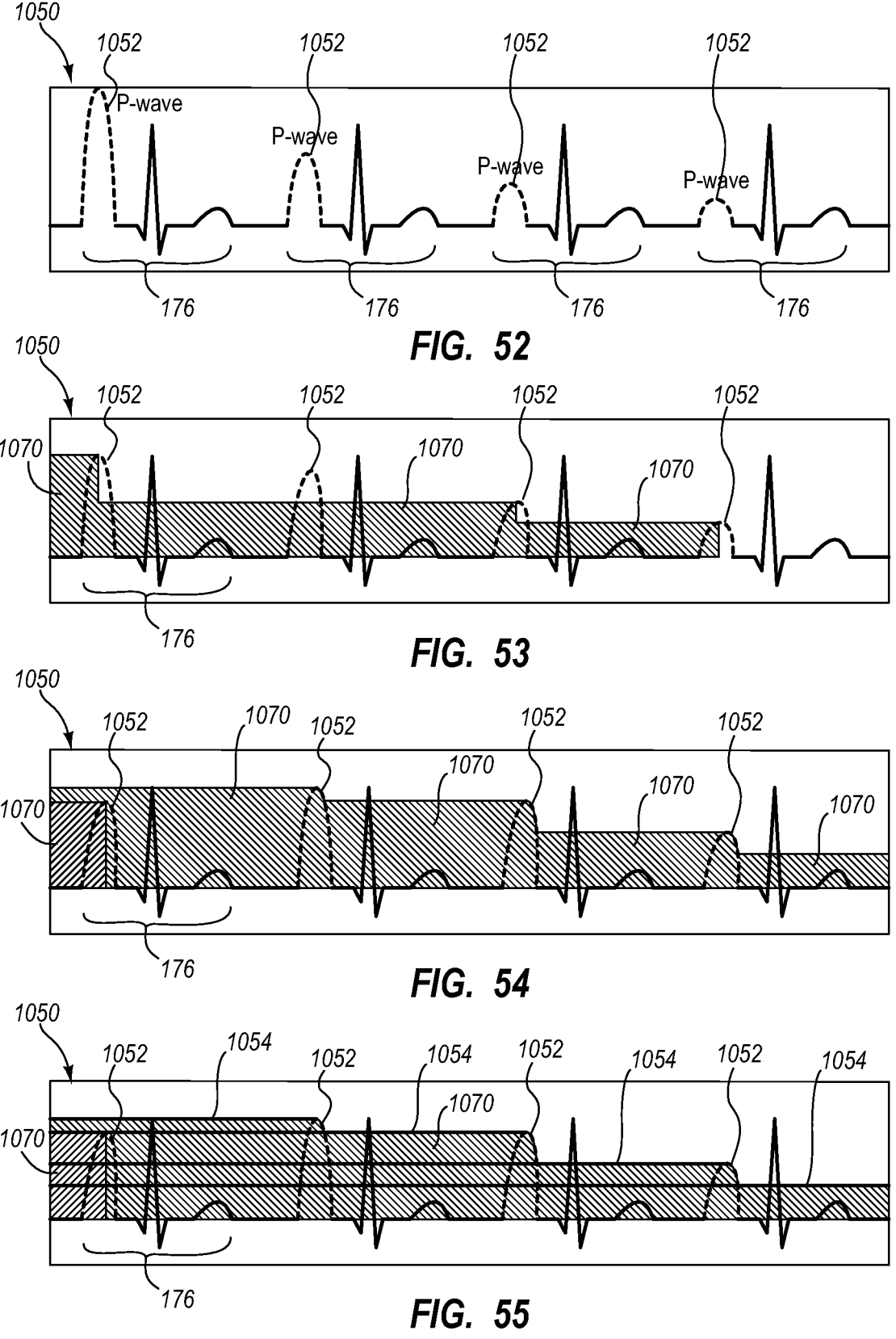
FIGS. 52-55 are ECG traces showing additional P-wave characteristics according to embodiments of the present disclosure.

FIGS. 52-55 give further examples of visual output that can be correlated with aspects of ECG signal data, such as P-wave amplitude of each detected ECG waveform, using the method depicted in FIG. 51. For instance, FIG. 52 shows one display implementation wherein the P-wave 1052 of each ECG waveform 176 is identified and highlighted with a color to differentiate the P-wave from other portions of the waveform. In one embodiment, the color can change according to changes in P-wave amplitude.

In FIG. 53, the peak amplitude of the P-wave 1052 in each waveform 176 is traced as a colored or shaded shadowing 1070 on the ECG trace 1050 as a function of time. In particular, during catheter insertion the P-waves 1052 of successive ECG waveforms 176 often vary in magnitude as the ECG sensor assembly of the catheter assembly (e.g., the catheter and/or stylet) approaches the SA node or other node of the heart. It is often useful to display the magnitude of the P-waves 1052 on the system display 30 as such changes take place. A line or colored bar can be used to trace out the magnitude of past peaks. In this way, a comparison between current and former peak magnitudes can be conveniently made. This display mode can be employed whether the trace move across the display or if the traces remain stationary and are refreshed by a moving bar that sweeps across the display.

FIG. 54 shows that once the P-wave 1052 falls below a previous level, another color or shade of shadowing 1070 can be used, as seen in the left-most portion of the ECG trace 1050 of FIG. 54, to illustrate the difference between the most recent peaks and previous peaks. Optionally, a horizontal line 1074 can be used to trace out the peak of each P-wave 1052, as in FIG. 55. The line 1074 can be used either with or without the shadowing 1070. Of course, many other such tracing implementations and visual indicia can be devised in accordance with these principles.

Reference is made to FIGS. 56A-57B in describing aspects of scaling control of the ECG trace 150 as displayed in the trace history window 182 of the system display 30, for instance. In typical ECG devices, the rate of ECG waveform display is constant. However, human heart rates are not constant and ECG waveform formation and spacing vary from person to person. It may be beneficial to the observer to be able to change the number of waveforms and/or amount of time waveforms are displayed on the system display 30 or other suitable device. This allows more or fewer ECG waveforms to be displayed. In one embodiment, the clinician can adjust display settings to determine how many ECG waveforms 176 are displayed or how much time the waveforms are to be displayed. In one embodiment, the user can select from a series of pre-determined, discrete display time or waveform options, or the settings can be user-defined. In another embodiment, the control over the display settings of the ECG trace 1050 can be dynamically or statically controlled autonomously by the system 10.

Figures 56A, 56B, 57A, 57B:
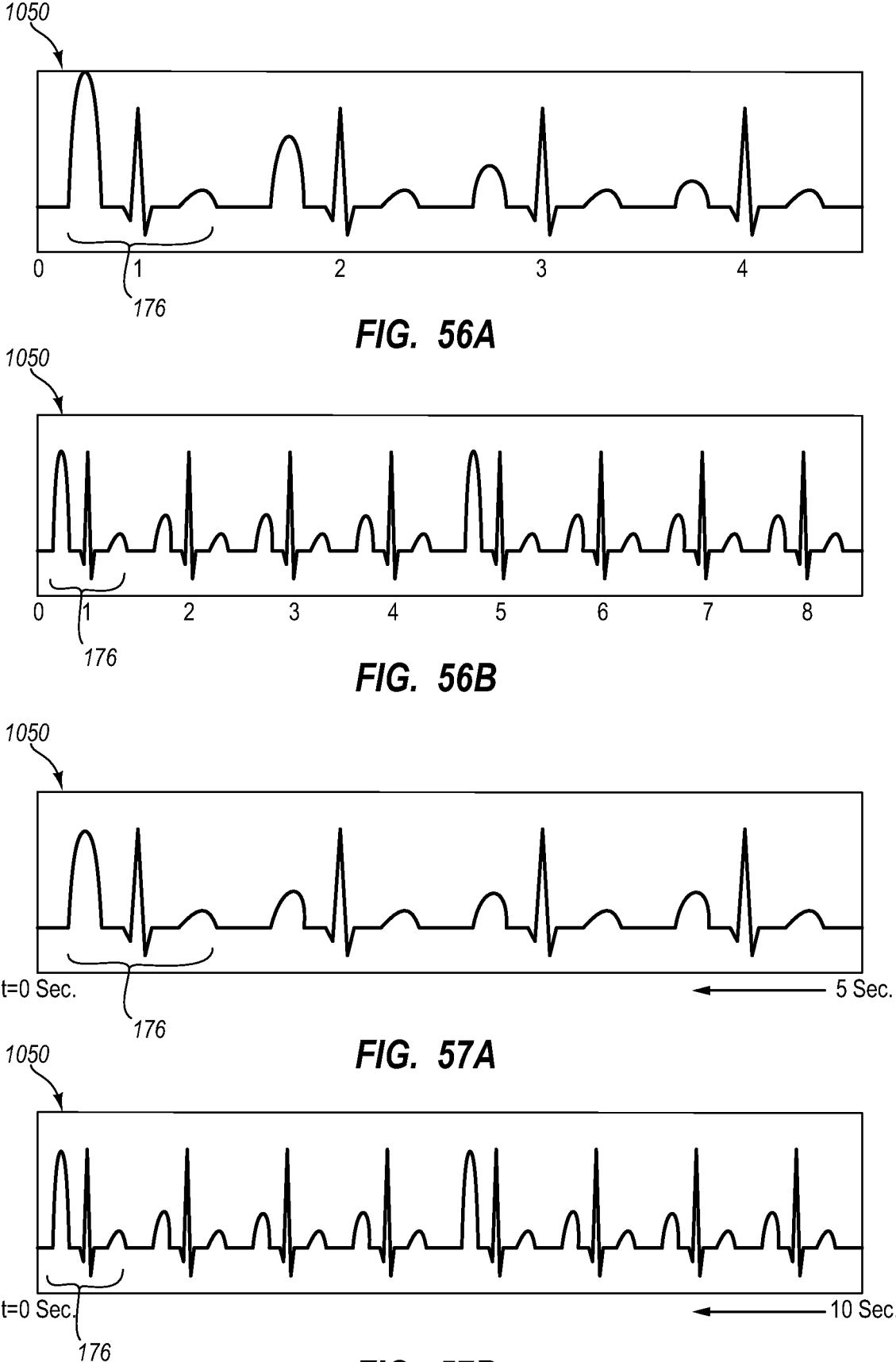

As examples of the above ECG trace time window variability, FIG. 56A shows the ECG waveforms 176 displayed as part of the ECG trace 1050 at a standard rate of four waveforms in the window, while FIG. 56B shows an increased ECG trace window including eight waveforms. Similarly, FIG. 57A shows ECG waveform data being displayed at a standard trace rate of five seconds, i.e., each waveform 176 remains displayed for approximately five seconds; while FIG. 57B shows the ECG waveforms displayed at a relatively longer rate of approximately 10 seconds, i.e., double the standard trace rate, such that the peaks appear relatively closer together. As shown in FIGS. 56A-57B, the physical width of the ECG trace window stays the same, with only the amount of waveforms displayed therein being modified.

Figure 58:
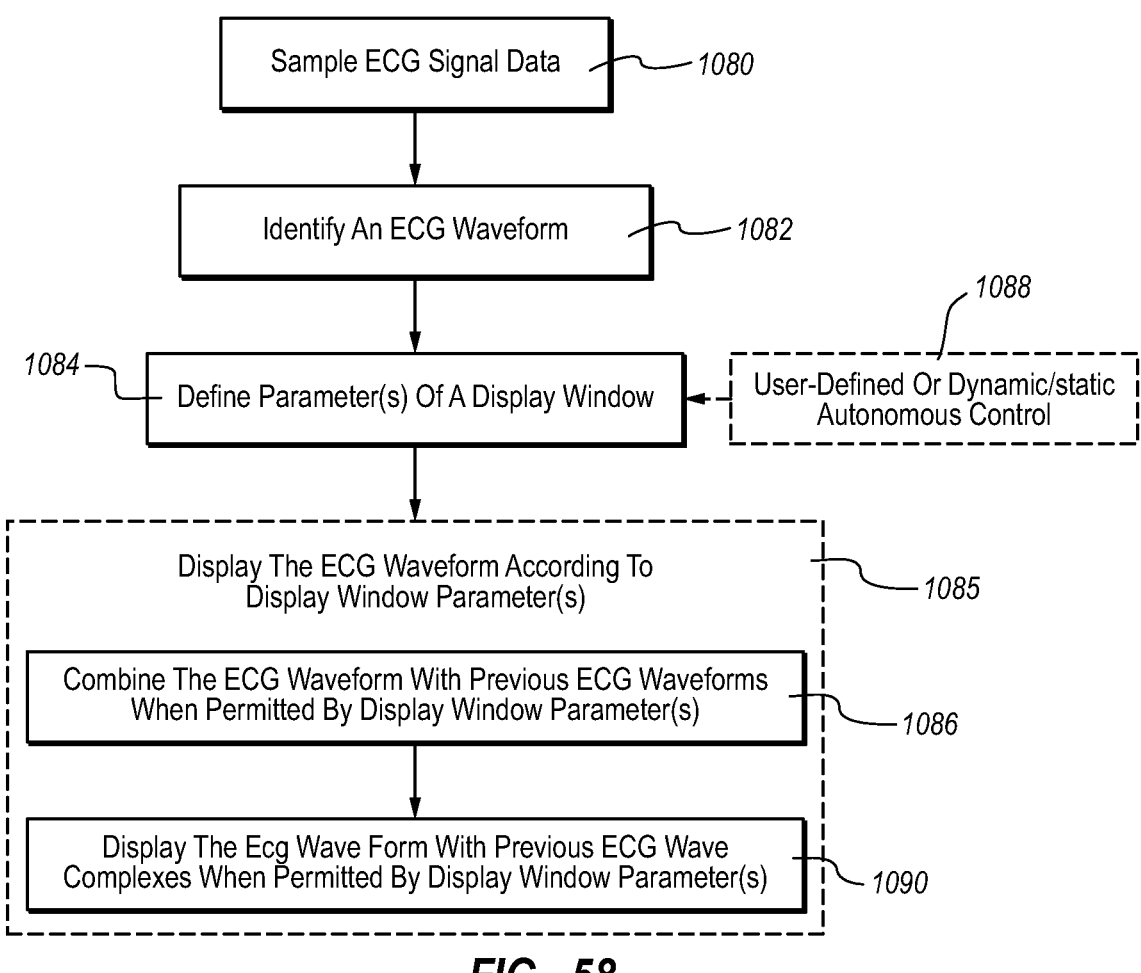
FIG. 58 is a flow chart describing one method according to one embodiment.

FIG. 58 shows a flow chart depicting one embodiment of a method for displaying ECG signal data in the manner described above in connection with FIGS. 56A-57B. Note that this method in whole or in part can be performed and/or controlled by suitable components of the system 10, e.g., circuitry included in the external sensor 50 or console 20, or other suitable catheter or medical device placement system. In stage 1080, ECG signal data is sampled in a manner such as has been described above in connection with use of the system 10 during catheter placement procedures. In stage 1082, an ECG waveform, such as the waveform 176 in FIGS. 56A-57B, is identified from the sampled ECG signal data. In stage 1084, parameters of a display window, such as the trace history window 182 shown in FIG. 17 for displaying the ECG trace 1050 of FIGS. 56A-57B, are defined. These parameters may be, for instance, the number of ECG waveforms to be included in the window, or the amount of time each waveform remains on screen. As stage 1088 shows, the parameters can be user-defined or autonomously defined and controlled in a static (e.g., pre-set at factory) or dynamic (e.g., automatically adjusted by the system according to feedback) manner. It is appreciated that the parameters can concern other display aspects of the ECG trace or waveforms, including for example waveform height, line width, etc. Further the parameters can be defined such that zero, one, two, or more ECG waveforms are displayed in the trace window before being refreshed, for instance.

In stage 1085, the ECG waveform is displayed according to the defined display window parameters. As shown, in one embodiment stage 1085 can include stages 1086 and 1090. In stage 1086 the ECG waveform is combined with previous waveforms if permitted by the parameters defined in stage 1084. In stage 1090, the ECG waveform is displayed together with any previous waveforms as permitted by the parameters defined in stage 1084.

Figure 59:
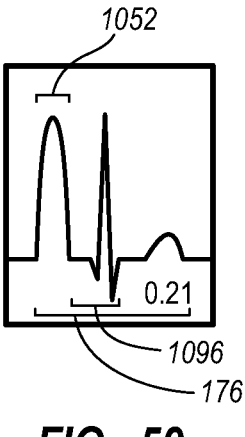
FIG. 59 is a display window including aspects of a single ECG waveform according to one embodiment.

FIG. 59 shows an individual trace window wherein a single ECG waveform 176 is displayed and is periodically refreshed as new waveforms are identified by the system 10 during catheter placement procedures, as has been described. Such a trace window is used, for example, for the current ECG waveform window 180 and windows 184A, 184B, and 184 C of the system display 30, as reflected by the display screenshot 178 shown in FIG. 17. As has been described, the ECG waveform 176 includes the P-wave 1052, and a QRS complex 1096. A ratio between the magnitude of the peak of the P-wave 1052 and the magnitude of the QRS complex 1096 can be displayed in the trace window as a numeric (as shown in FIG. 59) or other suitable format to assist the clinician in determining the change of the ECG waveform as the catheter 72 is advanced through the vasculature of the patient 70. The ratio is updated as each new ECG waveform is depicted in the individual trace window.

Figure 60:
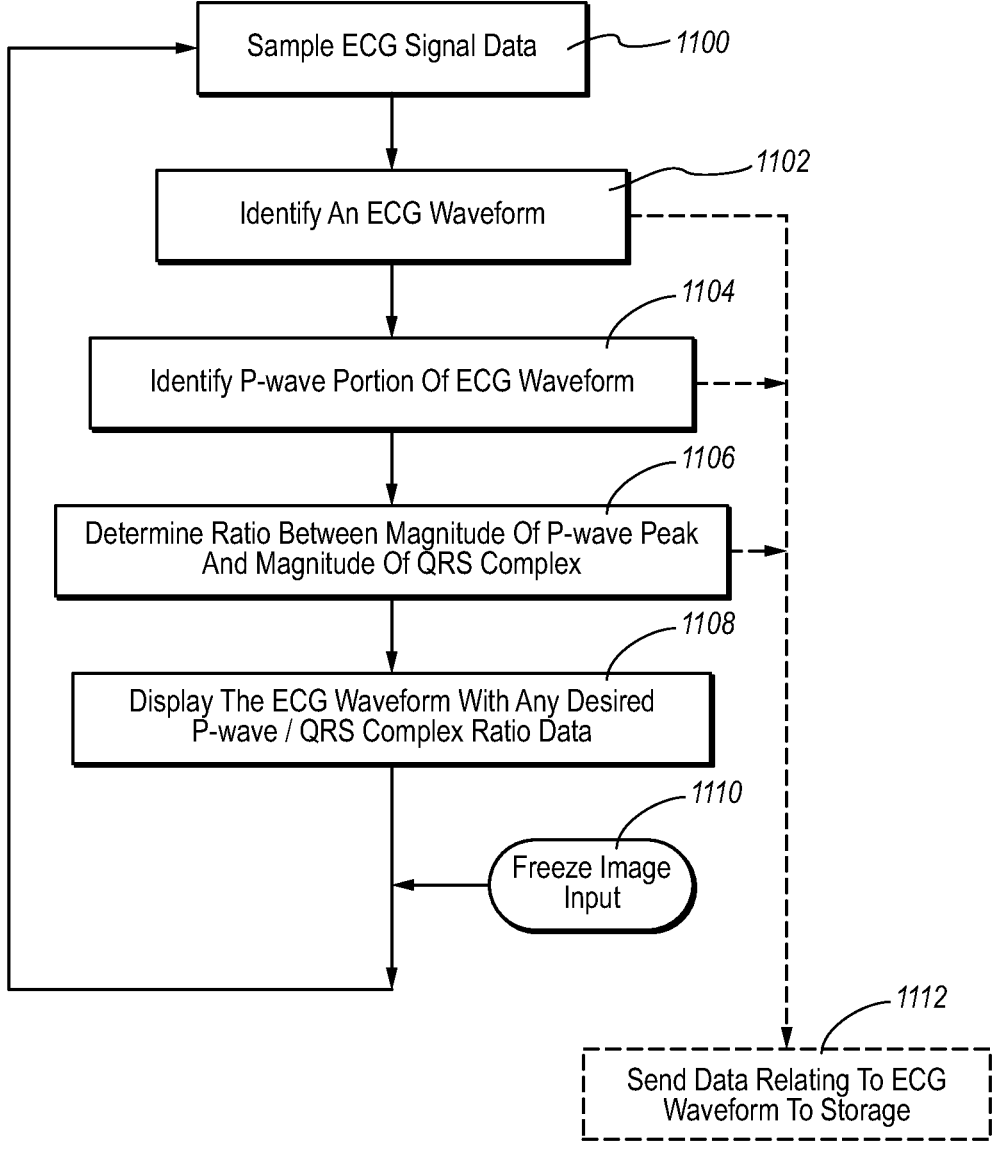
FIG. 60 is a flow chart describing one method according to one embodiment.

FIG. 60 shows a flow chart depicting one embodiment of a method for displaying an ECG waveform in the manner described above in connection with FIG. 59. Note that this method in whole or in part can be performed and/or controlled by suitable components of the system 10, e.g., circuitry included in the external sensor 50 or console 20, or other suitable catheter or medical device placement system. In stage 1100, ECG signal data is sampled in a manner such as has been described above in connection with use of the system 10 during catheter placement procedures. In stage 1102, an ECG waveform, such as the waveform 176 in FIG. 59, is identified from the sampled ECG signal data. In stage 1104, a P-wave portion of the ECG waveform 176 is identified. This can be accomplished, for instance, by comparing portions of the waveform with a standard, pre-loaded P-wave template to determine the existence and location of the P-wave 1052.

In stage 1106, a ratio between the magnitude of the P-wave amplitude and a magnitude of the QRS complex amplitude 1096 is determined. In one embodiment, this stage may include determining the amplitude peak of the P-wave, identifying the QRS complex 1096 from the ECG waveform 176 and determining the magnitude of the QRS complex magnitude. In stage 1108, the ECG waveform 176 is displayed, such as in the current ECG waveform window 180 or one of the windows 184A, 184B, and 184 C of the system display 30 (FIG. 17). The waveform 176 can be displayed with the P-wave/QRS complex ratio data acquired via stage 1106, if desired. As shown in FIG. 60, the process flow can be looped so as to acquire and display new ECG waveforms as they are produced and detected.

Stage 1110 includes a freeze image input option, wherein a user can select the displayed ECG waveform 176 and freeze it in the display, thus interrupting the looping of the process flow, or optionally preventing newly-acquired waveforms from being displayed. Also, during the process flow stage 1112 can be executed, wherein data relating to the identified ECG waveform is sent to a storage location or device. The stored image can then be displayed if desired, such as in one of the windows 184A, 184B, and 184 C of the system display 30 (FIG. 17).

Figure 61:
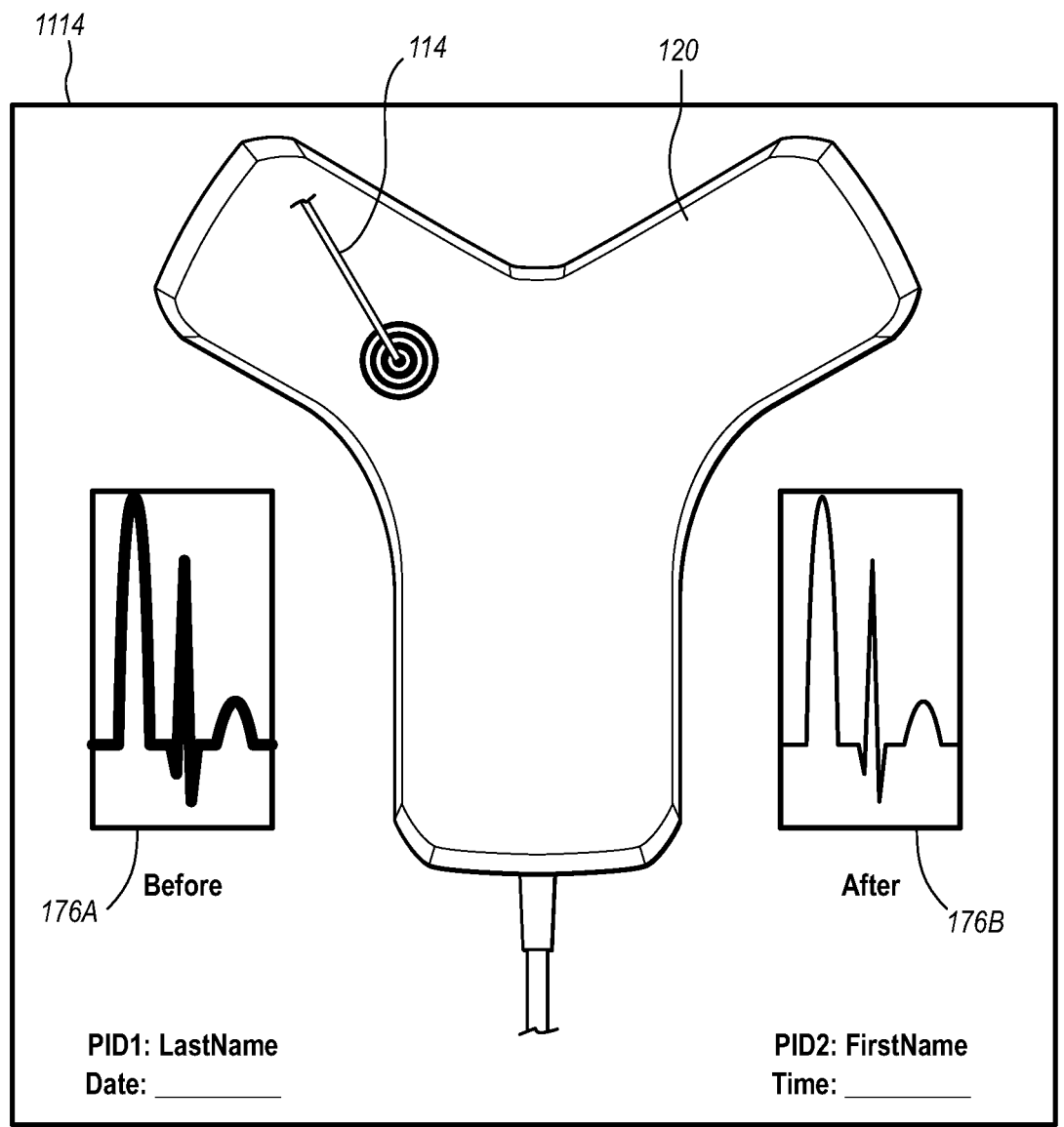
FIG. 61 is a catheter placement record configured according to one embodiment.

FIG. 61 shows one example of a catheter placement record 1114 that can be printed and used for record keeping/documentation purposes to verify proper placement of the catheter 72 within the vasculature of the patient 70. The record 1114 can include, in one embodiment, a beginning ECG waveform 176A representing the ECG waveform when the catheter 72 is first introduced into the patient vasculature, and a final ECG waveform 176B representing the ECG waveform when the distal end of the catheter is positioned in its desired location proximate the patient's heart or other suitable location. An image representation 120 of the sensor 50 can be included with a stylet distal end icon 114 depicted on the sensor image to represent final placement of the stylet, and thus catheter as well. Date, time, patient ID, etc. can also be included in the record 1114. In one embodiment, a location for the clinician or responsible party to sign can also be included. The record 1114 can be user-modifiable via the system 10 in one embodiment so as to allow for customization for various hospital and clinic procedures and requirements. Printout of the record 1114 can be performed via an appropriate button included on the US probe 40, system console 20, etc. In another embodiment, the foot-switch 1116 shown in FIG. 27 or other suitable interface can be used to capture and print the record 1114, if desired.

Figure 62:
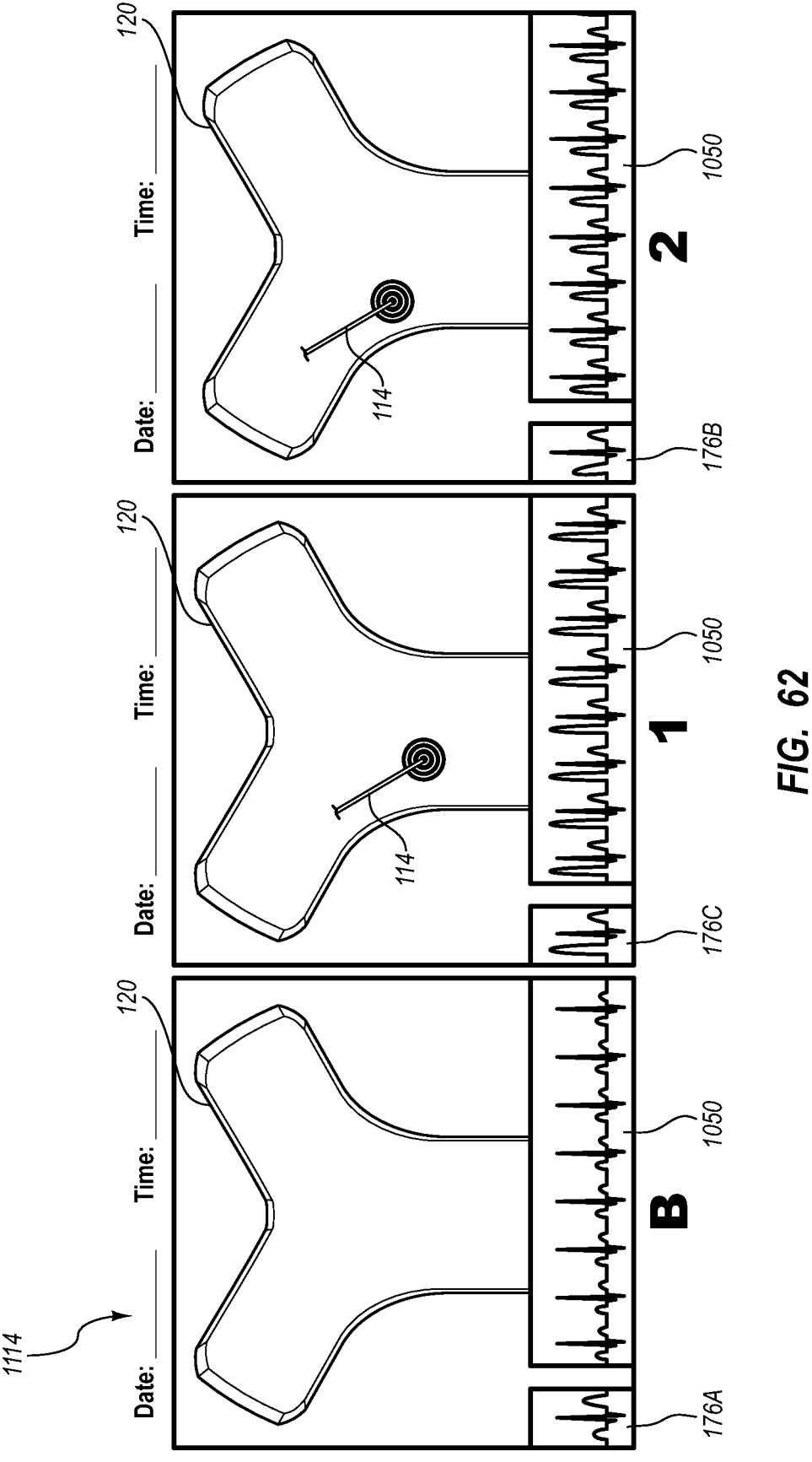
FIG. 62 is another catheter placement record configured according to one embodiment.

FIG. 62 shows yet another example of the catheter place-ment record 1114 that can be printed and used for record keeping/documentation purposes to verify proper placement of the catheter 72. The record 1114 can include, in one embodiment, three windows, with each window depicting the sensor image 120 and selected tip location and ECG waveform data. For instance, the record 1114 in FIG. 62 shows a left window including the beginning ECG wave-form 176A and the corresponding ECG trace 1050 when the catheter 72 is first introduced to the vasculature, a middle window including the revised ECG trace 1050 and an intermediate ECG waveform 176C representing the ECG waveform when the catheter is positioned as indicated by the stylet distal end icon 114, and a right window including the updated ECG trace 1050 and final position ECG waveform 176B representing the ECG waveform when the catheter is finally positioned as indicated by the stylet distal end icon 114. Of course, other configurations/information can be included in the record.

The various data acquired via use of the system 10 as described herein can be stored and/or evaluated for current or later use. In particular, in one embodiment both the TLS magnetic element tracking data and ECG signal detection data acquired via use of the system 10 can be stored for use as appreciated by those skilled in the art. In one embodi-ment, the TLS magnetic element tracking data for the catheter 72 and the ECG signal detection data can be associated with catheter position within the vasculature as a function of time so that a record of the catheter placement can be constructed in real time or at a later time via storage of the data. Such data can be stored in real time during the catheter placement procedure to operate as a fail-safe mode should the system temporarily and unexpectedly shut down during placement. Further, the data can be useful to pinpoint stylet position relative to the peak P-wave amplitude of the ECG signal by calculating the distance between the current stylet distal tip position and the position where P-wave amplitude is maximized. The data can also be employed to provide three dimensional information regarding the path along which the catheter is advanced within the patient vasculature.

Iconic Representations of Aspects of the Catheter or Medical Device

Figures 63, 64:
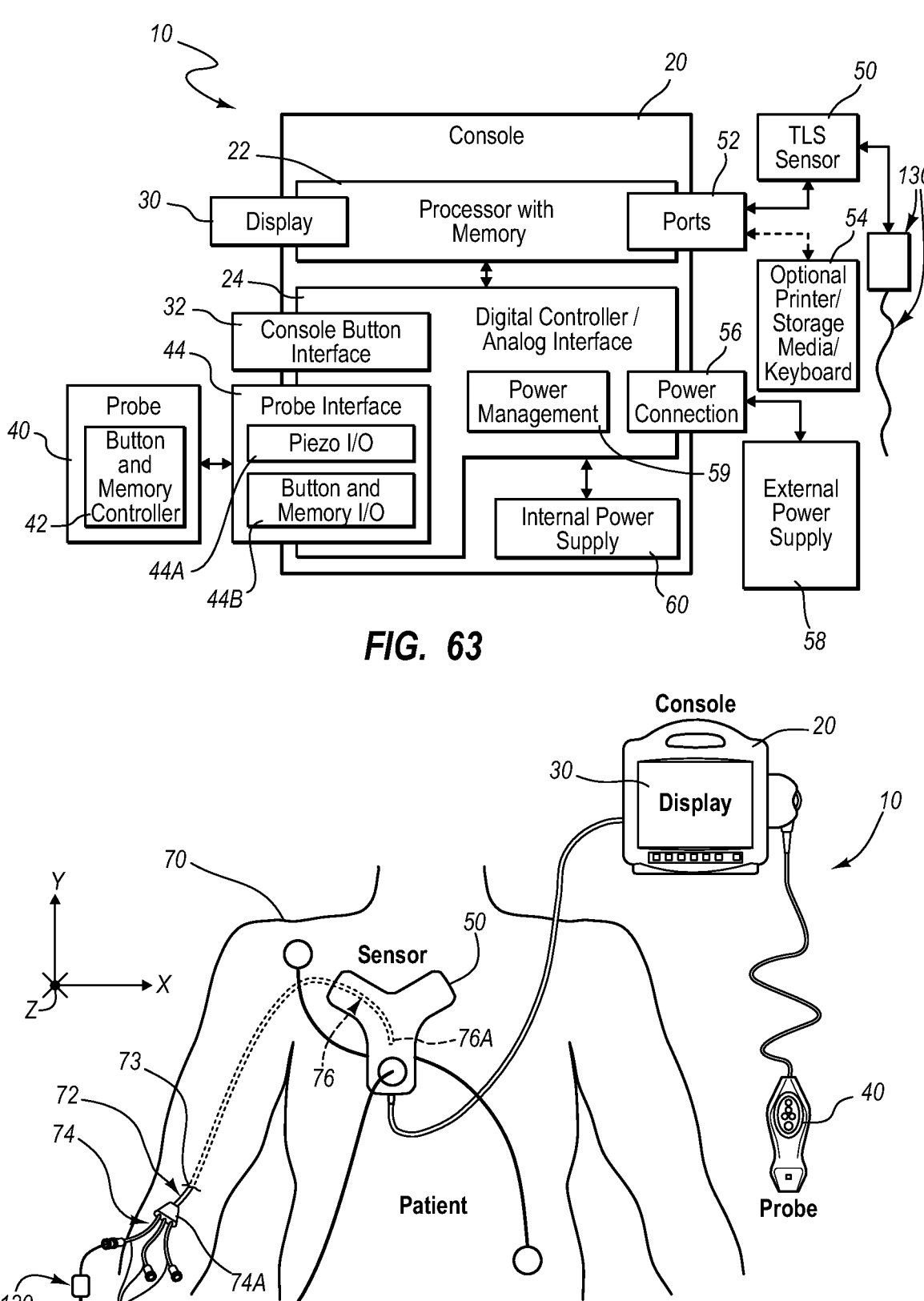
FIG. 63 is a block diagram depicting various elements of an integrated system for intravascular placement of a catheter as one example environment where embodiments of the present invention can be practiced.
FIG. 64 is a simplified view of a patient and a catheter being inserted therein with assistance of the integrated system of FIG. 63.

Reference is now made to FIGS. 63 and 64, which depict various components of the placement system ("system") 10, configured in accordance with one embodiment. As shown, the system 10 generally includes a console 20, display 30, probe 40, and sensor 50, each of which is described in further detail below. As the system 10 is similar in many respect to the systems already described above, only selected features are discussed below.

FIG. 64 shows the general relation of these components to a patient 70 during a procedure to place a catheter 72 into the patient vasculature through a skin insertion site 73. FIG. 64 shows that the catheter 72 generally includes a proximal portion 74 that remains exterior to the patient and a distal potion 76 that resides within the patient vasculature after placement is complete. In the present embodiment, the system 10 is employed to ultimately position a distal tip 76A of the catheter 72 in a desired position within the patient vasculature. In one embodiment, the desired position for the catheter distal tip 76A is proximate the patient's heart, such as in the lower one-third ($\frac{1}{3}^{rd}$) portion of the Superior Vena Cava ("SVC"). Of course, the system 10 can be employed to place the catheter distal tip in other locations. The catheter proximal portion 74 further includes a hub 74A that provides fluid communication between the one or more lumens of the catheter 72 and one or more extension legs 74B extending proximally from the hub.

An example implementation of the console 20 is shown in FIG. 8C above, though it is appreciated that the console can take one of a variety of forms. A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 and buttons included on the probe 40 can be used to immediately call up a desired mode to the display 30 by the clinician to assist in the placement procedure. In one embodiment, information from multiple modes, such as TLS and ECG, may be displayed simultaneously. Thus, the single display 30 of the system console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 30 is an LCD device.

The probe 40 is employed in connection with the first modality mentioned above, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, etc.

As such, in one embodiment a clinician employs the first, US, modality to determine a suitable insertion site and establish vascular access, such as with a needle or introducer, then with the catheter. The clinician can then seamlessly switch, via button pushes on the probe button pad, to the second, TLS, modality without having to reach out of the sterile field. The TLS mode can then be used to assist in advancement of the catheter 72 through the vasculature toward an intended destination.

FIG. 63 shows that the probe 40 further includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Note that while a vein is typically depicted on the display during use of the system 10 in the US modality, other body lumens or portions can be imaged in other embodiments. Note that the US mode can be simultaneously depicted on the display 30 with other modes, such as the TLS mode or ECG mode, if desired. In addition to the visual display 30, aural information, such as beeps, tones, etc., can also be employed by the system 10 to assist the clinician during catheter placement. Moreover, the buttons included on the probe 40 and the console button interface 32 can be configured in a variety of ways, including the use of user input controls in addition to buttons, such as slide switches, toggle switches, electronic or touch-sensitive pads, etc. Additionally, US, TLS, and ECG activities can occur simultaneously or exclusively during use of the system 10.

As just described, the handheld ultrasound probe 40 is employed as part of the integrated catheter placement system 10 to enable US visualization of the peripheral vasculature of a patient in preparation for transcutaneous introduction of the catheter. In the present example embodiment, however, the probe is also employed to control functionality of the TLS portion, or second modality, of the system 10 when navigating the catheter toward its desired destination within the vasculature as described below. Again, as the probe 40 is used within the sterile field of the patient, this feature enables TLS functionality to be controlled entirely from within the sterile field. Thus the probe 40 is a dual-purpose device, enabling convenient control of both US and TLS functionality of the system 10 from the sterile field. In one embodiment, the probe can also be employed to control some or all ECG-related functionality, or third modality, of the catheter placement system 10, as described further below.

The catheter placement system 10 further includes the second modality mentioned above, i.e., the magnetically-based catheter TLS, or tip location system. The TLS enables the clinician to quickly locate and confirm the position and/or orientation of the catheter 72, such as a peripherally-inserted central catheter ("PICC"), central venous catheter ("CVC"), or other suitable catheter or medical device, during initial placement into and advancement through the vasculature of the patient 70. Specifically, the TLS modality detects a magnetic field generated by a magnetic element-equipped tip location stylet, which is pre-loaded in one embodiment into a longitudinally defined lumen of the catheter 72, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

As mentioned, the TLS utilizes a stylet to enable the distal end of the catheter 72 to be tracked during its advancement through the vasculature. In one embodiment, the stylet includes a proximal end and a distal end, with a handle included at the proximal end and a core wire extending distally therefrom. A magnetic assembly is disposed distally of the core wire. The magnetic assembly includes one or more magnetic elements disposed adjacent one another proximate the stylet distal end and encapsulated by tubing. In the present embodiment, a plurality of magnetic elements is included, each element including a solid, cylindrically shaped ferromagnetic stacked end-to-end with the other magnetic elements. An adhesive tip can fill the distal tip of the tubing, distally to the magnetic elements.

Note that in other embodiments, the magnetic elements may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845 titled "Medical Instrument Location Means," which is incorporated herein by reference in its entirety. Yet other examples of stylets including magnetic elements that can be employed with the TLS modality can be found in U.S. Pat. No. 8,784,336 titled "Stylet Apparatuses and Methods of Manufacture," which is incorporated herein by reference in its entirety. These and other variations are therefore contemplated by embodiments of the present invention. It should be appreciated herein that "stylet" as used herein can include any one of a variety of devices configured for removable placement within a lumen of the catheter to assist in placing a distal end of the catheter in a desired location within the patient's vasculature. In one embodiment, the stylet includes a guidewire.

FIG. 64 shows disposal of a stylet 130 substantially within a lumen in the catheter 72 such that the proximal portion thereof extends proximally from the catheter lumen, through the hub 74A and out through a selected one of the extension legs 74B. So disposed within a lumen of the catheter, the distal end 100B of the stylet 100 in the present embodiment is substantially co-terminal with the distal catheter end 76A such that detection by the TLS of the stylet distal end correspondingly indicates the location of the catheter distal end. In other embodiments, other relationships between the distal ends of the stylet and catheter or medical device are possible.

The TLS sensor 50 is employed by the system 10 during TLS operation to detect a magnetic field produced by the magnetic elements 106 of the stylet 100. As seen in FIG. 2, the TLS sensor 50 is placed on the chest of the patient during catheter insertion. The TLS sensor 50 is placed on the chest of the patient in a predetermined location, such as through the use of external body landmarks, to enable the magnetic field of the stylet magnetic elements, disposed in the catheter 72 as described above, to be detected during catheter transit through the patient vasculature. Again, as the magnetic elements of the stylet magnetic assembly are co-terminal with the distal end 76A of the catheter 72 (FIG. 64), detection by the TLS sensor 50 of the magnetic field of the magnetic elements provides information to the clinician as to the position and orientation of the catheter distal end during its transit.

In greater detail, the TLS sensor 50 is operably connected to the console 20 of the system 10 via one or more of the ports 52, as shown in FIG. 63. Note that other connection schemes between the TLS sensor and the system console can also be used without limitation. As just described, the magnetic elements are employed in the stylet 100 to enable the position of the catheter distal end 76A (FIG. 64) to be observable relative to the TLS sensor 50 placed on the patient's chest. Detection by the TLS sensor 50 of the stylet magnetic elements 106 is graphically displayed on the display 30 of the console 20 during TLS mode. In this way, a clinician placing the catheter is able to generally determine the location of the catheter distal end 76A within the patient vasculature relative o the TLS sensor 50 and detect when catheter malposition, such as advancement of the catheter along an undesired vein, is occurring.

As discussed above, the system 10 includes additional functionality in the present embodiment wherein determination of the proximity of the catheter distal tip 76A relative to a sino-atrial ("SA") or other electrical impulse-emitting node of the heart of the patient 70 can be determined, thus providing enhanced ability to accurately place the catheter distal tip in a desired location proximate the node. Also referred to herein as "ECG" or "ECG-based tip confirmation," this third modality of the system 10 enables detection of ECG signals from the SA node in order to place the catheter distal tip in a desired location within the patient vasculature. Note that the US, TLS, and ECG modalities are seamlessly combined in the present system 10, but can be employed in concert or individually to assist in catheter placement. In one embodiment, it is understood that the ECG modality as described herein can be included in a stand-alone system without the inclusion of the US and TLS modalities. Thus, the environments in which the embodiments herein are described are understood as merely example environments and are not considered limiting of the present disclosure.

As described, the catheter stylet 130 is removably predisposed within the lumen of the catheter 72 being inserted into the patient 70 via the insertion site 73. The stylet 130, in addition to including a magnetic assembly for the magnetically-based TLS modality, includes a sensing component, i.e., an ECG sensor assembly, proximate its distal end and including a portion that is co-terminal with the distal end of the catheter tip for sensing ECG signals produced by the SA node. The stylet 130 includes a tether 134 extending from its proximal end that operably connects to the TLS sensor 50. As will be described in further detail, the stylet tether 134 permits ECG signals detected by the ECG sensor assembly included on a distal portion of the stylet 130 to be conveyed to the TLS sensor 50 during confirmation of the catheter tip location as part of the ECG signal-based tip confirmation modality. Reference and ground ECG electrodes attach to the body of the patient 70 in the present embodiment and are operably attached to the TLS sensor 50 to enable the system to filter out high level electrical activity unrelated to the electrical activity of the SA node of the heart, thus enabling the ECG-based tip confirmation functionality. Together with the reference and ground signals received from the ECG electrodes placed on the patient's skin, the ECG signals sensed by the stylet ECG sensor assembly are received by the TLS sensor 50 positioned on the patient's chest (FIG. 10) or other designated component of the system 10. The TLS sensor 50 and/or console processor 22 can process the ECG signal data to produce one or more electrocardiogram waveform, or traces, on the display 30, as will be described. In the case where the TLS sensor 50 processes the ECG signal data, a processor is included therein to perform the intended functionality. If the console 20 processes the ECG signal data, the processor 22, controller 24, or other processor can be utilized in the console to process the data.

Thus, as it is advanced through the patient vasculature, the catheter 72 equipped with the stylet 130 as described above can advance under the TLS sensor 50, which is positioned on the chest of the patient as shown in FIG. 10. This enables the TLS sensor 50 to detect the position of the magnetic assembly of the stylet 130, which is substantially co-terminal with the distal tip 76A of the catheter as located within the patient's vasculature. The detection by the TLS sensor 50 of the stylet magnetic assembly is depicted on the display 30 during ECG mode. The display 30 can further depict during ECG mode an ECG electrocardiogram trace produced as a result of patient heart's electrical activity as detected by the ECG sensor assembly (also referred to herein as an ECG sensor component) of the stylet 130. In greater detail, the ECG electrical activity of the SA node, including the P-wave of the trace, is detected by the ECG sensor assembly of the stylet and forwarded to the TLS sensor 50 and console 20. The ECG electrical activity is then processed for depiction on the display 30. A clinician placing the catheter can then observe the ECG data to determine optimum placement of the distal tip 76A of the catheter 72, such as proximate the SA node in one embodiment. In one embodiment, the console 20 includes the electronic components, such as the processor 22 (FIG. 63), necessary to receive and process the signals detected by the stylet ECG sensor assembly. In another embodiment, the TLS sensor 50 can include the necessary electronic components processing the ECG signals.

As already discussed, the display 30 is used to display information to the clinician during the catheter placement procedure. The content of the display 30 changes according to which mode the catheter placement system is in: US, TLS, or ECG. Any of the three modes can be immediately called up to the display 30 by the clinician, and in some cases information from multiple modes, such as TLS and ECG, may be displayed simultaneously. In one embodiment, as before, the mode the system is in may be controlled by the control buttons included on the handheld probe 40, thus eliminating the need for the clinician to reach out of the sterile field (such as touching the button interface 32 of the console 20) to change modes. Thus, in the present embodiment the probe 40 is employed to also control some or all ECG-related functionality of the system 10. Note that the button interface 32 or other input configurations can also be used to control system functionality. Also, in addition to the visual display 30, aural information, such as beeps, tones, etc., can also be employed by the system to assist the clinician during catheter placement.

In light of the above discussion relating to FIGS. 63 and 64, FIGS. 65-75 depict various details regarding systems and methods for depicting multi-dimensional position and orientation information relating to a distal portion of a catheter (or other indwelling medical device) during procedures for placing the catheter within the body of a patient. In one embodiment, the multi-dimensional position and orientation information is embodied in an icon depicted on the display 30 of the system 10, which is configured for accurately placing the catheter within the vasculature of a patient, as described above. In one embodiment, the system 10 employs the tip location/navigation system ("TLS mode") employing magnetically-based tracking of the catheter tip during its advancement through the tortuous vasculature path to detect and facilitate correction of any tip malposition during such advancement. In addition, the system 10 includes in one embodiment other modalities for improving catheter placement accuracy, including ultrasound-assisted guidance ("US mode") for introducing the catheter into the patient's vasculature, and ECG signal-based catheter tip guidance ("ECG mode") to enable guidance of the catheter tip to a desired position with respect to a node of the patient's heart from which the ECG signals originate. Such ECG-based positional assistance is also referred to herein as "tip confirmation." Depiction of the icon on the system display 30 can occur in connection with TLS mode, ECG mode, or another suitable mode executed by the system 10, as appreciated by one skilled in the art.

As described above and in connection with the embodiments already discussed, the icon 114 is depicted by the system 10 on the display 30 to convey information relating to detection of the distal portion of the stylet 130 disposed in the catheter 72. The icons to be discussed below can be used in the embodiments already discussed in connection with the system 10.

Figure 65:
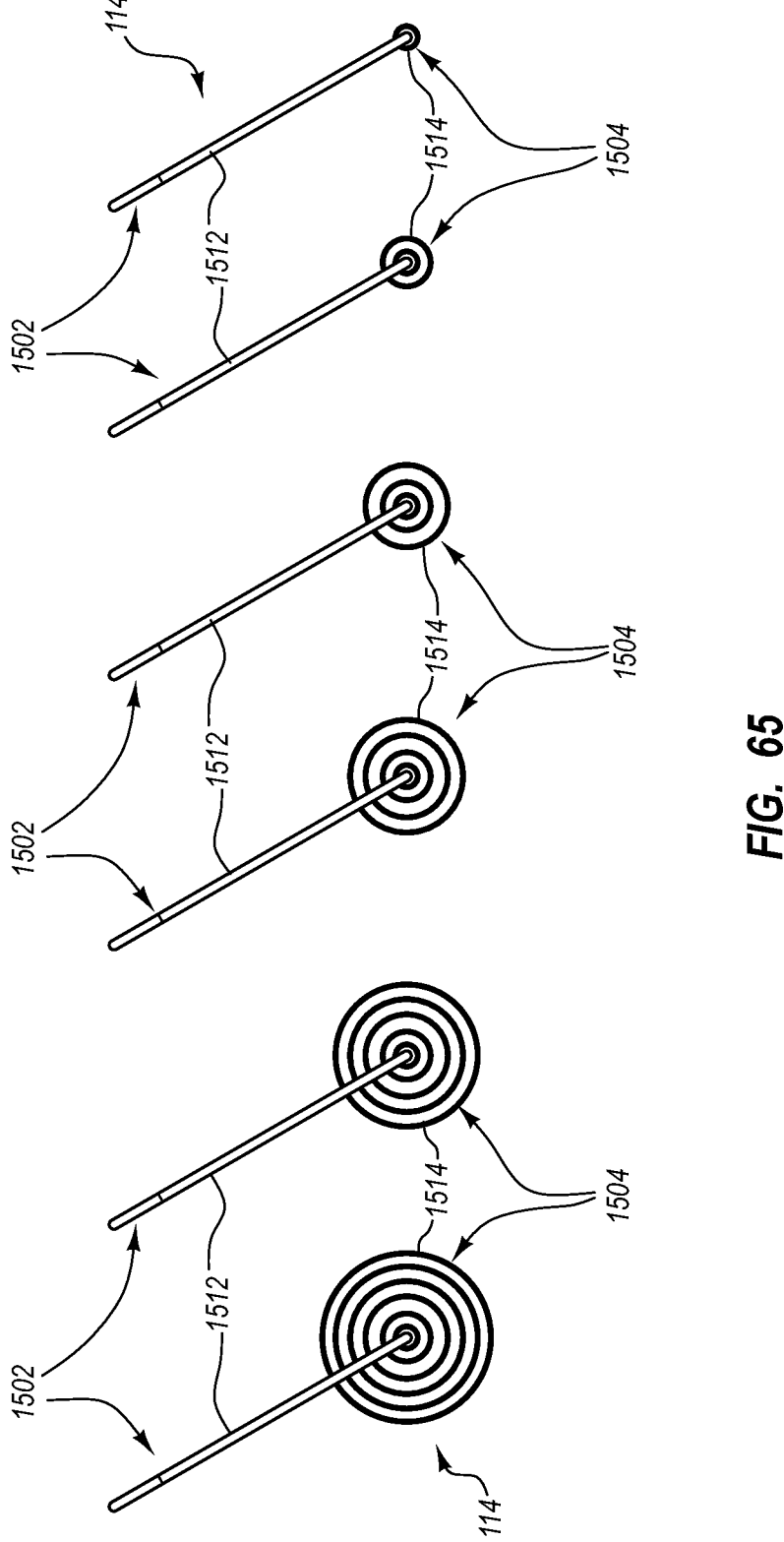
FIG. 65 shows various icons for depiction on the display of the integrated system of FIG. 63, indicating a four-dimensional position and orientation of a distal end of a stylet associated with the catheter of FIG. 64 during catheter tip placement procedures.

In accordance with one embodiment, the icon 114 can visually indicate various pieces of information regarding the position, orientation, and other aspects of the stylet distal end, and thus the distal end of the catheter itself, as already described. FIG. 65 show various examples of the icon 114 in depicting both position and orientation information of the stylet distal end as detected by the system 10 in TLS and/or ECG mode. In particular, the various views of the icon 114 in FIG. 65 include both an orientation indicator 1502, which depicts the orientation of a distal portion of the stylet 130 (FIG. 63, 64), and a position and depth indicator 1504, which depicts indicate the position and depth of the stylet distal end.

In greater detail and as mentioned, the orientation indicator 1502 of the icon 114 depicts on the display 30 the orientation, or "yaw," of the stylet, i.e., the direction the stylet tip is pointing, as detected by the sensor 50 (FIGS. 63, 64). In the present embodiment, the orientation indicator 1502 is implemented as an elongate rod 1512, as shown. The orientation of the rod 1512 as depicted on the display 30 during system operation represents the portion of the stylet proximal to the distal end thereof, thus indicating the direction from which the stylet distal end has advanced. As the stylet moves within the vasculature, the icon 114 and its rod 1512 correspondingly move on the display 30.

The position and depth indicator 1504 of the icon 114 denotes both the two-dimensional position of the stylet distal tip, i.e., the tip position in the x-y plane of the x-y-z coordinate axis as shown in FIG. 64, as well as the depth of the stylet tip within the patient, as detected by the sensor 50 (FIG. 64). In the present embodiment, the position and depth indicator 1504 is implemented as a concentric circle array ("circle array") 1514, as shown.

The center of the circle array 1514 indicates the x-y position of the stylet distal tip within the patient body and with respect to the sensor 50, while the relative size of the circle array indicates the depth thereof. For instance, the left-most icon 114 in FIG. 65 includes relatively many concentric circles included in its circle array 1514, indicating that the stylet distal tip is relatively proximate to the sensor 50, or at a relatively shallow depth within the patient body, which corresponds to a position along the vertical, or z-axis, of the x-y-z coordinate axis shown in FIG. 64.

In contrast, the right-most icon 114 includes relatively few concentric circles in its circle array 1514, indicating that the stylet distal tip is relatively far from the sensor 50, or at a relatively deeper depth within the patient body. Thus, the appearance of the rod 1512 and circle array 1514 of the icon 114 on the display 30 can indicate to a user of the system 10 the spatial status of the stylet distal end in four-dimensions: its x-y-z axis position and depth three-dimensional location, and its yaw orientation (i.e., the fourth dimension). Such an icon depiction provides useful and readily identifiable information to the clinician placing the catheter, wherein the depth indication provided by the icon 114 described above can be used to determine when the catheter is malpositioned within the vasculature. Of course, other medical devices can be similarly tracked, other shapes and configurations for the orientation and position/depth indicators can be used, and stylet tip aspects in addition to orientation, position, and depth can be depicted, as will be seen.

Figure 70:
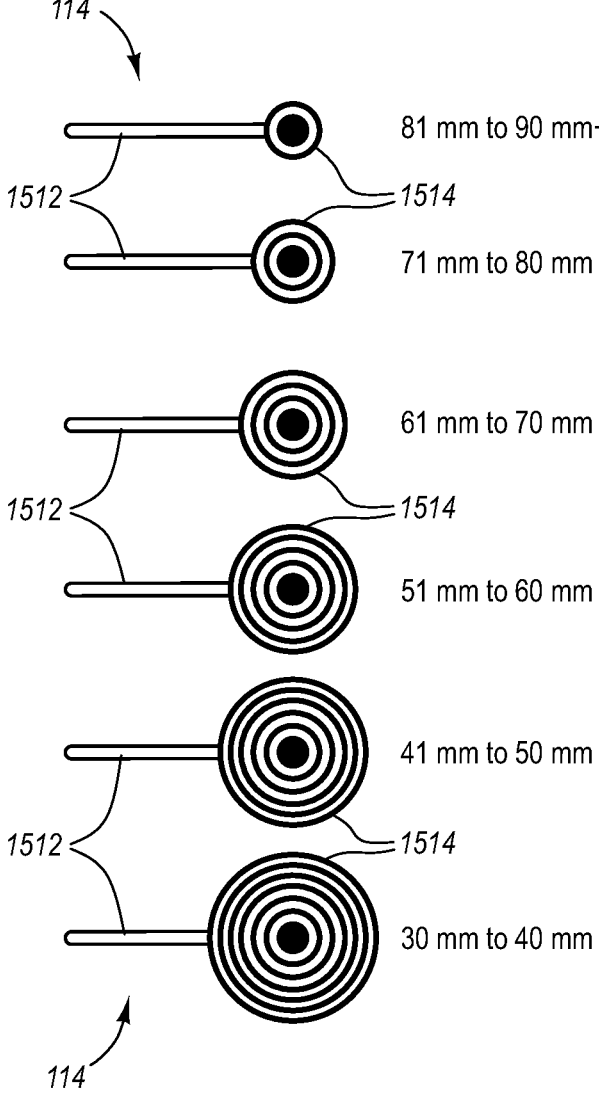
FIG. 70 shows further possible icons including multi-dimensional information according to one embodiment.

FIG. 70 depicts the icon 114 and its corresponding orientation indicating rod 1512 and position/depth indicating circle array 1514 according to the present embodiment, together with examples of corresponding stylet distal tip depths within the patient body as detected by the system sensor 50 (FIG. 64). Of course, this is merely one example of icon size-to-depth correspondence; others are also possible. In addition, the icon features shown herein can be employed to represent other aspects of the detected stylet tip or other suitable indwelling medical device, in other embodiments.

FIG. 66 depicts a method 1530 in which the system 10 or other suitable device can detect, calculate, and depict the icon 114, according to one embodiment. In stage 1532 multiple strength measurements are taken from the various sensor components included in the sensor 50 from their detection of the magnetic assembly of the stylet in TLS mode (FIG. 64). These measurements are used in stage 1534 to calculate position and orientation data for the stylet distal tip. Particularly, in stages 1536 and 1538 the x and y positions of the stylet distal tip are calculated, then depicted on the display 30 of the system 10 at stage 1540. As mentioned, in the embodiment shown in FIG. 65, the x-y position of the stylet distal tip is displayed as the center of the circle array 1514 of the icon 114.

Similarly, in stage 1542 the z position of the stylet distal tip is calculated, then depicted on the display 30 at stage 1544. As mentioned, in the embodiment shown in FIG. 65, the z position of the stylet distal tip is displayed as the circle array 1514 of the icon 114, with a relatively larger array size indicating a shallower stylet distal tip z position within the patient body.

In stage 1546 the orientation of the stylet distal tip is calculated, then depicted on the display 30 at stage 1548. As mentioned, in the embodiment shown in FIG. 65, the orientation of the distal portion of the stylet is displayed as the rod 1512, with the longitudinal extension thereof indicating the direction from which the stylet distal tip has immediately travelled within the patient body. Stages in addition to or instead of the stages discussed here can also be included in the method 1530, in one embodiment. Note that the calculations of stages 1536, 1538, 1542, and 1546 can be performed by the processor 22 of the system console 20 (FIG. 63) in one embodiment, or by another suitable system component.

FIGS. 67A-67F depict examples of other possible configurations for the icon 114 in depicting four-dimensional information relating to the three-dimensional position and orientation (i.e., the fourth dimension) of the stylet distal end. FIG. 67A shows the icon 114 including the rod 1512 and the concentric circle array 1514, as was discussed in connection with FIG. 65. In FIG. 67B, the icon 114 includes the rod 1512 as an orientation indicator and a position and depth indicator implemented as a concentric circle array. In particular, the circle array can include both solid rings 1514A and faded rings 1514B. As stylet distal depth increases, the number of faded rings 1514B increases, replacing formerly present solid rings 1514A.

In FIG. 67C, the icon 114 includes the rod 1512, which serves as an orientation indicator, and a fixed-size concentric circle array 1510A that serves as a tip icon 1510 to show x-y stylet distal tip position. A bar graph 1554 is included adjacent the tip icon 1510. Relatively more of the bars of the bar graph 1554 are solidly filled (in black & white scheme, color, etc.) or otherwise altered when the stylet distal tip is positioned in a shallow depth relative the sensor 50, and vice versa. Instead of a bar graph, the embodiment shown in FIG. 67D includes a vertical scale 1564 with an arrow 1566 that slides along the vertical scale to indicate stylet distal tip depth, wherein the arrow slides lower on the vertical scale as tip depth increases.

In FIG. 67E, the icon 114 includes the rod 1512 to indicate stylet distal tip orientation and the fixed tip icon 1510 to indicate x-y tip position. In addition, the length of the rod 1512 varies according to tip depth, with a relatively shorter rod length indicating deeper tip depth. In FIG. 67F, the rod 1512 includes a plurality of rod segments 1574 that vary in number according to stylet distal tip depth, with a relatively fewer number of rod segments visible indicating deeper tip depth. Note that the various icon elements described herein can be utilized to indicate other aspects of the stylet distal tip, catheter, or other medical device. For instance, the bar graph 1554 used to indicate stylet tip depth in the icon 114 of FIG. 67C can be used in another embodiment to indicate a confidence level (determined by the system 10) with regard to the position, orientation, etc., of the stylet distal tip. Likewise, the rod segments 1574 used to indicate stylet tip depth in the icon 114 of FIG. 67F can be used in another embodiment to indicate the confidence level of the stylet distal tip as determined by the system. These and other variations are therefore contemplated for the various elements and indicators of the icon 114.

Figure 68A:
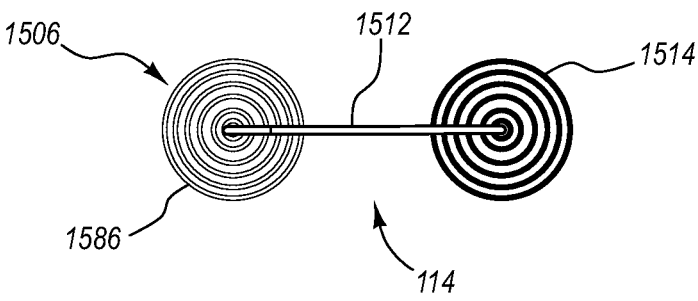
FIGS. 68A and 68B show an example icon for depiction on the display of the integrated system of FIG. 63, indicating a five-dimensional position and orientation of the distal end of a stylet associated with the catheter of FIG. 64 during catheter tip placement procedures.
Figure 68B:
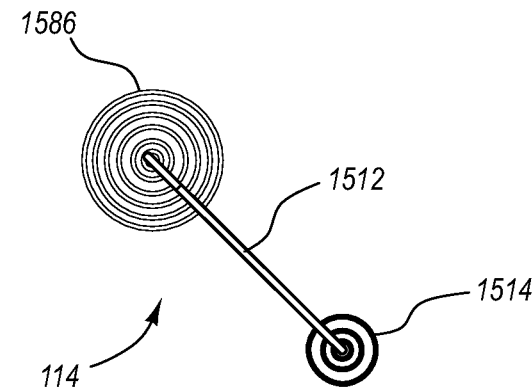
Figure 69:
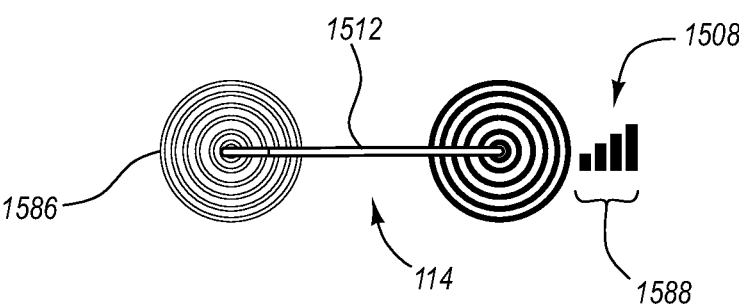
FIG. 69 shows an example icon for depiction on the display of the integrated system of FIG. 63, indicating a six-dimensional position and orientation of a distal end of the stylet associated with the catheter of FIG. 64 during catheter tip placement procedures.

FIGS. 68A-69 depict examples of other possible configurations for the icon 114 in depicting four and five-dimensional information, respectively, relating to: the three-dimensional position of the stylet distal tip; its orientation (i.e., the fourth dimension); pitch, or angle of deviation of the stylet distal portion in the z-direction from the perspective of the x-y-z coordinate axis shown in FIG. 64, also referred to as a fifth dimension of stylet information, and indicating the angle at which the stylet distal end is approaching or departing from the sensor 50 (FIG. 64); and confidence level, i.e., of the correctness of stylet position as determined by the system 10, also referred to herein as a sixth dimension of stylet information.

In FIGS. 68A and 68B, for example, the icon 114 includes the rod 1512 indicating stylet distal portion orientation, and the concentric circle array 1514 indicating stylet distal tip three-dimensional position and depth. In addition, a pitch indicator 1506 is included, implemented as a concentric circle array 1586 disposed at an end of the rod 1512 opposite the circle array 1514. The circle array 1586 includes concentric circles of a different color or solidness from those of the circle array 1514. The circle array 1586 works in conjunction with the circle array 1514 to indicate stylet distal portion pitch. For instance, FIG. 68A depicts a situation where the stylet distal portion has a substantially zero pitch, i.e., a level attitude with respect to the sensor 50. In contrast, FIG. 68B depicts a situation where the stylet distal portion has a downward pitch, indicated by the relatively deeper position of the stylet distal tip (as indicated by the relatively fewer circles of the circle array 1514) with respect to the more shallow more proximal portion of the stylet distal portion (as indicated by the relatively greater number of circles in the circle array 1586. In this way, the icon 114 can indicate pitch to a system user.

FIG. 69 adds the above-mentioned sixth-dimensional confidence level to the embodiment of the icon 114 shown in FIGS. 68A and 68B by adding a confidence indicator 1508 thereto. In the present embodiment, the confidence indicator 1508 is implemented as a confidence bar graph 1588, wherein the number of bars present or solidly filled in indicate the level of confidence in the stylet distal position, orientation, etc., as determined by the system 10 (i.e., fewer bars indicating a lower level of confidence). Confidence described here is also referred to herein as "strength."

As such, it is appreciated that the icons described herein are only examples of various iconic indicators that can be employed to indicate positional and other characteristics of an indwelling device or component. Indeed, in other embodiments, other types of graphs, symbols, shapes, other indicators, and indicator configurations can be employed to represent the various characteristics of the stylet distal tip, including any one or more of the six dimensional characteristics described herein.

Figure 71:
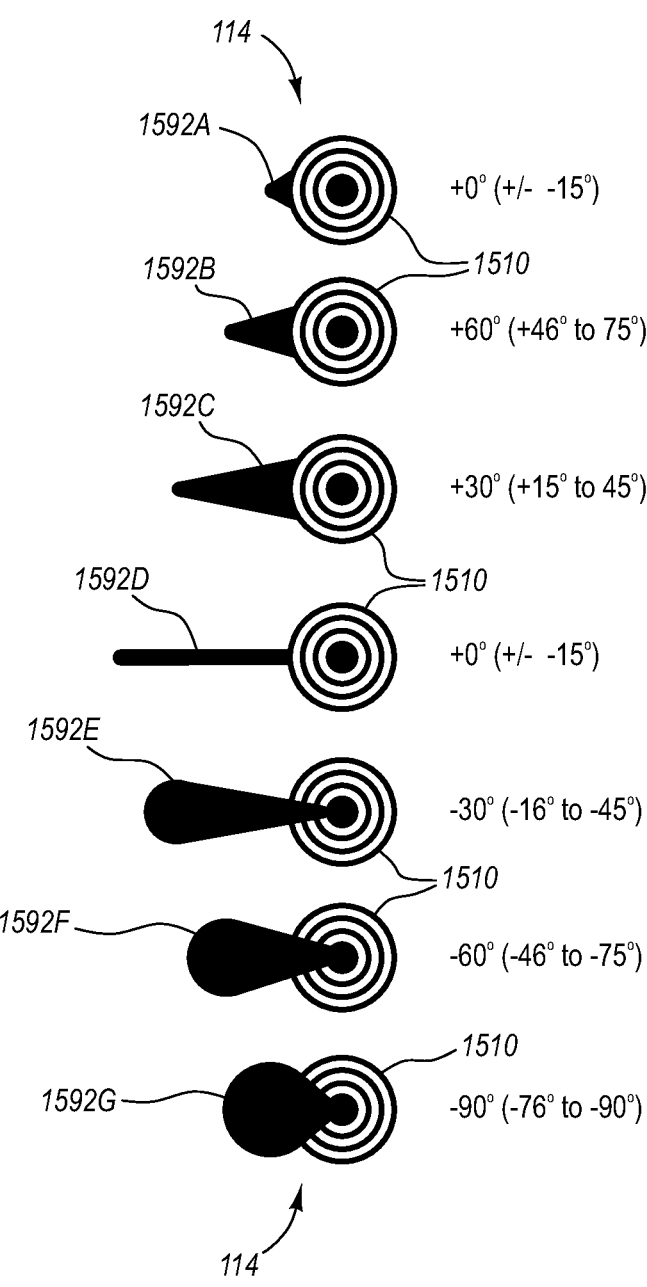
FIG. 71 shows further possible icons including multi-dimensional information according to one embodiment.

FIG. 71 depicts another example of the icon 114 in depicting five-dimensional stylet distal tip data according to one embodiment, wherein three dimensional stylet tip position and depth information is shown by the circle array 1514 of the icon, and the fourth-dimensional stylet distal portion orientation is shown by a rod 1592. In addition, the rod 1592 is given an angled perspective when depicted on the display 30 so as to visually indicate the pitch (i.e., the fifth dimension of stylet distal tip information) of the distal portion of the stylet. For instance, the angled rod 1592A indicates that the angle of the pitch is steeply positive, that is, the stylet tip is steeply approaching the sensor 50 in the z direction. Angled rods 1592B and 1592C also depict positive-pitch stylet tips, though at relatively less steep angles, as indicated in FIG. 71. The angled rod 1592D shows a zero pitch, while angled rods 1592E through 1592G depict negative-pitch stylet tips, i.e., the stylet distal portion is downwardly departing in the z direction from the sensor 50.

Figure 72:
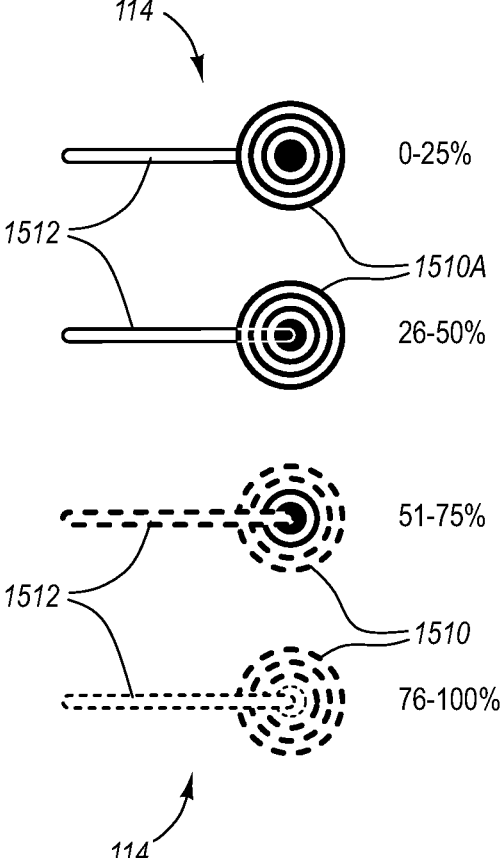
FIG. 72 shows further possible icons including multi-dimensional information according to one embodiment.

FIG. 72 depicts another example of the icon 114 in depicting a characteristic of the stylet distal tip, such as an uncertainty level regarding the position, orientation, etc., of the tip. As shown, the icon 114 includes the rod 1512 and a fixed tip icon 1510. The rod 1512, tip icon 1510, or both can fade in color, visibility, shading, etc. according to the level of uncertainty as determined by the system 10, shown to the right of the corresponding icons in FIG. 72. This is but one example of an additional characteristic that can be represented by the icon 114 when depicted on the system display 30. Thus, multiple aspects or pieces of information can be represented by one or more indicators of the icons as described herein. Note that as used herein, uncertainty is a value opposite to that of confidence, which is discussed above; the two terms are therefore inverses of one another, in one embodiment.

Note that the various indicators shown and described herein are depicted as integrated with or grouped physically proximate/adjacent to one another. In another embodiment, it is appreciated that the various aspects of the icons could be depicted separately from one another.

Figure 73:
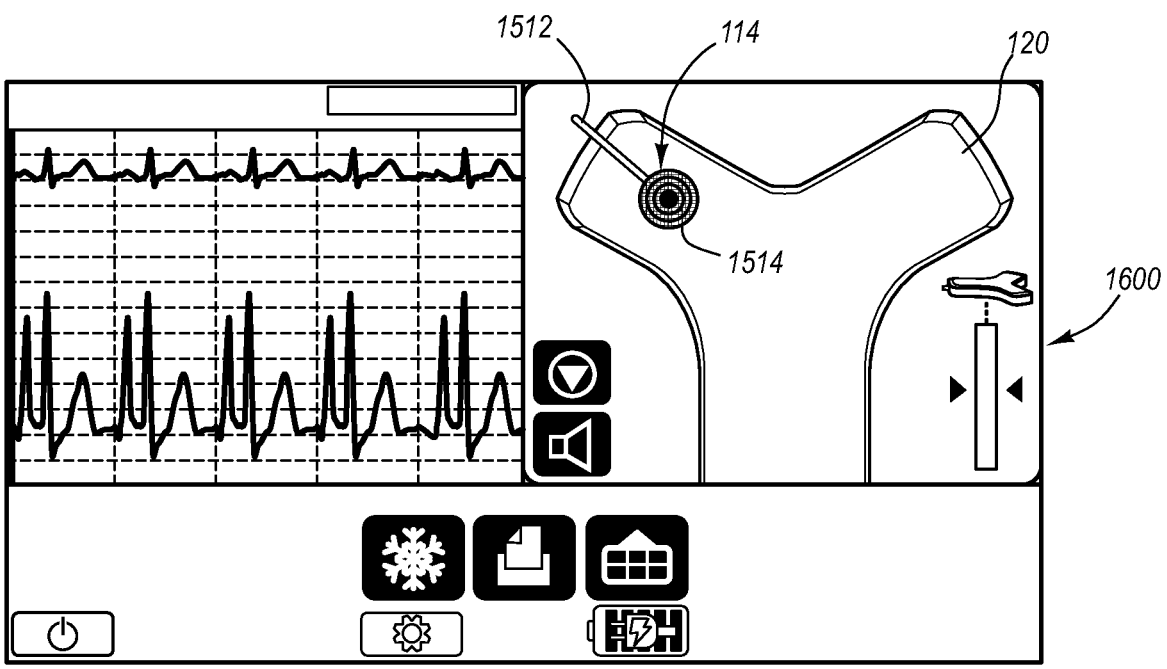
FIG. 73 shows a screenshot with one example of an icon indicating information relating to a position of an indwelling device according to one embodiment.
Figure 74:
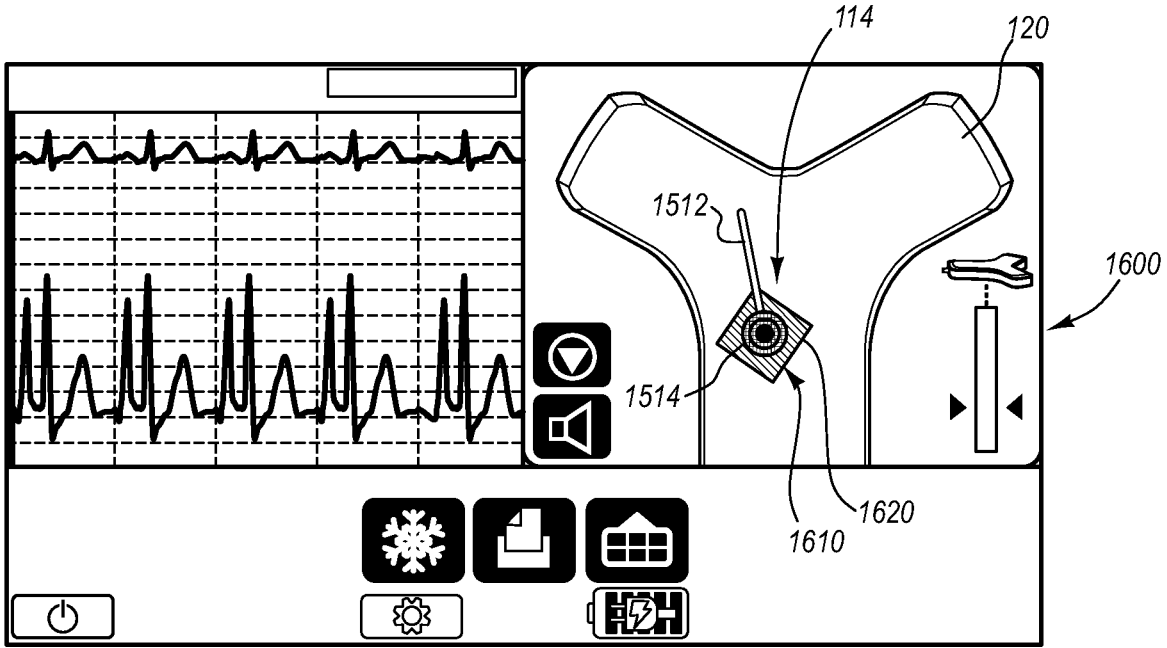
FIG. 74 shows a screenshot with one example of an icon indicating information relating to a position of an indwelling device according to one embodiment.

In FIG. 73, a screenshot 1600 of the system display 30 while the system is in the third modality referenced further above, i.e., ECG-based tip position confirmation, is shown. In particular, the icon 114 is shown, representing the distal catheter tip as it advances through the vasculature of the patient, superimposed upon the representative image 120 of the sensor 50 (FIG. 64). In accordance with one embodiment, the shape, color, etc., of the icon 114 can change according to the proximity of the tip to an intended intravascular location as determined or known by the system 10, such as the lower 1/3$^{rd}$ portion of the SVC. FIG. 73 shows that, before arriving at the intended destination, the icon 114 is similar to icons discussed above and includes the rod 1512 to indicate stylet distal tip orientation and the concentric circle array 1514 indicating the position and depth of the stylet tip. FIG. 74 shows that, once the system 10 has determined that the catheter distal tip has arrived at the lower 1/3$^{rd}$ portion of the SVC (or other suitable intended destination), a location indicator 1610 can be displayed, which in the present embodiment is implemented as a diamond 1620 that is superimposed on the rod 1512 and circle array 1514. In the present embodiment, the diamond 1620 is colored green, though other coloring, shading, and shapes can be used. This indicates to an observer that the catheter distal tip is correctly positioned.

Figure 75:
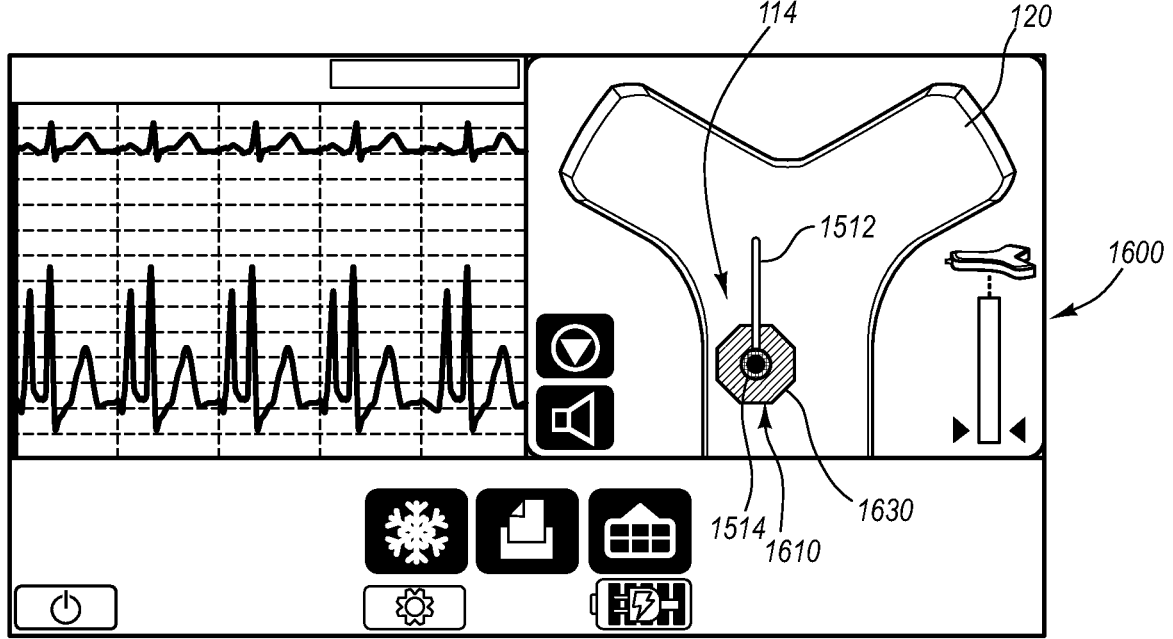
FIG. 75 shows a screenshot with one example of an icon indicating information relating to a position of an indwelling device according to one embodiment.

FIG. 75 shows that, when the catheter distal tip has advanced past the intended destination, the location indicator 1610 can change to an octagon 1630 superimposed on the rod 1512 and circle array 1514, and which can be colored red. The shape and color of the icon location indicator 1610 here is suggestive of a "STOP" traffic sign to indicate to an observer that advancement of the catheter distal tip should stop and perhaps be retracted a suitable amount. In one embodiment, a gray circle or other suitable indicator can be superimposed on the icon 114 if insufficient data exists to depict the location indicator with a suitable level of confidence.

Note that the location indicators 1610 described in connection with FIGS. 73-75 include differing shapes in addition to the differing colors to enable differentiation even to color-blind observers or when printed out in black-and-white. Note also that the above-described icons are only representative of a wider range of possible icons that can be employed in indicating various aspects of the position, orientation, etc., of the indwelling device or component.

Generally, note that in other embodiments, the magnetic element(s) described above may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845 titled "Medical Instrument Location Means," which is incorporated herein by reference in its entirety. Yet other examples of stylets including magnetic elements that can be employed with the TLS modality can be found in U.S. Pat. No. 8,784,336 titled "Stylet Apparatuses and Methods of Manufacture," which is incorporated herein by reference in its entirety. These and other variations are therefore contemplated by embodiments of the present invention. It should be appreciated herein that "stylet" as used herein can include any one of a variety of devices configured for removable placement within a lumen of the catheter to assist in placing a distal end of the catheter in a desired location within the patient's vasculature, and can include guidewires. Additionally, it is appreciated that the catheter placement system described herein can take many forms and can include varying configurations from what is described herein. Further, the icons can be employed in describing aspects of indwelling medical devices other than stylets or be used with systems that employ other modalities, including impedance-based systems, pressure-based systems, systems with varying different frames of reference (e.g., from other than the TLS sensor's frame of reference), etc. Finally, it is appreciated that audio signals can accompany the depiction and movement of the icon on the display. For instance, in one embodiment a first audio tone can be sounded when the icon is near but not atop the sensor image 120 (FIGS. 73-75) such as is seen in FIG. 8B, a second audio tone when the icon is depicted in the top half of the sensor image such as in FIG. 73, a third tone when the icon is depicted in the middle portion of the sensor image such as in FIG. 74, and a fourth tone (such as a chirp) when the icon indicates that the stylet tip has passed the intended destination within the patient vasculature such as in FIG. 75. Note that the icons and tones described here are used in one embodiment to track the stylet distal tip using the ECG modality described further above. Thus, these and other audio-related icons are appreciated as falling within the present disclosure.

Embodiments of the present invention may comprise a special purpose or general-purpose computer including computer hardware. Embodiments within the scope of the present disclosure also include computer-readable media for carrying or having computer-executable instructions or data structures stored thereon. Such computer-readable media can be any available media that can be accessed by a general purpose or special purpose computer. By way of example, and not limitation, computer-readable media can include physical (or recordable-type) computer-readable storage media, such as, RAM, ROM, EEPROM, CD-ROM or other optical disk storage, magnetic disk storage or other magnetic storage devices, non-volatile and flash memory, or any other medium which can be used to store desired program code means in the form of computer-executable instructions or data structures and which can be accessed by a general purpose or special purpose computer.

In this description and in the following claims, a "network" is defined as one or more data links that enable the transport of electronic data between computer systems and/ or modules. When information is transferred or provided over a network or another communications connection (either hardwired, wireless, or a combination of hardwired or wireless) to a computer, the computer properly views the connection as a computer-readable medium. Thus, by way of example, and not limitation, computer-readable media can also include a network or data links which can be used to carry or store desired program code means in the form of computer-executable instructions or data structures and which can be accessed by a general purpose or special purpose computer.

Computer-executable instructions comprise, for example, instructions and data which cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments of the present invention may be practiced in computing environments with one or more types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, and the like. Embodiments may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A system for guiding and placing a catheter in a patient, the system comprising:

a sensor designed for positioning on a chest of the patient;

a stylet designed for insertion into a lumen of the catheter; and a console, comprising:

one or more processors; and a display communicatively coupled to the one or more processors, the display designed to depict current positional information relating to the catheter during insertion of the catheter and the stylet into the patient, the current positional information depicted by an icon comprising:

(i) a position indicator designed to indicate a position of the catheter and the stylet in a x-y plane, (ii) an orientation indicator designed to indicate a direction the catheter and the stylet are pointing, (iii) a depth indicator designed to indicate a depth of the catheter and the stylet, and (iv) a confidence indicator that indicates a level of confidence determined by the console relating to at least one of the position indicator, the orientation indicator, and the depth indicator.

2. The system according to claim 1, wherein the confidence indicator is depicted as at least one of the position indicator, the orientation indicator, and the depth indicator having a more solid appearance at a higher confidence level and a more faded appearance at a lower confidence level.

3. The system according to claim 1, wherein the orientation indicator is depicted on the display as an elongate rod and the confidence indicator is depicted on the elongate rod as a plurality of rod segments.

4. A system for guiding and placing a catheter in a patient, the system comprising:

a sensor designed for positioning on a chest of the patient;

a stylet designed for insertion into a lumen of the catheter; and a console, comprising:

one or more processors;

a display communicatively coupled to the one or more processors; and a non-transitory storage device communicatively coupled to the one or more processors, the non-transitory storage device having stored thereon logic, that when executed by the one or more processors, causes performance of operations including:

depicting an icon on the display, the icon designed to indicate at least six-dimensions of information with respect to a current position of the catheter and the stylet with respect to the sensor when the catheter and the stylet are inserted together into the patient, the icon including:

(i) a position indicator designed to indicate the current position of the catheter and the stylet in a x-y plane, (ii) an orientation indicator designed to indicate a direction the catheter and the stylet are pointing, (iii) a depth indicator designed to indicate a depth of the catheter and the stylet, and (iv) a confidence indicator that indicates a level of confidence determined by the console relating to at least one of the position indicator, the orientation indicator, and the depth indicator;

receiving updated positioning information as the catheter and the stylet are moved with respect to the sensor; and depicting the icon in an updated state on the display according to the updated positioning information.

5. The system according to claim 4, wherein the orientation indicator is depicted on the display as an elongate rod.

6. The system according to claim 5, wherein the position indicator and the depth indicator are depicted on the display as a concentric circle array.

7. The system according to claim 6, wherein the position indicator is depicted as a center of the concentric circle array, and wherein the depth indicator is depicted as one or more circles, and wherein a greater number of circles indicates a closer proximity to the sensor.

8. The system according to claim 5, wherein the confidence indicator is depicted on the elongate rod as a plurality of rod segments.

9. The system according to claim 4, wherein the orientation indicator has a first shape designed to indicate a first pitch of the catheter and the stylet, and a second shape different from the first shape to indicate a second pitch different from the first pitch.

10. The system according to claim 4, further comprising a pitch indicator to indicate a direction of a distal portion of the catheter and the stylet, the pitch indicator comprising a first concentric circle array.

11. The system according to claim 10, wherein the depth indicator is depicted as a second concentric circle array spaced from the first concentric circle array.

12. The system according to claim 11, wherein the icon further comprises an angle indicator designed to indicate an angle at which the distal portion of the catheter and the stylet are moving toward or away from the sensor, the angle indicator comprising a shape connecting the first concentric circle array to the second concentric circle array.

13. The system according to claim 4, wherein the icon further comprises a location indicator that indicates a proximity of the catheter to an intended destination within the patient.

14. The system according to claim 13, wherein the location indicator is depicted as one of a diamond and an octagon.

15. The system according to claim 14, wherein the diamond is colored green and wherein the octagon is colored red.

16. The system according to claim 4, wherein the confidence indicator is depicted as a bar graph.

17. The system according to claim 4, wherein the confidence indicator is depicted as one or both of the position indicator and the depth indicator having a more solid appearance at a higher confidence level and a more faded appearance at a lower confidence level.

18. The system according to claim 17, wherein the position indicator and the depth indicator are solid in a confidence range of 75% to 100%.

19. The system according to claim 18, wherein the position indicator and the depth indicator are dotted lines in a confidence range of 0% to 24%.

\* \* \* \* \*